(12) United States Patent
Beaulieu et al.

(10) Patent No.: US 7,439,258 B2
(45) Date of Patent: *Oct. 21, 2008

(54) VIRAL POLYMERASE INHIBITORS

(75) Inventors: Pierre Louis Beaulieu, Rosemere (CA); Gulrez Fazal, Rosemere (CA); James Gillard, Rosemere (CA); George Kukolj, Mont-Royal (CA); Volkhard Austel, Biberach (DE)

(73) Assignee: Boehringer Ingelheim (Canada) Ltd, Laval (CA)

( * ) Notice: Subject to any disclaimer, the term of this patent is extended or adjusted under 35 U.S.C. 154(b) by 395 days.

This patent is subject to a terminal disclaimer.

(21) Appl. No.: 10/851,710

(22) Filed: May 21, 2004

(65) Prior Publication Data

US 2004/0224955 A1    Nov. 11, 2004

Related U.S. Application Data

(60) Continuation of application No. 10/238,282, filed on Sep. 10, 2002, now Pat. No. 6,794,404, which is a division of application No. 09/995,099, filed on Nov. 27, 2001, now Pat. No. 6,479,508, which is a division of application No. 09/898,297, filed on Jul. 3, 2001, now Pat. No. 6,448,281.

(60) Provisional application No. 60/281,343, filed on Apr. 5, 2001, provisional application No. 60/274,374, filed on Mar. 8, 2001, provisional application No. 60/216,084, filed on Jul. 6, 2000.

(51) Int. Cl.
*A61K 31/4439* (2006.01)
*C07D 401/04* (2006.01)

(52) U.S. Cl. ............... 514/338; 546/273.4; 546/256; 548/181; 548/304.7; 548/306.1; 514/333; 514/365; 514/394

(58) Field of Classification Search ............ 514/338, 514/333, 365, 394; 546/273.4, 256; 548/181, 548/304.7, 306.1
See application file for complete search history.

(56) References Cited

U.S. PATENT DOCUMENTS 4,146,725 A    3/1979    Meyer et al.

(Continued)

FOREIGN PATENT DOCUMENTS

CA    1111695    11/1981

(Continued)

OTHER PUBLICATIONS

Mayer, et al; "Solid-Phase Synthesis of Benzimidazoles"; Tetrahedron Letters 39 (1998) 6655-6658.

(Continued)

*Primary Examiner*—Charanjit S. Aulakh
(74) *Attorney, Agent, or Firm*—Michael Morris; Mary-Ellen M. Devlin; David Dow

(57) ABSTRACT

A compound of the formula I:

(I)

wherein: X is CH or N; Y is O or S; Z is OH, $NH_2$, $NMeR^3$, $NHR^3$; $OR^3$ or 5- or 6-membered heterocycle, having 1 to 4 heteroatoms selected from O, N and S, said heterocycle being optionally substituted with from 1 to 4 substituents; A is N, $COR^7$ or $CR^5$, wherein $R^5$ is H, halogen, or ($C_{1-6}$) alkyl and $R^7$ is H or ($C_{1-6}$ alkyl), with the proviso that X and A are not both N; $R^6$ is H, halogen, ($C_{1-6}$ alkyl) or $OR^7$, wherein $R^7$ is H or ($C_{1-6}$ alkyl);

$R^1$ is selected from the group consisting of 5- or 6-membered heterocycle having 1 to 4 heteroatoms selected from O, N, and S, phenyl, phenyl($C_{1-3}$)alkyl, ($C_{2-6}$)alkenyl, phenyl ($C_{2-6}$)alkenyl, ($C_{3-6}$)cycloalkyl, ($C_{1-6}$)alkyl, $CF_3$, 9- or 10-membered heterobicycle having 1 to 4 heteroatoms selected from O, N and S, wherein said heterocycle, phenyl, phenyl($C_{2-6}$)alkenyl and phenyl($C_{1-3}$)alkyl), alkenyl, cycloalkyl, ($C_{1-6}$)alkyl, and heterobicycle are all optionally substituted with from 1 to 4 substituents;

$R^2$ is selected from ($C_{1-6}$)alkyl, ($C_{3-7}$)cycloalkyl, ($C_{3-7}$)cycloalkyl($C_{1-3}$)alkyl, ($C_{6-10}$)bicycloalkyl, adamantyl, phenyl, and pyridyl, all of which is optionally substituted with from 1 to 4 substituents;

$R^3$ is selected from H, ($C_{1-6}$)alkyl, ($C_{3-6}$)cycloalkyl, ($C_{3-6}$) cycloalkyl($C_{1-6}$)alkyl, ($C_{6-10}$)aryl, ($C_{6-10}$)aryl($C_{1-6}$)alkyl, ($C_{2-6}$)alkenyl, ($C_{3-6}$)cycloalkyl($C_{2-6}$)alkenyl, ($C_{6-10}$)aryl ($C_{2-6}$)alkenyl, $N\{(C_{1-6})alkyl\}_2$, $NHCOO(C_{1-6})$alkyl ($C_{6-10}$) aryl, $NHCO(C_{6-10})$aryl, ($C_{1-6}$)alkyl-5- or 10-atom heterocycle, having 1 to 4 heteroatoms selected from O, N and S, and 5- or 10-atom heterocycle having 1 to 4 heteroatoms selected from O, N and S;

wherein said alkyl, cycloalkyl, aryl, alkenyl and heterocycle are all optionally substituted with from 1 to 4 substituents; n is zero or 1; or a detectable derivative or salt thereof.

The compounds of the invention may be used as inhibitors of hepatitis C virus replication.

The invention further provides a method for treating or preventing hepatitis C virus infection.

30 Claims, 1 Drawing Sheet

U.S. PATENT DOCUMENTS

| | | | |
|---|---|---|---|
| 4,250,317 A | 2/1981 | Meyer et al. | |
| 4,264,325 A * | 4/1981 | Meyer et al. | 8/648 |
| 4,360,679 A | 11/1982 | Meyer et al. | |
| 4,384,121 A | 5/1983 | Meyer | |
| 4,432,886 A | 2/1984 | Meyer | |
| 4,433,975 A | 2/1984 | Meyer | |
| 4,859,684 A | 8/1989 | Raeymaekers et al. | |
| 5,216,003 A | 6/1993 | Vazquez | |
| 5,482,956 A | 1/1996 | Lunkenheimer et al. | |
| 6,448,281 B1 * | 9/2002 | Beaulieu et al. | 514/394 |
| 6,770,666 B2 | 8/2004 | Hashimoto et al. | |
| 6,794,404 B2 * | 9/2004 | Beaulieu et al. | 514/394 |
| 2004/0097438 A1 | 5/2004 | Hashimoto et al. | |

FOREIGN PATENT DOCUMENTS

| | | |
|---|---|---|
| CA | 2067112 | 2/1992 |
| CA | 2150812 | 6/1994 |
| CA | 2158996 | 10/1994 |
| CA | 2143040 | 8/1995 |
| CA | 2124169 | 11/1995 |
| CA | 2164394 | 6/1996 |
| CA | 2223585 | 12/1996 |
| CA | 2241186 | 6/1997 |
| CH | 511 873 | 10/1971 |
| DE | 26 41 060 A1 | 3/1978 |
| DE | 35 22 230 A1 | 1/1987 |
| DE | 195 07 913 A1 | 9/1996 |
| EP | 0 011 824 A1 | 6/1980 |
| EP | 0 012 291 A1 | 6/1980 |
| EP | 0 014 411 A1 | 8/1980 |
| EP | 0 010 063 A2 | 12/1982 |
| EP | 0 209 707 A2 | 1/1987 |
| EP | 0 318 084 A2 | 5/1989 |
| EP | 0 353 606 A2 | 2/1990 |
| EP | 0 429 240 A1 | 5/1991 |
| EP | 0 439 356 A1 | 7/1991 |
| EP | 0 459 334 A1 | 12/1991 |
| EP | 0 546 713 A1 | 6/1993 |
| EP | 0 549 175 A1 | 6/1993 |
| EP | 0 563 910 A1 | 10/1993 |
| EP | 0 583 665 A2 | 2/1994 |
| EP | 0 607 439 A1 | 7/1994 |
| EP | 0 615 159 A1 | 9/1994 |
| EP | 0 750 226 A1 | 12/1996 |
| EP | 1 162 196 A1 | 12/2001 |
| FR | 1 604 809 | 5/1972 |
| FR | 2 291 749 | 6/1976 |
| GB | 1094903 | 12/1967 |
| GB | 1186504 | 4/1970 |
| GB | 1436089 | 5/1976 |
| GB | 1 509 527 | 5/1978 |
| GB | 2 203 420 A | 10/1988 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 6297858 | 10/1994 |
| JP | 7140604 | 6/1995 |
| JP | 7228530 | 8/1995 |
| JP | 9328678 | 12/1997 |
| JP | 10204059 | 8/1998 |
| JP | 10265478 | 10/1998 |
| JP | 11021693 | 1/1999 |
| JP | 11177218 | 7/1999 |
| WO | WO 91 16313 A1 | 10/1991 |
| WO | WO 92 10097 A1 | 6/1992 |
| WO | WO 93 06828 A1 | 4/1993 |
| WO | WO 94 11349 A1 | 5/1994 |
| WO | WO 95 07263 A1 | 3/1995 |
| WO | WO 96 39391 A1 | 12/1996 |
| WO | WO 97 12613 A1 | 4/1997 |
| WO | WO 98 01436 A1 | 1/1998 |
| WO | WO 99 61020 A1 | 12/1999 |
| WO | WO 99 65886 A1 | 12/1999 |
| WO | WO 00 06566 A1 | 2/2000 |
| WO | WO 00 10573 A1 | 3/2000 |
| WO | WO 00 13708 A1 | 3/2000 |
| WO | WO 00 18231 A1 | 4/2000 |
| WO | WO 01/47883 A1 | 7/2001 |

OTHER PUBLICATIONS

Wu, et al; "'One-pot' nitro reduction-cyclisation solid phase route to benzimidazoles"; Tetrahedron Letters 41 (2000) 9871-9874.
CAS Registry No. 214150-93-3 Registry Copyright 2001 ACS.
CAS Registry No. 214150-90-0 Registry Copyright 2001 ACS.
CAS Registry No. 115577-24-7 Registry Copyright 2001 ACS.
CAS Registry No. 66630-73-7 Registry Copyright 2001 ACS.
CAS Registry No. 66315-52-4 Registry Copyright 2001 ACS.
CAS Registry No. 66315-51-3 Registry Copyright 2001 ACS.
CAS Registry No. 66315-47-7 Registry Copyright 2001 ACS.
U.S. Appl. No. 10/180,558, filed Jun. 26, 2002.

* cited by examiner

FIGURE 1

AMINO ACID SEQUENCE OF HCV NS5B (SEQ ID NO. 1)

MSYYHHHHHHDYDIPTTENLYFQGAMDPEFSMSYTWTGALITPCAAEESQLPINALSNSLV
RHRNMVYSTTSRSAALRQK
KVTFDRLQVLDDHYRDVLKEMKAKASTVKAKLLSVEEACKLTPPHSAKSKFGYGAKDVRNL
SSKAVDHIRSVWKDLLEDT
ETPIDTTIMAKNEVFCVQPEKGGRKPARLIVFPDLGVRVCEKMALYDVVSTLPQAVMGSSY
GFQYSPKQRVEFLVNAWKS
KKCPMGFSYDTRCFDSTVTESDIRVEESIYQCCDLAPEARQAIKSLTERLYIGGPLTNSKGQ
NCGYRRCRASGVLTTSCG
NTLTCYLKASAACRAAKLQDCTMLVNGDDLVVICESAGTQEDAANLRVFTEAMTRYSAPPG
DLPQPEYDLELITSCSSNV
SVAHDASGKRVYYLTRDPTTPLARAAWETARHTPINSWLGNIIMYAPTLWARMVLMTHFFSI
LLAQEQLEKALDCQIYGA
CYSIEPLDLPQIIERLHGLSAFSLHSYSPGEINRVASCLRKLGVPPLRVWRHRARSVRAKLLS
QGGRAATCGKYLFNWAV
RTKLKLTPIPAASRLDLSGWFVAGYNGGDIYHSLSRARPRWFMLCLLLLSVGVGIYLLPNR

SEQUENCE LISTING

```
<160> NUMBER OF SEQ ID NOS: 1

<210> SEQ ID NO 1
<211> LENGTH: 621
<212> TYPE: PRT
<213> ORGANISM: Hepatitis C Virus

<400> SEQUENCE: 1

Met Ser Tyr Tyr His His His His His His Asp Tyr Asp Ile Pro Thr
 1               5                   10                  15

Thr Glu Asn Leu Tyr Phe Gln Gly Ala Met Asp Pro Glu Phe Ser Met
             20                  25                  30

Ser Tyr Thr Trp Thr Gly Ala Leu Ile Thr Pro Cys Ala Ala Glu Glu
         35                  40                  45

Ser Gln Leu Pro Ile Asn Ala Leu Ser Asn Ser Leu Val Arg His Arg
     50                  55                  60

Asn Met Val Tyr Ser Thr Thr Ser Arg Ser Ala Ala Leu Arg Gln Lys
 65                  70                  75                  80

Lys Val Thr Phe Asp Arg Leu Gln Val Leu Asp Asp His Tyr Arg Asp
                 85                  90                  95

Val Leu Lys Glu Met Lys Ala Lys Ala Ser Thr Val Lys Ala Lys Leu
            100                 105                 110

Leu Ser Val Glu Glu Ala Cys Lys Leu Thr Pro Pro His Ser Ala Lys
        115                 120                 125

Ser Lys Phe Gly Tyr Gly Ala Lys Asp Val Arg Asn Leu Ser Ser Lys
    130                 135                 140

Ala Val Asp His Ile Arg Ser Val Trp Lys Asp Leu Leu Glu Asp Thr
145                 150                 155                 160

Glu Thr Pro Ile Asp Thr Thr Ile Met Ala Lys Asn Glu Val Phe Cys
                165                 170                 175

Val Gln Pro Glu Lys Gly Gly Arg Lys Pro Ala Arg Leu Ile Val Phe
            180                 185                 190
```

-continued

```
Pro Asp Leu Gly Val Arg Val Cys Glu Lys Met Ala Leu Tyr Asp Val
        195                 200                 205

Val Ser Thr Leu Pro Gln Ala Val Met Gly Ser Ser Tyr Gly Phe Gln
    210                 215                 220

Tyr Ser Pro Lys Gln Arg Val Glu Phe Leu Val Asn Ala Trp Lys Ser
225                 230                 235                 240

Lys Lys Cys Pro Met Gly Phe Ser Tyr Asp Thr Arg Cys Phe Asp Ser
                245                 250                 255

Thr Val Thr Glu Ser Asp Ile Arg Val Glu Glu Ser Ile Tyr Gln Cys
            260                 265                 270

Cys Asp Leu Ala Pro Glu Ala Arg Gln Ala Ile Lys Ser Leu Thr Glu
        275                 280                 285

Arg Leu Tyr Ile Gly Gly Pro Leu Thr Asn Ser Lys Gly Gln Asn Cys
    290                 295                 300

Gly Tyr Arg Arg Cys Arg Ala Ser Gly Val Leu Thr Thr Ser Cys Gly
305                 310                 315                 320

Asn Thr Leu Thr Cys Tyr Leu Lys Ala Ser Ala Ala Cys Arg Ala Ala
                325                 330                 335

Lys Leu Gln Asp Cys Thr Met Leu Val Asn Gly Asp Asp Leu Val Val
            340                 345                 350

Ile Cys Glu Ser Ala Gly Thr Gln Glu Asp Ala Ala Asn Leu Arg Val
        355                 360                 365

Phe Thr Glu Ala Met Thr Arg Tyr Ser Ala Pro Pro Gly Asp Leu Pro
    370                 375                 380

Gln Pro Glu Tyr Asp Leu Glu Leu Ile Thr Ser Cys Ser Ser Asn Val
385                 390                 395                 400

Ser Val Ala His Asp Ala Ser Gly Lys Arg Val Tyr Tyr Leu Thr Arg
                405                 410                 415

Asp Pro Thr Thr Pro Leu Ala Arg Ala Ala Trp Glu Thr Ala Arg His
            420                 425                 430

Thr Pro Ile Asn Ser Trp Leu Gly Asn Ile Ile Met Tyr Ala Pro Thr
        435                 440                 445

Leu Trp Ala Arg Met Val Leu Met Thr His Phe Phe Ser Ile Leu Leu
    450                 455                 460

Ala Gln Glu Gln Leu Glu Lys Ala Leu Asp Cys Gln Ile Tyr Gly Ala
465                 470                 475                 480

Cys Tyr Ser Ile Glu Pro Leu Asp Leu Pro Gln Ile Ile Glu Arg Leu
                485                 490                 495

His Gly Leu Ser Ala Phe Ser Leu His Ser Tyr Ser Pro Gly Glu Ile
            500                 505                 510

Asn Arg Val Ala Ser Cys Leu Arg Lys Leu Gly Val Pro Pro Leu Arg
        515                 520                 525

Val Trp Arg His Arg Ala Arg Ser Val Arg Ala Lys Leu Leu Ser Gln
    530                 535                 540

Gly Gly Arg Ala Ala Thr Cys Gly Lys Tyr Leu Phe Asn Trp Ala Val
545                 550                 555                 560

Arg Thr Lys Leu Lys Leu Thr Pro Ile Pro Ala Ala Ser Arg Leu Asp
                565                 570                 575

Leu Ser Gly Trp Phe Val Ala Gly Tyr Asn Gly Gly Asp Ile Tyr His
            580                 585                 590
```

```
Ser Leu Ser Arg Ala Arg Pro Arg Trp Phe Met Leu Cys Leu Leu Leu
        595                 600                 605

Leu Ser Val Gly Val Gly Ile Tyr Leu Leu Pro Asn Arg
610                 615                 620
```

VIRAL POLYMERASE INHIBITORS

RELATED APPLICATIONS

This application is a continuation of Ser. No. 10/238,282, filed Sep. 10, 2002 now U.S. Pat. No. 6,794,404, which is a divisional of U.S. application Ser. No. 09/995,099, filed on Nov. 27, 2001 now U.S. Pat. No. 6,479,508, which is a divisional of U.S. application Ser. No. 09/898,297, filed on Jul. 3, 2001 now U.S. Pat. No. 6,448,281, which claims benefit of U.S. Provisional Application Ser. No. 60/216,084, filed on Jul. 6, 2000, U.S. Provisional Application Ser. No. 60/274,374, filed on Mar. 8, 2001, and U.S. Provisional Application Ser. No. 60/281,343, filed on Apr. 5, 2001, are hereby claimed, each of which is incorporated by reference in its entirety.

TECHNICAL FIELD OF THE INVENTION

The invention relates to inhibitors of RNA dependent RNA polymerases, particularly those viral polymerases within the Flaviviridae family, and more particularly the NS5B polymerase of HCV.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051*). HCV is not easily cleared by the hosts' immunological defences; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S*). There are an estimated 170 million HCV carriers world-wide, and HCV-associated end-stage liver disease is now one of the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection. Prolonged treatment of chronically infected patients with interferon or interferon and ribavirin is the only currently approved therapy, but it achieves a sustained response in fewer than 50% of cases (Lindsay, K. L.; 1997; *Hepatology* 26: 71S-77S*, and Reichard, O.; Schvarcz, R.; Weiland, O.; 1997 *Hepatology* 26: 108S-111S*).

HCV belongs to the family Flaviviridae, genus *hepacivirus*, which comprises three genera of small enveloped positive-strand RNA viruses (Rice, C. M.; 1996; "Flaviviridae: the viruses and their replication"; pp. 931-960 in *Fields Virology*; Fields, B. N.; Knipe, D. M.; Howley, P. M. (eds.); Lippincott-Raven Publishers, Philadelphia Pa. *). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274-288*). The HCV polyprotein is cleaved co- and post-translationally into at least 10 individual polypeptides (Reed, K. E.; Rice, C. M.; 2000; *Curr. Top. Microbiol. Immunol.* 242: 55-84*). The structural proteins result from signal peptidases in the N-terminal portion of the polyprotein. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22*; and Lohmann, V.; Körner, F.; Herian, U.; Bartenschlager, R.; 1997; *J. Virol.* 71: 8416-8428*). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051*).

* incorporated herein by reference

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 00/06529 reports inhibitors of NS5B which are α,γ-diketoacids.

WO 00/13708, WO 00/10573, and WO 00/18231 report inhibitors of NS5B proposed for treatment of HCV.

SUMMARY OF THE INVENTION

The present invention reduces the difficulties and disadvantages of the prior art by providing a novel class of compounds useful for the treatment and prevention of hepatitis C virus (HCV) infection. The aforesaid compounds have been found to inhibit an RNA dependent RNA polymerase encoded by HCV.

In a first aspect, the invention provides a compound of formula I:

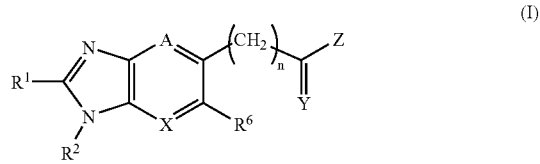

(I)

wherein:

X is CH or N;

Y is O or S;

Z is OH, $NH_2$, $NMeR^3$, $NHR^3$; $OR^3$ or 5-or 6-membered heterocycle, having 1 to 4 heteroatoms selected from O, N and S, said heterocycle being optionally substituted with from 1 to 4 substituents selected from:
COOH and —O—($C_{6-10}$)aryl-($C_{2-6}$)alkenyl-COOH;

A is N, $COR^7$ or $CR^5$, wherein $R^5$ is H, halogen, or ($C_{1-6}$) alkyl and $R^7$ is H or ($C_{1-6}$ alkyl), with the proviso that X and A are not both N;

$R^6$ is H, halogen, ($C_{1-6}$ alkyl) or $OR^7$, wherein $R^7$ is H or ($C_{1-6}$alkyl);

$R^1$ is selected from the group consisting of 5- or 6-membered heterocycle having 1 to 4 heteroatoms selected from O, N, and S, phenyl, phenyl(C$_{1-3}$)alkyl, (C$_{2-6}$)alkenyl, phenyl(C$_{2-6}$)alkenyl, (C$_{3-6}$)cycloalkyl, (C$_{1-6}$)alkyl, CF$_3$, 9- or 10-membered heterobicycle having 1 to 4 heteroatoms selected from O, N and S, wherein said heterocycle, phenyl, phenyl(C$_{2-6}$)alkenyl and phenyl(C$_{1-3}$)alkyl), alkenyl, cycloalkyl, (C$_{1-6}$) alkyl, and heterobicycle are all optionally substituted with from 1 to 4 substituents selected from: OH, halogen, CF$_3$, amino, cyano, phenyl(C$_{1-4}$)alkoxy, COOH, —OCH$_2$CONHCH$_2$Ph, (C$_{1-4}$)alkyl, —OCH$_2$CONH (CH$_2$)$_{2-3}$N(CH$_3$)$_2$, (C$_{1-4}$)alkoxy, —OCH$_2$CO-(morpholino), pyrrolidinyl, carboxy(C$_{2-4}$)alkenyl, phenoxy, —NH(C$_{2-4}$)acyl, —O(CH$_2$)$_m$OH, m being an integer from 2 to 4, SO$_3$, and NO$_2$;

R$^2$ is selected from (C$_{1-4}$)alkyl, (C$_{3-7}$)cycloalkyl, (C$_{3-7}$)cycloalkyl(C$_{1-3}$)alkyl, (C$_{6-10}$)bicycloalkyl, norbornane, phenyl, and pyridyl, all of which is optionally substituted with from 1 to 4 substituents selected from halogen, (C$_{1-6}$)alkyl, —CH$_2$OH, O-benzyl and OH;

R$^3$ is selected from H, (C$_{1-6}$)alkyl, (C$_{3-6}$)cycloalkyl, (C$_{3-6}$)cycloalkyl(C$_{1-6}$)alkyl, (C$_{6-10}$)aryl, (C$_{6-10}$)aryl(C$_{1-6}$)alkyl, (C$_{2-6}$)alkenyl, (C$_{3-6}$)cycloalkyl(C$_{2-6}$)alkenyl, (C$_{6-10}$)aryl(C$_{2-6}$)alkenyl, N{(C$_{1-6}$)alkyl}$_2$, NHCOO(C$_{1-6}$)alkyl(C$_{6-10}$)aryl, NHCO(C$_{6-10}$)aryl, (C$_{1-6}$)alkyl-5- or 10-atom heterocycle, having 1 to 4 heteroatoms selected from O, N and S, and 5- or 10-atom heterocycle having 1 to 4 heteroatoms selected from O, N and S;

wherein said alkyl, cycloalkyl, aryl, alkenyl and heterocycle are all optionally substituted with from 1 to 4 substituents selected from:

OH, COOH, COO(C$_{1-6}$)alkyl, (C$_{1-6}$)alkyl, (C$_{1-6}$)alkyl-hydroxy, phenyl, benzyloxy, halogen, (C$_{2-4}$)alkenyl, (C$_{2-4}$)alkenyl-(C$_{1-6}$)alkyl-COOH, and carboxy(C$_{2-4}$)alkenyl, 5- or 6-membered heterocycle having 1 to 4 heteroatoms selected from O, N and S, said heterocycle being optionally substituted with from 1 to 4 substituents selected from:

(C$_{1-6}$ alkyl), CF$_3$, OH, (CH$_2$)$_p$COOH, COOH, NHCH(C$_{1-6}$alkyl)$_2$, NHCO(C$_{1-6}$ alkyl), NH$_2$, NH(C$_{1-6}$ alkyl), and N(C$_{1-6}$ alkyl)$_2$, wherein p is an integer from 1 to 4;

9- or 10-membered heterobicycle having 1 to 4 heteroatoms selected from O, N and S, said heterobicycle being optionally substituted with from 1 to 4 substituents selected from:

halogen, OPO$_3$H, sulfonamido, SO$_3$H, SO$_2$CH$_3$, —CONH$_2$, —COCH$_3$, (C$_{1-3}$)alkyl, (C$_{2-4}$alkenyl)COOH, tetrazolyl, COOH, —CONH$_2$, OH, NO$_2$, NH$_2$, —O(CH$_2$)$_p$COOH, hydantoin, benzoyle-neurea, triazolyl, (C$_{1-4}$)alkoxy, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCOCONH$_2$, —NHCOCONHCH$_3$, —NHCO(C$_{1-6}$)alkyl-COOH, —NHCOCONH(C$_{1-6}$)alkyl-COOH, —NHCO(C$_{3-7}$)cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, —NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$)aryl-COOH, —NHCH$_2$COOH, —NHCONH$_2$, —NHCO(C$_{1-6}$)hydroxyalkyl COOH, —OCO(C$_{1-6}$) hydroxyalkyl COOH, (C$_{3-6}$)cycloalkyl COOH,

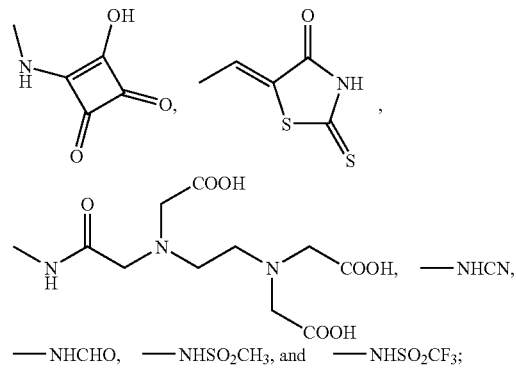

6- or 10-membered aryl being optionally substituted with from 1 to 4 substituents selected from:

halogen, OPO$_3$H, sulfonamido, SO$_3$H, SO$_2$CH$_3$, nitro, —CONH$_2$, —COCH$_3$, (C$_{1-3}$)alkyl, (C$_{2-4}$alkenyl)COOH, tetrazolyl, COOH, —CONH$_2$, OH, NH$_2$, —O(CH$_2$)$_p$COOH, hydantoin, benzoyle-neurea, triazolyl, (C$_{1-4}$)alkoxy, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCOCONH$_2$, —NHCOCONHCH$_3$, —NHCO(C$_{1-6}$)alkyl-COOH, —NHCOCONH(C$_{1-6}$)alkyl-COOH, —NHCO(C$_{3-7}$)cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$) aryl-COOH, —NHCH$_2$COOH, —NHCONH$_2$, —NHCO(C$_{1-6}$)hydroxyalkyl COOH, —OCO (C$_{1-6}$) hydroxyalkyl COOH, (C$_{3-6}$)cycloalkyl COOH,

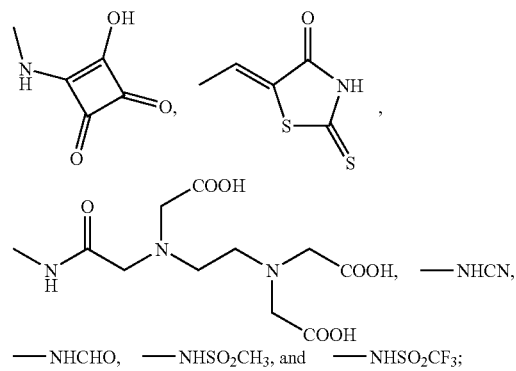

coumarin, (C$_{1-6}$)alkyl-amino, di-(C$_{1-6}$)alkyl-amino, C(halogen)$_3$, —NH(C$_{2-4}$)acyl, —NH(C$_{6-10}$)aroyl, —CONHCH(CH$_2$OH)$_2$, —CO(C$_{1-6}$)alkyl-COOH, —CO—NH-alanyl, —(CH$_2$)$_p$COOH, —OCH$_2$Ph, —CONHbenzyl, —CONHpyridyl, —CONHCH$_2$pyridyl, —CONH(C$_{2-4}$)alkylN(C$_{1-6}$ alkyl)$_2$, —CONH(C$_{2-4}$)alkyl-morpholino, —CONH (C$_{2-4}$)alkyl-pyrrolidino, —CONH(C$_{2-4}$)alkyl-N-methylpyrrolidino, —CONH($C_{2-4}$) alkyl-(COOH)-imidazole, —CONHCH$_2$CH(OH)CH$_2$OH, —CONH($C_{1-6}$)alkyl-COOH, —CONH($C_{6-10}$)aryl-COOH, —CONH($C_{6-10}$)aryl-COO($C_{1-6}$)alkyl, —CONH($C_{1-6}$) alkyl-COO($C_{1-6}$)alkyl, —CONH($C_{6-10}$)aryl-($C_{1-6}$)alkyl-COOH, —CONH($C_{6-10}$)aryl-($C_{2-6}$)alkenyl-COOH, —CONH($C_{2-6}$)alkyl-CONH-9 or 10-membered heterobicycle having 1 to 4 heteroatoms selected from O, N, and S, said heterobicycle being optionally substituted with from 1 to 4 substituents selected from;

COOH, ($C_{6-10}$)aryl and (CH$_2$)$_p$COOH, wherein p is an integer from 1 to 4;

—CONH($C_{6-10}$) aryl-5- or 6-membered heterocycle having 1 to 4 heteroatoms selected from O, N and S, said heterocycle being optionally substituted with from 1 to 4 substituents selected from:

COOH and (CH$_2$)$_p$COOH, wherein p is an integer from 1 to 4;

—CONH($C_{1-6}$alkyl)CONH($C_{6-10}$aryl), said aryl being optionally substituted with from 1 to 4 substituents selected from:

COOH and (CH$_2$)$_p$COOH, wherein p is an integer from 1 to 4;

—O(CH$_2$)$_p$tetrazolyl, wherein p is an integer from 1 to 4; and n is zero or 1;

or a detectable derivative or salt thereof;

with the proviso that if X is CH, Y is O, Z is OH, n=0, and R$^2$ is alkyl or hydroxyalkyl, then R$^1$ is not a five membered heterocycle containing S and N;

and with the further proviso that if X is CH, Y is O, Z is OH, n=0, and R$^1$ is ($C_{2-10}$)alkyl, ($C_{3-10}$)alkenyl, ($C_{3-6}$)cycloalkyl or phenyl, then R$^2$ is not phenyl;

and with the further proviso that if X is CH, Y is O, Z is OH, n=0, and R$^2$ is alkyl or hydroxyalkyl, then R$^1$ is not 5-nitro-2-furyl;

and with the further proviso that if X is CH, Y is O, Z is OH, n=0, and R$^2$ is optionally substituted alkyl or cycloalkyl, then R$^1$ is 5-aryl-2-furyl;

and with the further proviso that if X is CH, Y is O, Z is OH, n=0, and R$^2$ is alkyl or cycloalkyl, then R$^1$ is not 6-phenyl-benzofuran-2-yl;

and with the further proviso that if X is CH, Y is O, Z is OH, n=0, and R$^2$ is n-Pr, then R$^1$ is not 2,3-benzofuranyl or phenyl;

and with the further proviso that if X is CH, Y is O, Z is OH, n=0, and R$^2$ is Me, then R$^1$ is not phenyl or methoxy-2,3-benzofuranyl;

and with the further proviso that if X is CH, Y is O, Z is OH, n=0, and R$^2$ is Et, then R$^1$ is not methoxy-2,3-benzofuranyl;

and with the further proviso that if X is CH, Y is O, Z is OH, n=0, and R$^2$ is ($C_{1-8}$)alkyl, then R$^1$ is not ethenyl;

and with the further proviso that if X is CH, Y is O, Z is OH, n=0, and R$^2$ is lower alkyl, then R$^1$ is not substituted or unsubstituted phenyl, heteroaryl, CHCHphenyl, CHCHfuryl, CHCHpyridyl or CHCHquinolinyl;

and with the further proviso that if X is CH, Y is O, Z is OH, n=0, and R$^2$ is lower alkyl, cycloalkyl or hydroxyalkyl, then R$^1$ is not alkenyl;

and with the further proviso that if X is CH, Y is O, Z is OH, n=0, and R$^2$ is alkyl, then R$^1$ is not aryl, pyridyl, 2-hydroxyphenyl or alkenyl;

and with the further proviso that if X is CH, Y is O, Z is OH, n=0, and R$^2$ is ($C_{1-4}$)alkyl or hydroxy($C_{1-4}$)alkyl, then R$^1$ is not ($C_{5-15}$)aryl, ($C_{2-6}$)alkenyl or ($C_{3-10}$)heteroarylene;

and with the further proviso that if X is CH, Y is O, Z is OH, n=0, and R$^2$ is ($C_{1-12}$)alkyl, then R$^1$ is not phenyl or aryl;

and with the further proviso that if X is CH, Y is O, Z is OH, n=0, and R$^2$ is alkyl or cycloalkyl, then R$^1$ is not 2-hydroxyphenyl;

and with the further proviso that if X is CH, Y is O, Z is OH, n=1, then R$^1$ is not methyl, ethyl or vinyl;

and with the further proviso that if X is CH, Y is O, Z is OH, n=1, then R$^1$ is not 5-azabenzimidazol-2-yl;

and with the further proviso that if X is CH, Y is O, Z is OH, n=0 or 1, and R$^2$ is ($C_{1-4}$)alkyl or hydroxy($C_{1-4}$)alkyl then R$^1$ is not $C_{1-4}$alkyl optionally substituted by OH, COOH or halo;

and with the further proviso that if X is CH, Y is O, Z is OH, n=0 or 1, R$^1$ is heteroaryl or phenyl, then R$^2$ is not heteroaryl or phenyl;

and with the further proviso that if X is CH, Y is O, Z is NHR$^3$ wherein R$^3$ is ($C_{1-3}$)alkyl, substituted with COOH, COOalkyl or tetrazol-5-yl, and further substituted with aryl or heteroaryl, n=0 or 1, and R$^1$ is ($C_{2-10}$)alkyl, ($C_{3-6}$)cycloalkyl or phenyl, then R$^2$ is not optionally substituted phenyl;

and with the further proviso that if X is CH, Y is O, Z is NMeR$^3$ or NHR$^3$ [wherein R$^3$ is alkyl], n=0, and R$^2$ is alkyl, cycloalkyl or aryl, then R$^1$ is not a substituted 2-benzofuryl group;

and with the further proviso that if X is CH, Y is O, Z is NHR$^3$ wherein R$^3$ is alkyl, n=0, and R$^2$ is alkyl or cycloalkyl, then R$^1$ is not a substituted benzofuryl group or benzofuran-2-yl;

and with the further proviso that if X is CH, Y is O, Z is NHR$^3$ wherein R$^3$ is Me, n=0, and R$^2$ is Me, then R$^1$ is not methoxy-2,3-benzofuranyl;

and with the proviso that if X is CH, Y is O, Z is NHR$^3$ [wherein R$^3$ is alkyl or aryl], n=0, and R$^2$ is alkyl not substituted with OH, then R$^1$ is not aryl or heterocycle;

and with the further proviso that if X is CH, Y is O, Z is NHR$^3$ [wherein R$^3$ is alkyl, cycloalkyl, aryl or heteroaryl], n=0, and R$^2$ is alkyl or cycloalkyl, then R$^1$ is not aryl, heteroaryl or alkyl;

and with the further proviso that if X is CH, Y is O, Z is OH or NHR$^3$ or NMeR$^3$ [wherein R$^3$ is ($C_{1-4}$)alkyl], n=0, and R$^2$ is ($C_{1-4}$)alkyl, then R$^1$ is not phenyl bearing an N-substituted sulfonamido group;

and with the further proviso that if X is CH, Y is O, Z is OH or NHR$^3$ wherein R$^3$ is alkyl, cycloalkyl, aryl or heterocycle, n=0, and R$^2$ is alkyl or cycloalkyl, then R$^1$ is not 3,4-dialkoxyphenyl, 3,4-dialkoxyphenylphenylene or 3,4-dialkoxyphenylalkylene;

and with the further proviso that if X is CH, Y is O, Z is OH or NHR$^3$ wherein R$^3$ is H, alkyl, allyl, cycloalkyl, cycloalkylalkyl, phenyl or benzyl, n=0, and R$^2$ is alkyl, cycloalkyl or hydroxyalkyl, then R$^1$ is not tetrazolyl;

and with the further proviso that if X is CH, Y is O, Z is OH or NHR$^3$ wherein R$^3$ is alkyl, halogenoalkyl, alkoxyalkyl, alkylcarbonyl, arylcarbonyl, arylsulphonyl, arylaminocarbonyl or arylmethylsulphonyl, n=0, and R$^2$ is lower alkyl, then R1 is not substituted phenyl or heteroaryl;

and with the further proviso that if X is CH, Y is O, Z is OH or NHR$^3$ wherein R$^3$ is H, alkyl, phenyl or benzyl, n=0, and R$^2$ is ($C_{1-4}$)alkyl, then R$^1$ is not phenyl;

and with the further proviso that if X is CH, Y is O, Z is OH or NH$_2$, n=0, and R$^2$ is alkyl or hydroxyalkyl, then R$^1$ is not fluoroalkyl;

and with the further proviso that if X is CH, Y is O, Z is OH or NH$_2$, n=0, and R$^2$ is alkyl, then R1 is not alkenyl or aryl;

and with the further proviso that if X is CH, Y is O, Z is NHR³ [wherein R³ is thiazolyl], n=1, and R² is $(C_{1-8})$alkyl, $(C_{1-6})$haloalkyl, $(C_{3-7})$cycloalkyl, phenyl or heteroaryl, then R1 is not phenyl, phenyl$(C_{2-4})$alkenyl, heteroaryl, heterocycle, $(C_{1-8})$alkyl, $(C_{2-6})$alkenyl, or $(C_{3-7})$cycloalkyl;

and with the further proviso that if X is CH, Y is O, Z is OH or NH₂, n=1, and R² is $(C_{1-5})$alkyl, then R¹ is not methyl or optionally halogenated phenyl;

and with the further proviso that if X is CH, Y is O, Z is NH₂, n=0, and R² is n-Pr, then R¹ is not phenylethenyl;

and with the further proviso that if X is CH, Y is O, Z is NH₂, n=0, and R² is alkyl, then R¹ is not substituted phenyl or naphthyl;

and with the further proviso that if X is CH, Y is O, Z is NH₂ or NHR³ wherein R³ is $(C_{1-4})$alkyl, benzyl or p-fluorophenylmethyl, n=0, and R² is $(C_{1-4})$alkyl, then R¹ is not phenyl substituted with acylamino.

Alternatively, the first aspect of the invention also provides a compound of formula Ia:

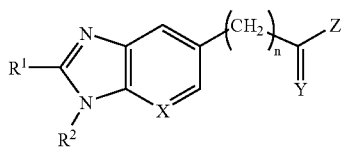

(Ia)

wherein:
X is CH or N;
Y is O or S;
Z is OH, NH₂, NMeR³ or NHR³;
and wherein
R¹ is selected from 5- or 6-membered heteroaryl or heterocycle having 1 to 4 heteroatoms selected from O, N, and S, phenyl, phenyl$(C_{1-3})$alkyl, $(C_{2-6})$alkenyl, phenyl$(C_{2-6})$alkenyl, $(C_{3-6})$cycloalkyl, $(C_{1-6})$alkyl, 9- or 10-atom heterobicycle having 1 to 4 heteroatoms selected from O, N and S, wherein said heteroaryl, phenyl phenylalkenyl, phenylalkyl, alkenyl, cycloalkyl, $(C_{1-6})$alkyl, and heterobicycle are all optionally substituted with 1 to 4 substituents selected from: OH, halogen, cyano, phenyl $(C_{1-4})$alkoxy, COOH, —OCH₂CONHCH₂Ph, $(C_{1-4})$alkyl, —OCH₂CONH(CH₂)$_{2-3}$N(CH₃)₂, $(C_{1-4})$alkoxy, —OCH₂CO-(morpholino), pyrrolidinyl, carboxy$(C_{2-4})$alkenyl, phenoxy, —NH$(C_{2-4})$acyl, —O(CH₂)$_m$OH, m being an integer from 2 to 4, SO₃ and NO₂;

R² is selected from $(C_{1-6})$alkyl, $(C_{3-7})$cycloalkyl, $(C_{3-7})$cycloalkyl$(C_{1-3})$alkyl, $(C_{6-10})$bicycloalkyl, norbornane, phenyl, and pyridyl, all of which is optionally substituted with from 1 to 4 substituents selected from: halogen, $(C_{1-6})$alkyl, —CH₂OH, O-benzyl and OH;

R³ is selected from $(C_{1-6})$alkyl, $(C_{3-6})$cycloalkyl, $(C_{3-6})$cycloalkyl$(C_{1-6})$alkyl, $(C_{6-10})$aryl, $(C_{6-10})$aryl$(C_{1-6})$alkyl, $(C_{2-6})$alkenyl, $(C_{3-6})$cycloalkyl$(C_{2-6})$alkenyl, $(C_{6-10})$aryl$(C_{2-6})$alkenyl, and 5- to 10-membered heterocycle having 1 to 4 heteroatoms selected from O, N and S;

wherein said alkyl, cycloalkyl, aryl, alkenyl and heterocycle are all optionally substituted with from 1 to 4 substituents selected from:
OH, COOH, COO$(C_{1-6})$alkyl, $(C_{1-6})$alkyl, phenyl, benzyloxy, halogen, $(C_{2-4})$alkenyl, carboxy$(C_{2-4})$alkenyl, 5- to 6-membered heterocycle having 1 to 4 heteroatoms selected from O, N and S, said heterocycle being optionally substituted with from 1 to four substituents selected from:
CH₃, CF₃, OH, CH₂COOH and COOH;

9- to 10-membered heterobicycle having 1 to 4 heteroatoms selected from O, N and S said heterobicycle being optionally substituted with from 1 to 4 substituents selected from:
halogen, $(C_{1-3})$alkyl, $(C_{1-3})$alkoxy, tetrazolyl, COOH, —CONH₂, triazolyl, OH, and —O$(C_{1-3})$alkyl-COOH; $(C_{1-4})$alkoxy, cyano, amino, azido, $(C_{1-6})$alkyl-amino, di-$(C_{1-6})$alkyl-amino, OPO₃H, sulfonamido, SO₃H, SO₂CH₃, nitro, C(halo)₃, —NH$(C_{2-4})$acyl, —NHCOCOOH, —NHCH₂COOH, —NHCONH₂,

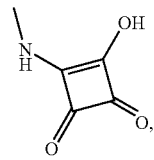

—NHCN, —NHCHO, —NHSO₂CH₃, —NHSO₂CF₃, —NH$(C_{6-10})$aroyl, —CONH₂, —CO—N H-alanyl, —(CH₂)$_p$COOH, —OCH₂Ph, —O—$(C_{1-6})$alkyl COOH, —NHCO $(C_{1-6})$hydroxyalkyl COOH, —OCO$(C_{1-6})$hydroxyalkyl COOH, $(C_{3-6})$cycloalkyl COOH, —CONHbenzyl, —CONHpyridyl, —CONHCH₂pyridyl, —CONH$(C_{2-4})$alkylN (CH₃)₂, —CONH$(C_{2-4})$alkylmorpholino and —O(CH₂)$_p$tetrazolyl, p being an integer from 1 to 4; and n is zero or 1; or a salt thereof;

with the proviso that if X is CH, Y is O, Z is OH, n=0, and R² is alkyl or hydroxyalkyl, then R¹ is not a five membered heterocycle containing S and N;

and with the further proviso that if X is CH, Y is O, Z is OH, n=0, and R¹ is $(C_{2-10})$alkyl, $(C_{3-10})$alkenyl, $(C_{3-6})$cycloalkyl or phenyl, then R² is not phenyl;

and with the further proviso that if X is CH, Y is O, Z is OH, n=0, and R² is alkyl or hydroxyalkyl, then R¹ is not 5-nitro-2-furyl;

and with the further proviso that if X is CH, Y is O, Z is OH, n=0, and R² is optionally substituted alkyl or cycloalkyl, then R¹ is 5-aryl-2-furyl;

and with the further proviso that if X is CH, Y is O, Z is OH, n=0, and R² is alkyl or cycloalkyl, then R¹ is not 6-phenyl-benzofuran-2-yl;

and with the further proviso that if X is CH, Y is O, Z is OH, n=0, and R² is n-Pr, then R¹ is not 2,3-benzofuranyl or phenyl;

and with the further proviso that if X is CH, Y is O, Z is OH, n=0, and R² is Me, then R¹ is not phenyl or methoxy-2,3-benzofuranyl;

and with the further proviso that if X is CH, Y is O, Z is OH, n=0, and R² is Et, then R¹ is not methoxy-2,3-benzofuranyl;

and with the further proviso that if X is CH, Y is O, Z is OH, n=0, and R² is $(C_{1-8})$alkyl, then R¹ is not ethenyl;

and with the further proviso that if X is CH, Y is O, Z is OH, n=0, and R² is lower alkyl, then R¹ is not substituted or unsubstituted phenyl, heteroaryl, CHCHphenyl, CHCHfuryl, CHCHpyridyl or CHCHquinolinyl;

and with the further proviso that if X is CH, Y is O, Z is OH, n=0, and $R^2$ is lower alkyl, cycloalkyl or hydroxyalkyl, then $R^1$ is not alkenyl;

and with the further proviso that if X is CH, Y is O, Z is OH, n=0, and $R^2$ is alkyl, then $R^1$ is not aryl, pyridyl, 2-hydroxyphenyl or alkenyl;

and with the further proviso that if X is CH, Y is O, Z is OH, n=0, and $R^2$ is $(C_{1-4})$alkyl or hydroxy$(C_{1-4})$alkyl, then $R^1$ is not $(C_{5-15})$aryl, $(C_{2-6})$alkenyl or $(C_{3-10})$heteroarylene;

and with the further proviso that if X is CH, Y is O, Z is OH, n=0, and $R^2$ is $(C_{1-2})$alkyl, then $R^1$ is not phenyl or aryl;

and with the further proviso that if X is CH, Y is O, Z is OH, n=0, and $R^2$ is alkyl or cycloalkyl, then $R^1$ is not 2-hydroxyphenyl;

and with the further proviso that if X is CH, Y is O, Z is OH, n=1, then $R^1$ is not methyl, ethyl or vinyl;

and with the further proviso that if X is CH, Y is O, Z is OH, n=1, then $R^1$ is not 5-azabenzimidazol-2-yl;

and with the further proviso that if X is CH, Y is O, Z is OH, n=0 or 1, and $R^2$ is $(C_{1-4})$alkyl or hydroxy$(C_{1-4})$alkyl then $R^1$ is not $C_{1-4}$alkyl optionally substituted by OH, COOH or halo;

and with the further proviso that if X is CH, Y is O, Z is OH, n=0 or 1, $R^1$ is heteroaryl or phenyl, then $R^2$ is not heteroaryl or phenyl;

and with the further proviso that if X is CH, Y is O, Z is $NHR^3$ wherein $R^3$ is $(C_{1-3})$alkyl, substituted with COOH, COOalkyl or tetrazol-5-yl, and further substituted with aryl or heteroaryl, n=0 or 1, and $R^1$ is $(C_{2-10})$alkyl, $(C_{3-6})$cycloalkyl or phenyl, then $R^2$ is not optionally substituted phenyl;

and with the further proviso that if X is CH, Y is O, Z is $NMeR^3$ or $NHR^3$ [wherein $R^3$ is alkyl], n=0, and $R^2$ is alkyl, cycloalkyl or aryl, then $R^1$ is not a substituted 2-benzofuryl group;

and with the further proviso that if X is CH, Y is O, Z is $NHR^3$ wherein $R^3$ is alkyl, n=0, and $R^2$ is alkyl or cycloalkyl, then $R^1$ is not a substituted benzofuryl group or benzofuran-2-yl;

and with the further proviso that if X is CH, Y is O, Z is $NHR^3$ wherein $R^3$ is Me, n=0, and $R^2$ is Me, then $R^1$ is not methoxy-2,3-benzofuranyl;

and with the proviso that if X is CH, Y is O, Z is $NHR^3$ [wherein $R^3$ is alkyl or aryl], n=0, and $R^2$ is alkyl not substituted with OH, then $R^1$ is not aryl or heterocycle;

and with the further proviso that if X is CH, Y is O, Z is $NHR^3$ [wherein $R^3$ is alkyl, cycloalkyl, aryl or heteroaryl], n=0, and $R^2$ is alkyl or cycloalkyl, then $R^1$ is not aryl, heteroaryl or alkyl;

and with the further proviso that if X is CH, Y is O, Z is OH or $NHR^3$ or $NMeR^3$ [wherein $R^3$ is $(C_{1-4})$alkyl], n=0, and $R^2$ is $(C_{1-4})$alkyl, then $R^1$ is not phenyl bearing an N-substituted sulfonamido group;

and with the further proviso that if X is CH, Y is O, Z is OH or $NHR^3$ wherein $R^3$ is alkyl, cycloalkyl, aryl or heterocycle, n=0, and $R^2$ is alkyl or cycloalkyl, then $R^1$ is not 3,4-dialkoxyphenyl, 3,4-dialkoxyphenylphenylene or 3,4-dialkoxyphenylalkylene;

and with the further proviso that if X is CH, Y is O, Z is OH or $NHR^3$ wherein $R^3$ is H, alkyl, allyl, cycloalkyl, cycloalkylalkyl, phenyl or benzyl, n=0, and $R^2$ is alkyl, cycloalkyl or hydroxyalkyl, then $R^1$ is not tetrazolyl;

and with the further proviso that if X is CH, Y is O, Z is OH or $NHR^3$ wherein $R^3$ is alkyl, halogenoalkyl, alkoxyalkyl, alkylcarbonyl, arylcarbonyl, arylsulphonyl, arylaminocarbonyl or arylmethylsulphonyl, n=0, and $R^2$ is lower alkyl, then $R^1$ is not substituted phenyl or heteroaryl;

and with the further proviso that if X is CH, Y is O, Z is OH or $NHR^3$ wherein $R^3$ is H, alkyl, phenyl or benzyl, n=0, and $R^2$ is $(C_{1-4})$alkyl, then $R^1$ is not phenyl;

and with the further proviso that if X is CH, Y is O, Z is OH or $NH_2$, n=0, and $R^2$ is alkyl or hydroxyalkyl, then $R^1$ is not fluoroalkyl;

and with the further proviso that if X is CH, Y is O, Z is OH or $NH_2$, n=0, and $R^2$ is alkyl, then $R^1$ is not alkenyl or aryl;

and with the further proviso that if X is CH, Y is O, Z is $NHR^3$ [wherein $R^3$ is thiazolyl], n=1, and $R^2$ is $(C_{1-8})$alkyl, $(C_{1-6})$haloalkyl, $(C_{3-7})$cycloalkyl, phenyl or heteroaryl, then $R^1$ is not phenyl, phenyl$(C_{2-4})$alkenyl, heteroaryl, heterocycle, $(C_1)$alkyl, $(C_{2-6})$alkenyl, or $(C_{3-7})$cycloalkyl;

and with the further proviso that if X is CH, Y is O, Z is OH or $NH_2$, n=1, and $R^2$ is $(C_{1-5})$alkyl, then $R^1$ is not methyl or optionally halogenated phenyl;

and with the further proviso that if X is CH, Y is O, Z is $NH_2$, n=0, and $R^2$ is n-Pr, then $R^1$ is not phenylethenyl;

and with the further proviso that if X is CH, Y is O, Z is $NH_2$, n=0, and $R^2$ is alkyl, then $R^1$ is not substituted phenyl or naphthyl;

and with the further proviso that if X is CH, Y is O, Z is $NH_2$ or $NHR^3$ wherein $R^3$ is $(C_{1-4})$alkyl, benzyl or p-fluorophenylmethyl, n=0, and $R^2$ is $(C_{1-4})$alkyl, then $R^1$ is not phenyl substituted with acylamino.

In a second aspect, the invention provides an inhibitor of NS5B having the formula I, or Ia, without the provisos.

In a third aspect, the invention provides an inhibitor of HCV replication having the formula I, or Ia, without the provisos.

In a fourth aspect, the invention provides a method of treating or preventing HCV infection in a mammal, comprising administering to the mammal an effective amount of a compound of formula I, or Ia, without the provisos.

In a fifth aspect, the invention provides a pharmaceutical composition for the treatment or prevention of HCV infection, comprising an effective amount of a compound of formula I, or Ia, without the provisos, and a pharmaceutically acceptable carrier.

In a sixth aspect, the invention provides a use for the manufacture of a medicament of formula I, or Ia, without the provisos, for the treatment of HCV infection.

In a seventh aspect, the invention provides a use of a compound of formula I, or Ia, without the provisos, as an inhibitor of NS5B.

In an eighth aspect, the invention provides a use of a compound of formula I, or Ia, without the provisos, as an inhibitor of HCV replication.

In a ninth aspect, the invention provides a method of treating HCV infection in a mammal, comprising giving instructions to a third party to administer a compound of formula I, or Ia, without the provisos to a subject suffering from HCV infection.

BRIEF DESCRIPTION OF THE DRAWINGS

Having thus generally described the invention, reference will now be made to the accompanying drawing, showing by way of illustration a preferred embodiment thereof, and in which:

FIG. 1 shows an amino acid sequence of full length NS5B (SEQ ID NO 1) of HCV.

DETAILED DESCRIPTION OF THE INVENTION

Definitions

The following definitions apply unless otherwise noted:

As used herein, the term "detectable derivative" is intended to refer to substituents, which "label" compounds of the present invention such that when the compound is associated with the polymerase target, the presence of the compound can be detected, measured and quantified. Examples of such "labels" are intended to include, but are not limited to, fluorescent labels, calorimetric labels, and radioactive isotopes.

As used herein, the terms "$(C_{1-3})$alkyl", "$(C14)$alkyl" or "$(C_{1-6})$alkyl", either alone or in combination with another radical, are intended to mean acyclic straight chain alkyl radicals containing up to three, four and six carbon atoms respectively. Examples of such radicals include methyl, ethyl, propyl, butyl, hexyl, 1-methylethyl, 1-methylpropyl, 2-methylpropyl, 1,1-dimethylethyl.

As used herein, the term "$(C_{2-4})$alkenyl", either alone or in combination with another radical, is intended to mean an unsaturated, acyclic straight chain radical containing two to four carbon atoms.

As used herein, the term "$(C_{3-7})$ cycloalkyl", either alone or in combination with another radical, means a cycloalkyl radical containing from three to seven carbon atoms and includes cyclopropyl, cyclobutyl, cyclopentyl, cyclohexyl and cycloheptyl.

As used herein, the term "aryl", either alone or in combination with another radical means aromatic radical containing six, or nine or ten carbon atoms, for example phenyl.

As used herein, the term "heterocycle" or "Het", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "heterobicyclic" as used herein, means a heterocycle as defined above fused to one or more other cycle, be it a heterocycle or any other cycle. Examples of such heterocycles include, but are not limited to, pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyridine-N-oxide, pyrimidine, thiazolo[4,5-b]-pyridine, quinoline, or indole, or the following heterocycles:

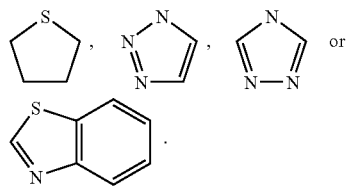

As used herein, the term "halo" means a halogen atom and includes fluorine, chlorine, bromine and iodine.

As used herein, the term "pharmaceutically acceptable salt" includes those derived from pharmaceutically acceptable bases and is non-toxic. Examples of suitable bases include choline, ethanolamine and ethylenediamine. Na$^+$, K$^+$, and Ca$^{++}$ salts are also contemplated to be within the scope of the invention (also see Pharmaceutical salts, Birge, S. M. et al., J. Pharm. Sci., (1977), 66, 1-19, incorporated herein by reference).

Preferred Embodiments

Compounds of the invention act as inhibitors of NS5B RNA dependent RNA polymerase-type activity in vitro and in HCV infected individuals.

According to the first embodiment of this invention preferably compounds of the invention have the following formula:

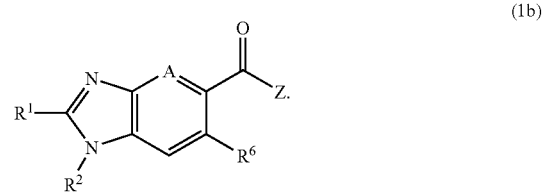

(1b)

Preferably A is N or CR$^5$, wherein R$^5$ is H or (C$_{1-6}$ alkyl). More preferably A is N, CCH$_3$, or CH. Most preferably A is CH.

Preferably R$^6$ is H or (C$_1$)alkyl. More preferably R$^6$ is CH$_3$ or H. Most preferably R$^6$ is H.

Preferably Z is NHR$^3$, OR$^3$, or OH. Most preferably Z is NHR$^3$.

Alternatively preferably, compounds of the invention have the following formulae:

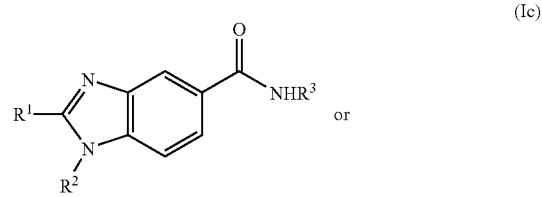

(Ic)

or

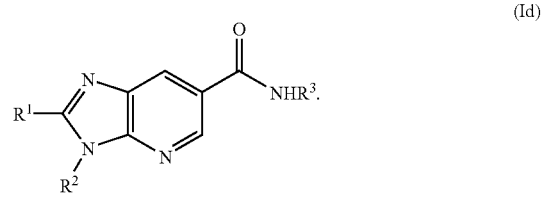

(Id)

With respect to compounds of formula (I), (Ia), (Ib), (Ic), and (Id), preferably R$^1$ is selected from the group consisting of 5- or 6-membered heterocycle having 1 to 4 heteroatoms selected from O, N, and S, phenyl, phenyl(C$_{1-3}$)alkyl, (C$_{2-6}$)alkenyl, phenyl(C$_{2-6}$)alkenyl, (C$_{3-6}$)cycloalkyl, (C$_{1-6}$)alkyl, CF$_3$, 9- or 10-membered heterobicycle having 1 to 4 heteroatoms selected from O, N and S, wherein said heterocycle, phenyl, phenyl(C$_{2-6}$)alkenyl and phenyl(C$_{1-3}$)alkyl), alkenyl, cycloalkyl, (C$_1$)alkyl, and heterobicycle are all optionally substituted with from 1 to 4 substituents selected from: OH, halogen, $CF_3$, amino, cyano, phenyl($C_{1-4}$)alkoxy, COOH, —$OCH_2CONHCH_2Ph$, ($C_{1-4}$)alkyl, —$OCH_2CONH(CH_2)_{2-3}N(CH_3)_2$, ($C_{1-4}$)alkoxy, —$OCH_2CO$-(morpholino), pyrrole, pyrrolidinyl, carboxy($C_{2-4}$)alkenyl, phenoxy, —$NH(C_{2-4})$acyl, —$O(CH_2)_mOH$, m being an integer from 2 to 4, $SO_3H$, and $NO_2$.

More preferably $R^1$ is furyl, tetrahydrofuranyl, pyridyl, N-methylpyrrolyl, pyrrolyl, pyrazine, imidazole, isoquinoline, thiazole, pyrimidine, thiadiazole, pyrazole, isoxazole, indole, thiophenyl, 1,3-benzodioxazole, 1,4-benzodioxan, $CF_3$, phenyl;

wherein said furanyl, tetrahydrofuranyl, pyridyl, N-methylpyrrolyl, pyrrolyl, pyrazine, isoquinoline, thiazole, pyrimidine, pyrazole, isoxazole, indole, thiophenyl, 1,3-benzodioxazole, 1,4-benzodioxan or phenyl being optionally substituted with from 1 to 4 substituents selected from: ($C_{1-6}$alkyl), ($C_{1-4}$)alkoxy, —$OCH_2CONH(CH_2)_{2-3}N(CH_3)_2$, COOH, OH, halogen, $CF_3$, cyano, phenoxy, pyrrolidinyl, —$NH(C_{2-4})$acyl, —$O(CH_2)_2OH$, $NO_2$, $SO_3H$,

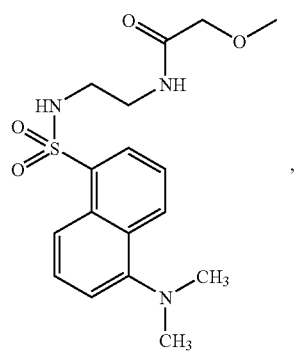,

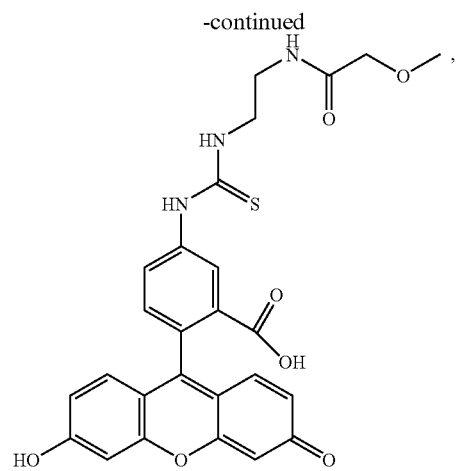

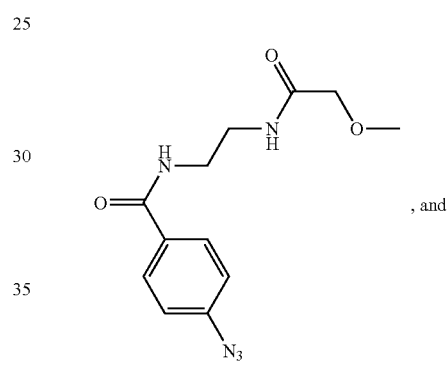, and

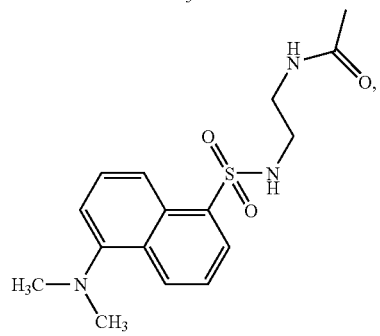

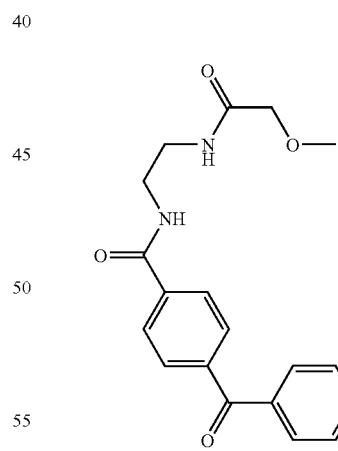

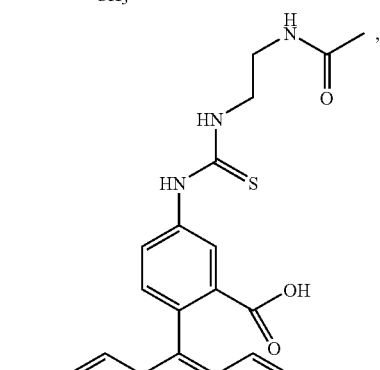,

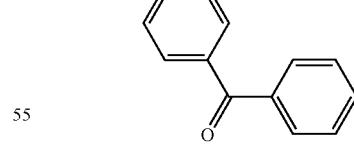

Even more preferably $R^1$ is furanyl, pyridinyl, phenyl, pyridyl, thiophene, thiadiazole, 1,3-benzodioxazole, pyrazine, imidazole, pyrazole, isoxazole, wherein said furan, pyridinyl, phenyl, thiophenyl, thiadiazole, 1,3-benzodioxazole, pyrazine, imidazole, pyrazole, isoxazole being optionally substituted with from 1 to 4 substituents selected from: ($C_{1-6}$alkyl), halogen,

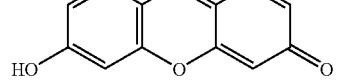

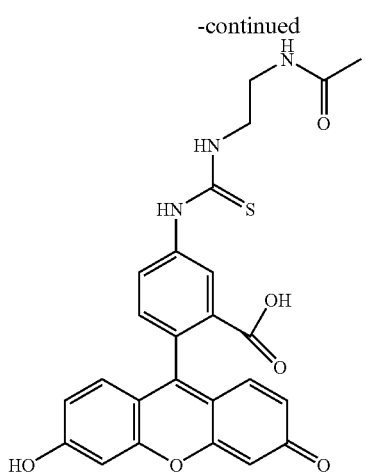

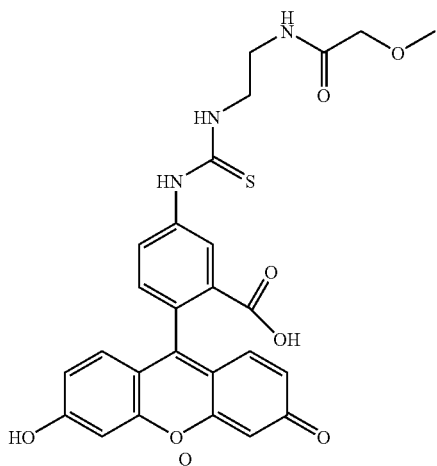

, and

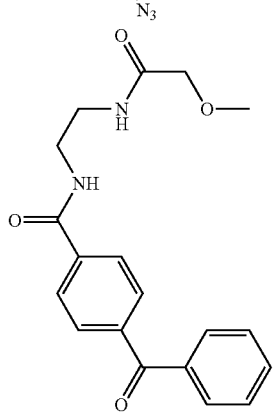

Most preferably R¹ is furanyl, pyridinyl, thiophenyl and phenyl.

With respect to compounds of formula (I), (Ia), (Ib), (Ic), and (Id), preferably R² is selected from $(C_{1-6})$alkyl, $(C_{3-7})$cycloalkyl, $(C_{3-7})$cycloalkyl$(C_{1-3})$alkyl, $(C_{6-10})$bicycloalkyl, adamantyl, phenyl, and pyridyl, all of which is optionally substituted with from 1 to 4 substituents selected from:

halogen, $(C_{1-6})$alkyl, —CH$_2$OH, O-benzyl and OH.

More preferably R² is $(C_{1-6}$ alkyl), norbornane, cyclobutyl, cyclopentyl, cyclohexyl, cycloheptyl,

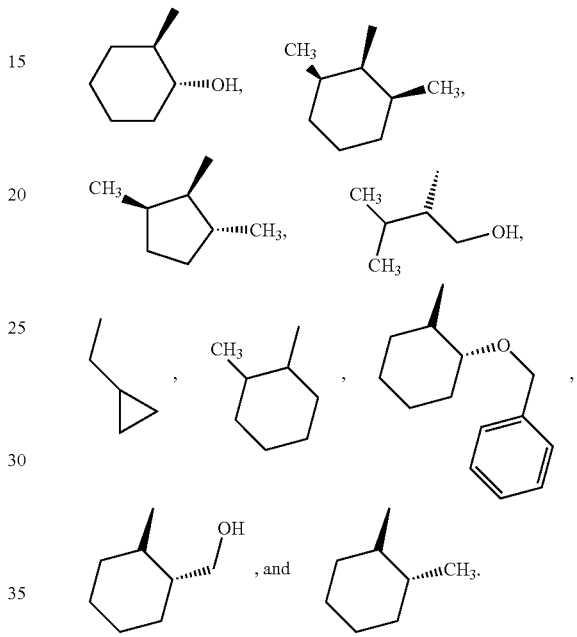

Most preferably R² is cyclohexyl or cyclopentyl.

With respect to compounds of formula (I), (Ia), (Ib), (Ic), and (Id), preferably R³ is selected from H, $(C_{1-6})$alkyl, $(C_{3-6})$cycloalkyl, $(C_{3-6})$cycloalkyl$(C_{1-6})$alkyl, $(C_{6-10})$aryl, $(C_{6-10})$aryl$(C_{1-6})$alkyl, $(C_{2-6})$alkenyl, $(C_{3-6})$cycloalkyl$(C_{2-6})$alkenyl, $(C_{6-10})$aryl$(C_{2-6})$alkenyl, N{$(C_{1-6})$alkyl}$_2$, NHCOO$(C_{1-6})$alkyl$(C_{6-10})$aryl, NHCO$(C_{6-10})$aryl, $(C_{1-6})$alkyl-5- or 10-atom heterocycle, having 1 to 4 heteroatoms selected from O, N and S, and 5- or 10-atom heterocycle having 1 to 4 heteroatoms selected from O, N and S;

wherein said alkyl, cycloalkyl, aryl, alkenyl and heterocycle are all optionally substituted with from 1 to 4 substituents selected from:

OH, COOH, COO$(C_{1-6})$alkyl, $(C_{1-6})$alkyl, $(C_{1-6})$alkyl-hydroxy, phenyl, benzyloxy, halogen, $(C_{2-4})$alkenyl, $(C_{2-4})$alkenyl-$(C_{1-6})$alkyl-COOH, and carboxy$(C_{2-4})$alkenyl, 5- or 6-membered heterocycle having 1 to 4 heteroatoms selected from O, N and S, said heterocycle being optionally substituted with from 1 to 4 substituents selected from:

$(C_{1-6}$ alkyl), CF$_3$, OH, (CH$_2)_p$COOH, COOH, NHCH$(C_{1-6}$alkyl)$_2$, NHCO$(C_{1-6}$ alkyl), NH$_2$, NH$(C_{1-6}$ alkyl), and N$(C_{1-6}$ alkyl)$_2$, wherein p is an integer from 1 to 4;

9- or 10-membered heterobicycle having 1 to 4 heteroatoms selected from O, N and S, said heterobicycle being optionally substituted with from 1 to 4 substituents selected from:

halogen, OPO₃H, sulfonamido, SO₃H, SO₂CH₃, nitro, —CONH₂, —COCH₃, (C$_{1-3}$)alkyl, (C$_{2-4}$alkenyl) COOH, tetrazolyl, COOH, —CONH₂, OH, NH₂, —O(CH₂)$_p$COOH, hydantoin, benzoyleneurea, triazolyl, (C$_{1-4}$)alkoxy, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCO-CONH₂, —NHCOCONHCH₃, —NHCO(C$_{1-6}$)alkyl-COOH, —NHCOCONH(C$_{1-6}$)alkyl-COOH, —NHCO(C$_{3-7}$)cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, —NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$)aryl-COOH, —NHCH₂COOH, —NHCONH₂, —NHCO(C$_{1-6}$)hydroxyalkyl COOH, —OCO(C$_{1-6}$)hydroxyalkyl COOH, (C$_{3-6}$)cycloalkyl COOH,

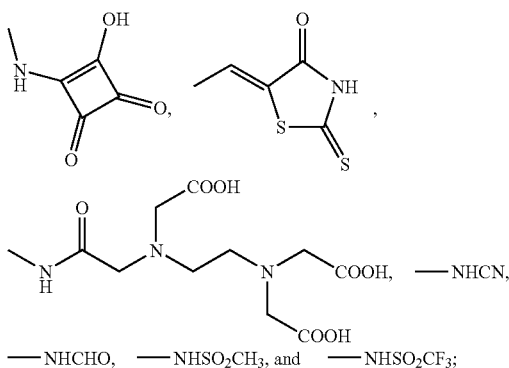

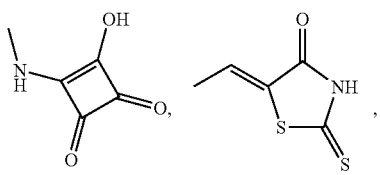

—NHCHO, —NHSO₂CH₃, and —NHSO₂CF₃;

6- or 10-membered aryl being optionally substituted with from 1 to 4 substituents selected from:
halogen, OPO₃H, sulfonamido, SO₃H, SO₂CH₃, nitro, —CONH₂, —COCH₃, (C$_{1-3}$)alkyl, (C$_{2-4}$alkenyl) COOH, tetrazolyl, COOH, —CONH₂, triazolyl, OH, NH₂, —O(CH₂)$_p$COOH, hydantoin, benzoyleneurea, (C$_{1-4}$)alkoxy, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCO-CONH₂, —NHCOCONHCH₃, —NHCO(C$_{1-6}$)alkyl-COOH, —NHCOCONH(C$_{1-6}$)alkyl-COOH, —NHCO(C$_{3-7}$)cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, —NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$)aryl-COOH, —NHCH₂COOH, —NHCONH₂, —NHCO(C$_{1-6}$)hydroxyalkyl COOH, —OCO(C$_{1-6}$)hydroxyalkyl COOH, (C$_{3-6}$)cycloalkyl COOH,

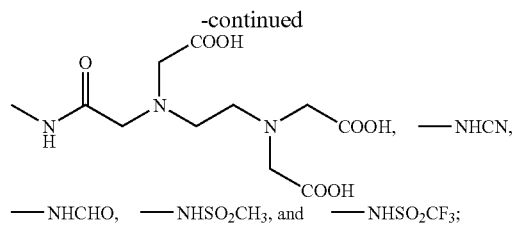

—NHCHO, —NHSO₂CH₃, and —NHSO₂CF₃;

coumarin, (C$_{1-6}$)alkyl-amino, di-(C$_{1-6}$)alkyl-amino, C(halogen)₃, —NH(C$_{2-4}$)acyl, —NH(C$_{6-10}$)aroyl, —CONHCH(CH₂OH)₂, —CO(C$_{1-6}$)alkyl-COOH, —CO—N H-alanyl, —(CH₂)$_p$COOH, —OCH₂Ph, —CONHbenzyl, —CONHpyridyl, —CONHCH₂pyridyl, —CONH(C$_{2-4}$)alkylN(C$_{1-6}$ alkyl)₂, —CONH(C$_{2-4}$)alkyl-morpholino, —CONH(C$_{2-4}$) alkyl-pyrrolidino, —CONH(C$_{2-4}$)alkyl-N-methylpyrrolidino, —CONH(C$_{2-4}$)alkyl-(COOH)-imidazole, —CONHCH₂CH(OH)CH₂OH, —CONH(C$_{1-6}$) alkyl-COOH, —CONH(C$_{6-10}$)aryl-COOH, —CONH(C$_{6-10}$)aryl-COO(C$_{16}$)alkyl, —CONH(C$_{1-6}$)alkyl-COO(C$_{1-6}$)alkyl, —CONH(C$_{6-10}$)aryl-(C$_{1-6}$)alkyl-COOH, —CONH(C$_{6-10}$)aryl-(C$_{2-6}$)alkenyl-COOH, —CONH(C$_{2-6}$)alkyl-CONH-9 or 10-membered heterobicycle having 1 to 4 heteroatoms selected from O, N, and S, said heterobicycle being optionally substituted with from 1 to 4 substituents selected from:
COOH, (C$_{6-10}$)aryl and (CH₂)$_p$COOH;
—CONH(C$_{6-10}$)aryl-5- or 6-membered heterocycle having 1 to 4 heteroatoms selected from O, N and S, said heterocycle being optionally substituted with from 1 to 4 substituents selected from:
COOH and (CH₂)$_p$COOH;
—CONH(C$_{1-6}$alkyl)CONH(C$_{6-10}$aryl), said aryl being optionally substituted with from 1 to 4 substituents selected from:
COOH and (CH₂)$_p$COOH; and
—O(CH₂)$_p$tetrazolyl;
wherein p is an integer from 1 to 4.
More preferably, R³ is

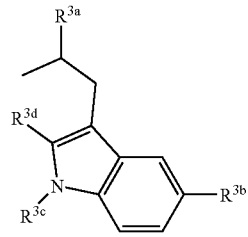

wherein preferably R³, is selected from H, 5- to 10-atom heterocycle having 1 to 4 heteroatoms selected from O, N and S;
COOH, COO(C$_{1-6}$)alkyl, said heterocycle being optionally substituted with from 1 to 4 substituents selected from the group consisting of: CH₃, CF₃, OH, CH₂COOH, COOH, NHCH(CH₃)₂, NHCOCH₃, NH₂, NHCH₃, and N(CH₃)₂, —CONH₂, —COCH₃—(CH₂)$_p$COOH, —OCH₂Ph, —CH₂—(C$_{6-10}$)aryl-COOH, —CONHpyridyl, —CONHCH₂pyridyl, —CONH(C$_{2-4}$)alkylN(CH₃)₂.

Most preferably $R^{3a}$ is $COOR^{3g}$, $CONHR^{3f}$, or

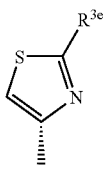

wherein preferably $R^3$, is H, ($C_{1-6}$ alkyl), amino, $NH(C_{1-6}$ alkyl), $N\{(C_{1-6}$ alkyl)$\}_2$, or $NHCO(C_{1-6}$ alkyl).

Preferably $R^{3f}$ is H, —$(C_{2-4})$alkyl-morpholino, —$(C_{2-4})$alkyl-pyrrolidino, —$(C_{2-4})$ alkyl-N-methylpyrrolidino; $(C_{1-6}$ alkyl)$N(CH_3)_2$, $(C_{1-6}$ alkyl)OH, $CH(CH_2OH)_2$ or $CH_2C(OH)CH_2OH$.

Most preferably $R^{3f}$ is H

Preferably $R^{3g}$ is H or ($C_{1-6}$ alkyl). More preferably $R^{3g}$ is H or $CH_3$.

Preferably $R^{3b}$ is selected from H, OH, amino, 5- to 10-atom heterocycle having 1 to 4 heteroatoms selected from O, N and S; said heterocycle being optionally substituted with OH, COOH, $CH_3$, $CF_3$, $CH_2COOH$, —$O(C_{1-3})$alkylCOOH, —NHCOCOOH, —$NHSO_2CH_3$, —$NHSO_2CF_3$,

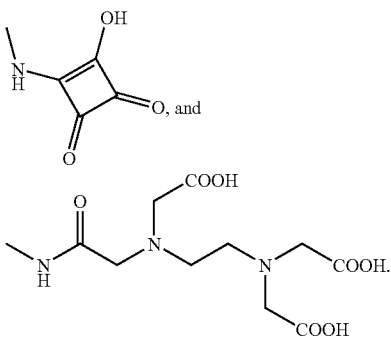

Most preferably $R^{3b}$ is $OCH_2COOH$ or OH.

Preferably $R^{3c}$ is selected from H, $(C_{1-6})$alkyl or —$(CH_2)_p$COOH, wherein p is an integer from 1 to 4. More preferably $R^{3c}$ is H, $CH_3$ or —$CH_2COOH$.

Preferably $R^{3d}$ is H or ($C_{1-6}$ alkyl). More preferably $R^{3d}$ is H or $CH_3$. Most preferably $R^{3d}$ is H.

Alternatively more preferably, $R^3$ is:

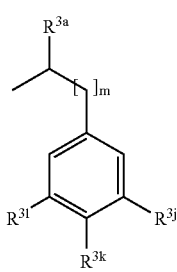

wherein $R^{3a}$ is as defined above.

Preferably $R^{3j}$ is $(C_{1-4})$alkoxy, OH, $O(C_{1-6}$ alkyl)COOH, $(C_{1-6}$ alkyl), halogen; $(C_{2-6})$alkenylCOOH, $(C_{1-6})$alkyl-hydroxy, COOH, or azido.

Preferably $R^{3k}$ is OH, $(CH_2)_p$COOH where p is an integer from 1 to 4, amino, $(C_{1-4})$alkoxy, NHCOCOOH, $NH(C_{1-6}$ alkyl)COOH, $O(C_{1-6}$ alkyl)COOH, COOH, 5- or 6-membered heterocycle having 1 to 4 heteroatoms selected from O, N and S, said heterocycle being optionally substituted with from 1 to 4 substituents selected from the group consisting of: $CH_3$, $CF_3$, OH, $CH_2COOH$, COOH; —O—$(C_{1-6})$alkyl COOH,

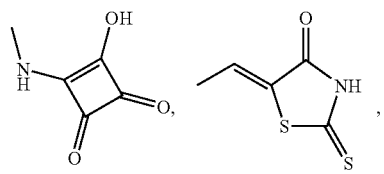

$NHCONH_2$, NHCN, NHCHO, $NHSO_2CF_3$, $NHCOCH_3$, $NHSO_2CH_3$, $CONH_2$, $(C_{3-6})$cycloalkylCOOH, $(C_{2-6})$alkenylCOOH, and NHCOCH(OH)COOH.

Preferably $R^{3l}$ is $O(C_{1-6}$ alkyl)COOH, $(C_{1-6}$ alkyl), or halogen.

Preferably m is an integer from 0 to 4. Most preferably m is 1.

Alternatively even more preferably, $R^3$ is:

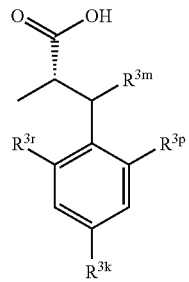

wherein $R^{3k}$ is as defined above.

Preferably $R^{3m}$ is H or OH.

Preferably $R^{3p}$ is H, halogen, or $(C_{1-6}$alkyl).

Preferably $R^{3r}$ is H, halogen, or $(C_{1-6}$ alkyl).

Alternatively more preferably, $R^3$ is

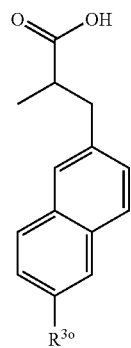

Preferably $R^{3o}$ is OH or $O(C_{1-6}$ alkyl)COOH.
Alternatively more preferably, $R^3$ is:

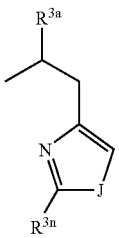

wherein $R^{3a}$ is as defined above.

Preferably J is S or $N(C_{1-6}$alkyl). More preferably J is S or $N(CH_3)$

Preferably $R^{3n}$ is H or amino.

Alternatively even more preferably, compounds of the invention have the following formula:

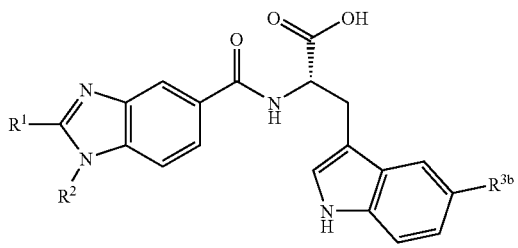

wherein $R^1$, $R^2$ and $R^{3b}$ are as defined above.

Alternatively even more preferably, compounds of the invention have the following formula:

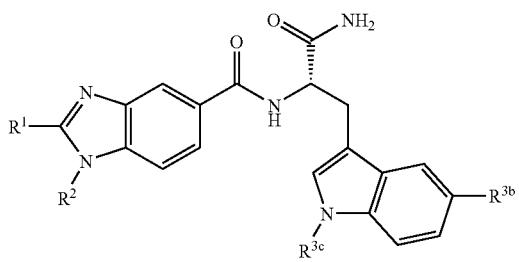

wherein $R^1$, $R^2$, $R^{3b}$, and $R^{3c}$ are as defined above.

Alternatively even more preferably, compounds of the invention have the following formula:

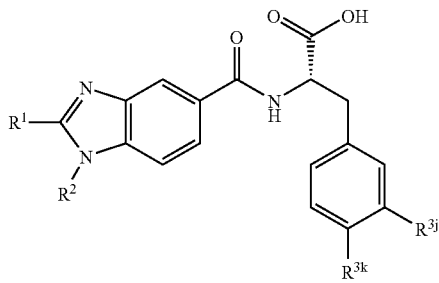

wherein $R^1$, $R^2$, $R^{3j}$, and $R^{3k}$ are as defined above.

According to a second aspect of the invention, the compounds of formula (Ib), (Ic), and (Id), or pharmaceutically acceptable salts thereof, are effective as inhibitors of RNA dependent RNA polymerase activity of the enzyme NS5B, encoded by HCV.

According to a third aspect of the invention, the compounds of formula (Ib), (Ic), and (Id), or pharmaceutically acceptable salt thereof, are effective as inhibitors of HCV replication.

According to a fourth aspect of the invention, there is provided a method of treating or preventing HCV infection in a mammal, comprising administering to the mammal an effective amount of the compounds of formula (Ib), (Ic), and (Id), or pharmaceutically acceptable salts thereof.

According to a fifth aspect of the invention, there is provided a pharmaceutical composition for the treatment or prevention of HCV infection, comprising an effective amount of a compound of formula (Ib), (Ic) or (Id), or a pharmaceutically acceptable salt thereof, and a pharmaceutically acceptable carrier.

According to a sixth aspect of the invention, there is provided a use for the manufacture of a medicament of formula (Ib), (Ic), and (Id), for the treatment of HCV infection.

According to a seventh aspect of the invention, there is provided a use of a compound of formula (Ib), (Ic), and (Id), as an inhibitor of NS5B.

According to an eighth aspect of the invention, there is provided a use of the compounds of formula (Ib), (Ic), and (Id), as an inhibitor of HCV replication.

According to a ninth aspect of the invention, there is provided a method of treating HCV infection in a mammal, comprising giving instructions to a third party to administer a compound of formula (Ib), (Ic), and (Id), to a subject suffering from HCV infection.

Specific Embodiments

Included within the scope of this invention are all compounds of formula (I), (Ia), (Ib), (Ic), or (Id), as presented in Tables 1 to 22.

Anti-NS5B Activity

The ability of the compounds of formula (I) to inhibit RNA synthesis by the RNA dependent RNA polymerase of HCV, NS5B, can be demonstrated by any assay capable of measuring RNA dependent RNA polymerase activity. A suitable assay is described in the examples.

Specificity for RNA Dependent RNA Polymerase Activity

To demonstrate that the compounds of the invention act by specific inhibition of NS5B, the compounds may be tested for the lack of inhibitory activity in other RNA dependent RNA polymerase assays or DNA dependant RNA polymerase assays.

When a compound of formula (I), or one of its therapeutically acceptable salts, is employed as an antiviral agent, it is administered orally, topically or systemically to mammals, e.g. humans, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula (I) is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in pharmaceutical texts, e.g. in "Remington's The Science and Practice of Pharmacy", 19th ed., Mack Publishing Company, Easton, Penn., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

For systemic administration, the compound of formula (I) is administered at a dosage of 10 mg to 150 mg per kilogram of body weight per day, although the aforementioned variations will occur. A dosage level that is in the range of from about 10 mg to 100 mg per kilogram of body weight per day is most desirably employed in order to achieve effective results.

Although the formulations disclosed hereinabove are indicated to be effective and relatively safe medications for treating HCV infections, the possible concurrent administration of these formulations with other antiviral medications or agents to obtain beneficial results also included. Such other antiviral medications or agents include interferon or interferon and ribavirin.

Methodology and Synthesis

Benzimidazole derivatives or analogs according to the present invention can be prepared from known starting materials by following Scheme 1, shown below wherein $R^1$, $R^2$ and $R^3$ are as previously described.

Scheme 1

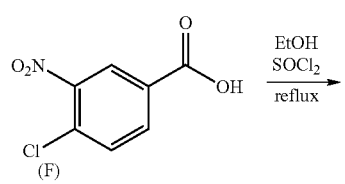

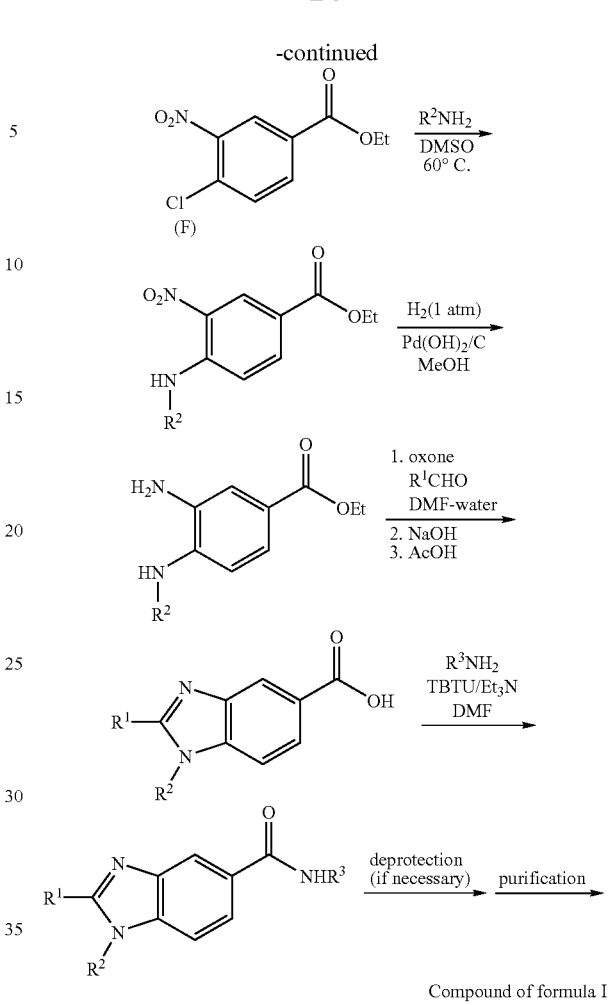

Compound of formula I

In carrying out the route illustrated in Scheme 1, illustrated above, a suitably protected form of 4-chloro-3-nitrobenzoic acid or 4-fluoro-3-nitrobenzoic acid is reacted with a primary amine $R^2NH_2$. Amines are of commercial sources or can be prepared by literature methods. This reaction is carried out in a suitable solvent such as DMSO, DMF or the like, at temperatures ranging from 20° C. to 170° C., or alternatively without solvent by heating the two components together. The nitro group of these derivatives is subsequently reduced to the corresponding aniline, using a reducing agent such as hydrogen gas in the presence of a catalyst (e.g. Pd metal and the like), metals in the presence of mineral acids (e.g. Fe or Zn with aqueous HCl), or metal salts ($SnCl_2$). The diamino derivatives that are obtained are condensed with commercially available aldehydes $R^1CHO$ in the presence of an oxidizing agent (e.g. air, oxygen, iodine, oxone®, quinones, peroxides etc.) to give benzimidazole 5-carboxylates.

Alternatively, other methods for benzimidazole ring construction can be employed, such as condensation of the diamino derivatives with carboxylic acids, nitriles or amides, in the presence or absence of a catalyst. Such methods are well known in the literature to those skilled in the art. Saponification of the ester protecting group of such derivatives using alkali metal hydroxides, followed by neutralization with weak acids (e.g. AcOH) generates free 5-carboxybenzimidazole derivatives of general formula I (X=CH, Y=O, Z=OH, n=0).

Derivatives of formula I in which Z=NHR³ may be obtained by condensation of 5-carboxybenzimidazoles of formula I (X=CH or N, Y=O, Z=OH) with amines H₂NR³ through formation of an amide bond. Amines H₂NR³ are from commercial sources or can be prepared following literature procedures. Condensation of the carboxylic acid with amine H₂NR³ can be accomplished using standard peptide bond forming reagents such as TBTU, BOP, EDAC, DCC, isobutyl chloroformate and the like, or by activation of the carboxyl group by conversion to the corresponding acid chloride prior to condensation with an amine. This coupling reaction can then be followed by elaboration of functional groups present in R³ and protecting groups are subsequently removed in the last stage of the synthesis, if necessary, to provide compounds of formula I.

Alternatively, benzimidazole derivatives or analogs according to the present invention can be prepared on a solid support as described in Scheme 2, below, wherein R¹, R² and R³ are as previously described.

In carrying out the synthetic route illustrated in Scheme 2, 4-fluoro-3-nitrobenzoic acid is converted to the acid chloride derivative using standard procedures (e.g. thionyl chloride, oxalyl chloride, phosgene and the like in the presence of a catalytic amount of DMF) in an inert solvent such as CH₂Cl₂.

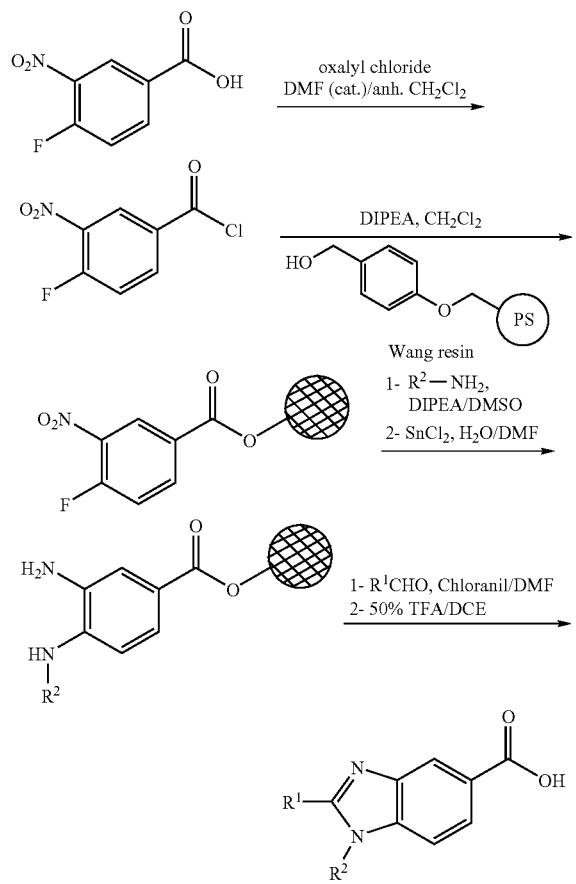

Scheme 2

Wang resin is esterified with this acid chloride by condensation in the presence of an organic tertiary amine such as triethylamine, N-methylmorpholine, DIEA and the like. Other types of resins are well known to those skilled in the art, for example Rink resin, which may be functionalized without deviating from the scope of the invention. The functionalised resin thus obtained is then elaborated to resin-bound benzimidazole carboxylate derivatives as described above for the solution-phase chemistry. Cleavage of the benzimidazole from the resin is carried out with strong acids (e.g. trifluoroacetic acid) to give benzimidazole 5-carboxylic acids of general formula I (X=CH or N, Y=O, Z=OH, n=0), within the scope of this invention. As described previously in solution phase, carboxylic acids of general formula I (X=CH or N, Y=O, Z=OH) can be elaborated to benzimidazole derivatives of general formula I (Z=NHR³) by condensation with amines R³NH₂.

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise. Mass spectral analyses were recorded using electrospray mass spectrometry. Abbreviations or symbols used herein include:

DIEA: diisopropylethylamine;
DMAP: 4-(dimethylamino)pyridine;
DMSO: dimethylsulfoxide;
DMF: N,N-dimethylformamide;
Et: ethyl;
EtOAc: ethyl acetate;
Et₂O: diethyl ether;
HPLC: high performance liquid chromatography;
$^i$Pr: isopropyl
Me: methyl;
MeOH: Methanol;
MeCN: acetonitrile;
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
MS (ES): electrospray mass spectrometry;
PFU: plaque forming units;
DEPC: diethyl pyrocarbonate;
DTT: dithiothreitol
EDTA: ethylenediaminetetraacetate
HATU: O-(7-azabenzotriazol-1-yl)-N,N,N',N'-tetramethyluronium hexafluorophosphate
BOP: benzotriazole-1-yloxy-tris(dimethylamino)phosphonium hexafluorophosphate
EDAC: see ECD
DCC: 1,3-Dicyclohexyl carbodiimide
HOBt: 1-Hydroxybenzotriazole
ES⁺: electro spray (positive ionization)
ES⁻: electro spray (negative ionization)
DCM: dichloromethane
TBME: tert-butylmethyl ether
TLC: thin layer chromatography
AcOH: acetic acid
EtOH: ethanol
DBU: 1,8-diazabicyclo[5.4.0]under-7-ene
BOC: tert-butyloxycarbonyl
Cbz: carbobenzyloxy carbonyl
BINAP: 2,2'-Bis(diphenylphosphine)-1,1'-binaphthyl
$^i$PrOH: isopropanol
NMP: N-methylpyrrolidone EDC: 1-(3-dimethylaminopropyl)-3-ethyl carbodiimide hydrochloride RNAsin: A ribonuclease inhibitor marketed by Promega Corporation Tris: 2-amino-2-hydroxymethyl-1,3-propanediol UMP: uridine 5′-monophosphate UTP: uridine 5′-triphosphate Examples 1-158 illustrate methods of synthesis of representative compounds of this invention.

Example 1

Entry 7021, Table 7

1-Cyclohexyl-2-pyridin-2-yl-1H-benzoimidazole-5-carboxylic Acid

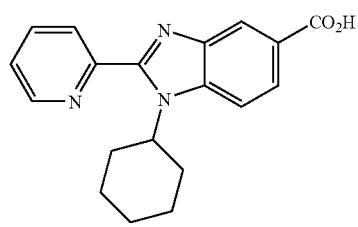

4-Chloro-3-nitrobenzoic acid, ethyl ester

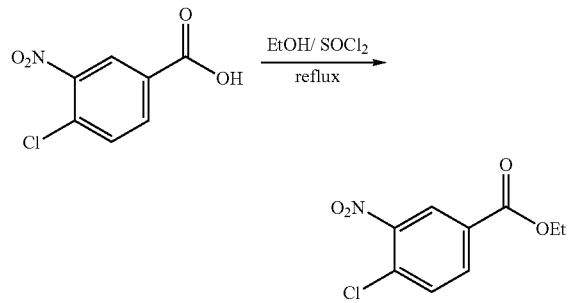

4-Chloro-3-nitrobenzoic acid (100.0 g, 0.496 mole) was suspended in ethanol (250 mL) and thionyl chloride (54 mL, 0.74 mole) was added drop-wise over 15 min. The mixture was then reflux for 2 h. After cooling to ambient temperature, volatiles were removed under reduced pressure and the residue was co-evaporated twice with ethanol (2×250 mL). The residue was crystallized from hot ethanol to give the desired ethyl ester as light yellow needles (109.8 g, 96% yield).

4-Cyclohexylamino-3-nitrobenzoic acid ethyl ester

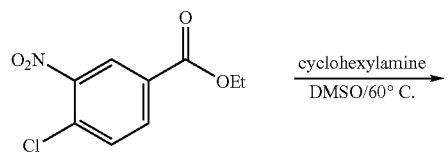

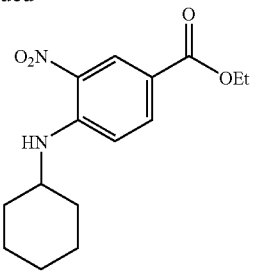

Ethyl 4-chloro-3-nitrobenzoate (20.00 g, 87 mmol) was dissolved in DMSO (50 mL) and cyclohexylamine (2.1 equiv. 21 mL, 183 mmol) was added and the mixture stirred at 60°C for 5 h. After cooling to ambient temperature, the reaction mixture was added drop-wise with vigorous stirring to water (500 mL). After stirring for an additional 15 min, the precipitated solid was collected by filtration, washed with water and dried. The title compound (25.67 g, 100% yield) was obtained as a bright yellow solid.

3-Amino-4-cyclohexylamino benzoic acid ethyl ester

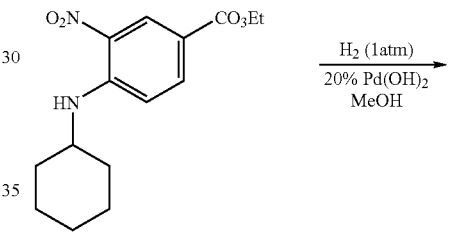

The nitro derivative from above (24.28 g, 83 mmol) was hydrogenated (1 atm $H_2$) over 20% Pd(OH)$_2$ on carbon (200 mg) in MeOH (150 mL) for 3 days. The catalyst was removed by filtration and volatiles removed under reduced pressure to give the title diamine (21.72 g, 100% yield) as a dark purple solid.

1-Cyclohexyl-2-pyridin-2-yl-1H-benzoimidazole-5-carboxylic acid

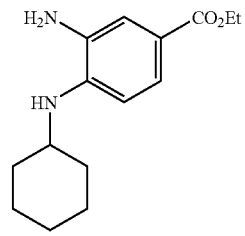

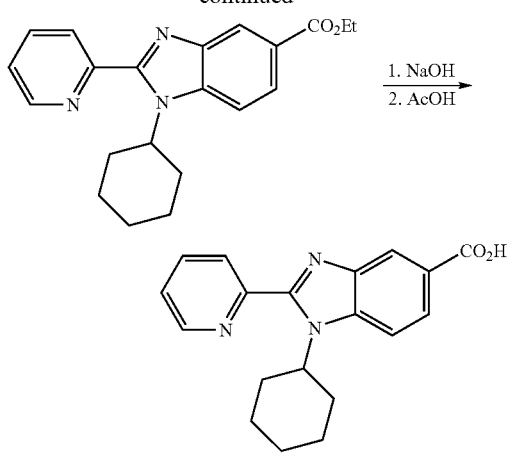

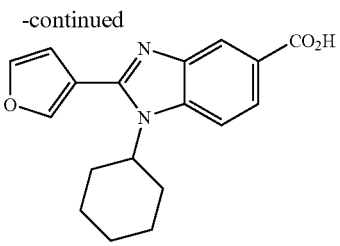

The diamine from above (3.20 g, 12.2 mmol) was dissolved in DMF (15 mL) and water (0.5 mL). 2-Pyridine carboxaldehyde (1.45 mL, 15 mmol) was added followed by oxone® (0.65 equivalent, 8 mmol, 4.92 g). The mixture was stirred 1 h at room temperature. Water (60 mL) was added, and the pH of the reaction mixture was brought up to 9 by addition of 1 N NaOH. The brown precipitate that formed was collected by filtration, washed with water and dried. The crude benzimidazole ethyl ester was obtained in 80% yield (3.43 g).

The ester from above (2.36 g, 7.53 mmol) was dissolved in MeOH (15 mL) and 2 N NaOH (20 mmol, 10 mL) was added. The mixture was stirred at 60° C. for 2 h and then cooled to room temperature. MeOH was removed under reduced pressure and the residue acidified to pH 4 with glacial AcOH. The precipitated carboxylic acid was collected by filtration, washed with water and dried to give the free acid as a beige solid (2.20 g, 91% yield).

Example 2

Entry 7018, Table 7

1-Cyclohexyl-2-furan-3-yl-1H-benzoimidazole-5-carboxylic acid

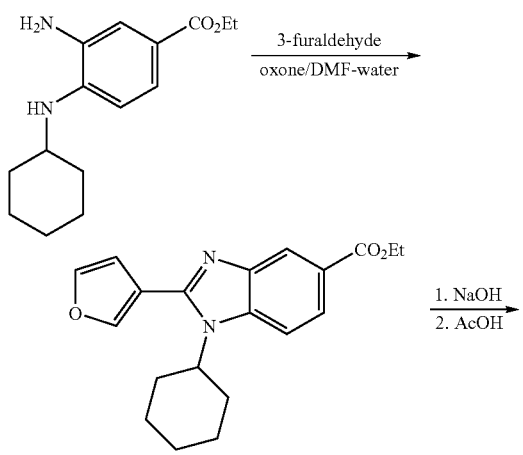

Ethyl 3-amino-4-(aminocyclohexyl)benzoate (3.67 g, 13.99 mmol) was dissolved in DMF (10 mL) and water (1 mL). Oxone® (9.8 mmol, 6.02 g) was added followed by 3-furaldehyde (1.44 g, 15 mmol). The mixture was stirred 45 min at room temperature. 4 N NaOH (20 mL) was added and the mixture stirred at 60° C. for 18 h. After cooling to room temperature, water (100 mL) was added and insoluble impurities removed by filtration through celite. AcOH was then added to precipitate the product as a beige solid. The precipitated carboxylic acid was collected by filtration, washed with water and dried to give the title compound as a beige solid (3.69 g, 85% yield).

Example 3

Entry 2108, Table 2

1-Cyclohexyl-2-pyridin-2-yl-1H-benzoimidazole-5-carboxylic acid [2-(3,4-dimethoxyphenyl)ethyl] amide

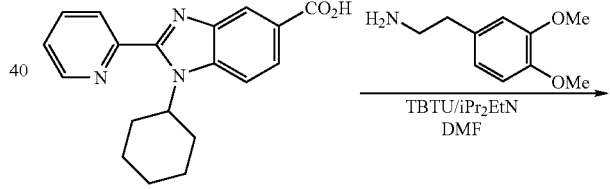

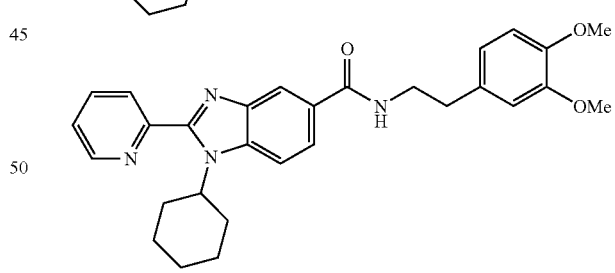

1-Cyclohexyl-2-pyridin-2-yl-1H-benzoimidazole-5-carboxylic acid (0.060 g, 0.19 mmol), 3,4-dimethoxyphenethylamine (35 µL, 0.21 mmol) and TBTU (0.090 g, 0.28 mmol) were dissolved in DMF (1 mL), and DIEA (330 µL, 1.9 mmol) was added. The mixture was stirred 1 h at room temperature, when HPLC analysis indicated completion of the coupling reaction. The reaction mixture was added drop-wise with vigorous stirring to 1 N NaOH (10 mL). The precipitated product was collected by filtration, washed with water and dried. The title amide derivative was obtained as a gray solid (0.056 g, 60% yield, 98% homogeneity by HPLC).

Example 4

General Procedure for the Preparation of Racemic α-alkylbenzylamine Derivatives

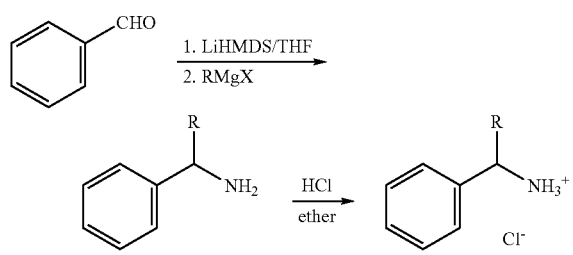

According to the general scheme shown above, and adapting the procedure of D. J. Hart et al. (*J. Org. Chem.* 1983, 48, 289), aromatic aldehydes are reacted first with lithium bis(trimethylsilyl)amide and then with a Grignard reagent in a suitable solvent such as $Et_2O$, tetrahydrofuran, toluene and the like, at temperatures ranging from 0° C. to 120° C. Following hydrolysis, the desired racemic x-alkylbenzylamines were isolated after conversion to their hydrochlorides. In this manner, a variety of racemic α-alkylbenzylamines were synthesized with substitution as previously described in this invention:

Dl-3,4-Dimethoxy-α-methylbenzylamine hydrochloride

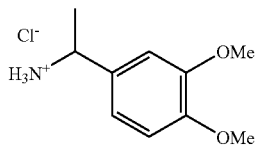

3,4-Dimethoxybenzaldehyde (5.00 g, 30 mmol) was dissolved in anhydrous THF (10 mL) and the solution cooled in ice under an argon atmosphere. Lithium bis(trimethylsilyl)amide (1 M in THF, 36 mmol, 36 mL) was added drop-wise and the resulting mixture stirred at 0° C. for 30 min. Methylmagnesium bromide (1.4 M in THF, 2 equiv., 72 mmol, 43 mL) was added and the solution allowed to warm up to room temperature. It was then reflux for 24 h. The reaction mixture was then cooled to room temperature and poured into saturated aqueous $NH_4Cl$ (200 mL). The mixture was extracted twice with DCM (75 mL) and the extract dried over $MgSO_4$. The solution was concentrated to a volume of about 25 mL under reduced pressure and diluted with an equal volume of $Et_2O$. Excess hydrogen chloride (4 M in dioxane) was added, and the resulting precipitate collected by filtration. It was washed with $Et_2O$ and dried in vacuo. DL-3,4-Dimethoxy-α-methylbenzylamine hydrochloride (5.1 g, 78% yield) was obtained as an orange solid.

Dl-3,4-Dimethoxy-α-ethylbenzylamine hydrochloride

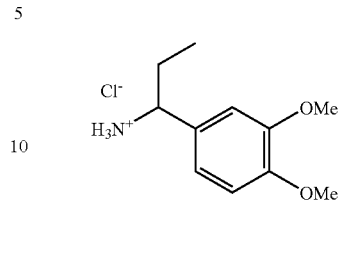

Following the general procedure, starting from 3,4-dimethoxybenzaldehyde and ethylmagnesium bromide, after a reaction time of 48 h, the title compound was obtained as a cream colored solid in 70% yield.

Dl-3,4-Dimethoxy-aisobutylbenzylamine hydrochloride

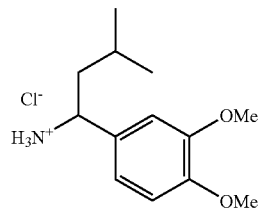

Following the general procedure, starting from 3,4-dimethoxybenzaldehyde and isobutylmagnesium bromide, after a reaction time of 48 h, the title compound was obtained as a pink solid in 81% yield.

Dl-3,4-Dimethoxy-α-(2-propenyl)benzylamine hydrochloride

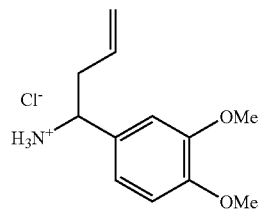

Following the general procedure, starting from 3,4-dimethoxybenzaldehyde and allylmagnesium bromide, after a reaction time of 48 h, the title compound was obtained as a cream colored solid in 89% yield.

Dl-3,4-Dimethoxy-aisopropylbenzylamine hydrochloride

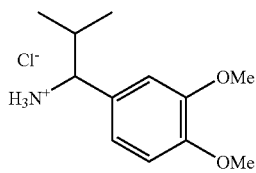

Following the general procedure, starting from 3,4-dimethoxybenzaldehyde and isopropylmagnesium chloride, after a reaction time of 72 h, the title compound was obtained as a cream colored solid in 75% yield.

DL-3,4-Dimethoxy-α-tert-butyl-benzylamine hydrochloride

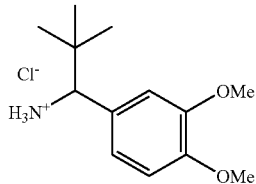

Following the general procedure, starting from 3,4-dimethoxybenzaldehyde and tert-butylmagnesium chloride, after a reaction time of 72 h, the title compound was obtained as a cream colored solid in quantitative yield.

DL-4-Methoxy-3-methyl-α-methylbenzylamine hydrochloride

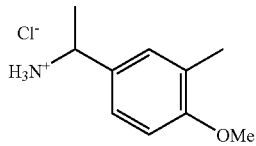

Following the general procedure, starting from 3-methyl-para-anisaldehyde and methylmagnesium bromide, after a reaction time of 48 h, the title compound was obtained as a cream colored solid in quantitative yield.

DL-4-Ethoxy-3-methoxy-amethylbenzylamine Hydrochloride

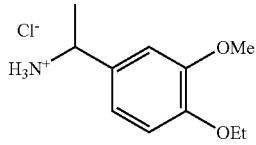

Following the general procedure, starting from 4-ethoxy-meta-anisaldehyde and methylmagnesium bromide, after a reaction time of 72 h, the title compound was obtained as a pink solid in 86% yield.

DL-3-Ethoxy-4-methoxy-α-methylbenzylamine hydrochloride

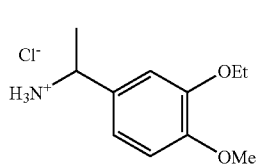

Following the general procedure, starting from 3-ethoxy-para-anisaldehyde and methylmagnesium bromide, after a reaction time of 96 h, the title compound was obtained as a light brown solid in 82% yield.

DL-3,4-Diethoxy-α-methylbenzylamine hydrochloride

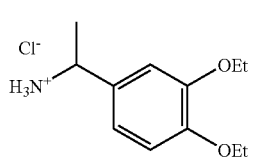

Following the general procedure, starting from 3,4-diethoxybenzaldehyde and methylmagnesium bromide, after a reaction time of 96 h, the title compound was obtained as a pink solid in 75% yield.

Example 5

Entry 2042, Table 2

1-Cyclohexyl-2-pyridin-2-yl-1h-benzoimidazole-5-carboxylic acid [(R)-1-(3,4-dimethoxyphenyl)ethyl] amide

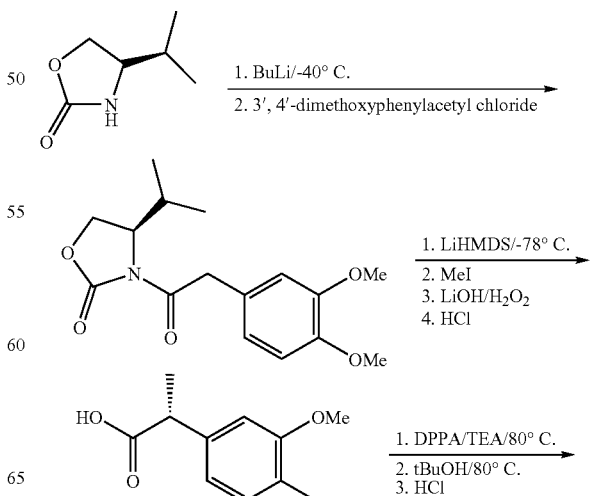

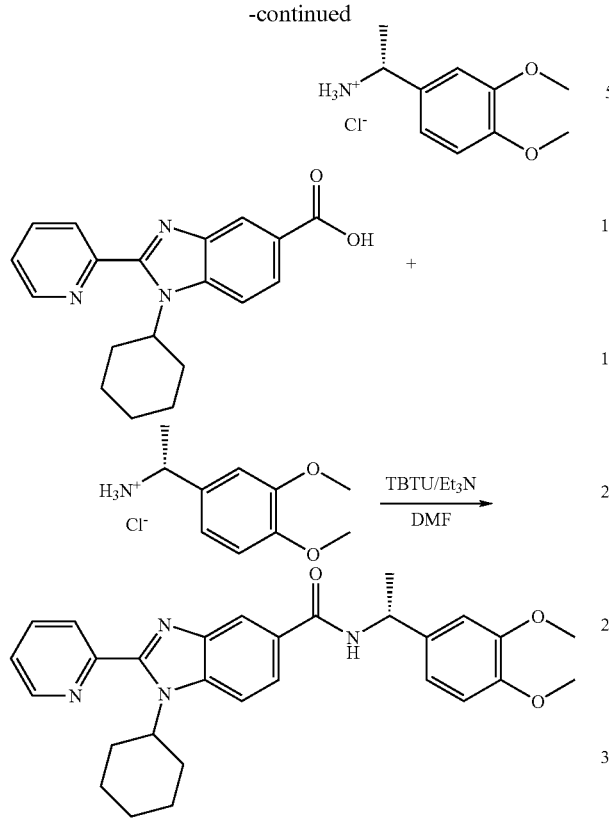

3',4'-Dimethoxyphenylacetyl chloride

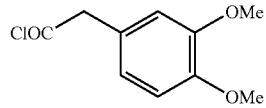

3',4'-Dimethoxyphenylacetic acid (10.00 g, 51 mmol) was dissolved in DCM (100 mL) and DMF (100 μL) was added. Oxalyl chloride (1.05 equiv., 53.5 mmol, 4.67 mL) was added drop-wise and the mixture stirred at room temperature until gas evolutions ceased. The solution was then refluxed for 30 min, cooled to room temperature and concentrated under reduced pressure. The crude acid chloride was used directly in the next step.

(R)-3-[2-(3,4-Dimethoxyphenyl)-ethanoyl]-4-isopropyl-oxazolidin-2-one

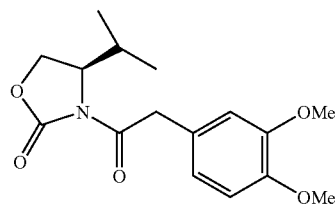

(R)-4-Isopropyl-2-oxazolidinone (6.59 g, 51 mmol) was dissolved in anhydrous THF (95 mL) under an argon atmosphere. The solution was cooled to −50° C. and n-BuLi (2.3 M in hexane, 51 mmol, 22 mL) was added drop-wise. The resulting white suspension was stirred for 30 min at −40° C. and then cooled further to −78° C. The acid chloride from above (51 mmol) in THF (10 mL+5 mL rinse) was added drop-wise over 5 min and the mixture stirred for 30 min at −78° C. The reaction mixture was then allowed to warm to 0° C. and stirred an additional 1 h at that temperature. After quenching with saturated aqueous NH$_4$Cl (25 mL), THF was removed under reduced pressure, water (25 mL) was added and the product extracted with EtOAc (150 mL). The extract was washed with 5% aqueous NaHCO$_3$ (2×50 mL) and brine (50 mL), and dried over MgSO$_4$. Volatiles were removed under reduced pressure, and the residue purified by flash chromatography on silica gel using 40% EtOAc in hexane as eluent (11.06 g, 70% yield).

(R)-3-[2-(3,4-Dimethoxyphenyl)-propanoyl]-4-isopropyl-oxazolidin-2-one

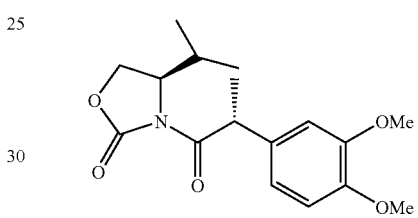

The oxazolidinone from above (5.24 g, 17 mmol) was dissolved in anhydrous THF (75 mL) and the solution cooled to −78° C. under an argon atmosphere. Lithium bis(trimethylsilyl)amide (1 M in THF, 1.15 equiv., 19.6 mmol, 19.6 mL) was added drop-wise and the mixture stirred 30 min at −78° C. Iodomethane (17 mmol, 1.06 mL) was added and the reaction mixture stirred 1 h at −78° C. and then at room temperature for 2 h. After quenching with 1 M KHSO$_4$ (25 mL), THF was removed under reduced pressure and the product extracted with EtOAc (150 mL). The extract was washed successively with 1 M KHSO$_4$ (25 mL), 10% aqueous NaHCO$_3$ (2×25 mL) and brine (25 mL). After drying (MgSO$_4$) and removal of volatiles under reduced pressure, the crude product was purified by flash chromatography on silica gel using 30% EtOAc in hexane as eluent to give the title compound as a white solid (2.93 g, 53% yield). $^1$H NMR analysis indicates a 9:1 mixture of diastereomers in favor of the desired (R,R)-isomer.

(R)-2-(3,4-Dimethoxyphenyl)propionic acid

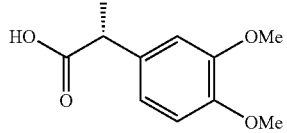

The oxazolidinone from above (2.72 g, 8.5 mmol) was dissolved in THF (40 mL) and water (15 mL) was added, followed by 30% hydrogen peroxide (4.36 mL, 42 mmol) and LIOH monohydrate (0.426 g, 10.2 mmol). The mixture was stirred for 1 h. THF was removed under reduced pressure and saturated aqueous NaHCO$_3$ (10 mL) was added. The solution was washed with DCM (2×25 mL) and then acidified to pH 1 with 6 N HCl. The product was extracted with EtOAc (2×50 mL) and the extract dried over MgSO$_4$. After evaporation of the solvent, the crude title compound (1.855 g) was obtained as a clear oil.

[(R)-1-(3,4-Dimethoxyphenyl)-ethyl]-carbamic acid tert-butyl ester

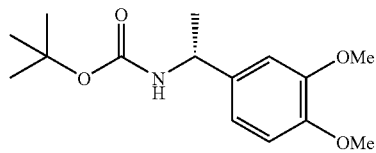

(R)-3',4'-Dimethoxy-2-methylphenylAcetic acid (1.505 g, 7.16 mmol) was dissolved in toluene (20 mL). Diphenylphosphoryl azide (1.70 mL, 7.87 mmol) and triethylamine (1.20 mL, 8.59 mmol) were added and the mixture stirred at room temperature for 20 min and then at 80° C. for 3 h. tert-Butanol (5 equiv., 39.2 mmol, 3.75 mL) was added and the heating to 80° C. continued for 20 h. The reaction mixture was then cooled to room temperature, diluted with Et$_2$O (100 mL) and washed successively with 1 M KHSO$_4$ (2×25 mL), saturated aqueous NaHCO$_3$ (2×25 mL) and brine (25 mL). After drying (MgSO$_4$), solvents were removed under reduced pressure and the residue purified by flash chromatography on silica gel using 15-20% EtOAc in hexane as eluent. The title amine carbamate was obtained as a white solid (0.72 g)

(R)-1-(3,4-Dimethoxyphenyl)-ethyl-ammonium chloride

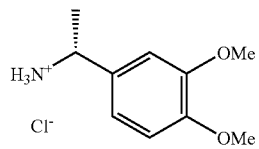

(R)-N-tert-Butyloxycarbonyl-3',4'-dimethoxy-α-methyl-benzylamine from above (0.653 g, 2.3 mmol) was stirred for 1 h in 4 N hydrogen chloride-dioxane (4 mL). Volatiles were removed under reduced pressure to give the title amine hydrochloride as a white solid (0.518 g).

1-Cyclohexyl-2-pyridin-2-yl-1H-benzoimidazole-5-carboxylic acid [(R)-1-(3,4-dimethoxyphenyl)-ethyl] amide hydrochloride

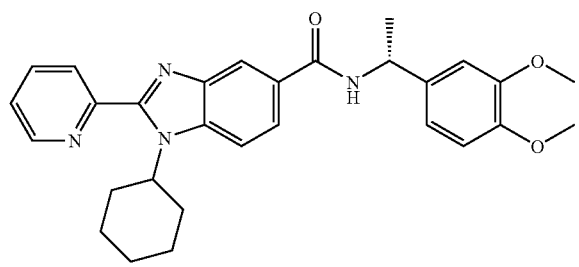

The carboxylic acid of example 1 (0.075 g, 0.23 mmol), TBTU (1.5 equiv., 0.34 mmol, 0.111 g) and triethylamine (5 equiv., 1.15 mmol, 0.16 mL) were dissolved in DMF (0.5 mL) and the (R)-amine hydrochloride from above (0.051 g, 0.23 mmol) was added. The mixture was stirred for 1 h at room temperature and quenched by addition of 1 N NaOH (5 mL) and water (10 mL). The gummy precipitate was extracted into EtOAc (75 mL), washed with brine and dried (MgSO$_4$). The solvent was evaporated under reduced pressure and the residue dissolved in EtOAc (1 mL). TBME (10 mL) was added followed by hexane (10 mL). The precipitate that formed was collected by filtration, washed with 1:1 TBME/hexane and dried. The product was further purified by flash chromatography on silica gel using EtOAc as eluent and then converted to its hydrochloride salt by reaction with hydrogen chloride in ether. The title compound was obtained as a white solid (0.065 g).

Example 6

General Procedure for the Preparation of Racemic Phenylglycine Methyl Ester Hydrochloride Derivatives

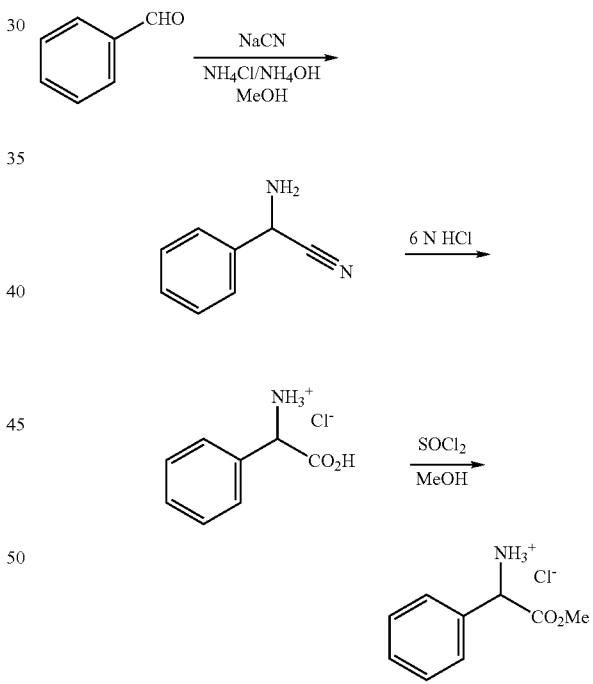

Aromatic aldehydes, substituted according to the scope of the present invention, were reacted with an alkali metal cyanide (preferably sodium or potassium cyanide) in a mixture of aqueous ammonium chloride and ammonium hydroxide and a co-solvent such as MeOH or ethanol. The aminonitriles formed were hydrolyzed to the corresponding racemic phenylglycines in boiling aqueous mineral acid (preferably hydrochloric acid), and then converted to the racemic phenylglycine methyl ester hydrochlorides by reaction with MeOH in the presence of either thionyl chloride, oxalyl chloride, acetyl chloride, phosgene, hydrogen chloride or the like.

Racemic Piperonylglycine Methyl Ester Hydrochloride

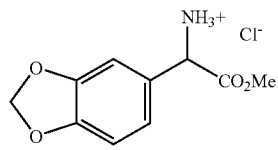

Piperonal (8.50 g, 56.6 mmol) was dissolved in MeOH (25 mL) and a solution of NaCN (2.77 g, 56.6 mmol) and ammonium chloride (3.33 g, 62 mmol) in 30% aqueous ammonium hydroxide was added. After stirring overnight at room temperature, the supernatant was decanted from oily polymeric residues and MeOH removed from the aqueous phase under reduced pressure. The aqueous phase was then extracted with EtOAc. The aminonitrile present in the extract was then extracted into 6 N HCl (2×50 mL), the aqueous acid phases combined and refluxed for 8 h. Water was removed under reduced pressure to precipitate out the phenylglycine derivative as the hydrochloride salt that was collected by filtration and dried in vacuo (2.20 g).

The crude amino acid from above (1.00 g, 4.3 mmol) was dissolved in MeOH (10 mL) and thionyl chloride (1.5 equiv., 0.48 mL) was added drop-wise. The mixture was refluxed for 3 h, and then volatiles were removed under reduced pressure. The residue was co-evaporated 3 times with MeOH (25 mL) and the residual solid triturated with $Et_2O$. The white solid was collected and dried (0.98 g, 92% yield).

Racemic 3,4-dimethoxyphenylglycine methyl ester hydrochloride

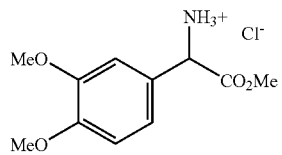

Following the general procedure and starting from 3,4-dimethoxybenzaldehyde, the phenylglycine hydrochloride was obtained in 29% yield, and the corresponding methyl ester hydrochloride in 96% yield.

Racemic 3,4,5-trimethoxyphenylglycine methyl ester hydrochloride

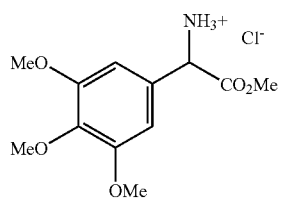

Following the general procedure and starting from 3,4,5-trimethoxybenzaldehyde, the phenylglycine hydrochloride was obtained in 72% yield, and the corresponding methyl ester hydrochloride in 92% yield.

Racemic 4-methoxyphenylglycine methyl ester hydrochloride

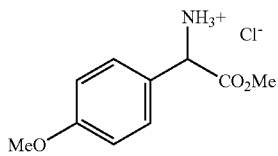

Following the general procedure and starting from 4-methoxybenzaldehyde, the phenylglycine hydrochloride was obtained in 25% yield, and the corresponding methyl ester hydrochloride in 95% yield.

Racemic 3-methoxyphenylglycine methyl ester hydrochloride

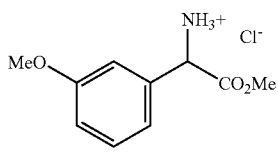

Following the general procedure and starting from 3-methoxybenzaldehyde, the phenylglycine hydrochloride was obtained in 43% yield, and the corresponding methyl ester hydrochloride in 99% yield.

Racemic 2-methoxyphenylglycine methyl ester hydrocloride

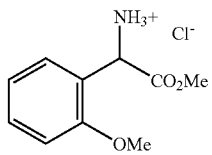

Following the general procedure and starting from 2-methoxybenzaldehyde, the phenylglycine hydrochloride was obtained in 11% yield, and the corresponding methyl ester hydrochloride in 92% yield.

Racemic 3,4-diethoxyphenylglycine methyl ester hydrocloride

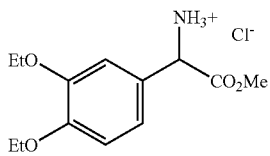

Following the general procedure and starting from 3,4-diethoxybenzaldehyde, the phenylglycine hydrochloride was obtained in 9% yield, and the corresponding methyl ester hydrochloride in 99% yield.

Racemic 3,4-dimethylphenylglycine methyl ester hydrocloride

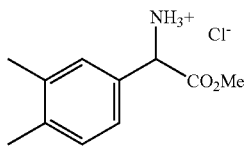

Following the general procedure and starting from 3,4-dimethylbenzaldehyde, the phenylglycine hydrochloride was obtained in 56% yield, and the corresponding methyl ester hydrochloride in 97% yield.

Racemic 4-isopropylphenylglycine methyl ester hydrocloride

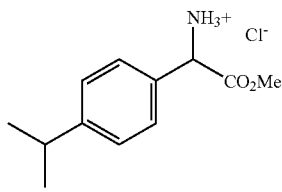

Following the general procedure and starting from 4-isopropylbenzaldehyde, the phenylglycine hydrochloride was obtained in 10% yield, and the corresponding methyl ester hydrochloride in 99% yield.

Racemic 4-trifluoromethylphenylglycine methyl ester hydrocloride

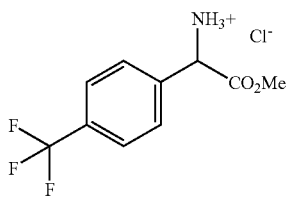

Following the general procedure and starting from 4-trifluoromethylbenzaldehyde, the phenylglycine hydrochloride was obtained in 53% yield, and the corresponding methyl ester hydrochloride in 78% yield.

Racemic 4-chlorophenylglycine methyl ester hydrocloride

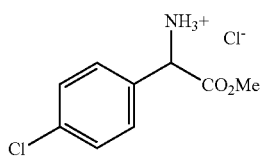

Following the general procedure and starting from 4-chlorobenzaldehyde, the phenylglycine hydrochloride was obtained in 27% yield, and the corresponding methyl ester hydrochloride in 83% yield.

Racemic 2-chlorophenylglycine methyl ester hydrocloride

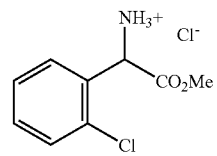

Following the general procedure and starting from 2-chlorobenzaldehyde, the phenylglycine hydrochloride was obtained in 25% yield, and the corresponding methyl ester hydrochloride in 93% yield.

Example 7

Entry 16006, Table 16

(S)-{[1-(1-Cyclohexyl-2-furan-3-yl-1H-benzoimidazole-5-yl)-methanoyl]-amino}-(3,4-dimethoxyphenyl)acetic acid:

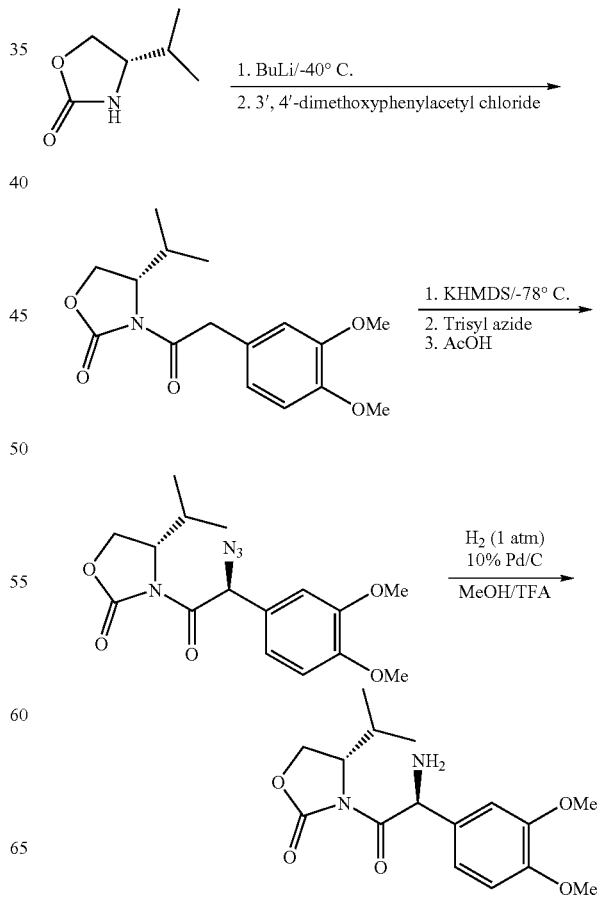

-continued

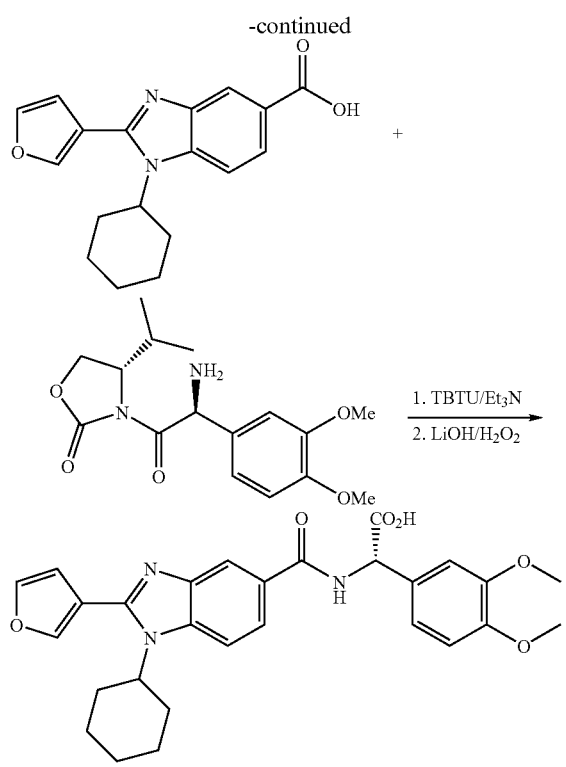

(S)-3-[(S)-2-Azido-2-(3,4-dimethoxyphenyl)-ethanoyl]-4-isopropyl-oxazolidin-2-one:

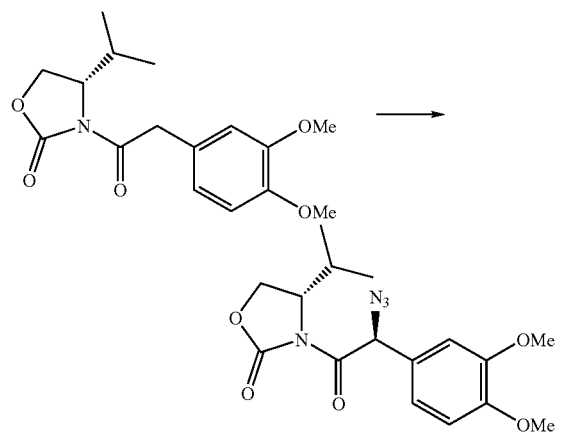

The (S)-N-acyloxazolidinone was prepared as in example 5 but starting from (S)-4-isopropyl-2-oxazolidinine. Following the procedure of D. A. Evans et al. (*J. Am. Chem. Soc.* 1990, 112, 4011), potassium bis(trimethylsilyl)amide (0.5 M in toluene, 7.2 mL, 3.6 mmol) was diluted with anhydrous THF (10 mL), and the solution was cooled under argon to −78° C. The oxazolidinone (1.00 g, 3.25 mmol) in THF (10 mL), also at −78° C., was cannulated into the base solution. After stirring at −78° C. for 30 min, a solution of trisyl azide (3.9 mmol, 1.21 g) in THF (10 mL) also at −78° C., was cannulated into the reaction mixture. The mixture was then stirred until completion (TLC) and then the reaction was quenched at −78° C. with glacial AcOH (0.86 mL, 15 mmol).

The reaction was warmed to room temperature and stirred overnight. Volatiles were removed under reduced pressure and the residue extracted into EtOAc. After washing with water, drying (MgSO$_4$) and concentration, the residue was purified by flash chromatography on silica gel using 30% EtOAc in hexane (61% yield).

(S)-3-[(S)-2-Amino-2-(3,4-dimethoxyphenyl)-ethanoyl]-4-isopropyl-oxazolidin-2-one

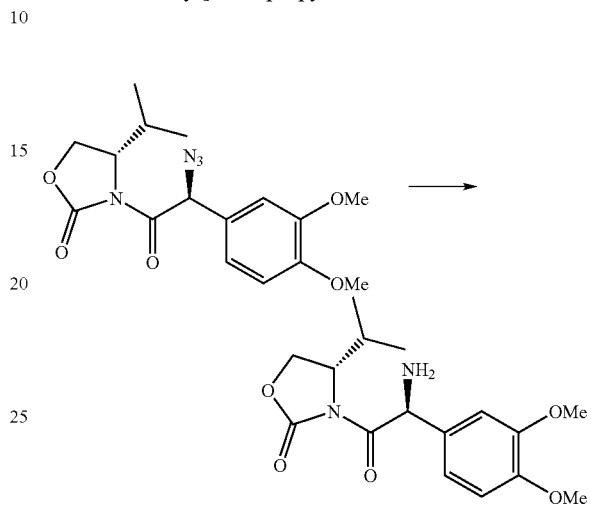

Following the procedure of D. A. Evans et al. (*J. Am. Chem. Soc.* 1990, 112, 4011), the azido derivative from above (0.100 g, 0.28 mmol) and 20% palladium hydroxide on carbon (20 mg) were suspended in MeOH (5 mL) and trifluoroacetic acid (3 equivalents, 0.86 mmol, 66 µL) was added. The mixture was hydrogenated under 1 atm of hydrogen gas for 3 h. The mixture was filtered and volatiles removed under vacuo, to give the desired amine in quantitative yield, as a white solid.

(S)-{[1-(1-Cyclohexyl-2-furan-3-yl-1H-benzoimidazole-5-yl)-methanoyl]-amino}-(3,4-dimethoxyphenyl)acetic acid

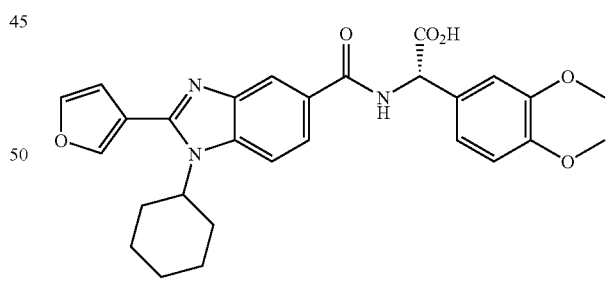

The acid derivative of example 2 (0.100 g, 0.32 mmol), the amine derivative from above (1.1 equivalent, 0.114 g, 0.36 mmol) and TBTU (1.3 equivalent, 0.134 g, 0.42 mmol) were dissolved in DMF (0.5 mL) and triethylamine (4 equivalents, 180 µL, 1.29 mmol) was added. The mixture was stirred at room temperature until reaction was complete as determined by HPLC analysis. 1 N NaOH (0.5 mL) was then added and the reaction mixture added to water (25 mL) with vigorous stirring. The resulting precipitate was collected, washed with water and dried (198 mg, 95% yield). This material was dissolved in THF (2.5 mL) and water (0.75 mL) was added.

The solution was cooled in ice and 30% aqueous hydrogen peroxide (4 equivalents, 151 µL) was added followed by LiOH monohydrate (2 equivalents, 0.016 g). After stirring for 4 h at 0° C., the reaction was quenched by addition of sodium bisulfite (3 equivalents) and the THF layer separated. This solution was diluted with DMSO and the product isolated by preparative HPLC (45 mg).

Example 8

Entry 1040, Table 1
(S)-2-{[1-(1-Cyclohexyl-2-furan-3-yl-1H-benzoimidazol-5-yl)methanoyl]amino}-3-(4-hydroxyphenyl)propionic acid

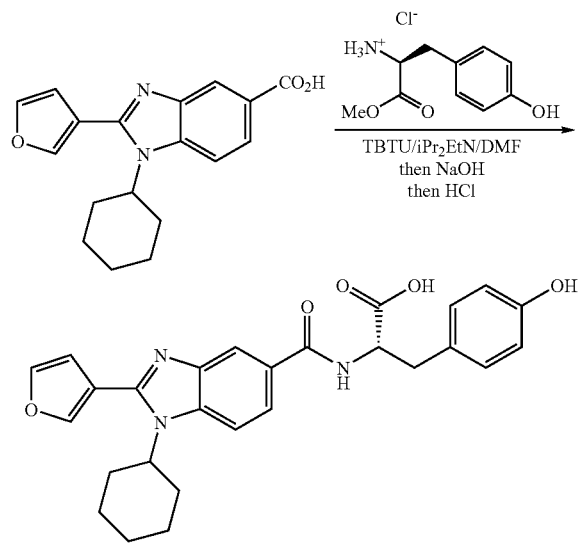

The carboxylic acid of example 2 (0.075 g, 0.24 mmol) and TBTU (1.2 equiv., 0.29 mmol, 0.093 g) were dissolved in DMF (0.5 mL) and DIEA (5 equiv., 1.2 mmol, 0.21 mL) was added followed by tyrosine methyl ester hydrochloride (1.2 equiv., 0.29 mmol, 0.036 g). The mixture was stirred 30 min at room temperature. The reaction mixture was added drop-wise to 1 N NaOH (10 mL) and the mixture stirred until complete hydrolysis of the methyl ester (as determined by HPLC analysis). The pH of the solution was then adjusted to 5-6 by drop-wise addition of 1 N HCl. The gray precipitate that formed was collected by filtration, washed with water and dried (125 mg). The solid was further purified by reversed-phase HPLC using 0.1% TFA—0.1% TFA in acetonitrile gradients to give after lyophilisation, the TFA salt of the title compound as a white amorphous solid (35 mg).

Example 9

Entry 16011, Table 16
(S)-3-(4-Carboxymethoxyphenyl)-2-{[1-(1-cyclohexyl-2-furan-3-yl-1H-benzoimidazol-5-yl)methanoyl]amino}propionic acid

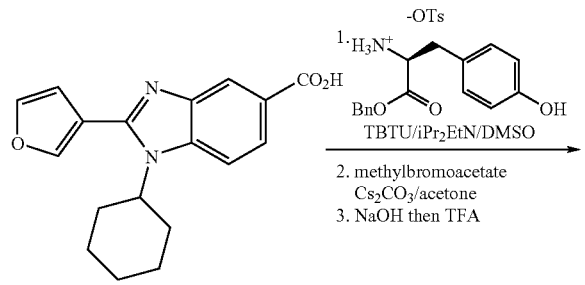

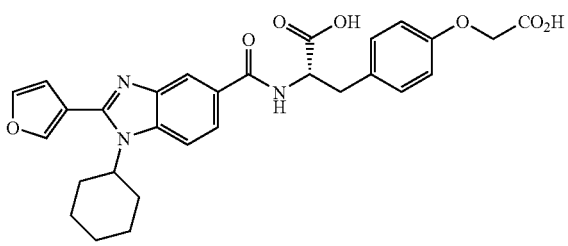

The carboxylic acid of example 2 (0.075 g, 0.24 mmol) and TBTU (1.3 equiv., 0.31 mmol, 0.100 g) were dissolved in DMSO (0.5 mL) and DIEA (5 equiv., 1.2 mmol, 0.21 mL) was added followed by tyrosine benzyl ester para-toluenesulfonate (1.3 equiv., 0.31 mmol, 0.137 g). The mixture was stirred overnight at room temperature and then added drop-wise to a solution of AcOH (0.3 mL) in water (15 mL). The gray precipitate that formed was collected by filtration, washed with water and dried (137 mg).

A portion of the tyrosine benzyl ester derivative from above (0.030 g, 0.043 mmol) was dissolved in acetone (1.5 mL) and $Cs_2CO_3$ (6 equiv., 0.26 mmol, 0.090 g) and methylbromoacetate (2 equiv., 0.086 mmol, 0.08 mL) were added. The mixture was stirred at 50° C. for 30 min and volatiles removed under reduced pressure. The residue was dissolved in DMSO (0.30 mL) and 5 N NaOH (50 µL) and water (50 µL) were added. The mixture was stirred at room temperature for 30 min, acidified with TFA (50 µL) and diluted with DMSO (0.15 mL). The mixture was directly purified by reversed-phase HPLC using 0.1% TFA—0.1% TFA in acetonitrile gradients to give after lyophilisation, the TFA salt of the title compound as a white amorphous solid (18 mg).

In a similar fashion, the tyrosine phenolic group could be alkylated with ethyl 4-bromopyruvate or methyl 5-bromovalerate to give inhibitors with homologated alkylcarboxyl chains.

Example 10

Entry 16017, Table 16

(S)-2-{[1-(1-Cyclohexyl-2-furan-3-yl-1H-benzoimidazol-5-yl)methanoyl]amino}-3-[4-(1H-tetrazol-5-yl)phenyl]propionic acid:

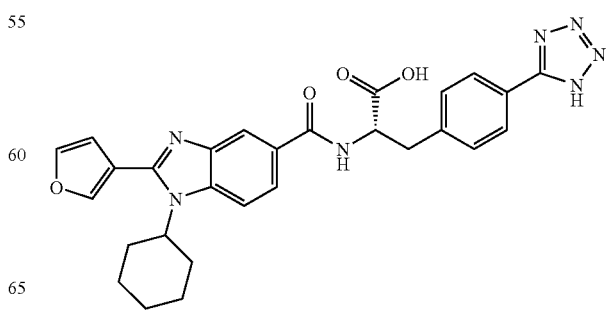

(S)-4-Cyanophenylalanine ethyl ester hydrocloride

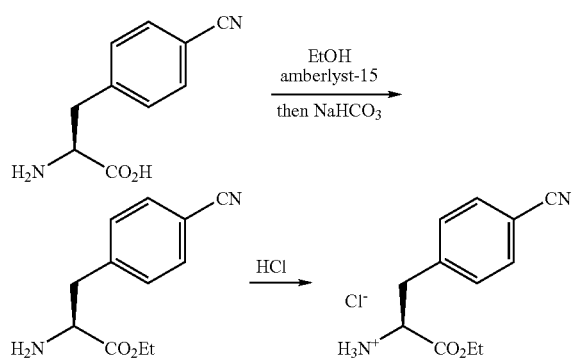

(S)-4-Cyanophenylalanine (0.630 g, 3.31 mmol) was suspended in EtOH (25 mL) and amberlyst-15 ion-exchange resin (10 g) was added. The mixture was stirred for two days at room temperature and quenched by addition of 10% aqueous $NaHCO_3$ (50 mL). The mixture was extracted twice with DCM (50 mL) and the organic extract dried over $MgSO_4$. Hydrogen chloride in $Et_2O$ (1 M, 10 mL) was added and volatiles removed under reduced pressure to give (S)-4-cyanophenylalanine ethyl ester hydrochloride as a white solid (0.800 g, 94% yield).

(S)-3-(4-Cyanophenyl)-2-{[1-(1-cyclohexyl-2-furan-3-yl-1H-benzoimidazol-5-yl)-methanoyl]amino}propionic acid ethyl ester

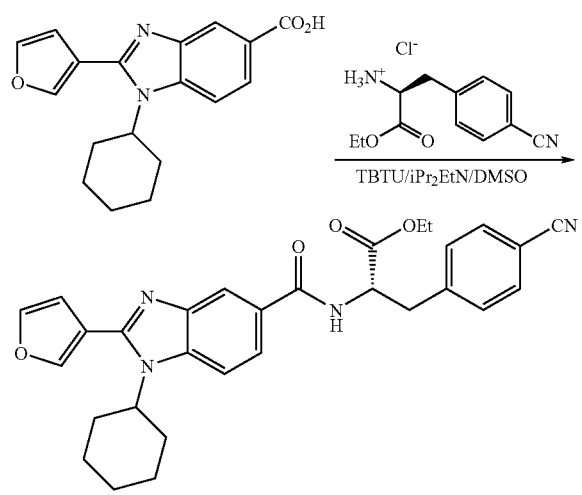

The carboxylic acid of example 2 (0.060 g, 0.20 mmol) and TBTU (1.3 equiv., 0.26 mmol, 0.084 g) were dissolved in DMSO (0.6 mL) and DIEA (5 equiv., 1.0 mmol, 0.18 mL) was added followed by (S)-4-cyanophenylalanine ethyl ester hydrochloride (1.3 equiv., 0.26 mmol, 0.065 g). The mixture was stirred at room temperature for 1 h and quenched with water. The precipitated solid was collected by filtration, washed with water and dried. The title amide (0.081 g) was obtained as a beige solid.

(S)-2-{[1-(1-Cyclohexyl-2-furan-3-yl-1H-benzoimidazol-5yl)methanoyl]amino}3-[4-(1H-tetrazol-5-yl)phenyl]propionic acid ethyl ester

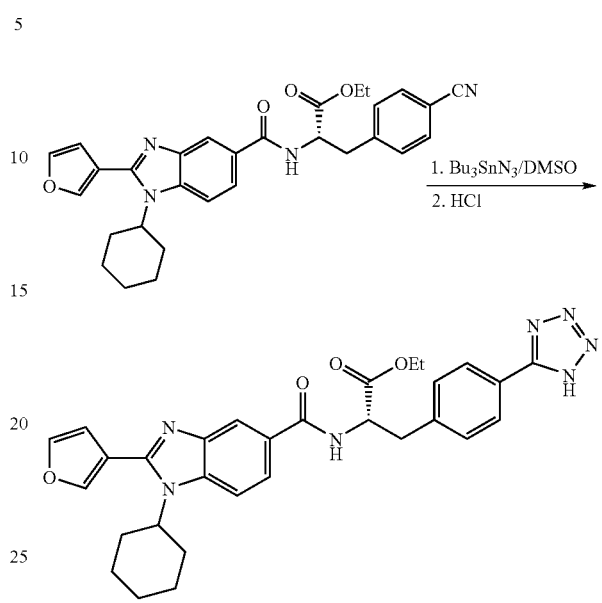

(S)-3-(4-Cyanophenyl)-2-{[1-(1-cyclohexyl-2-furan-3-yl-1H-benzoimidazol-5-yl)-methanoyl]-amino}-propionic acid ethyl ester from above (0.260 g, 0.51 mmol) and tributyltin azide (4 equiv., 2.0 mmol, 0.650 g) were dissolved in DMSO (2 mL) and the solution stirred at 80° C. for 48 h. The reaction was then quenched with 1 N HCl (10 mL) and stirred for an additional 40 min. The aqueous phase was decanted and the oily residue dissolved in DMSO and purified by reversed-phase HPLC using 0.1% TFA—0.1% TFA in acetonitrile gradients to give after lyophilisation, the TFA salt of the title compound as a white amorphous solid (97 mg).

(S)-2-{[1-(1-Cyclohexyl-2-furan-3-yl-1H-benzoimidazol-5-yl)methanoyl]amino}-3-[4-(1H-tetrazol-5-yl)phenyl]propionic acid

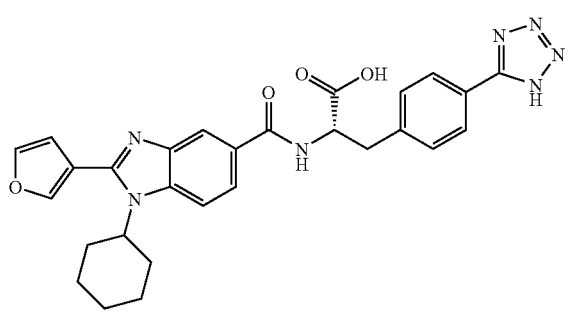

The ethyl ester prepared as above (0.16 mmol) was dissolved in DMSO (1 mL) and aqueous KOH was added (pH 10). After stirring for 30 min at room temperature, the mixture was acidified with TFA and the precipitate collected by filtration. The product was purified by reversed-phase HPLC using 0.1% TFA—0.1% TFA in acetonitrile gradients to give after lyophilisation, the TFA salt of the title compound as a white amorphous solid (15 mg).

Example 11

2,6-Dimethyl-DL-tyrosine methyl ester hydrocloride

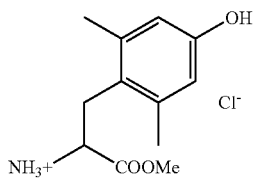

The amino acid of example 11 was prepared in racemic form following the procedure of Dygos et al. (*Synthesis* 1992, 741). Bis(1,5-cyclooctadiene)rhodium (I) trifluoromethanesulfonate was used as catalyst and 1,2-bis(diphenylphosphino)ethane as ligand for the hydrogenation step. The amino acid was converted to its methyl ester hydrochloride in the usual manner (MeOH/SOCl$_2$). This amino acid derivative was used to prepare inhibitors in the usual manner.

Example 12

3,5-Dimethyl-DL-tyrosine methyl ester hydrocloride

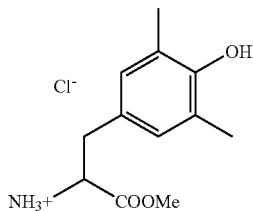

This compound was prepared from 2,6-dimethyl-4-iodophenol, using the procedure described for example 11.

Example 13

N-Boc-4-(2-Carboethoxyethenyl)-L-phenylalanine benzyl ester and N-Boc-4-(2-Carboethoxycyclopropyl)-L-phenylalanine benzyl ester

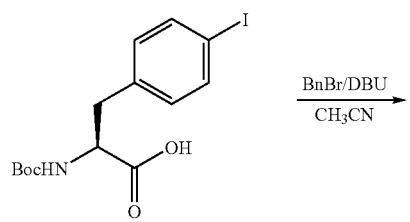

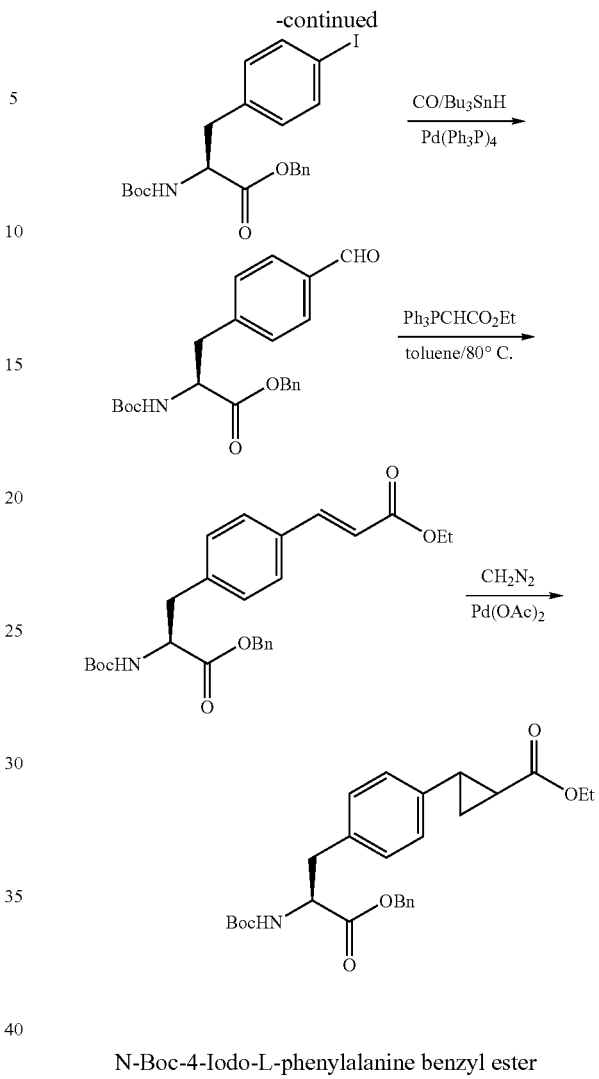

N-Boc-4-Iodo-L-phenylalanine benzyl ester

N-Boc-4-iodophenylalanine was dissolved in acetonitrile and DBU (1 equivalent) was added followed by benzyl bromide (1 equivalent). The mixture was stirred for 2 h at room temperature. After removal of the solvent under reduced pressure, the residue was dissolved in EtOAc and the solution washed with 10% aqueous HCl and water. Drying (MgSO$_4$) and concentration under reduced pressure gave a crude product that was purified by crystallization from hexane.

N-Boc-4-Formyl-L-phenylalanine benzyl ester

The iodo derivative from above (6.16 g, 12.8 mmol) was dissolved in dry THF (50 mL). The system was purged with carbon monoxide gas. Tetrakis(triphenylphosphine)palladium (300 mg) was added and the mixture stirred for 10 min at room temperature, and then brought to 50° C. Tributyltin hydride (4.10 g, 14 mmol) in THF (20 mL) was added dropwise over 2.5 h while CO gas was slowly bubbled through the solution. After completion, THF was removed under reduced pressure and the residue purified by flash chromatography using 20% EtOAc in hexane as eluent. The title compound was obtained as a tan-colored solid (4.33 g, 88% yield).

51

(E)-3-[4-((S)-2-Benzyloxycarbonyl-2-tert-butoxycarbonylamino-ethyl)-phenyl]-acrylic acid ethyl ester The aldehyde from above (0.500 g, 1.3 mmol) and (carbethoxymethylene) triphenylphosphorane (0.905 g, 2.60 mmol) were suspended in toluene (4 mL) and the mixture heated to 80° C. for 2 h. Toluene was removed under reduced pressure and the residue purified by flash chromatography on silica gel using 30-50% EtOAc in hexane as eluent. The unsaturated ester was obtained as a solid in quantitative yield.

2-[4-((S)-2-Benzyloxycarbonyl-2-tert-butoxycarbonylamino-ethyl)-phenyl]-cyclopropane carboxylic acid ethyl ester The ester from above (0.040 g, 0.088 mmol) was dissolved in 1:1 DCM-Et$_2$O (0.5 mL) and palladium acetate (10 mg) was added. The solution was cooled to −5° C. and excess diazomethane in Et$_2$O was added slowly. After stirring for 15 min, the solution was flushed with air, filtered and concentrated in vacuo. The title compound was obtained in quantitative yield.

Example 14

(R)-2-(4-Hydroxyphenyl)-1-methyl-ethyl-ammonium chloride

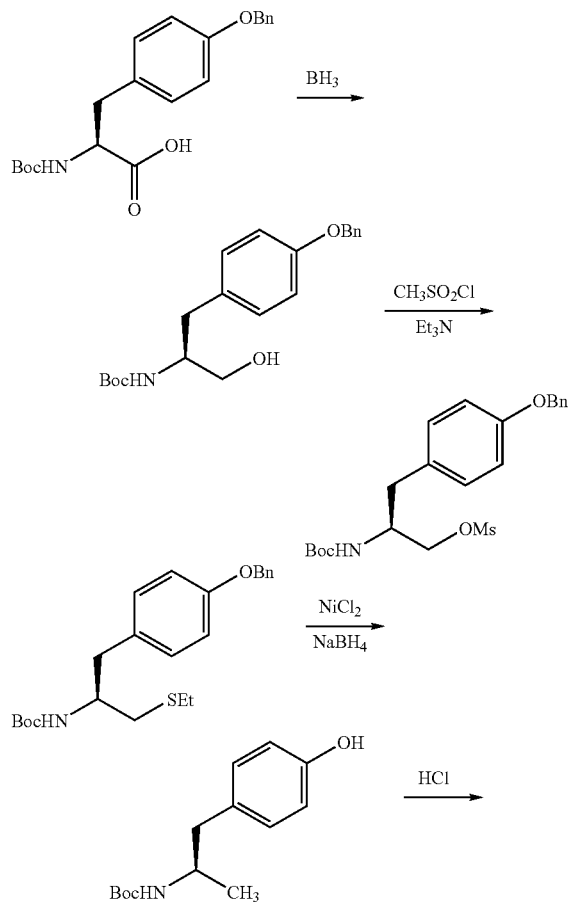

52

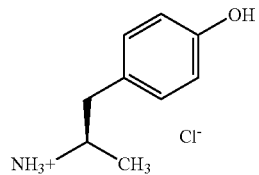

N-Boc-(O-benzyl)-L-tyrosine was reduced to the corresponding amino alcohol, converted to the mesylate and then the ethyl sulfide, following the procedure of Donner (*Tetrahedron Lett.* 1995, 36, 1223). The ethyl sulfide was reduced to a methyl group using nickel boride according to Euerby and Waigh (*Synth. Commun.* 1986, 16, 779). The O-benzyl protecting group was also cleaved in this step.

The N-Boc protecting group was removed with hydrogen chloride to give the crude amine hydrochloride salt that was used without purification.

Example 15

(S)-1-Methoxycarbonyl-2-[4-(4-methoxycarbonyl-1,2,3]triazol-1-yl)-phenyl]-ethyl ammonium chloride

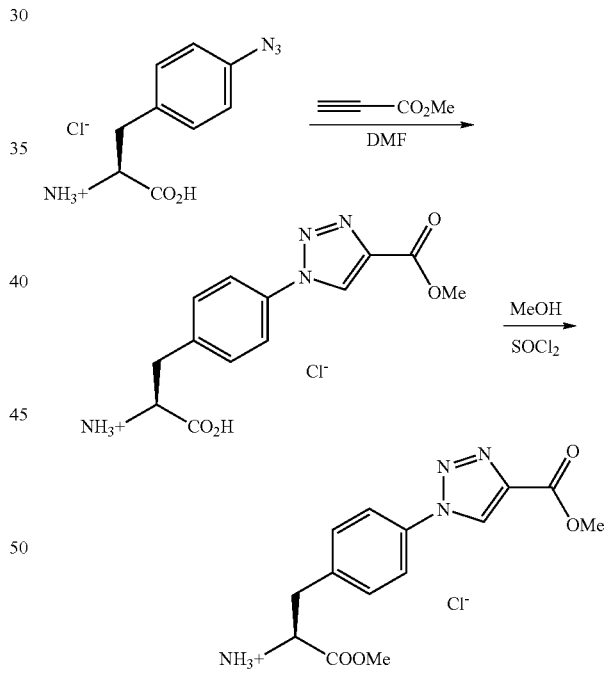

4-Azido-L-phenylalanine hydrochloride (0.242 g, 1 mmol) was dissolved in dry DMF (1 mL) and methyl propiolate (0.420 g, 5 mmol) was added. The suspension was stirred 24 h at 45° C. After cooling to room temperature, the solid was filtered, washed with EtOAc and dried (175 mg). The material was suspended in MeOH (15 mL) and thionyl chloride (0.5 mL) was added drop-wise. The mixture was refluxed for 3 h, cooled and concentrated under reduced pressure. The residue was triturated with ether to give the title compound as a white solid (175 mg, 53% yield).

Example 16
Entry 1083, Table 1
[4-((S)-2-Carboxy-2-{[1-(1-cyclohexyl-2-furan-3-yl-1H-benzoimidazol-5-yl)-methanoyl]aminoethyl)-phenyl]-trifluoromethyl-3H-[1,2,3]triazole-4-carboxylic acid:
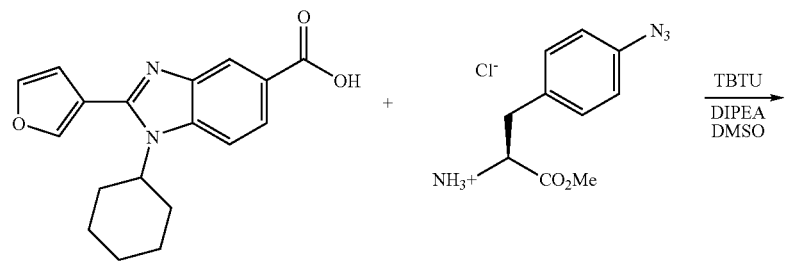
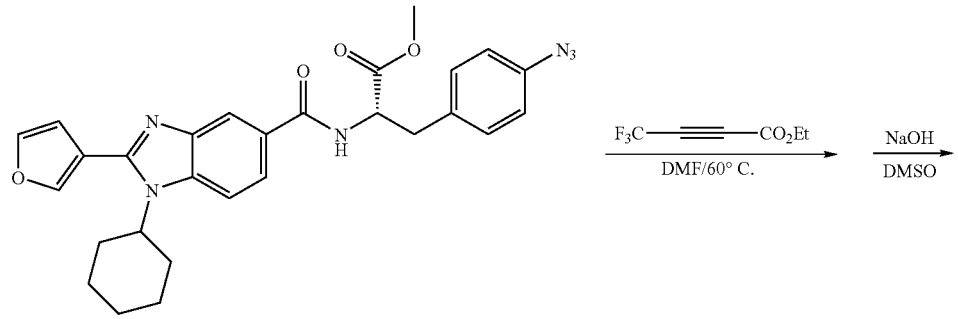
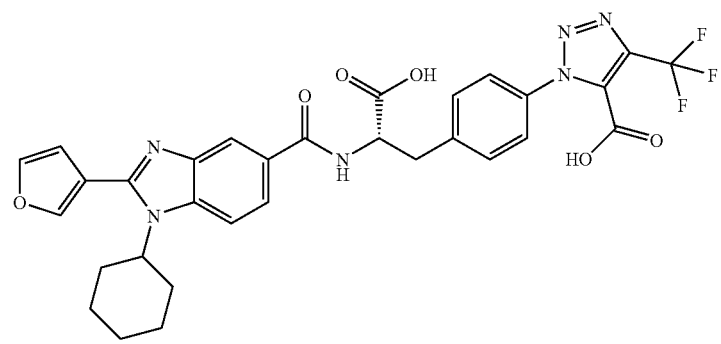

The carboxylic acid of example 2 was coupled to 4-azido-L-phenylalanine methyl ester hydrochloride using the usual procedure. The resulting amide derivative (0.020 g, 0.039 mmol) was dissolved in DMF (0.3 mL) and ethyl 4,4,4-trifluoro-2-butynoate (0.014 g, 0.084 mmol) was added. The mixture was stirred overnight at 60° C. The reaction mixture was then evaporated under high vacuum and the residue dissolved in DMSO (0.3 mL). Aqueous 5 N NaOH (0.2 mL) was added and the mixture stirred at room temperature for 1 h. The title compound was isolated by preparative HPLC of the reaction mixture.

Example 17

Entry 16022, Table 16

(S)-2-{[1-(1-Cyclohexyl-2-furan-3-yl-1H-benzoimidazol-5-yl)-methanoyl]-amino}-3-[4-(1H-tetrazol-5-ylmethoxy)-phenyl]-propionic acid

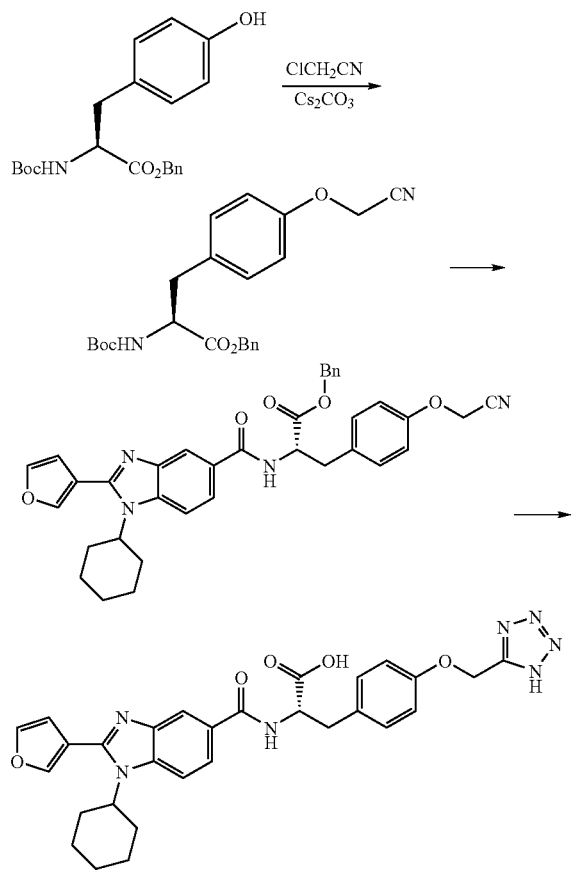

(S)-2-tert-Butoxycarbonylamino-3-(4-cyanomethoxyphenyl)-propionic acid benzyl ester N-Boc-L-tyrosine benzyl ester (0.371 g, 1 mmol) was dissolved in acetone (5 mL) and cesium carbonate (0.650 g, 2 mmol) was added followed by chloroacetonitrile (0.150 g, 2 mmol). The mixture was then reflux for 2 h. The reaction was cooled to room temperature and insoluble salts removed by filtration using acetone for washings. Volatiles were removed under reduced pressure and the residue dissolved in DCM. The solution was washed with brine, dried (MgSO$_4$) and concentrated to give the desired product as an oil (450 mg).

Coupling with Carboxylic Acid of Example 2

The above ester was stirred for 1 h in 4 N HCl-dioxane. Volatiles were removed under reduced pressure and the residue triturated with Et$_2$O to give the amine hydrochloride salt as a tan-colored solid (350 mg).

The hydrochloride salt (0.080 g, 0.26 mmol) was added to a mixture of the carboxylic acid of example 2 (0.060 g, 0.2 mmol), TBTU (0.080 g, 0.26 mmol) and DIPEA (150 μL) in DMSO (0.9 mL). The mixture was stirred for 1 h at room temperature and then poured into water. The precipitated material was collected by filtration, washed with water and dried. It was purified by flash chromatography on silica gel using EtOAc as eluent, to give the desired amide derivative (50 mg).

(S)-2-{[1-(1-Cyclohexyl-2-furan-3-yl-1H-benzoimidazol-5-yl)-methanoyl]-amino}-3-[4-(1H-tetrazol-5-ylmethoxy)-phenyl]-propionic acid The cyano derivative from above (0.040 g, 0.066 mmol) and tributyltin azide (300 mg) were dissolved in DMSO (0.5 mL) and the mixture stirred at 80° C. for 24 h. Aqueous 6 N HCl (1 mL) was added and the mixture stirred for 1 h at room temperature. The mixture was basified to pH 10 with 5 N NaOH, and after stirring for 30 min, the solution was acidified with TFA and the precipitated material collected by filtration. The title compound was isolated by preparative HPLC (6.6 mg).

Example 18

4-Aminophenylalanine derivatives

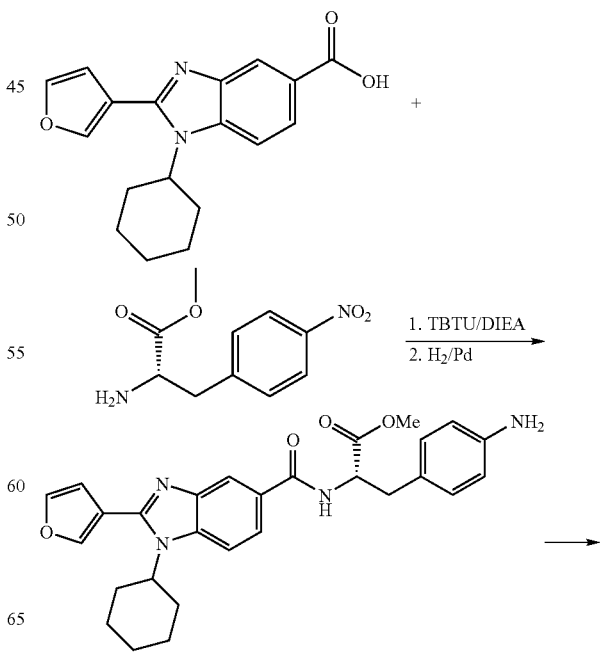

-continued

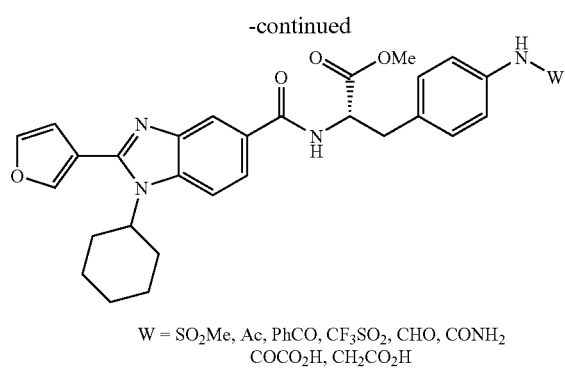

W = SO₂Me, Ac, PhCO, CF₃SO₂, CHO, CONH₂
COCO₂H, CH₂CO₂H (S)-2-{[1-(1-Cyclohexyl-2-furan-3-yl-1H-benzoimidazol-5-yl)-methanoyl]-amino}-3-(4-nitrophenyl)-propionic acid methyl ester The carboxylic acid of example 2 (0.500 g, 1.61 mmol), TBTU (0.621 g, 1.94 mmol) and 4-nitro-L-phenylalanine methyl ester hydrochloride (0.461 g, 1.77 mmol) were dissolved in DMSO (2.0 mL) and DIEA (6.44 mmol, 1.12 mL) was added. The mixture was stirred for 2 h at room temperature (HPLC: complete). The reaction mixture was added drop-wise with stirring to a mixture of water (45 mL) and AcOH (0.8 mL). The precipitate that formed was collected by filtration, washed with water and dried (0.768 g, 92% yield).

(S)-3-(4-Aminophenyl)-2-{[1-(1-cyclohexyl-2-furan-3-yl-1H-benzoimidazol-5-yl)-methanoyl]-amino}-propionic acid methyl ester The nitro derivative from above (0.765 g, 1.48 mmol) was hydrogenated in MeOH (25 mL) over 10% palladium on carbon (150 mg) under 1 atm $H_2$ for 6 h (HPLC: complete). The catalyst was removed by filtration and volatiles removed under vacuum to give the desired aniline in quantitative yield as a greenish-brown solid.

(Entry 16032, Table 16): (S)-2-({[1-(1-Cyclohexyl-2-furan-3-yl-1H-benzoimidazol-5-yl)-methanoyl]-amino}-3-(4-methanesulfonylaminophenyl)-propionic acid (W=SO₂CH₃):

The aniline derivative from above (0.050 g, 0.10 mmol) was dissolved in DCM (5 mL). DIEA (1.1 equivalent, 0.11 mmol, μL) was added and the solution cooled in ice. Methanesulfonyl chloride (1.1 equivalent, 0.11 mmol, 9 μL) was added. Stir 1 h at 0° C. Add DIEA (20 μL) and methanesulfonyl chloride (4 μL) and stir an additional h at room temperature. Evaporate DCM under reduced pressure and dissolved residue in DMSO (1.4 mL). 2.5 N Aqueous NaOH (200 μL) was added and the mixture stirred 1 h at room temperature (hydrolysis of methyl ester complete by HPLC). TFA (100 μL) was added, the solution was filtered and the product isolated by prep HPLC (17 mg).

(Entry 16031, Table 16): (S)-3-(4-Acetylaminophenyl)-2-{[1-(1-Cyclohexyl-2-furan-3-yl-1H-benzoimidazol-5-yl)-methanoyl]-amino}-propionic acid (W=COCH₃)

The procedure described above was followed, using acetyl chloride as acylating agent.

(Entry 1080, Table 1): (S)-2-{[1-(1-Cyclohexyl-2-furan-3-yl-1H-benzoimidazol-5-yl)-methanoy]amino}-3-(4-[(1-phenylmethanoyl)-amino]-phenyl}-propionic acid (W=COPh)

The procedure described above was followed, using benzoyl chloride as acylating agent.

(Entry 16030, Table 16): (S)-2-{[1-(1-Cyclohexyl-2-furan-3-yl-1H-benzoimidazol-5-yl)-methanoyl]amino}-3-(4-trifluoromethanesulfonylaminophenyl)-propionic acid (W=SO₂CF₃):

The procedure described above was followed, using trifluoromethanesulfonic anhydride as acylating agent.

(Entry 16009, Table 16): (S)-3{4-[(1-Carboxymethanoyl)amino]phenyl)-2-{[1-(1-cyclohexyl-2-furan-3-yl-1H-benzoimidazol-5-yl)-methanoyl]-amino}-propionic acid (W=COCO₂H)

The procedure described above was followed, using methyloxalyl chloride as acylating agent.

(Entry 16028, Table 16): (S)-2-([1-(1-Cyclohexyl-2-furan-3-yl-1H-benzoimidazol-5-yl)-methanoyl]-amino}-3-(4-formylaminophenyl)-propionic acid (W=CHO)

The aniline derivative described at the start of example 18 (0.050 g, 0.103 mmol) was dissolved in MeOH (1 mL) and methyl formate (300 μL) was added. The mixture was stirred for 48 h at 50° C. (HPLC indicates 75% conversion). Volatiles were removed under reduced pressure and the residue was dissolved in a mixture of DMSO (1 mL) and 2.5 N NaOH (200 μL). After stirring for 1 h at room temperature, TFA (100 μL) was added and the product isolated by prep HPLC (16 mg).

(Entry 16026, Table 16): (S)-2-{[1-(1-Cyclohexyl-2-furan-3-yl-1H-benzoimidazol-5-yl)-methanoyl]-amino}-3-(4-ureidophenyl)-propionic acid (W=CONH₂)

The aniline derivative described at the start of example 18 (0.050 g, 0.103 mmol) was dissolved in AcOH (0.5 mL) and KOCN (3 equivalent, 0.309 mmol, 0.024 g) was added. The mixture was stirred for 2 h at room temperature (HPLC: complete). Volatiles were removed under vacuo and the residue was dissolved in a mixture of DMSO (0.5 mL) and 2.5 N NaOH (200 μL). The mixture was stirred for 1 h at room temperature and TFA (100 μL) was added. The product was isolated by Prep HPLC (22 mg).

(Entry 16010, Table 16): (S)-3-[4-(Carboxymethylamino)phenyl]-2-{[1-(1-cyclohexyl-2-furan-3-yl-1H-benzoimidazol-5-yl)-methanoyl]-amino}-propionic acid (W=CH$_2$CO$_2$H)

The aniline derivative described at the start of example 18 (0.040 g, 0.082 mmol) was dissolved in a mixture of DCM (2 mL) and DMSO (0.5 mL). DIEA (2 equivalent, 0.16 mmol, 29 μL) and methyl bromoacetate (1.1 equivalent, 0.09 mmol, 9 μL) were then added and the mixture stirred 48 h at room temperature. DCM was removed under reduced pressure and 5 N NaOH (50 μL) was added. After stirring for 0.5 h at room temperature, the reaction mixture was acidified with TFA (50 μL) and the product was isolated by prep HPLC (7 mg).

Example 19

Entry 16029, Table 16
(S)-2-{[1-(1-Cyclohexyl-2-furan-3-yl-1H-benzoimidazol-5-yl)-methanoyl]amino}-3-[4-(2-hydroxy-3,4-dioxocyclobut-1-enylamino)-phenyl]-propionic acid

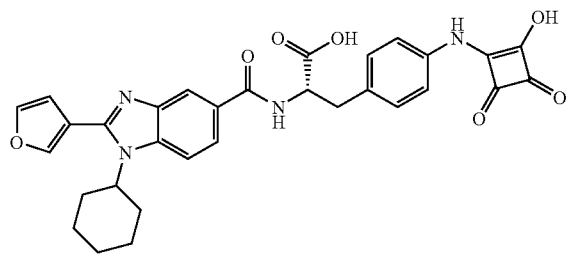

The aniline of example 17 (0.050 g, 0.103 mmol) was dissolved in MeOH (2 mL) and 3,4-dimethoxy-3-cyclobutene-1,2-dione (3 equivalents, 0.31 mmol, 0.044 g) was added. The mixture was refluxed for 2 h (HPLC: complete). MeOH was removed under reduced pressure and the residue purified by prep HPLC. The most polar component was isolated (corresponds to the methyl ester on the amino acid carboxyl group) and stirred with DMSO (0.5 mL) and 2.5 N NaOH (200 μL) for 0.5 h. TFA (100 μL) was added and the desired compound of example 19 was isolated by prep HPLC.

Example 20

Entry 11021, Table 11
(S)-2-(5-Hydroxy-1-methyl-1H-indol-3-y)-1-methoxycarbonyl-ethyl-ammonium chloride and (S)-2-({[1-(1-Cyclohexyl-2-furan-3-yl-1H-benzoimidazol-5-yl)-methanoyl]-amino}-3(5-hydroxy-1-methyl-1H-indol-3-yl)-propionic acid)

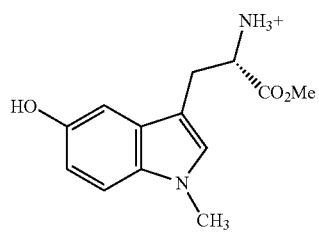

5-Benzyloxy-1-methylindole 5-benzyloxyindole (2.00 g, 8.96 mmol) was dissolved in DMF (20 mL) and the solution cooled in ice. Sodium hydride (60% oil dispersion, 1.2 equivalent, 10.7 mmol, 0.43 g) was added and the mixture stirred for 30 min. Iodomethane (1.2 equivalent, 10.7 mmol, 0.67 mL) was added and the reaction stirred at room temperature overnight. The reaction was then poured into water (150 mL) and the precipitated solid collected by filtration. After washing with water and drying, 5-benzyloxy-1-methylindole (1.913 g, 90% yield) was obtained as a white solid.

(S)-2-(5-Hydroxy-1-methyl-1H-indol-3-yl)-1-methoxycarbonyl-ethyl-ammonium chloride Following the procedure of Bennani et al. (*Synlett* 1998, 754), 5-benzyloxy-1-methylindole was converted to the N-Cbz protected tryptophan benzyl ester derivative in 20% yield: MS (ES$^+$) m/z 549 (MH$^+$). Protecting groups were removed by hydrogenolysis in MeOH over 10% palladium under 1 atm H$_2$ and the free amino acid converted to the corresponding methyl ester hydrochloride in the usual manner using MeOH/thionyl chloride.

(S)-2-{[1-(1-Cyclohexyl-2-furan-3-yl-1H-benzoimidazol-5-yl)-methanoyl]-amino}-3(5-hydroxy-1-methyl-1H-indol-3-yl)-propionic Acid The above tryptophan derivative was coupled in the usual manner to the carboxylic acid of example 2 to give the title compound after hydrolysis of the methyl ester.

Example 21

Entry 11020, Table 11

(S)-2-(5-Hydroxy-2-methyl-1H-indol-3-yl)-1-methoxycarbonyl-ethyl-ammonium chloride and (S)-2-{[1-(1-Cyclohexyl-2-furan-3-yl-1H-benzoimidazol-5-yl)-methanoyl]-amino}-3-(5-hydroxy-2-methyl-1H-indol-3-yl)-propionic acid

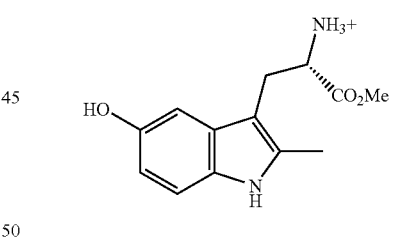

(S)-2(5-Hydroxy-1-methyl-1H-indol-3-yl)-1-methoxycarbonyl-ethyl-ammonium chloride Ethyl 5-hydroxy-2-methyl-3-carboxylate was converted to the 5-benzyloxy derivative (benzyl chloride/K$_2$CO$_3$/acetonitrile) and decarboxylated to give 5-benzyloxy-2-methylindole (R. V. Heinzelman et al., *J. Org. Chem.* 1960, 25,1548) which was then was converted to the corresponding tryptophan derivative as described for example 20.

(S)-2-{[1-(1-Cyclohexyl-2-furan-3-yl-1H-benzoimidazol-5-yl)-methanoyl]-amino}-3-(5-hydroxy-2-methyl-1H-indol-3-yl)-propionic acid The above tryptophan derivative was coupled in the usual manner to the carboxylic acid of example 2 to give the title compound after hydrolysis of the methyl ester.

Example 22

Entry 11022, Table 11

(S)-2-{[1-(1-Cyclohexyl-2-furan-3-yl-1H-benzoimidazol-5-yl)-methanoyl]-amino}-3-[5-(1H-tetrazol-5-yl)-1H-indol-3-yl]-propionic acid

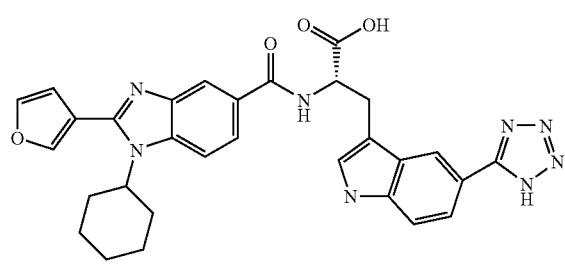

(S)-5-Cyanotryptophan methyl ester hydrochloride was prepared according to the procedure of Dua and Phillips (*Tetrahedron Lett.* 1992, 33, 29), and coupled to the carboxylic acid of example 2 in the usual manner. The cyano group was then converted into the corresponding tetrazole as described in example 10 and the title compound was isolated in the usual manner.

Example 23

3-((S)-2-Carboxy-2-{[1-(1-cyclohexyl-2-furan-3-yl-1H-benzoimidazol-5-yl)-methanoyl]-amino}-ethyl)-1H-indole-5-carboxylic acid (Entry 24, Table 1) and (S)-3-(5-carbamoyl-1H-indol-3-yl)-2-{[1-(1-cyclohexyl-2-furan-3-yl-1H-benzoimidazol-5-yl)-methanoyl]-amino}-propionic acid (Entry 11019, Table 11)

(S)-3-(1-Acetyl-5-cyano-1H-indol-3-yl)-2-methoxycarbonylamino-propionic acid methyl ester was prepared following the procedure of Dua and Phillips (*Tetrahedron Left.* 1992, 33, 29). The cyano derivative was stirred at 80° C. for 18 h with concentrated HCl. Removal of the volatiles under reduced pressure gave a 2:1 mixture of 5-carboxytryptophan and 5-tryptophan carboxamide. The mixture was converted to the methyl ester (MeOH/SOCl$_2$) and these were coupled to the carboxylic acid of example 2 in the usual manner. After hydrolysis of the methyl esters, the title compounds were separated by prep HPLC.

3-((S)-2-Carboxy-2-{[1-(1-cyclohexyl-2-furan-3-yl-1H-benzoimidazol-5-yl)-methanoyl]-amino}-ethyl)-1H-indole-5-carboxylic acid (Entry 11018, Table 11):

(S)-3-(5-carbamoyl-1H-indol-3-yl)-2-{[1-(1-cyclohexyl-2-furan-3-yl-1H-benzoimidazol-5-yl)-methanoyl]-amino}-propionic acid (Entry 11019, Table 11)

Example 24

Entry 2062, Table 2)

1-Cyclohexyl-2-{4-[(3-dimethylamino-propylcarbamoyl)-methoxy]-phenyl}-1H-benzoimidazole-5-carboxylic acid 3,4-dimethoxybenzyl amide

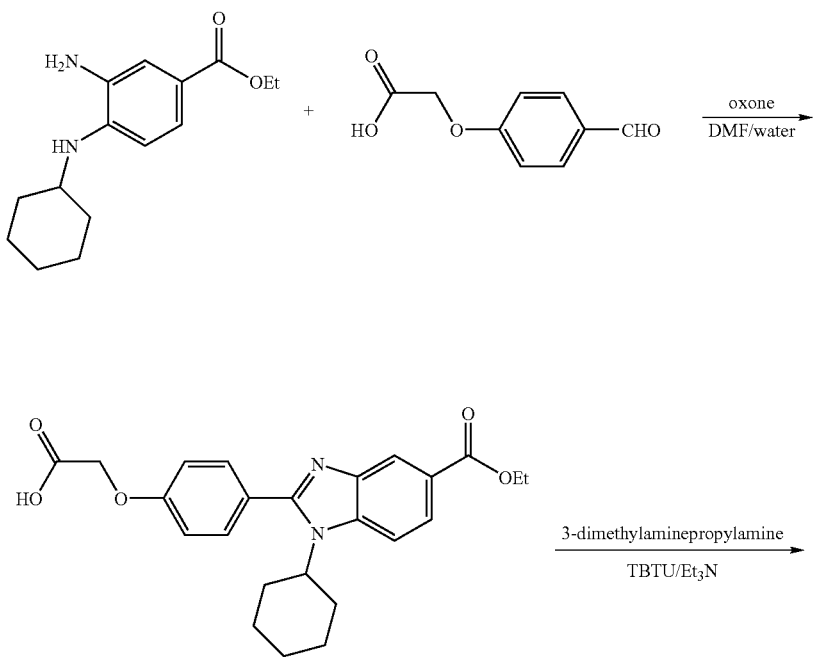

-continued

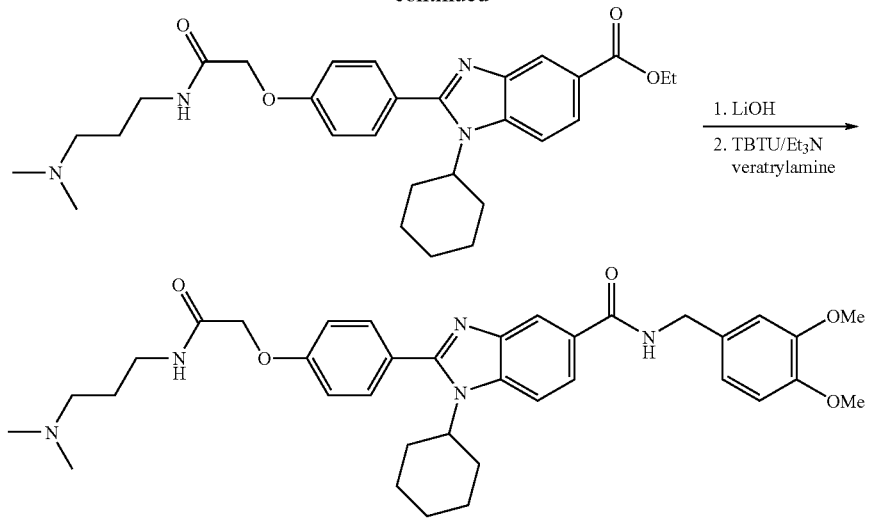

2-(4-Carboxymethoxy-phenyl)-1-cyclohexyl-1H-benzoimidazole-5-carboxylic acid ethyl ester (Entry 11007, Table 11)

Following the procedure of example 1, ethyl 3-amino-4-(aminocyclohexyl)benzoate (1.077 g, 4.1 mmol) and 4-formylphenoxyacetic acid (0.748 g, 4.15 mmol) were dissolved in a mixture of DMF (8 mL) and water (0.5 mL). Oxone® (0.7 equivalent, 2.87 mmol, 1.764 g) was added and the mixture stirred for 30 min at room temperature (HPLC complete). Water was added to precipitate the product, which was collected by filtration, washed with water and dried (1.130 g, 65% yield, brown solid).

1-Cyclohexyl-2-{4-[(3-dimethylamino-propylcarbamoyl)-methoxy]-phenyl}-1H-benzoimidazole-5-carboxylic acid ethyl ester The acid from above (0.975 g, 2.31 mmol), TBTU (0.963 g, 3.0 mmol) and triethylamine (0.98 mL, 7.0 mmol) were dissolved in DMF (4 mL) and 3-dimethylaminepropylamine (0.32 mL, 2.5 mmol) was added. The mixture was stirred for 6 h at room temperature and quenched with 1 N NaOH (1 mL). Water was added and the product extracted with EtOAc. The extract was washed with water, dried ($MgSO_4$) and concentrated to a dark purple oil.

1-Cyclohexyl-2-{4-[(3-dimethylamino-propylcarbamoyl)-methoxy]-phenyl}-1H-benzoimidazole-5-carboxylic acid 3,4-dimethoxybenzyl amide (Entry 2062, Table 2)

The above ethyl ester (0.598 g, 1.18 mmol) was dissolved in MeOH and 1 N LiOH (2 equivalent, 2.36 mmol, 2.36 mL) was added. The mixture was stirred overnight at room temperature, volatiles removed under reduced pressure and the residue dried in vacuo at 45° C.

The lithium salt from above (0.098 mmol) in DMSO (0.29 molar) was treated with TBTU (0.148 mmol, 0.047 g), triethylamine (0.197 mmol, 0.027 mL) and veratrylamine (0.108 mmol, 16 μL). The mixture was stirred overnight at room temperature, poured into 0.5 N NaOH (10 mL) and extracted into EtOAc. The extract was washed with water, dried ($MgSO_4$) and concentrated. The residue was purified by prep HPLC (29 mg).

Example 25

Entry 16035, Table 16

(S)-3-(4-Carbamoyl-phenyl)-2-{[1-(1-cyclohexyl-2-furan-3-yl-1H-benzoimidazol-5-yl)-methanoyl]-amino}-propionic acid

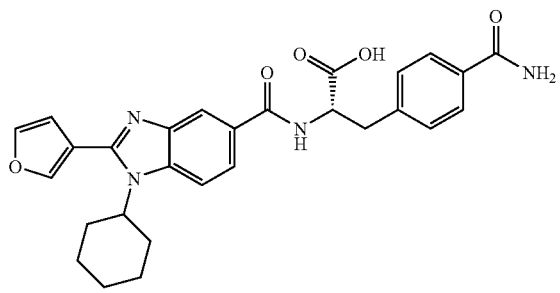

(S)-3-(4-Cyanophenyl)-2-{[1-(1-cyclohexyl-2-furan-3-yl-1H-benzoimidazol-5-yl)-methanoyl]-amino}-propionic acid ethyl ester from example 10 (0.120 g, 0.235 mmol) was dissolved in a mixture of acetone (5 mL) and water (3 mL). Urea-hydrogen peroxide complex (1.0 mmol, 0.094 g) and potassium carbonate (10 mg) were added and the mixture stirred until completion (HPLC). The reaction mixture was concentrated under reduced pressure, the residue was dissolved in DMSO (1.5 mL) and 5 N NaOH (0.2 mL) was added. After stirring for 30 min at room temperature, TFA (0.5 mL) was added and the product isolated by prep HPLC (18 mg).

Example 26
(E)-3-[5-((S)-2-Carboxy-2-{[1-(1-cyclohexyl-2-furan-3-yl-1H-benzimidazol-5-yl)-methanoyl]-amino}-ethyl)-2-hydroxyphenyl]-acrylic acid 26 (Entry 16064, Table 16) and (S)-3-[-3-(2-caboxyethyl)-4-hydroxy-phenyl]-2-{[1-(1-cyclohexyl-2-furan-3-yl-1H-benzoimidazol-5-yl)-methanoyl]-amino}-propionic acid (Entry 16065, Table 16)
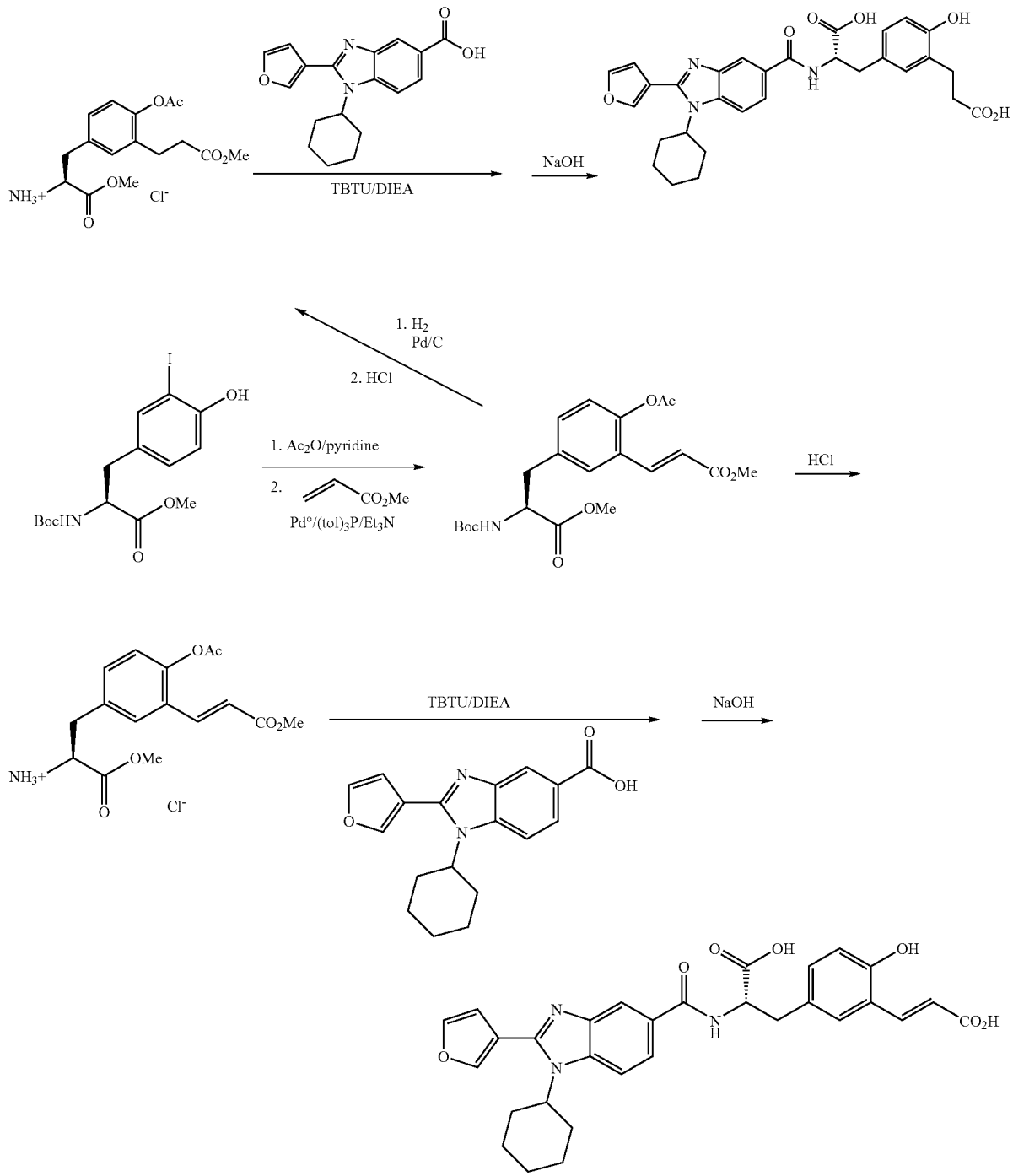

(S)-3-(4-Acetoxy-3-iodo-phenyl)-2-tert-butoxycarbonylamino-propionic acid methyl ester 3-Iodo-L-tyrosine was converted to the methyl ester and protected on nitrogen with a Boc group following standard procedures. The hydroxyl group was then acetylated with acetic anhydride in DMF, in the presence of DIEA.

(E)-3-[2-Acetoxy-5-((S)-2-tert-butoxycarbonylamino-2-methoxycarbonyl-ethyl)-phenyl]-acrylic acid methyl ester The iodo derivative from above (0.150 g, 0.32 mmol) was dissolved in MeCN (3 mL) and argon was bubbled through the solution for 15 min. Methyl acrylate (5 equivalent, 1.62 mmol, 146 μL), tri-o-tolylphosphine (50 mg), racemic BINAP (50 mg), DIEA (2.6 equivalent, 0.84 mmol, 146 μL) and palladium acetate (50 mg) were added and the mixture refluxed for 5 h. The reaction was cooled to room temperature and argon was bubbled again through the solution for 5 min. Fresh portions of methyl acrylate (146 μL), DIEA (146 μL), tri-o-tolylphosphine (50 mg), racemic BINAP (50 mg) and palladium acetate (50 mg) were added and refluxing resumed for another 16 h. Volatiles were then removed under reduced pressure and the residue dissolved in EtOAc. The solution was washed with 1 M KHSO$_4$, 5% NaHCO$_3$ and brine, dried (MgSO$_4$) and concentrated. The product was purified by flash chromatography using 10-25% EtOAc in hexane (122 mg, 90% yield).

(S)-3-[4-Acetoxy-3-(2-methoxycarbonyl-ethyl)-phenyl]-2-tert-butoxycarbonylamino-propionic acid methyl ester The acrylate from above (0.060 g, 0.14 mmol) was hydrogenated in iPrOH (3 mL) under 1 atm H$_2$ over 10% palladium on carbon (50 mg). After 16 h, the solution was filtered and volatiles removed under reduced pressure to give the saturated analogue (56 mg).

(E)-3-[5-((S)-2-Carboxy-2-{[1-(1-cyclohexyl-2-furan-3-yl-1H-benzimidazol-5-yl)-methanoyl]-amino}-ethyl)-2-hydroxyphenyl]-acrylic acid The acrylate derivative from above (0.060 g, 0.14 mmol) was stirred for 1 h in 4N HCl in dioxane (2 mL). Volatiles were then removed in vacuo and the residue dissolved in DMSO (1 mL). TBTU (1.5 equivalent, 0.067 mg, 0.21 mmol), DIEA (4 equivalent, 0.56 mmol, 97 μL) and the carboxylic acid of example 2 (1.2 equivalent, 0.17 mmol, 0.052 g) were added and the mixture stirred for 1.5 h at room temperature. 2 N NaOH (200 μL) and MeOH (400 μL) were added and the mixture stirred overnight at room temperature. The title compound was isolated by prep HPLC (27 mg).

(S)-3-[-3-(2-caboxyethyl)-4-hydroxy-phenyl]-2-{[1-(1-cyclohexyl-2-furan-3-yl-1H-benzoimidazol-5-yl)-methanoyl]-amino}-propionic acid The propanoate derivative from above (0.056 g, 0.13 mmol) was stirred for 1 h in 4N HCl in dioxane (2 mL). Volatiles were then removed in vacuo and the residue dissolved in DMSO (1 mL). TBTU (1.5 equivalent, 0.064 mg, 0.20 mmol), DIEA (4 equivalent, 0.53 mmol, 92 μL) and the carboxylic acid of example 2 (1.2 equivalent, 0.16 mmol, 0.049 g) were added and the mixture stirred for 1.5 h at room temperature. 2 N NaOH (200 μL) and MeOH (400 μL) were added and the mixture stirred overnight at room temperature. The title compound was isolated by prep HPLC (34 mg).

Example 27

Entry 16024, Table 16

(S)-2-{[1-(1-Cyclohexyl-2-furan-3-yl-1H-benzoimidazol-5-yl)-methanoyl]-amino}-3-[4-(4-oxo-2-thioxo-thiazolidin-5-ylidenemethyl)-phenyl]propionic acid

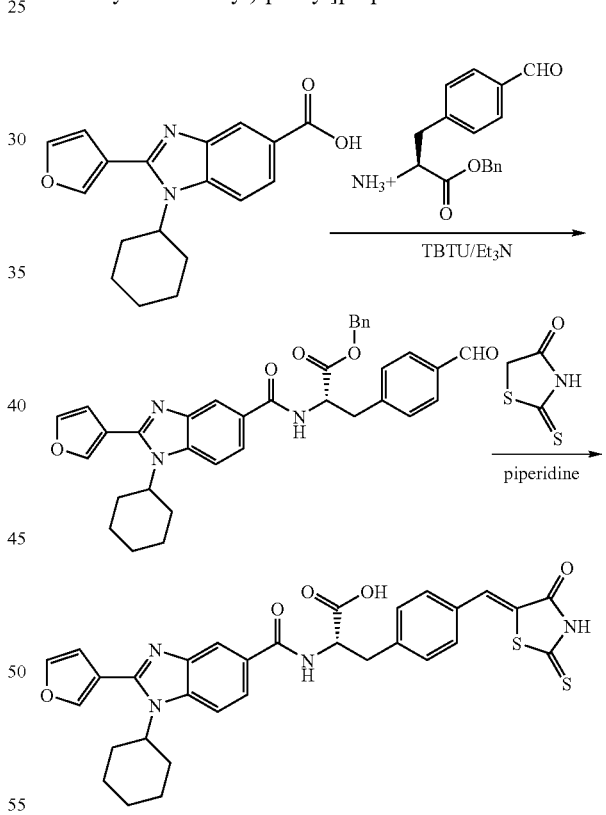

The acid of example 2 and 4-formyl-L-phenylalanine benzyl ester hydrochloride (example 13) were coupled with TBTU in the usual manner. The aldehyde derivative thus obtained (0.050 g, 0.087 mmol) and rhodamine (1.1 equivalent, 0.013 g, 0.095 mmol) were suspended in EtOH (0.5 mL) and piperidine (10 μL) was added. The mixture was refluxed for 3 h. DMSO (1 mL) and 2 N NaOH (0.3 mL) were added and the mixture stirred overnight at room temperature. The reaction mixture was neutralized with TFA and the product isolated by prep HPLC (6 mg).

Example 28

3-Cyclohexyl-2-pyridin-2-yl-3H-imidazo[4,5-b]pyridine-6-carboxylic acid

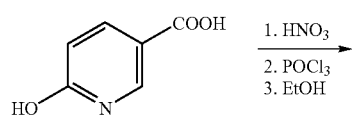

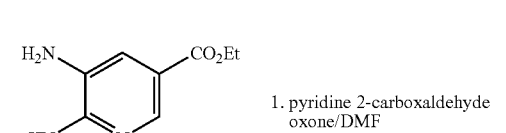

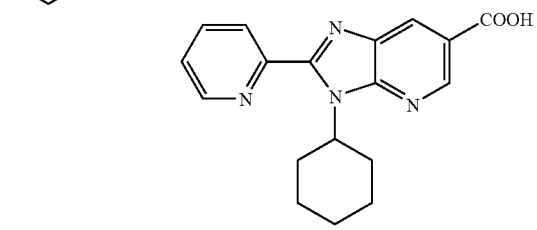

Ethyl 5-amino-6-cyclohexylaminonicotinate

Ethyl 6-chloro-5-nitronicotinate (1.00 g, 4.33 mmol) prepared according to A. H. Berrie et al. (*J. Chem. Soc.* 1951, 2590) was dissolved in DMSO (2 mL) and cyclohexylamine (0.54 g, 5.4 mmol) was added. The mixture was stirred for 1 h at room temperature, diluted with water and the yellow precipitated collected by filtration. The product was washed with water and dried (0.95 g, 74% yield). The nitro derivative from above (0.68 g, 2.32 mmol) was hydrogenated (1 atm $H_2$) in EtOAc (30 mL) over 5% palladium on charcoal (100 mg). After 2 h, the reaction (complete by HPLC) was filtered and concentrated under reduced pressure to give the title diamine (0.58 g, 94% yield.

3-Cyclohexyl-2-pyridin-2-yl-3H-imidazo[4,5-b]pyridine-6-carboxylic acid

The diamine from above (0.58 g, 2.2 mmol) and 2-pyridine carboxaldehyde (0.252 g, 2.4 mmol) were dissolved in a mixture of DMF (2 mL) and water (0.1 mL). Oxone® (1.24 g, 2 mmol) was added and the mixture stirred for 2 h at room temperature. The reaction was diluted with 5% aqueous $NaHCO_3$ and extracted with DCM. The extract was washed with water and brine, dried ($MgSO_4$) and concentrated to a brown oil.

The crude ester was dissolved in MeOH (30 mL) and KOH (300 mg) was added. The mixture was refluxed for 2 h, cooled and concentrated under reduced pressure. The residue was dissolved in water (20 mL) and the solution acidified with 4 N HCl until complete precipitation of the product as a purple solid. The crude product was collected, washed with water an dried. It was further purified by prep HPLC.

Example 29

Entry 16002, Table 16

(S)-3-(4-Carboxymethyl-phenyl)-2-{[1-(1-cyclohexyl-2-furan-3-yl-1H-benzoimidazol-5-yl)-methanoyl]-amino}propionic acid

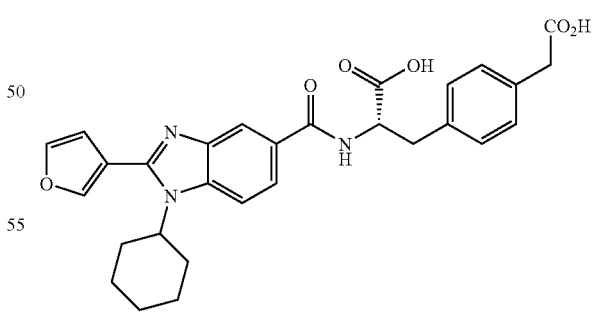

The protected 4-carboxymethyl-L-phenylalanine derivative was prepared by adaptation of the procedure of J. W. Tilley et al. (*J. Org. Chem.* 1990, 55, 906). Following deprotection on the carbamate function with HCl, the amine hydrochloride was coupled in the usual manner to the acid of example 2. Deprotection of all ester functions with NaOH and purification by prep HPLC gave the title compound:

Example 30
Racemic 1-Cyclohexyl-2-furan-3-yl-1H-benzimidazole-5-carboxylic acid [2,2,2-trifluoro-1-(4-hydroxybenzyl)-ethyl]-amide and [4-(2-({[1-(1-Cyclohexyl-2-furan-3-yl-1H-benzimidazol-5-yl)-methanoyl]-amino}-3,3,3-trifluoro-propyl)-phenoxy]-acetic acid (Entries 1122 and 1123, Table 1)
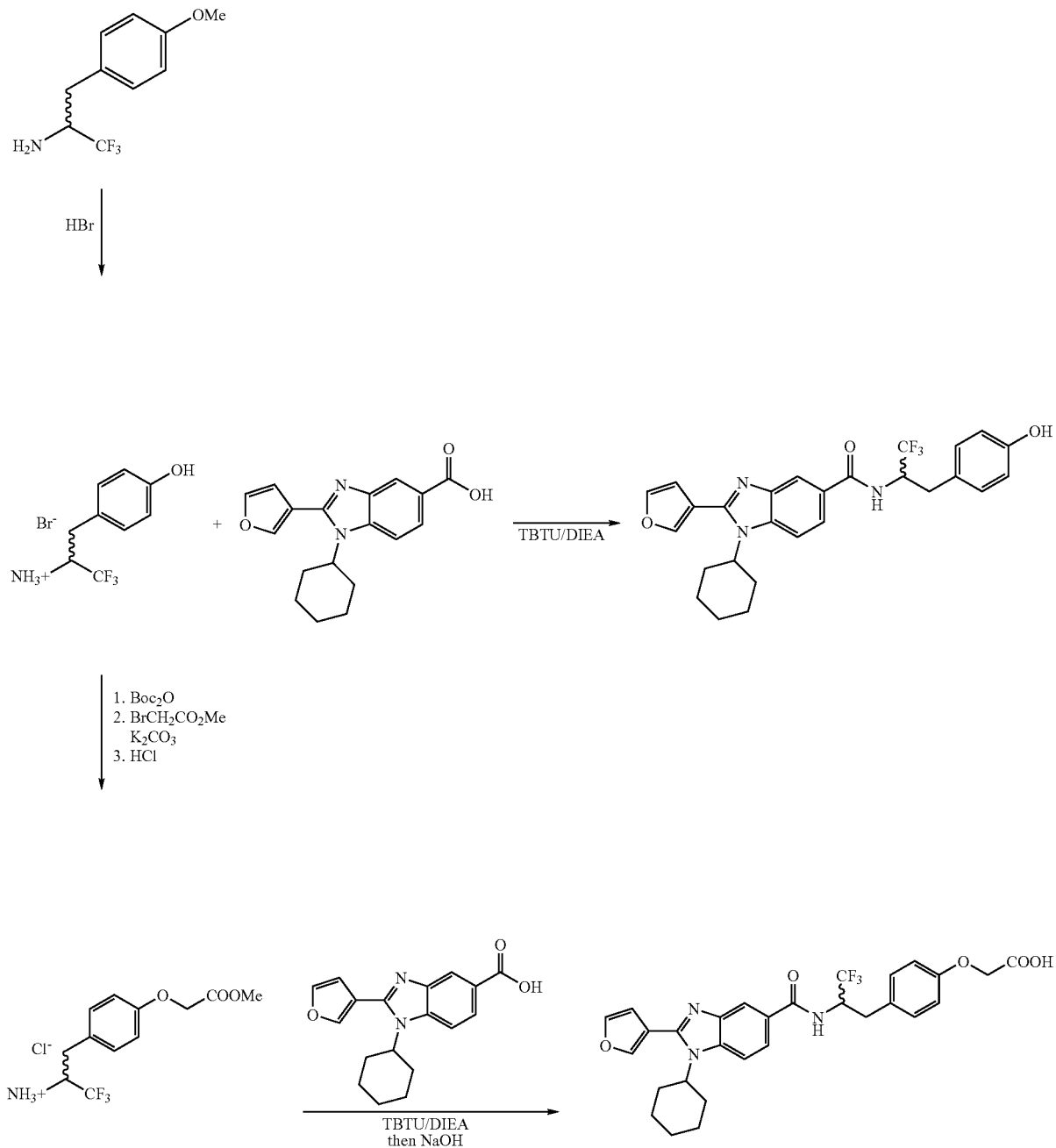

Racemic 1-cyclohexyl-2-furan-3-yl-1H-benzimidazole-5-carboxylic acid [2,2,2-trifluoro-1-(4-hydroxybenzyl)-ethyl]-amide (Entry 1122, Table 1)

The racemic O-methyl trifluoromethyl amine derivative, prepared by the procedure of R. M. Pinder et al. (*J. Med. Chem.* 1969, 12, 322), was deprotected by stirring with 48% aqueous HBr at 100° C. for two hours. The resulting hydrobromide salt was coupled in the usual manner to the acid of example 2 to give after preparative C18 reversed-phase HPLC purification the title phenolic compound.

Racemic [4-(2-{[1-(1-Cyclohexyl-2-furan-3-yl-1H-benzimidazol-5-yl)-methanoyl]-amino}-3,3,3-trifluoro-propyl)-phenoxy]-acetic acid: (Entry 1123, Table 1)

The racemic trifluoromethyl amine hydrobromide salt from above (0.64 g, 2.23 mmol) was dissolved in 80% aqueous MeCN and the solution cooled in ice. Sodium bicarbonate (0.50 g, 6 mmol) was added followed by di-tert-butyldicarbonate (0.48 g, 2.23 mmol), and the mixture was stirred for 15 min at 0° C. and 4 h at room temperature. The reaction mixture was then poured into water (60 mL) and extracted with EtOAc (3×). The extract was washed with water, dried (MgSO4) and concentrated to an oily residue that was purified by flash chromatography using 3:7 EtOAc/hexane as eluent (tan-colored solid, 270 mg).

The carbamate from above (0.260 g, 0.85 mmol) was dissolved in acetone (5 mL). Anhydrous potassium carbonate (0.280 g, 2.0 mmol) and methyl bromoacetate (0.150 g, 1 mmol) were added and the mixture was refluxed for 1.5 h. The reaction mixture was then diluted with acetone and filtered. Concentration of the filtrate gave the desired aryloxyacetate derivative as a white solid (0.31 g).

The carbamate from above (0.310 g, 0.82 mmol) was deprotected by stirring in 4N HCl-dioxane (10 mL) for 1 h at room temperature. Removal of volatiles under reduced pressure gave the amine hydrochloride salt as a yellow solid (0.250 g). The amine salt from above was coupled in the usual manner to the acid of example 2. Deprotection of the ester function with NaOH and purification by preparative C18 reversed-phase HPLC gave the title compound.

Example 31

2-[2-(4-{1-Cyclohexyl-5-[(S)-1-methoxycarbonyl-2-(5-methoxycarbonylmethoxy-1H-indol-3-yl)-ethylcarbamoyl]-1H-benzimidazol-2-yl}-phenoxy)-ethanoylamino]-ethyl-ammonium chloride

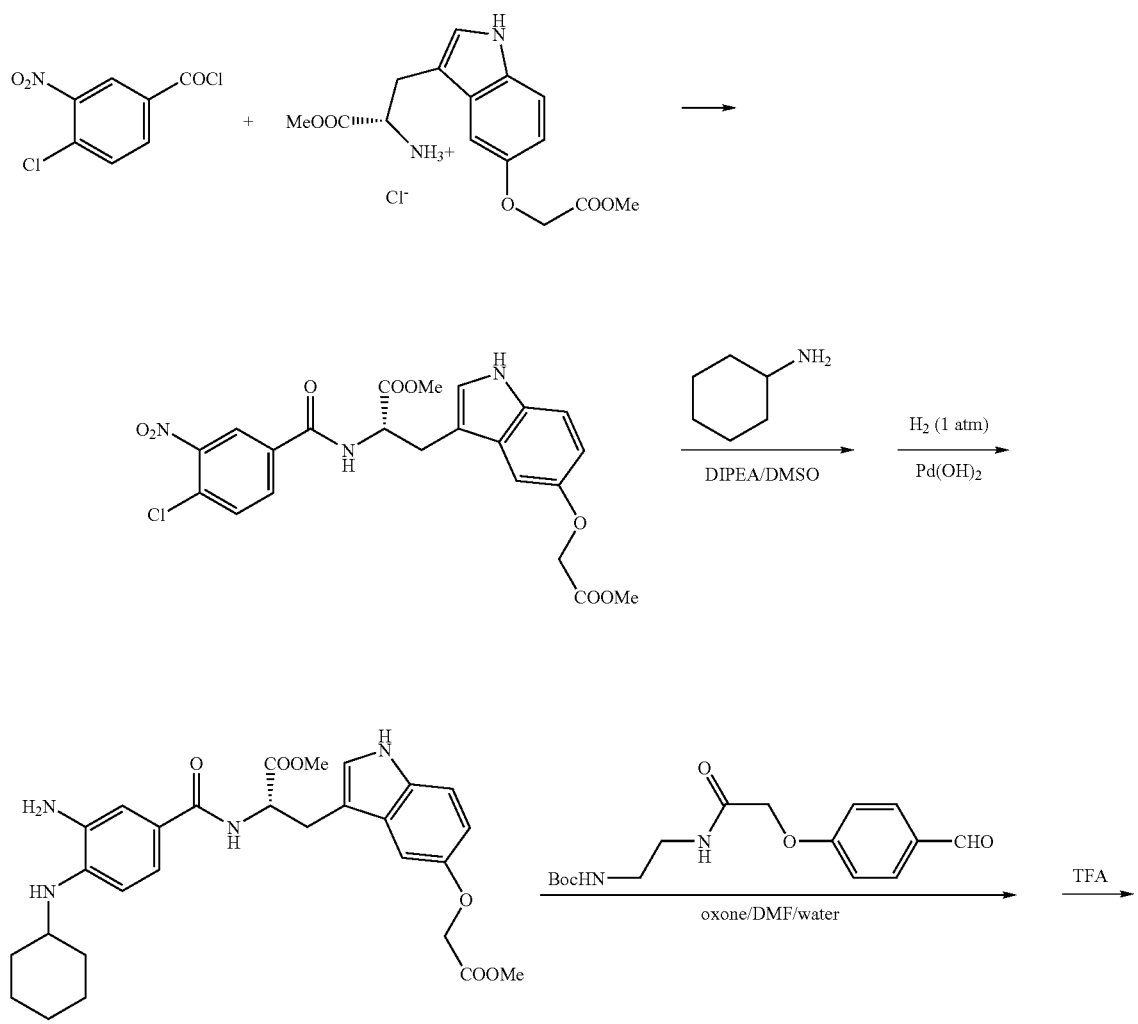

-continued

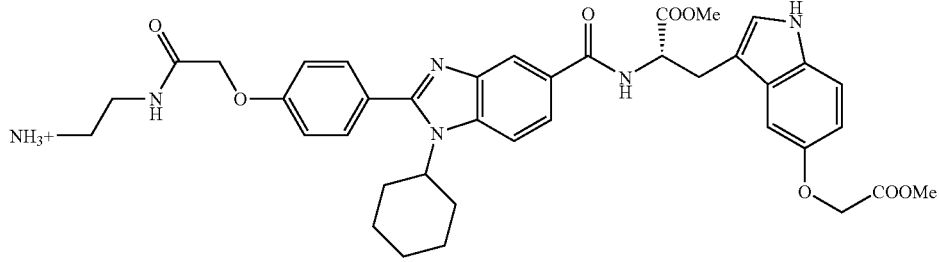

4-Chloro-3-nitrobenzoyl chloride

4-Chloro-3-nitrobenzoic acid (40.40 g, 0.20 mole) was suspended in DCM (100 mL) containing 3 drops of DMF. Oxalyl chloride (1.5 equivalents, 0.3 mole, 27 mL) was added in small portions and the mixture stirred overnight at room temperature. After refluxing for an additional hour to complete the reaction, volatiles were removed under reduced pressure and the residue was coevaporated twice with hexane to give the title compound as a light yellow solid.

(S)-1-Methoxycarbonyl-2-(5-methoxycarbonyl-methoxy-1H-indol-3-yl)-ethyl-ammonium chloride

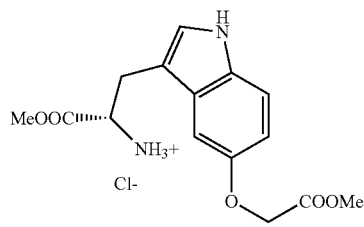

(S)-5-Hydroxytryptophan methyl ester hydrochloride (1.55 g, 5 mmol) was dissolved in 80% aqueous MeCN (25 mL) and the solution cooled in ice. Sodium bicarbonate (0.850 g, 10 mmol) was added followed by di-tert-butyidicarbonate (1.10 g, 5.1 mmol). The mixture was stirred for 2 h at room temperature, poured into water (200 mL) and extracted with EtOAc (3×). The combined extracts were washed with water and brine, dried (MgSO$_4$) and concentrated to give a beige solid (1.65 g). The crude product from above (1.50 g, 4.83 mmol) was dissolved in acetone (20 mL) and anhydrous potassium carbonate (1.5 g, 11 mmol) and methyl bromoacetate (0.76 g, 5 mmol) were added. The mixture was reflux for 4 h after which point additional methyl bromoacetate was added to complete the reaction (15 mg portions until complete by HPLC). The reaction mixture was then cooled and filtered to remove solid. Evaporation of the filtrate gave the desired carbamate as an oil (2.0 g).

The crude carbamate from above (2.0 g) was deprotected by stirring with 4N HCl—dioxane for 1 h at room temperature. Removal of volatiles in vacuo gave the desired tryptophan ester derivative as a tan-colored solid (1.51 g).

(S)-2-{[1-(4-Chloro-3-nitro-phenyl)-methanoyl]-amino}-3-(5-methoxycarbonylmethoxy-1H-indol-3-yl)-propionic acid methyl ester

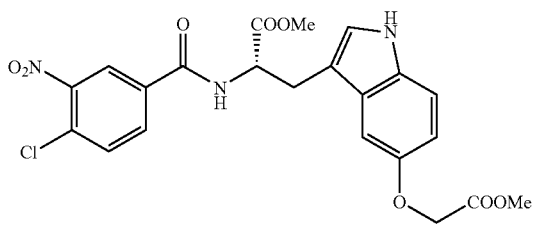

The tryptophan derivative from above (0.343 g, 1 mmol) was dissolved in 80% aqueous MeCN (10 mL) and sodium bicarbonate (3 equivalents, 0.260 g) was added. The solution was cooled in ice and 4-chloro-3-nitrobenzoyl chloride (0.220 g, 1 mmol) was added. The mixture was stirred for one hour at room temperature, concentrated under reduced pressure and the residue purified by flash chromatography (1:2 hexane/EtOAc as eluent) to give the title compound as a yellow foam (0.391 g).

(S)-2-{[1-(3-Amino-4-cyclohexylamino-phenyl)-methanoyl]-amino}-3-(5-methoxycarbonylmethoxy-1H-indol-3-yl)-propionic acid methyl ester

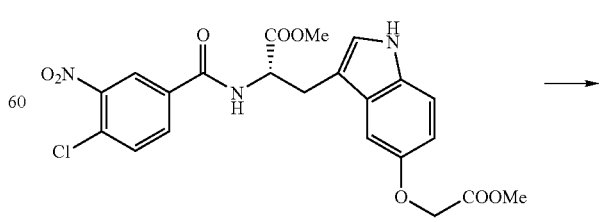

77

-continued

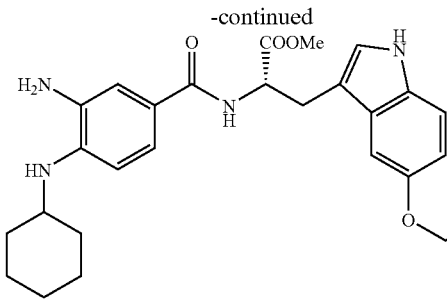

The 4-chlorobenzamide derivative from above (0.214 g, 0.45 mmol) was dissolved in DMSO (1 mL) and DIEA (0.2 mL) was added followed by cyclohexylamine (3 equivalents, 0.16 mL). The mixture was stirred at 60-65° C. for 4 h and subsequently diluted with water. The orange precipitate that formed was collected, washed with water and dried (0.200 g).

The crude material (0.200 g, 0.36 mmol) was hydrogenated (1 atm H$_2$) over 20% Pd(OH)$_2$ on charcoal (60 mg) in MeOH (15 mL). After 2 h, the suspension was filtered to remove the catalyst and concentrated under vacuo to give the title compound as a foam (0.16 g).

78

{2-[2-(4-Formyl-phenoxy)-ethanoylamino]-ethyl}-carbamic acid tert-butyl ester

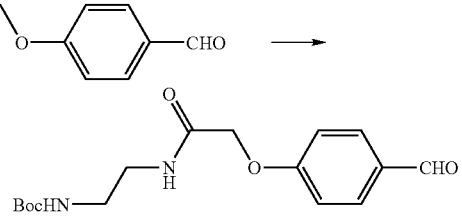

4-Formylphenoxyacetic acid (0.306 g, 1.70 mmol) was dissolved in DCM (5 mL). DIEA (0.524 g, 4 mmol) and TBTU (0.550 g, 1.70 mmol) were added followed by tert-butyl N-(2-aminoethyl)carbamate (0.250 g, 1.56 mmol). The mixture was stirred 2 h at room temperature, dissolved in EtOAc and washed sequentially with 5% aqueous K$_2$CO$_3$, KHSO$_4$, water and brine. The extract was dried (MgSO$_4$) and concentrated under reduced pressure to give a yellow solid (0.350 g).

2-[2-(4-{1-Cyclohexyl-5-[(S)-1-methoxycarbonyl-2-(5-methoxycarbonylmethoxy-1H-indol-3-yl)-ethyl-carbamoyl]-1H-benzimidazol-2-yl}-phenoxy)-ethanoylamino]-ethyl-ammonium chloride:

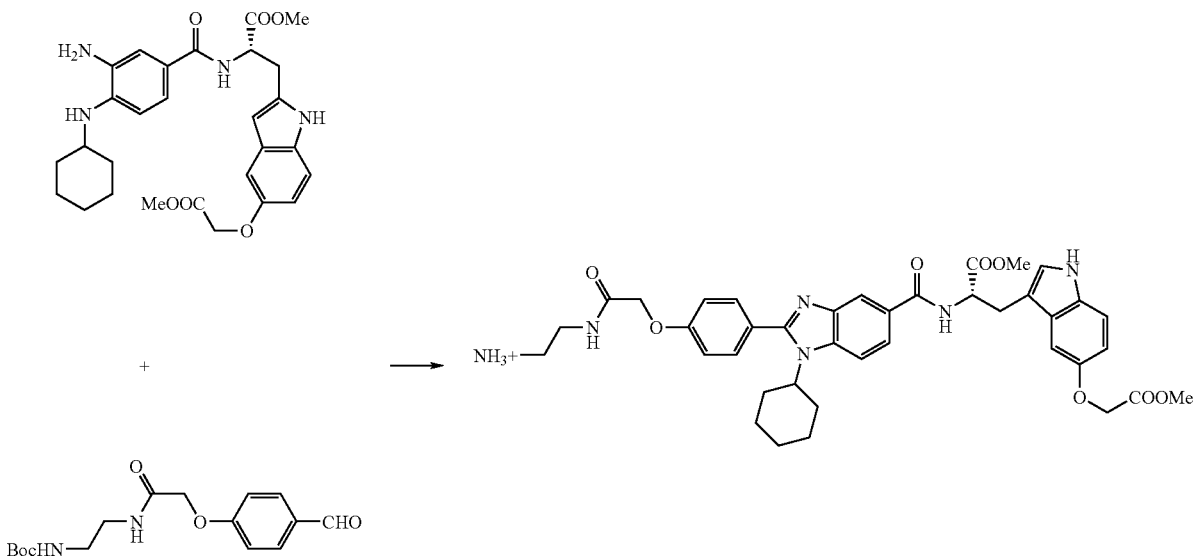

The diamine derivative (0.026 g, 0.05 mmol) and aldehyde (0.020 g, 0.06 mmol) were dissolved in DMF (0.3 mL) and water (0.03 mL) was added followed by oxone® (0.024 g, 0.04 mmol). The mixture was stirred 1 h at room temperature and then diluted with water. The resulting precipitate was collected by filtration, washed with water and dried to give a beige solid (0.020 g).

The crude carbamate from above was stirred with TFA for 30 min at room temperature. Volatiles were removed under reduced pressure and the residue was purified by preparative C18 reversed-phase HPLC to give the title compound of example 31 as the bis TFA salt.

Example 32

(S)-3-(5-Carboxymethoxy-1H-indol-3-yl)-2-({1-[1-cyclohexyl-2-(4-{[2-(5-dimethylamino-naphthalene-1-sulfonylamino)-ethylcarbamoyl]-methoxy}-phenyl)-1H-benzimidazol-5-yl]-methanoyl}-amino)-propionic acid (Entry 2129, Table 2,)

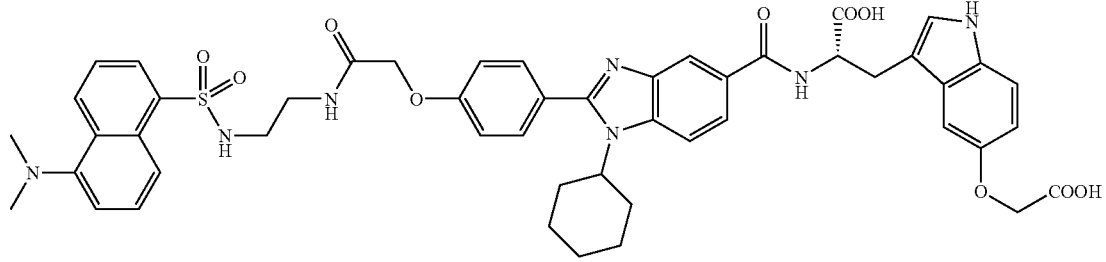

The amine salt of example 31 (0.019 g, 0.02 mmol) was dissolved in DMSO (0.3 mL) and DIEA (0.06 mL) was added followed by dansyl chloride (0.065 g, 0.02 mmol). The mixture was stirred for 1 h at room temperature. 5N NaOH (0.12 mL) and water (0.05 mL) were added and the saponification was allowed to proceed for 1 h at room temperature. Following acidification with TFA, the product was directly isolated from the reaction mixture by preparative C18 reversed-phase HPLC.

Example 33

5-(3-{2-[2-(4-{5-[(S)-1-Carboxy-2-(5-carboxymethoxy-1H-indol-3-yl)-ethylcarbamoyl]-1-cyclohexyl-1H-benzimidazol-2-yl}-phenoxy)-ethanoylamino]-ethyl}-thioureido)-2-(6-hydroxy-3-oxo-3H-xanthen-9-yl)-benzoic acid (Entry 12022, Table 12)

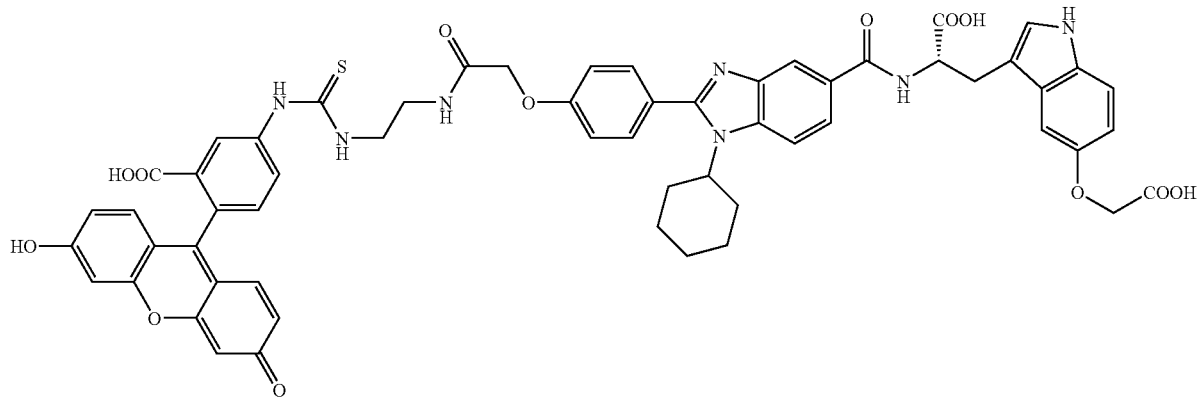

The amine salt of example 31 (0.06 mmol) was dissolved in DMSO (0.6 mL) and DIEA (0.3 mL) was added followed by fluorescein isothiocyanate isomer 1 (0.026 g, 0.066 mmol). The mixture was stirred for 1 h at room temperature. 5N NaOH (0.3 mL) and water (0.15 mL) were added and stirring resumed for an additional 30 min. Following acidification with TFA, the title compound was isolated directly by preparative C18 reversed-phase HPLC.

Example 34

(S)-2-{[1-(2-{4-[(2-{[1-(4-Azido-phenyl)-methanoyl]-amino}-ethylcarbamoyl)-methoxy]-phenyl}-1-cyclohexyl-1H-benzimidazol-5-yl)-methanoyl]-amino}-3-(5-carboxymethoxy-1H-indol-3-yl)-propionic acid (Entry 12025, Table 12)

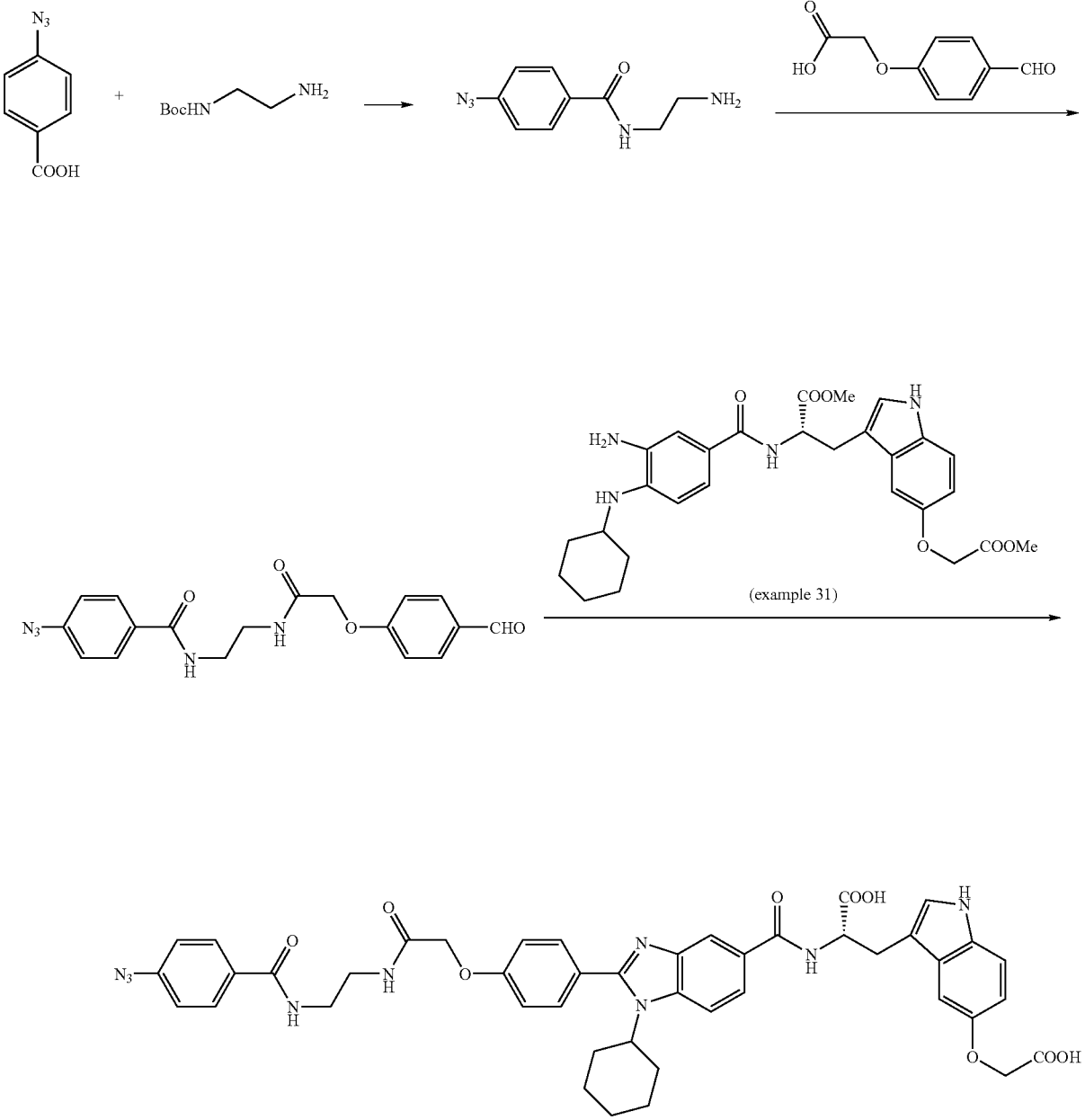

4-Azido-N-{2-[2-(4formyl-phenoxy)ethanoy-lamino]-ethyl}-benzamide

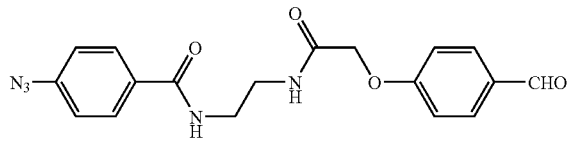

4-Azidobenzoic acid (0.160 g, 1 mmol) was dissolved in DCM (3 mL). DIEA (0.5 mL, 2.5 mmol) and TBTU (0.337 g, 1.05 mmol) were added followed by tert-butyl N-(2-amino-ethyl)carbamate (0.165 g, 1.03 mmol). The mixture was stirred 2.5 h at room temperature, dissolved in EtOAc and washed sequentially with 5% aqueous $K_2CO_3$, $KHSO_4$, water and brine. The extract was dried ($MgSO_4$) and concentrated under reduced pressure to give a yellow solid (0.257 g).

The crude carbamate (0.257 g, 0.84 mmol) was deprotected by stirring in 4N HCl—dioxane (15 mL) for 2 h at room temperature. Volatiles were removed under reduced pressure to give a pinkish solid. 4-Formylphenoxyacetic acid (0.200 g, 1.1 mmol) was dissolved in DCM (3 mL) and DIEA (0.5 mL) was added followed by TBTU (0.350 g, 1,1 mmol) and the amine salt from above (0.240 g, 1 mmol). The mixture was stirred 4 h at room temperature, dissolved in EtOAc and washed sequentially with 5% aqueous $K_2CO_3$, $KHSO_4$, water and brine. The extract was dried ($MgSO_4$) and concentrated under reduced pressure to give an off-white solid (0.162 g).

(S)-2-{[1-(2-{4-[(2-{[1-(4-Azido-phenyl)-metha-noyl]-amino}-ethylcarbamoyl)-methoxy]-phenyl}-1-cyclohexyl-1H-benzimidazol-5-yl)-methanoyl]-amino}-3-(5-carboxymethoxy-1H-indol-3-yl)-propionic acid

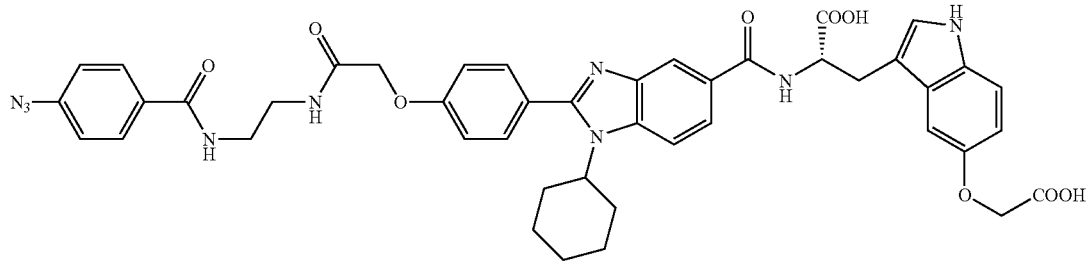

The benzaldehyde derivative from above (0.044 g, 0.12 mmol) and the diamine derivative of example 31 (0.052 g, 0.1 mmol) were dissolved in DMF (0.6 mL) and water (0.1 mL). Oxone® (0.050 g, 0.8 mmol) was added and the mixture stirred for 1 h at room temperature. 5N NaOH (0.2 mL) and water (0.1 mL) were added and saponification allowed to proceed for 1 h. The title compound of example 34 was isolated directly by preparative C18 reversed-phase HPLC (12.5 mg).

Example 35

(S)-3-(5-Carboxymethoxy-1H-indol-3-yl)-2-({1-[1-cyclohexyl-2-(4-{[2-({1-[4-(1-phenyl-methanoyl)-phenyl]-methanoyl}-amino)-ethylcarbamoyl]-methoxy}-phenyl)-1H-benzimidazol-5-yl]-methanoyl}-amino)-propionic acid (Entry 12026, Table 12)

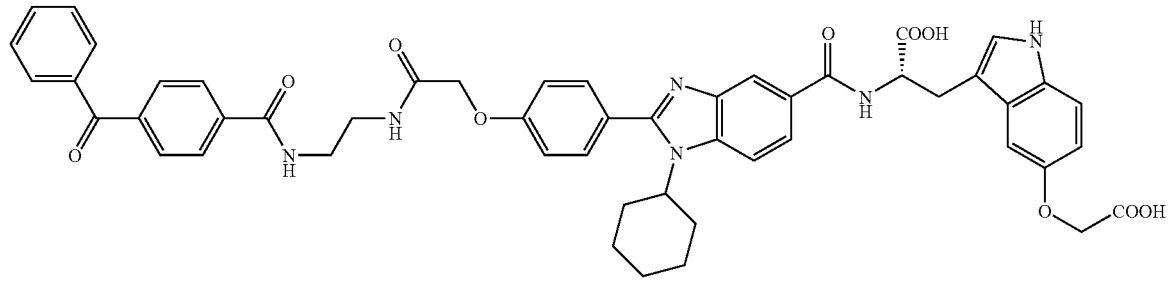

The title compounds was prepared following the procedures described for example 34 except that 4-benzoylbenzoic acid was used instead of 4-azidobenzoic acid.

Example 36

(S)-3-(5-Carboxymethoxy-1H-indol-3-yl)-2-{[1-(1-cyclohexyl-2{4-[2-(5-dimethylamino-naphthalene-1-sulfonylamino)-ethylcarbamoyl]-phenyl}-1H-benzimidazol-5-yl)-methanoyl]-amino}-propionic acid (Entry 2130, Table 2)

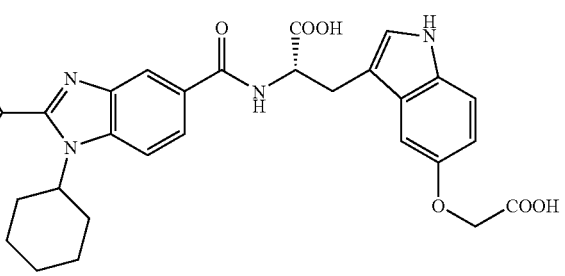

Following the procedures described for example 34, 4-carboxybenzaldehyde was coupled to tert-butyl N-(2-aminoethyl)carbamate. Following benzimidazole ring formation with the diamine derivative of example 34 using oxone®, the Boc protecting group was removed and the resulting amine condensed with dansyl chloride as described in example 32. The title compound was obtained following saponification of the ester group under the usual conditions and isolation by preparative C18 reversed-phase HPLC.

Example 37

5-[3-(2-{[1-(4-{5-[(S)-1-Carboxy-2-(5-carboxymethoxy-1H-indol-3-yl)-ethylcarbamoyl]-1-cyclohexyl-1H-benzimidazol-2-yl}-phenyl)-methanoyl]-amino}-ethyl)-thioureido]-2-(6-hydroxy-3-oxo-3H-xanthen-9-yl)-benzoic acid (Entry 12021, Table 12)

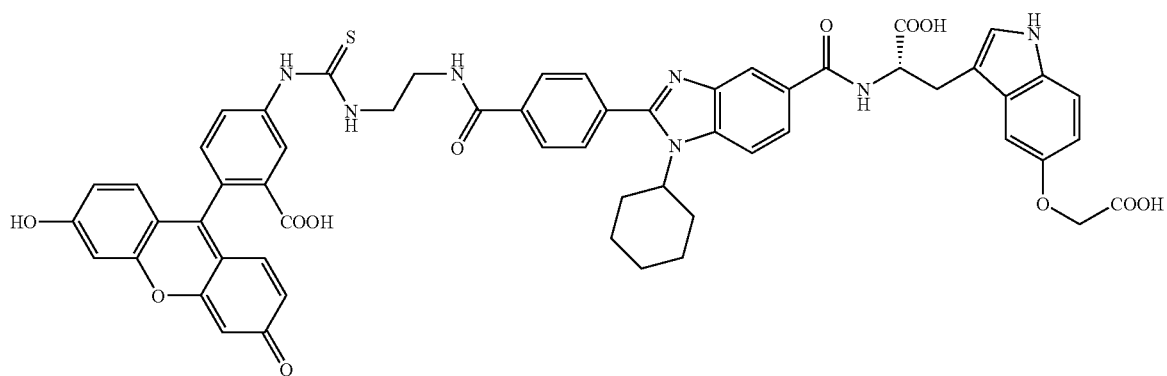

The procedure described for example 36 was used except that fluorescein isothiocyanate isomer 1 was used instead of dansyl chloride. The title compound of example 37 was obtained after purification by preparative C18 reversed-phase HPLC.

Example 38

Racemic 1-cyclohexyl-2-furan-3-yl-1H-benzimidazole-5-carboxylic acid [2-(4-hydroxy-phenyl)-1-pyridin-2-yl-ethyl]-amide (Entry 1231, Table 1)

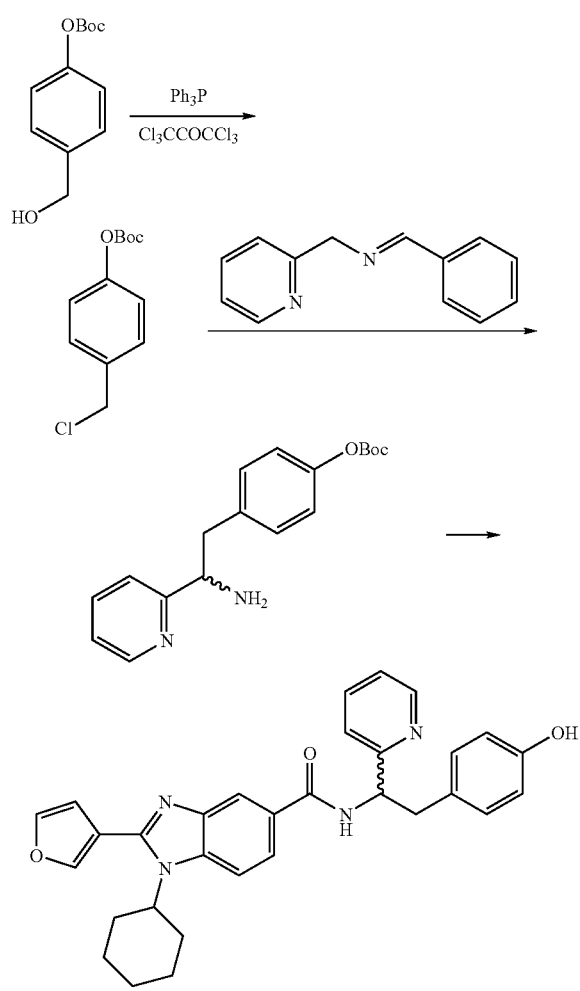

Triphosgene (5.45 g, 18.4 mmol) was added in small portions to an ice-cold solution of triphenylphosphine (12.60 g, 48 mmol) in DCM (180 mL). After stirring for 15 min, the solvent was removed under reduced pressure. A solution of 4-tert-butoxycarbonyloxy-benzyl alcohol (I. Cabrera et al., U.S. Pat. No. 5,356,752,1994) (9.89 g, 44 mmol) in DCM (75 mL) was then added to the above residue over a 15 min period and the mixture stirred for 20 min at room temperature. The solvent was then removed in vacuo and the residue triturated with pentane (200 mL). The solid was removed by filtration and washed with pentane. The combined extracts were concentrated to 50 mL and passed through a pad of silica gel using 1:2 EtOAc—hexane as eluent. 4-tert-Butoxycarbonyloxy-benzyl chloride was obtained as a clear yellow liquid (8.82 g).

2-(Aminomethyl)pyridine was converted to its benzaldehyde imine (benzaldehyde in DCM with 4A molecular sieves) and alkylated with 4-tert-butoxycarbonyloxy-benzyl chloride following an adaptation of the procedure described by Y. Wang et al. (*Synth. Commun.* 1992, 22, 265). The resulting racemic amine was coupled to the carboxylic acid of example 2 under the usual conditions, and deprotected with TFA to give the title compound of example 38 after purification by preparative C18 reversed-phase HPLC.

Example 39

Racemic 1-cyclohexyl-2-furan-3-yl-1H-benzimidazole-5-carboxylic acid [2-(4-hydroxy-phenyl)-1-phenyl-ethyl]-amide (Entry 1259, Table 1)

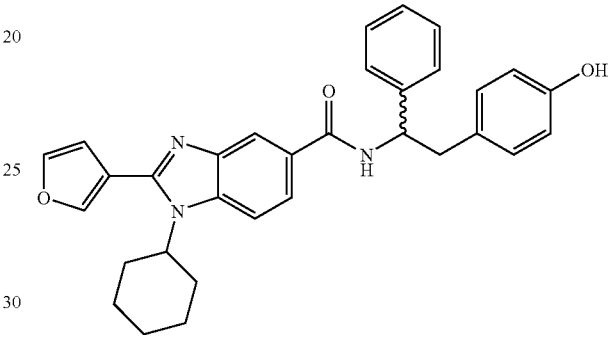

Following the general method of example 37, the benzaldehyde imine of benzylamine was alkylated with tert-butoxycarbonyloxy-benzyl chloride using lithium hexamethyldisilizane as a base at low temperature (−78° C.) in THF as solvent. Following the usual work up, the racemic amine was coupled to the carboxylic acid of example 2, to give after removal of the Boc group and purification by preparative C18 reversed-phase HPLC, the title compound of example 39.

Example 40

Racemic 1-cyclohexyl-2-furan-3-yl-1H-benzimidazole-5-carboxylic acid [2-(4-hydroxy-phenyl)-1-pyridin-3-yl-ethyl]-amide (Entry 1260, Table 1)

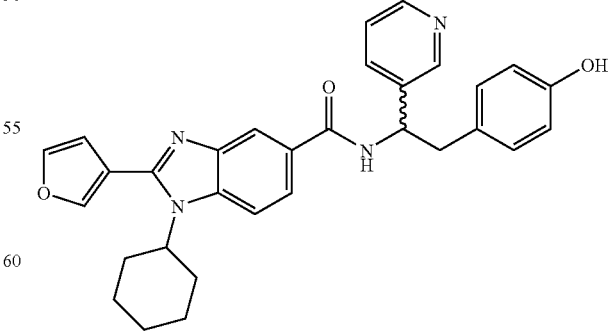

Following the procedure of example 39, but starting with 3-(aminomethyl)pyridine, the title compound of example 40 was obtained.

Example 41

3-Bromomethyl-5-tert-butoxycarbonyloxy-indole-1-carboxylic acid tert-butyl ester

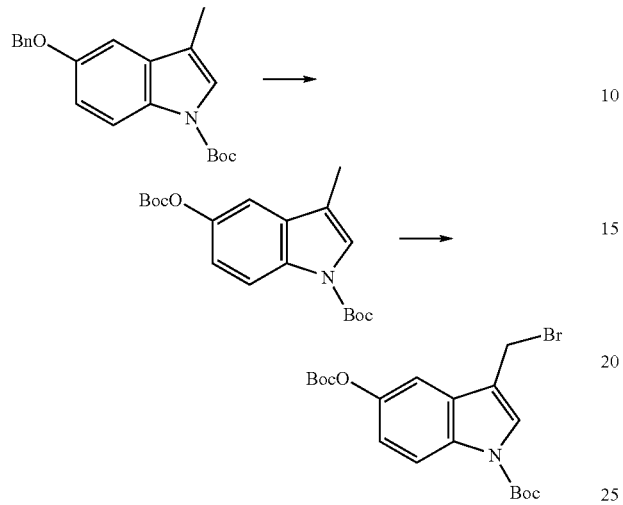

N-Boc-5-benzyloxy-3-methylindole was prepared according to the method of J. P. Marino et al. (*J. Am. Chem. Soc.* 1992, 114, 5566). This indole (4.00 g, 11.9 mmol) was dissolved in THF (60 mL) containing di-tert-butyldicarbonate (2.60 g, 11.9 mmol), anhydrous $K_2CO_3$ (3.20 g, 23 mmol), 18-crown-6 (10 mg) and 20% $Pd(OH)_2$ on charcoal (0.4 g). The suspension was stirred under a hydrogen atmosphere (1 atm) for 18 h at room temperature. The mixture was then filtered and the cake washed with THF. Removal of volatiles from the filtrate and purification by flash chromatography gave the Bis-Boc-protected indole (4.14 g).

The 3-methylindole derivative from above (3.80 g, 10.94 mmol) was dissolved in $CCl_4$ (200 mL) and N-bromosuccinimide (1.85 g, 10.4 mmol) and dibenzoyl peroxide (5 mg) were added. The mixture was refluxed under irradiation by a sun lamp for 3 h. After cooling and removal of insoluble solids by filtration, the solution was concentrated under reduced pressure and the residual yellow oil was purified by flash chromatography (6% EtOAc in hexane) to give the title compound of example 41 as a yellowish solid (2.28 g).

Example 42

Racemic 1-cyclohexyl-2-furan-3-yl-1H-benzimidazole-5-carboxylic acid [2-(5-hydroxy-1H-indol-3-yl)-1-pyridin-2-yl-ethyl]-amide (Entry 11032, Table 11)

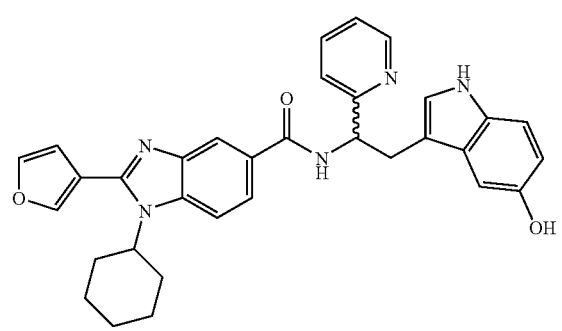

The procedure of example 39 was followed using 2-(aminomethyl)pyridine as starting material. Alkylation of the benzaldehyde imine derived from this compound with the bromomethyltryptophan derivative of example 41 gave after removal of Boc protecting groups the racemic amine as the dihydrochloride salt. The crude amine was coupled under usual conditions to the carboxylic acid derivative of example 2 to give the title compound of example 42 after purification by preparative C18 reversed-phase HPLC.

Example 43

Racemic 1-cyclohexyl-2-furan-3-yl-1H-benzimidazole-5-carboxylic acid [2-(5-hydroxy-1H-indol-3-yl)-1-pyridin-4-yl-ethyl]-amide (Entry 11033, Table 11)

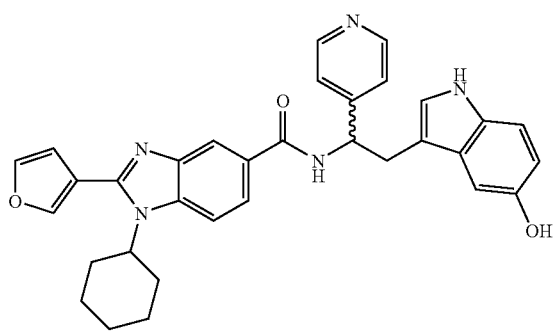

Following the above procedure for example 42, but starting with 4-(aminomethyl)pyridine, the title compound of example 43 was obtained.

Example 44

(S)-5-Hydroxytryptophan amide

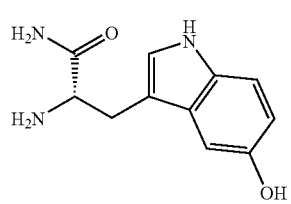

(S)-5-Hydroxytryptophan methyl ester hydrochloride (0.247 g, 0.91 mmol) was stirred overnight at room temperature in ammonium hydroxide (10 mL). After removal of volatiles under vacuum, the title compound of example 44 was obtained as a dark solid.

Example 45

1-Cyclohexyl-2-furan-3-yl-1H-benzimidazole-5-carboxylic acid [(S)-1-carbamoyl-2-(5-hydroxy-1H-indol-3-yl)-ethyl]-amide (Entry 13001, Table 13)

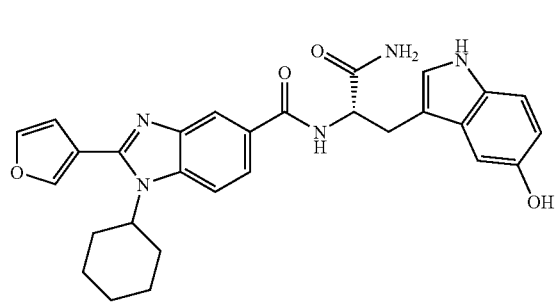

The tryptophan amide derivative of example 44 was coupled in the usual manner with the carboxylic acid of example 2 to give after purification by preparative C18 reversed-phase HPLC the title compound of example 45.

Example 46

2-[4-((S)-2-Carbamoyl-2-{[1-(1-cyclohexyl-2-furan-3-yl-1H-benzimidazol-5-yl)-methanoyl]-amino)-ethyl)-phenoxy]-2-methyl-propionic acid (Entry 1171, Table 1)

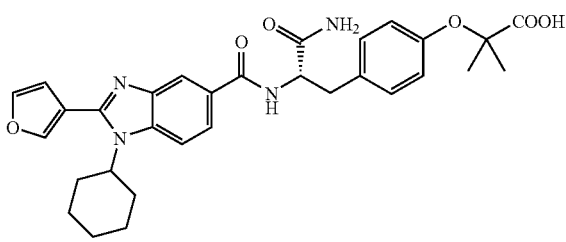

Tyrosine amide derivative (entry 16021, Table 16, BILB1028BS) (0.035 g, 0.074 mmol) was dissolved in acetone (0.5 mL). Cesium carbonate (0.072 g, 0.22 mmol) and tertbutylbromoacetate (0.050 g, 0.22 mmol) were added and the mixture stirred at 60° C. for 1.5 h. Additional bromoacetate was added and the reaction brought to completion (HPLC) by refluxing overnight. The reaction mixture was concentrated under reduced pressure and the residue treated with TFA (1 mL) for 1 h. The product was isolated directly by preparative C18 reversed-phase HPLC to give the title compound of example 46.

Example 47

(S)-2-{[1-(1-Cyclohexyl-2-furan-3-yl-1H-benzimidazol-5-yl)-methanoyl]-amino}-3-(5-nitro-1H-indol-3-yl)-propionic acid (Entry 1125, Table 1)

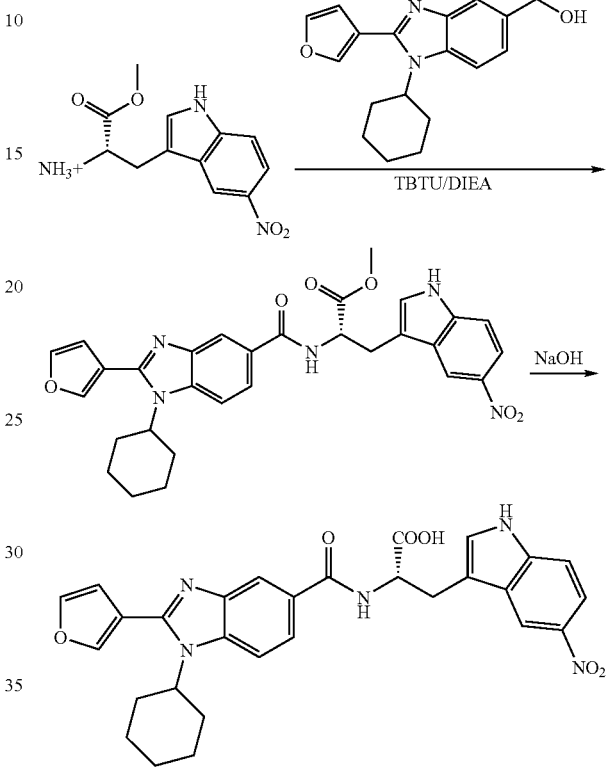

(S)-5-Nitrotryptophan methyl ester hydrochloride was prepared following adapted procedures of T. Hino et al. (*Chem. Pharm. Bull.* 1983,1856) and K. Irie et al. (*Chem. Pharm. Bull.* 1984, 2126). The amino ester derivative was coupled to the carboxylic acid of example 2 in the usual manner. Following saponification and purification by preparative C18 reversed-phase HPLC, the title compound of example 47 was obtained.

Example 48

(S)-3-(5-Amino-1H-indol-3-yl)-2-{[1-(1-cyclohexyl-2-furan-3-yl-1H-benzimidazol-5-yl)-methanoyl]-amino}-propionic acid (Entry 11023, Table 11)

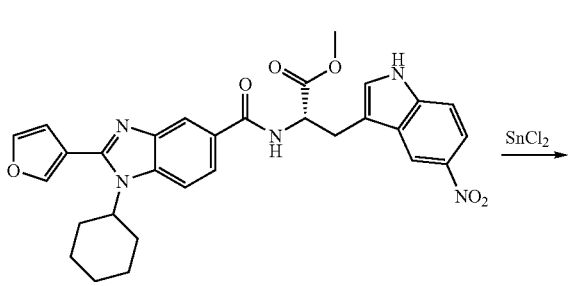

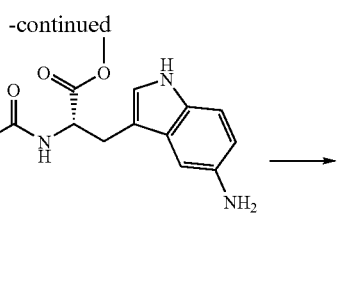

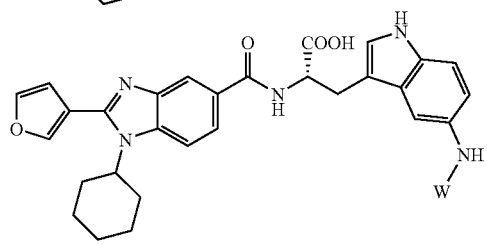

W = H, COCOOH, SO₂CH₃, SO₂CF₃

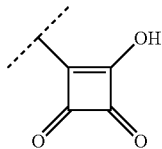

The 5-n itrotryptophan methyl ester intermediate of example 47 (0.400 g, 0.72 mmol) was dissolved in DMF (3 mL). Water (0.1 mL) and tin dichloride dihydrate (0.812 g, 3.6 mmol) were added and the mixture heated at 60° C. for 3 h and stirred overnight at room temperature. The reaction mixture was diluted with water (50 mL), saturated aqueous NaHCO₃ (20 mL) and EtOAc (50 mL). The mixture was vigorously stirred for 5 min and filtered to remove solids (wash cake with 50 mL of EtOAc). The organic layer from the filtrate was washed with water (3×50 mL) and brine (50 mL), and subsequently dried over MgSO₄. Volatiles were removed under reduced pressure and the residue was triturated with TBME (10 mL) to give the 5-aminotryptophan methyl ester derivative as a white solid (0.250 g).

Following saponification and purification by preparative C18 reversed-phase HPLC, the title compound of example 48 (W=H) was obtained.

Example 49

(S)-3-{5-[(1-Carboxy-methanol)-amino]-1H-indol-3-yl}-2-{[1-(1-cyclohexyl-2-furan-3-yl-TH-benzimidazol-5-yl)-methanoylt-aminot-propionic acid (Entry 11024, Table 11, W=COCOOH in example 48)

The 5-aminotryptophan methyl ester intermediate of example 48 (0.025 g, 0.048 mmol) was dissolved in DCM (1 mL) and DIEA (17 µL, 0.095 mmol) and oxalyl methyl chloride (5 µL, 0.053 mmol) were added. The mixture was stirred for 30 min and volatiles removed under reduced pressure. The residue was dissolved in DMSO (0.5 mL), 2.5 N NaOH (0.2 mL) was added and the mixture stirred at room temperature for 30 ml. After acidification with TFA, the title compound of example 49 was isolated directly by preparative C18 reversed-phase HPLC (0.020 g).

Example 50

(S)-2-([1-(1-Cyclohexyl-2-furan-3-yl-1H-benzimidazol-5-yl)-methanoyl]-amino}-3-(5-methanesulfonylamino-1H-indol-3-yl)-propionic acid (Entry 11025, Table 11, W=SO₂CH₃ in example 48)

Following the procedure described for example 49 and replacing oxalyl methyl chloride by methanesulfonyl chloride, the title compound of example 50 was obtained.

Example 51

(S)-2-([1-(Cyclohexyl-furan-3-yl-1H-benzimidazol-5-yl)-methanoyl]-amino}-3-(5-trifluoromethanesulfonylamino-1H-indol-3-yl)-propionic acid (Entry 11026, Table 11, W=SO₂CF₃ in example 48)

Following the procedure described for example 49 and replacing oxalyl methyl chloride by trifluoromethanesulfonic anhydride, the title compound of example 51 was obtained.

Example 52
(S)-2-{[1-(1-Cyclohexyl-2-furan-3-yl-1-H-benzimidazol-5-yl)-methanoyl]-amino}-3-[5-(2-hydroxy-3,4-dioxo-cyclobut-1-enylamino)-1H-indol-3-yl]-propionic acid (Entry 11027, Table 11, W=squaric acid in example 48)

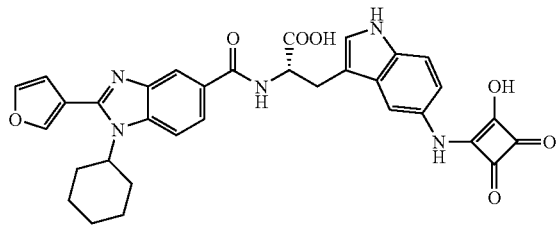

The 5-aminotryptophan methyl ester intermediate of example 48 (0.050 g, 0.095 mmol) was dissolved in MeOH (2 mL) and 3,4-dimethoxy-3-cyclobutene-1,2-dione (0.041 g, 0.28 mmol) was added. The mixture was stirred overnight at room temperature. Volatiles were then removed under reduced pressure and the protected derivative isolated by preparative C18 reversed-phase HPLC as a yellow solid. The material was dissolved in DMSO (0.5 mL) and treated with 2.5 N NaOH (0.2 mL) at room temperature for 30 min. Following acidification with TFA, the title compound of example 52 was isolated by preparative C18 reversed-phase HPLC (11 mg).

Example 53

(S)-5-Nitrotryptophan amide hydrocloride

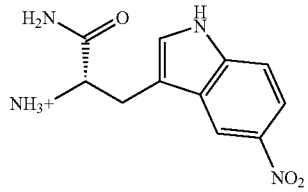

(S)-5-Nitrotryptophan methyl ester hydrochloride (see example 47) was converted to the corresponding amide derivative following the procedure described in example 44 for the 5-hydroxy derivative. The amino amide was then converted to its hydrochloride salt using 4N HCl in dioxane.

Example 54

1-Cyclohexyl-2-furan-3-yl-1H-benzimidazole-5-carboxylic acid [(S)-2-(5-amino-1H-indol-3-yl)-1-carbamoyl-ethyl]-amide (Entry 13005, Table 13)

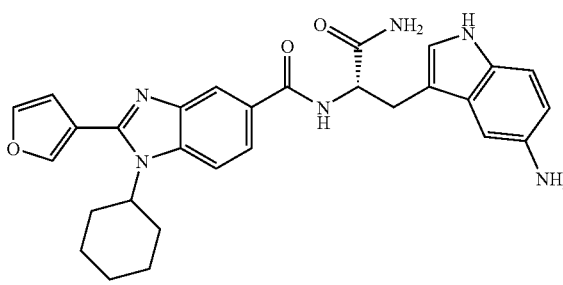

The 5-nitrotryptophan amide derivative of example 53 was coupled to the carboxylic acid of example 2 in the usual manner. The nitro group was then reduced to the corresponding amine using $SnCl_2$ dihydrate as described in example 48, to give the title compound of example 54 after purification by preparative C18 reversed-phase HPLC.

Example 55

1-Cyclohexyl-2-furan-3-yl-1H-benzimidazole-5-carboxylic acid [(S)-1-carbamoyl-2-(5-methanesulfonylamino-1H-indol-3-yl)-ethyl]-amide (Entry 13006, Table 13)

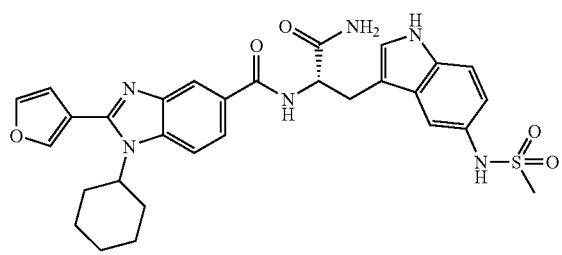

The 5-aminotryptophan derivative of example 54 was treated with methanesulfonyl chloride as described for example 50, to give the title compound of example 55.

Example 56

1-Cyclohexyl-2-furan-3-yl-1H-benzimidazole-5-carboxylic acid [(S)-1-carbamoyl-2-(5-trifluoromethanesulfonylamino-1H-indol-3-yl)-ethyl]-amide (Entry 13007, Table 13)

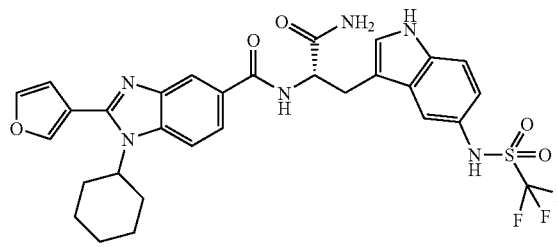

The 5-aminotryptophan derivative of example 54 was treated with trifluoromethanesulfonic anhydride as described for example 51, to give the title compound of example 56.

Example 57

N-[3-((S)-2-Carbamoyl-2-{[1-(1-cyclohexyl-2-furan-3-yl-1H-benzimidazol-5-yl)-methanoyl]-amino}-ethyl)-1H-indol-5-yl]-oxalamic acid (Entry 13008, Table 13)

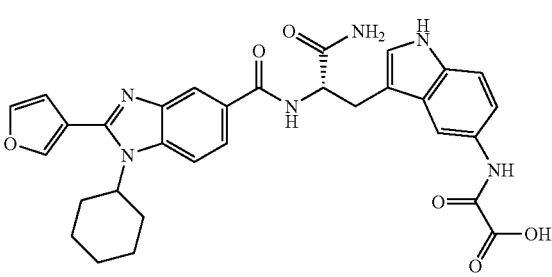

The 5-aminotryptophan derivative of example 54 was treated with methyl oxalyl chloride as described for example 49, to give the title compound of example 57.

Example 58

N-[3-((S)-2-Carbamoyl-2-{[1-(1-cyclohexyl-2-furan-3-yl-1H-benzimidazol-5-yl)-methanoyl]-amino}-ethyl)-1H-indol-5-yl]-oxalamide (Entry 13009, Table 13, W=H)

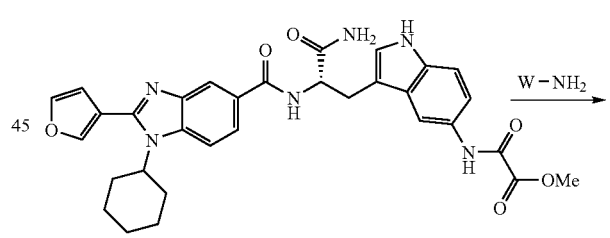

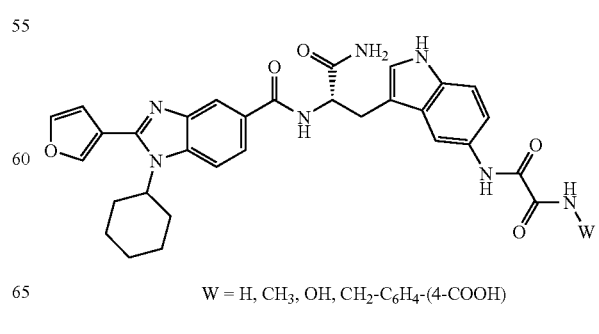

W = H, $CH_3$, OH, $CH_2$-$C_6H_4$-(4-COOH)

The 5-aminotryptophan derivative of example 54 was treated with methyl oxalyl chloride as described for example 49. The resulting methyl ester derivative was dissolved in MeOH and treated with excess aqueous ammonium hydroxide to give after isolation by preparative C18 reversed-phase HPLC the title compound of example 58.

Example 59

$N^1$-[3-((S)-2-Carbamoyl-2-{[1-(1-cyclohexyl-2-furan-3-yl-1H-benzimidazol-5-yl)-methanoyl]-amino}-ethyl)-1H-indol-5-yl]-$N^2$-methyl-oxalamide (Entry 13010, Table 13, W=$CH_3$ in example 58)

The procedure of example 58 was followed except that methylamine (2M in THF) was used instead of ammonium hydroxide, to give the title compound of example 59.

Example 60

$N^1$-[3-((S)-2-Carbamoyl-2-{[1-(1-cyclohexyl-2-furan-3-yl-1H-benzimidazol-5-yl)-methanoyl]-amino}-ethyl)-1H-indol-5-yl]-$N^2$-hydroxy-oxalamide (Entry 13011, Table 13, W=OH in example 58)

The procedure of example 58 was followed except that hydroxylamine hydrochloride and two equivalents of DIEA were used instead of ammonium hydroxide, to give the title compound of example 60.

Example 61

4-[({-[3-((S)-2-Carbamoyl-2-{[1-(1-cyclohexyl-2-furan-3-yl1H-benzimidazol-5-yl)-methanoyl]-amino}-ethyl)-1H-indol-5-ylcarbamoyl]-methanoyl}-amino)-methyl]-benzoic acid (Entry 13012, Table 13, W=$CH_2C_6H_4$-(4-COOH) in example 58)

The procedure of example 58 was followed except that 4-(aminomethyl)benzoic acid and two equivalents of DIEA were used instead of ammonium hydroxide, to give the title compound of example 61.

Example 62

1-Cyclohexyl-2-furan-3-yl-1H-benzimidazole-5-carboxylic acid {(S)-1-carbamoyl-2-[5-(2-hydroxy-3,4-dioxo-cyclobut-1-enylamino)-1H-indol-3-yl]-ethyl}-amide(Entry 13004, Table 13)

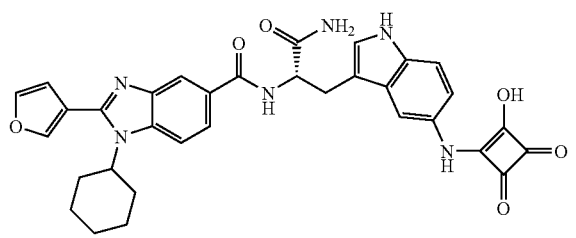

Following the procedure described in example 52, the 5-aminotryptophan derivative of example 54 was converted to the title compound of example 62.

Example 63

1-Cyclohexyl-2-furan-3-yl-1H-benzimidazole-5-carboxylic acid [(s)-1-carbamoyl-2-(5-ureido-1H-indol-3-yl)-ethyl]-amide (Entry 13013, Table 13)

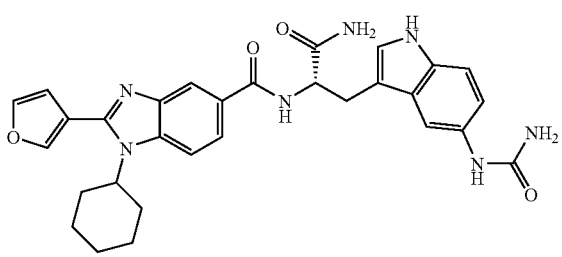

The 5-aminotryptophan derivative of example 54 (0.040 g, 0.078 mmol) and KOCN (0.019 g, 0.24 mmol) were dissolved in AcOH (2 mL) and the mixture was stirred for 1 h at room temperature. The urea derivative of example 63 was isolated directly by preparative C18 reversed-phase HPLC.

Example 64

Carbonic acid 4-[(S)-2-tert-butoxycarbonylamino-2-(2-methylamino-thiazol-4-yl)-ethyl]-phenyl ester tert-butyl ester

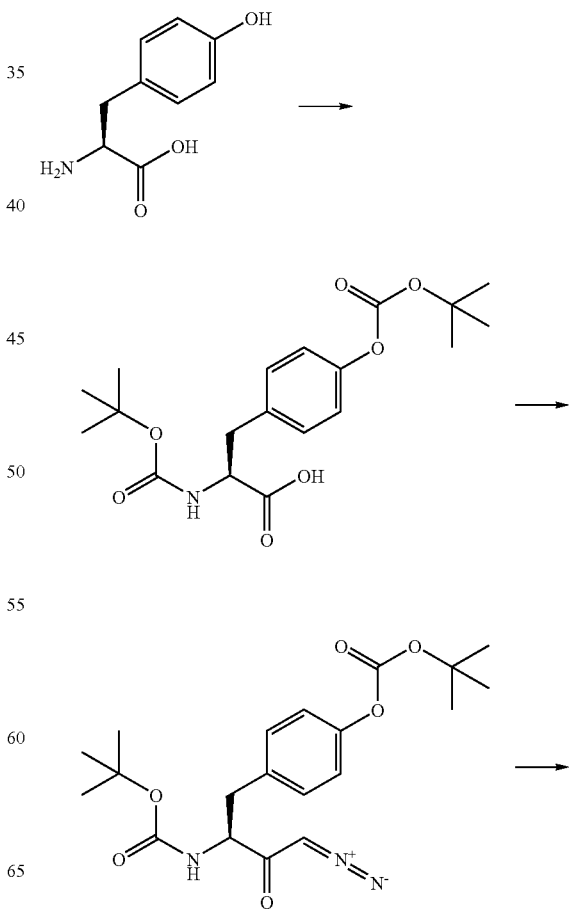

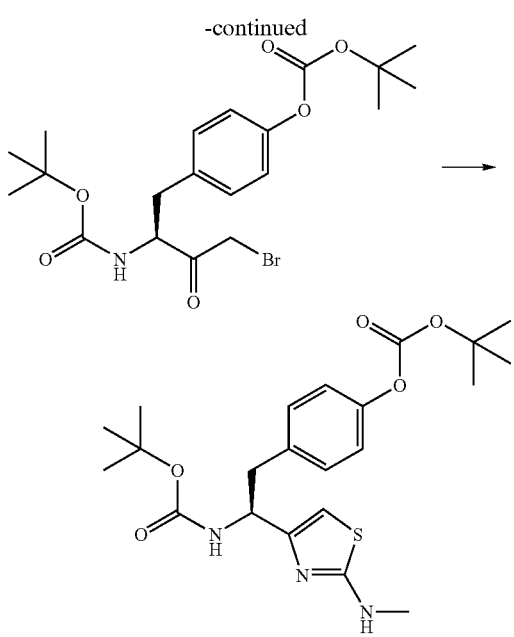

N,O-Bis-Boc-(S)-tyrosine

To a mechanically stirred suspension of L-tyrosine (50.00 g, 276 mmol) in 700 mL of water was added di-tert-butyldicarbonate (163.00 g, 745 mmol) dissolved in 400 mL of isopropanol. The pH was adjusted to 12.0 by adding a solution of 8N KOH and was subsequently maintained at this value by adding small volumes of the basic solution. After 4 h, di-tert-butyldicarbonate (100 g) was added and the mixture stirred overnight. The isopropanol was evaporated under reduced pressure, the residue diluted with 1 L of water, washed with Et₂O (500 mL) and a 1:1 mixture of Et₂O/hexane (2×500 mL). The aqueous solution was stirred with Et₂O (1 L), cooled in an ice bath and the pH was adjusted to 2.5 with conc. HCl. The organic layer was decanted, the aqueous layer re-extracted with Et₂O (2×500 mL), the organic fractions were pooled, washed with brine (500 mL), dried (MgSO₄) and the solvent evaporated to yield 96.85 g (92%) of a thick clear oil which crystallized on standing.

Carbonic acid 4-((S)-2-tert-butoxycarbonylamino-4-diazo-3-oxo-butyl)-phenyl ester tert-butyl ester N,O-Bis-Boc-(S)-tyrosine (6.00 g, 15.73 mmol) was dissolved in THF (40 mL), the solution stirred under an argon atmosphere and cooled in an ice bath. Isobutyl chloroformate (3.0 6 mL, 23.59 mmol) was added followed by DIEA (8.22 mL, 47.19 mmol). Additional isobutyl chloroformate (1 mL) was added after 1.5 and 2.5 h. To the cold suspension was then added a ca 0.6M Et₂O solution of diazomethane (80 mL) by portions. After 15 min. of stirring, nitrogen was diffused in the solution for 0.5 hr. The solvent was evaporated, the residue taken into EtOAc (75 ml) and the solution washed with 0.5M aqueous citric acid (2×50 mL), 5% aqueous sodium bicarbonate (2×50 mL) and brine (50 mL). After drying (MgSO₄) and evaporation of the solvent under reduced pressure, the residue was purified by flash chromatography (20% EtOAc/hexane) to give the title compound (5.52 g) of a yellowish solid.

Carbonic acid 4-((S)-4-bromo-2-tert-butoxycarbonylamino-3-oxo-butyl)-phenyl ester tert-butyl ester The diazoketone prepared above was dissolved in EtOAc (25 mL), the solution stirred under an argon atmosphere and cooled to −25° C. A solution of HBr in AcOH (45% w/v, 1.33 mL, 7.40 mmol) was then added in small portions over 20 min. After 10 min the suspension was diluted with EtOAc (50 mL), washed with 5% aqueous sodium bicarbonate (4×50 mL) and brine (50 mL). After drying (MgSO₄) and evaporation of the solvent, the title compound (2.75 g) was obtained as a clear oil which crystallized on standing.

Carbonic acid 4-[(S)-2-tert-butoxycarbonylamino-2-(2-methylamino-thiazol-4-yl)-ethyl]-phenyl ester tert-butyl ester To the bromoketone prepared above (0.750 g, 1.64 mmol) dissolved in MeCN (10 mL) was added N-methylthiourea (0.192 g, 2.13 mmol) and the mixture was stirred 18 h at room temperature. The solvent was evaporated to give the title compound (0.855 g, >100% yield) as a tan solid that was used directly for coupling to the carboxylic acid of example 2 (see example 69).

Example 65

Carbonic acid 4-[(S)-2-tert-butoxycarbonylamino-2-(2-dimethylamino-thiazol-4-yl)-ethyl]-phenyl ester tert-butyl ester

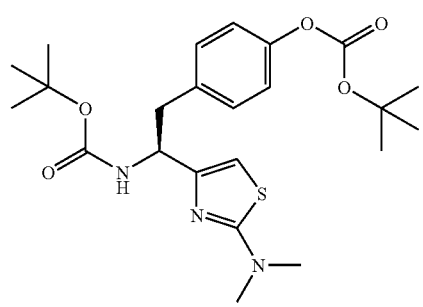

Prepared as described in example 64 except that N,N-dimethylthiourea was used instead of N-methylthiourea.

Example 66

Carbonic acid 4-[(S)-2-(2-acetylamino-thiazol-4-yl)-2-tert-butoxycarbonylamino-ethyl]-phenyl ester tert-butyl ester

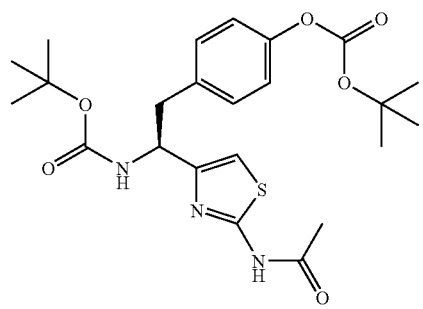

Prepared as described in example 64 except that N-acetyl-2-thiourea was used instead of N-methylthiourea.

Example 67
Carbonic acid 4-[(S)-2-(2-acetylamino-1H-imidazol-4-yl)-2-tert-butoxycarbonylamino-ethyl]-phenyl ester tert-butyl ester

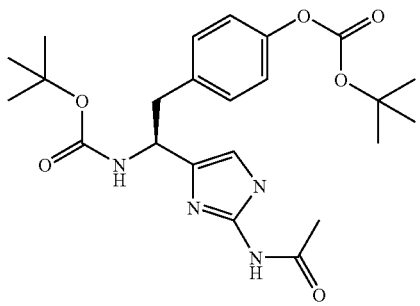

Prepared as described in example 64 except that 1-acetylguanidine was used instead of N-methylthiourea.

Example 68
Carbonic acid 4-((S)-2-tert-butoxycarbonylamino-2-thiazol-4-yl-ethyl)-phenyl ester tert-butyl ester

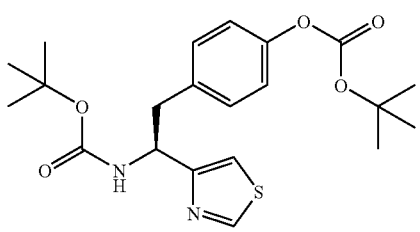

To a stirred suspension of $P_2S_5$ (0.89 g, 2.0 mmol) in dry dioxane (5 mL) was added dry formamide (433 μL, 10.9 mmol). The mixture was heated at 90° C. for 2.5 h (to maintain a free suspension occasional trituration was needed). The suspension was allowed to cool to RT, the solid filtered off and the bromoketone from example 64 (0.229 g, 0.5 mmol) was added to the filtrate. The solution was heated to 80° C. for 2 h then diluted with EtOAC (25 mL), washed with 5% aqueous citric acid (2×20 mL), 5% aqueous sodium bicarbonate (2×20 mL) and brine. After drying (MgSO$_4$) and removal of the solvent under reduced pressure, the title compound (186 g) was obtained as a brown solid.

Example 69
1-Cyclohexyl-2-furan-3-yl-1H-benzimidazole-5-carboxylic acid [(S)-2-(4-hydroxy-phenyl)-1-(2-methylamino-thiazol-4-yl)-ethyl]-amide (Entry 1240, Table 1)

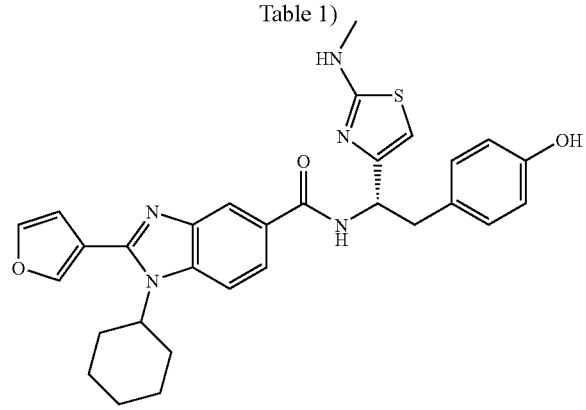

The crude protected aminothiazole derivative of example 69 (0.075 g, 0.17 mmol) was dissolved in dioxane (1 mL) and a 4N solution of HCl in dioxane was added. After 2.5 h the solvent was evaporated and the residue dried under high vacuum for 0.5 h. The resulting hydrochloride salt was coupled to the carboxylic acid of example 2 in the usual manner to give the title compound of example 69 after purification by preparative C18 reversed-phase HPLC.

Example 70
1-Cyclohexyl-2-furan-3-yl-1H-benzimidazole-5-carboxylic acid [(S)-1-(2-dimethylamino-thiazol-4-yl)-2-(4-hydroxy-phenyl)-ethyl]-amide (Entry 1241, Table 1)

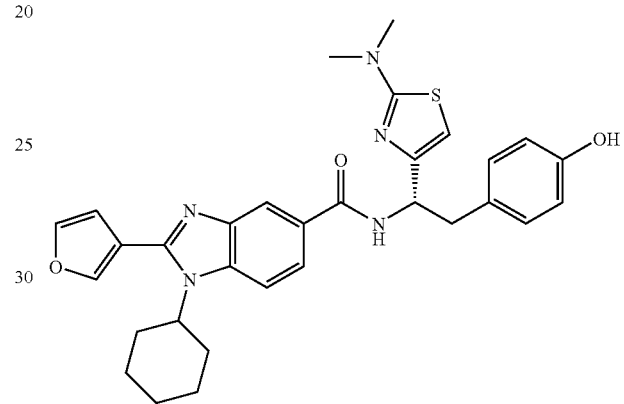

Prepared as described in example 69 from the aminothiazole derivative of example 65.

Example 71
1-Cyclohexyl-2-furan-3-yl-1H-benzimidazole-5-carboxylic acid [(S)-1-(2-acetylamino-thiazol-4-yl)-2-(4-hydroxy-phenyl)-ethyl]-amide (Entry 1242, Table 1)

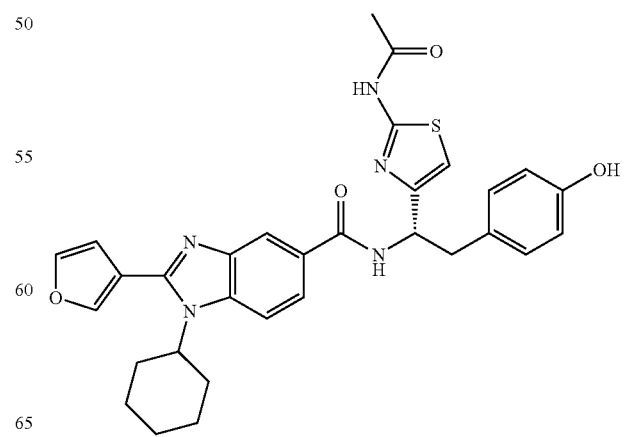

Prepared as described in example 69 from the aminothiazole derivative of example 66.

Example 72

1-Cyclohexyl-2-furan-3-yl-1H-benzimidazole-5-carboxylic acid [(S)-1-(2-acetylamino-1H-imidazol-4-yl)-2-(4-hydroxy-phenyl)-ethyl]-amide (Entry 1243, Table 1)

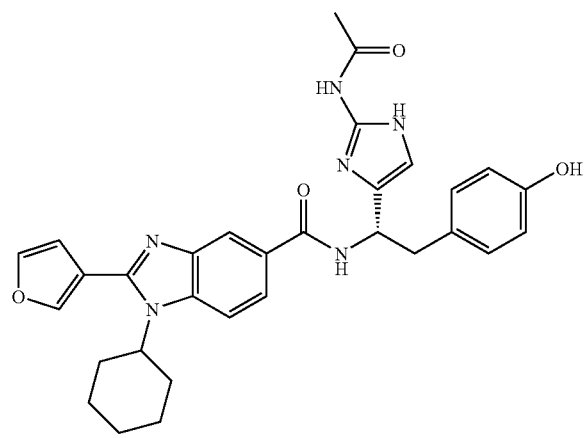

Prepared as described in example 69 from the imidazole derivative of example 67.

Example 73

1-Cyclohexyl-2-furan-3-yl-1H-benzimidazole-5-carboxylic acid [(S)-2-(4-hydroxy-phenyl)-1-thiazol-4-yl-ethyl]-amide (Entry 1250, Table 1)

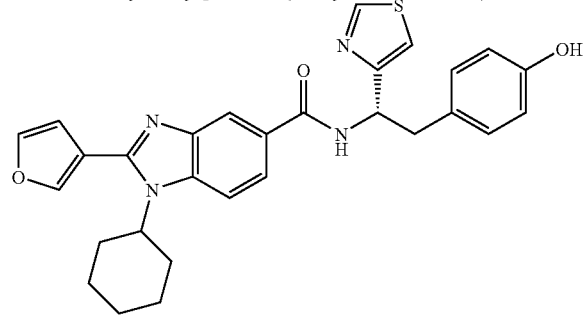

Prepared as described in example 69 from the aminothiazole derivative of example 68.

Example 74

Acetic acid 4-[(S)-2-(2-amino-thiazol-4-yl)-2-tert-butoxycarbonylamino-ethyl]-phenyl ester

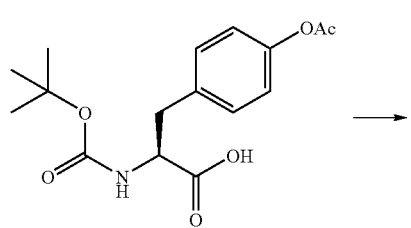

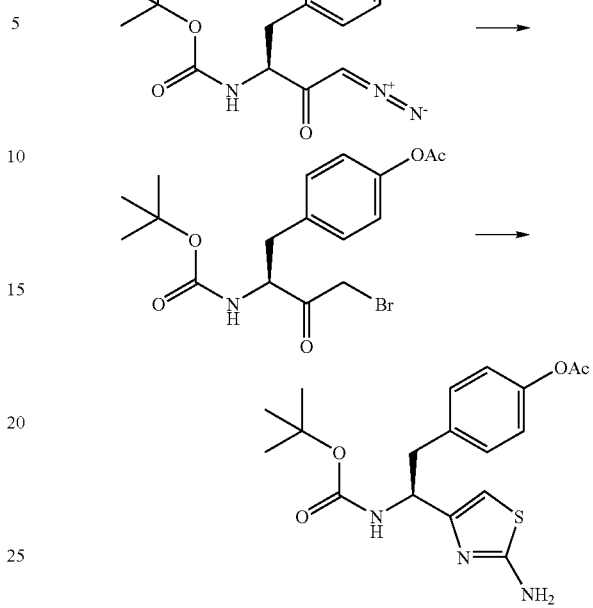

Acetic acid 4-((S)-2-tert-butoxycarbonylamino-4-diazo-3-oxo-butyl)-phenyl ester: A solution of Boc-(S)-Tyr(OAc)-OH (1.75 g, 5.4 mmol) in THF (20 mL) was stirred under argon and cooled to −5° C. DIEA (2.83 mL, 16.2 mmol) and isobutyl chloroformate (1.05 mL, 8.2 mmol) were added. After 1 h, additional isobutyl chloroformate (1 mL) was added and stirring continued for 1 h. To the cold suspension was then added an excess of a ca 0.6M $Et_2O$ solution of diazomethane (25 mL) in small portions. After 16 h of stirring nitrogen was diffused in the solution for 0.5 h. The solvent was evaporated, the residue taken in EtOAC (50 ml) and the solution washed with 0.5M aqueous citric acid (2×25 mL), 5% aqueous sodium bicarbonate (2×25 mL) and brine (25 mL). After drying ($MgSO_4$) and removal of the solvent, the residue was purified by flash chromatography (gradient 30 to 50% EtOAC/hexane) to yield 1.14 g (60%) of a yellowish solid.

Acetic acid 4-((S)$_4$-bromo-2-tert-butoxycarbonylamino-3-oxo-butyl)-phenyl ester: The title compound was prepared as in example 64 using the diazomethylketone from above.

Acetic acid 4-[(S)-2-(2-amino-thiazol-4-yl)-2-tert-butoxycarbonylamino-ethyl]-phenyl ester The bromoketone from above (0.600 g, 1.50 mmol) and thiourea (0.135 g, 1.80 mmol) were stirred at room temperature in MeCN (10 mL) for 18 hrs. The solid was filtered and dried under high vacuum to yield the title compound.

Example 75

Acetic acid 4-[(S)-2-tert-butoxycarbonylamino-2-(2-methyl-thiazol4-yl)-ethyl]-phenyl ester

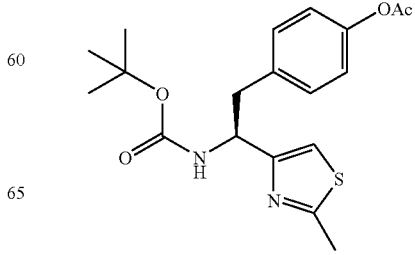

Prepared as described in example 74 except that thioacetamide was used instead of thiourea, and refluxing conditions were used for condensation with the bromomethyl ketone. Under those conditions, the N-Boc protecting group was cleaved. The crude reaction product was thus re-protected (di-tert-butyldicarbonate/aqueous 5% NaHCO$_3$/dioxane) to allow purification by flash chromatography.

Example 76

1-Cyclohexyl-2-furan-3-yl-1H-benzimidazole-5-carboxylic acid [(S)-1-(2-amino-thiazol-4-yl)-2-(4-hydroxy-phenyl)-ethyl]-amide (Entry 16060, Table 16)

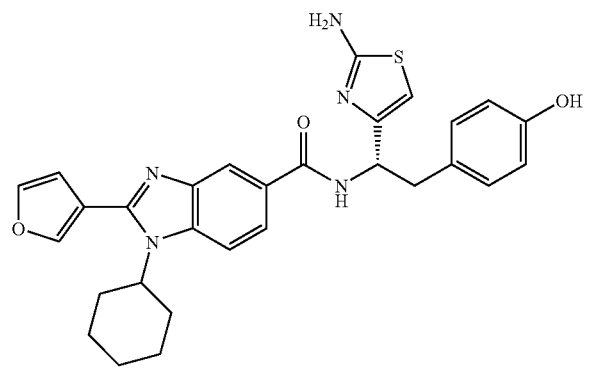

The protected aminothiazole derivative of example 74 was deprotected on nitrogen by stirring with 4N HCl—dioxane as in example 69. The resulting hydrochloride salt was coupled to the carboxylic acid of example 2 in the usual manner to give, after removal of the O-acetyl protecting group (NaOH) the title compound of example 75 after purification by preparative C18 reversed-phase HPLC.

Example 77

1-Cyclohexyl-furan-3-yl-1H-benzimidazole-5-carboxylic acid [(S)-2-(4-hydroxy-phenyl)-1-(2-methyl-thiazol-4-yl)-ethyl]-amide (Entry 1187, Table 1)

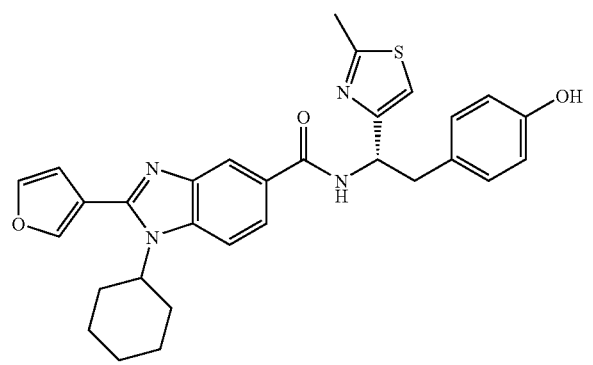

Prepared as described in example 76 except that the thiazole derivative of example 75 was used.

Example 78

1-Cyclohexyl-2-furan-3-yl-1H-benzimidazole-5-carboxylic acid [(S)-2-(5-hydroxy-1H-indol-3-yl)-1-(5-trifluoromethyl-1,2,4oxadiazol-3-yl)-ethyl]-amide (Entry 1298, Table 1)

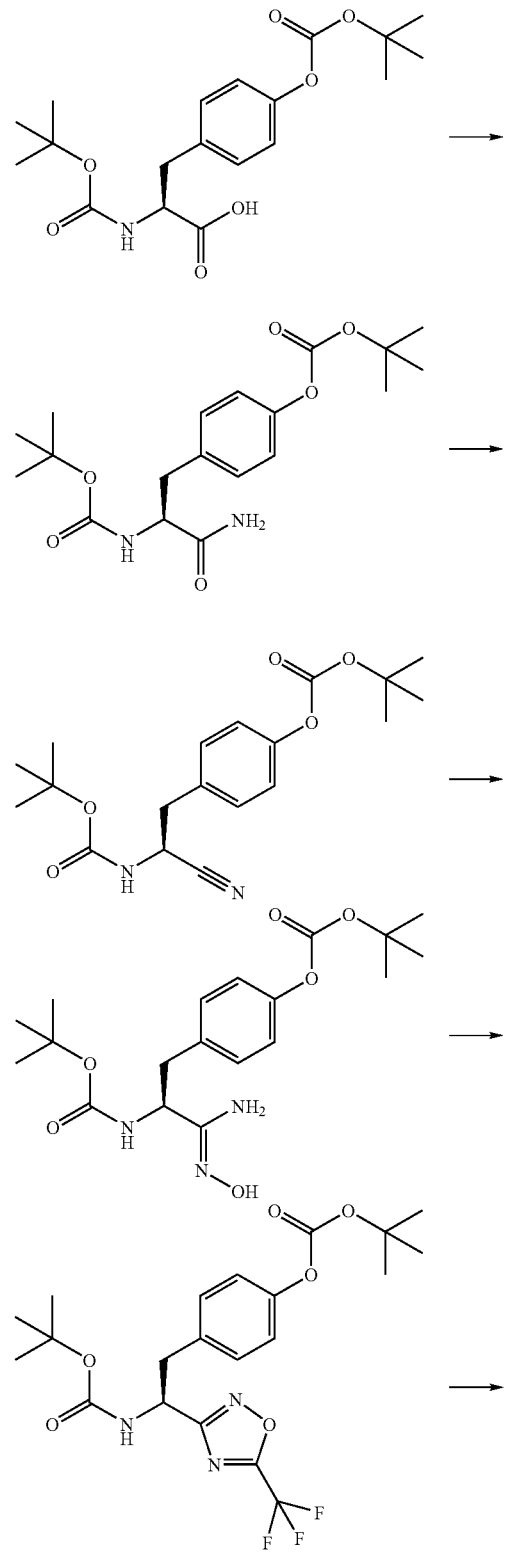

-continued

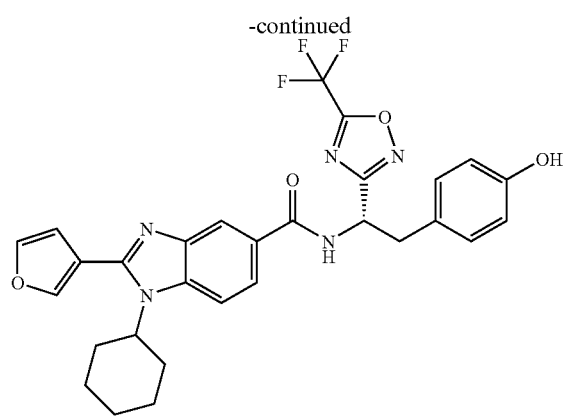

Carbonic acid 4-((S)-2-tert-butoxycarbonylamino-2-carbamoyl-ethyl)-phenyl ester tert-butyl ester: N,O-Bis-Boc-(S)-tyrosine from example 64 (5.00 g, 13.11 mmol) was dissolved in THF (20 mL), the solution stirred under an argon atmosphere and cooled in an ice bath. DIEA (5.70 mL, 32.7 mmol) was added followed by isobutylchloroformate (2.55 mL, 19.6 mmol). After 45 min a solution of 2M ammonia in isopropanol (39.3 mL, 78.6 mmol) was added and the mixture stirred at room temperature for 18 h. The solvent was evaporated, the residue taken in EtOAC (100 mL), washed with 5% aqueous citric acid (2×50 mL), 5% aqueous sodium bicarbonate (2×50 mL) and brine. After drying (MgSO$_4$) and evaporation of the solvent, the residue was dissolved in chloroform (15 mL), stirred vigorously and Et$_2$O (150 mL) was added. The suspension was stirred for 20 min. then the solid filtered and air dried to yield 3.10 g (62%) of the title compound.

Carbonic acid 4-((S)-2-tert-butoxycarbonylamino-2-cyano-ethyl)-phenyl ester tert-butyl ester The tyrosine amide from above (2.00 g, 5.3 mmol) was suspended in DCM (20 mL), stirred under argon and DMSO (1 mL) was added. The resulting solution was cooled to −78° C. and oxalyl chloride (554 μL, 6.31 mmol) was slowly added followed by DIEA (2.75 mL, 15.8 mmol). The mixture was stirred for 5 h at room temperature, re-cooled to −78° C., more oxalyl chloride (750 μL) was added and the mixture stirred at room temperature for 18 h. It was then diluted with DCM (20 mL), washed with 1 N HCl (2×20 mL), 5% aqueous sodium bicarbonate (2×20 mL) and brine (20 mL). The solution was dried (MgSO$_4$) and the solvent evaporated. The residue was purified by flash chromatography using 10 to 25% EtOAc/hexane to yield 683 mg (36%) of the title compound as an amorphous solid.

Carbonic acid 4-[(S)-2-tert-butoxycarbonylamino-2-(N-hydroxycarbamimidoyl)-ethyl]-phenyl ester tert-butyl ester: The nitrile prepared above (0.336 g, 0.93 mmol) was dissolved in MeOH (3 mL), hydroxylamine hydrochloride (0.070 g, 1.02 mmol) was added followed by sodium bicarbonate (0.156 g, 1.85 mmol). The mixture was stirred 18 h under an argon atmosphere. The solvent was evaporated, the residue taken up in EtOAc (25 mL), washed with 5% aqueous sodium bicarbonate and brine (20 mL) The solution was dried (MgSO$_4$) and the solvent evaporated to yield 353 mg (96%) of the title compound.

Carbonic acid 4-[(S)-2-tert-butoxycarbonylamino-2-(5-trifluoromethyl-1,2,4-oxadiazol-3-yl)-ethyl]-phenyl ester tert-butyl ester: The amidoxime prepared above (0.200 g, 0.51 mmol) was dissolved in THF (400 μL), trifluoroacetic anhydride (216 μL, 1.53 mmol) was added followed by TFA (39 μL, 0.51 mmol). The solution was heated to 70° C. for 2 h, allowed to cool to room temperature, diluted with EtOAc, washed with 5% aqueous sodium bicarbonate and brine. The solution was dried (MgSO$_4$) and the solvent evaporated to yield 237 mg (98%) of the title compound that was used directly in the next step.

1-Cyclohexyl-2-furan-3-yl-1H-benzimidazole-5-carboxylic acid [(S)-2-(5-hydroxy-1H-indol-3-yl)-1-(5-trifluoromethyl-1,2,4-oxadiazol-3-yl)-ethyl]-amide (Entry 1298, Table 1)

The protected heterocycle from above was deprotected as described in example 64 and coupled to the carboxylic acid of example 2 in the usual manner. The title compound of example 78 was obtained after purification by preparative C18 reversed-phase HPLC.

Example 79

1-Cyclohexyl-2-furan-3-yl-1H-benzimidazole-5-carboxylic acid [(S)-1-cyano-2-(4-hydroxy-phenyl)-ethyl]-amide (Entry 1170, Table 1)

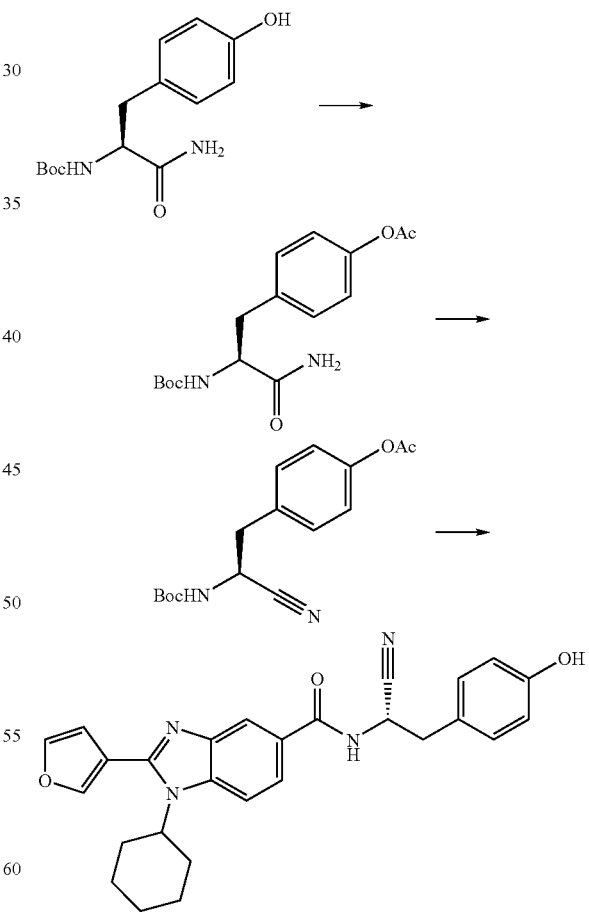

Acetic acid 4-((S)-2-tert-butoxycarbonylamino-2-carbamoyl-ethyl)-phenyl ester: To a solution of Boc-tyrosine amide (0.960 g, 3.4 mmol) in pyridine (10 mL) stirred under argon was added acetic anhydride (808 μL, 8.56 mmol). After 18 hrs of stirring the solvent was evaporated, the residue taken in EtOAc (30 mL) washed with 5% aqueous citric acid (3×20 mL) and brine. The solution was dried (MgSO₄) and the solvent evaporated to yield 949 mg (86%) of the title compound.

Acetic acid 4-((S)-2-tert-butoxycarbonylamino-2-cyanoethyl)-phenyl ester The amide from above was dissolved in a 4/1 mixture of DCM/DMSO, the solution stirred under an argon atmosphere and cooled to −78° C. Oxalyl chloride (65 µL, 0.74 mmol) was added dropwise, the solution stirred for 30 min and triethylamine (259 µL, 1.86 mmol) was added. After 1 h at −78° C. the solution was allowed to warm to room temperature and stirred for 1.5 h. EtOAc (40 mL) was added, the solution washed with 5% aqueous sodium bicarbonate (20 mL) and brine (20 mL). The solution was dried (MgSO₄) and the solvent evaporated. The residue was purified by flash chromatography (gradient 20 to 30% EtOAc/hexane) to yield 115 mg (61%) of the title compound.

1-Cyclohexyl-2-furan-3-yl-1H-benzimidazole-5-carboxylic acid [(S)-1-cyano-2-(4-hydroxy-phenyl)-ethyl]-amide (Entry 1170, Table 1): Following the procedure of example 76, the nitrile from above was coupled to the carboxylic acid of example 2 to give after purification by preparative C18 reversed-phase HPLC, the title compound of example 79.

Example 80

(S)-3-(3-Acetyl-4-hydroxy-phenyl)-2-({[1-(1-cyclohexyl-2-furan-3-yl-1H-benzimidazol-5-yl)-methanoyl]-amino}-propionic acid (Entry 1147, Table 1)

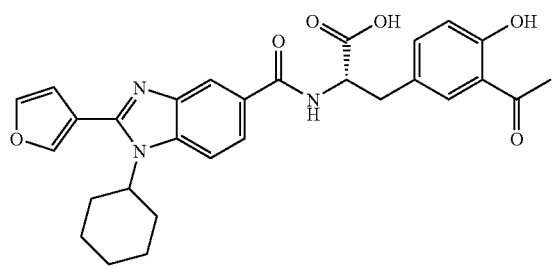

(S)-3-(3-Acetyl-4-hydroxyphenyl)alanine methyl ester hydrochloride was prepared according to the method of D. L. Boger et al. (*J. Org. Chem.* 1987, 52, 5283) and coupled to the carboxylic acid of example 2 in the usual manner.

Example 81

(S)-2-{[1-(1-Cyclohexyl-2-furan-3-yl-1H-benzimidazol-5-yl)-methanoyl]-amino}-3-[4-hydroxy-3 (RS)-(1-hydroxy-ethyl)-phenyl]-propionic acid (Entry 16052, Table 16)

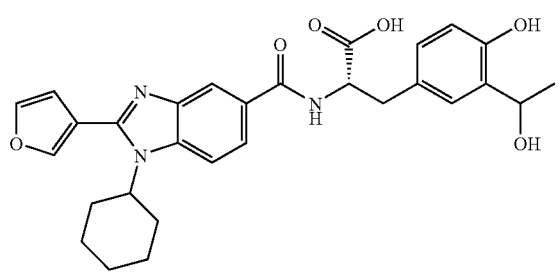

An aliquot from the coupling reaction of example 80 was treated with excess sodium borohydride at room temperature for 1 h. Following acidification with TFA, the title compound of example 81 was isolated as a mixture of epimers (carbinol center) by prep HPLC.

Example 82

(S)-2-{[1-(1-Cyclohexyl-2-furan-3-yl-1H-benzimidazol-5-yl)-methanoyl]-amino}-3-(4-methyl-2-oxo-2H-1-benzopyran-6-yl)-propionic acid (Entry 1126, Table 1)

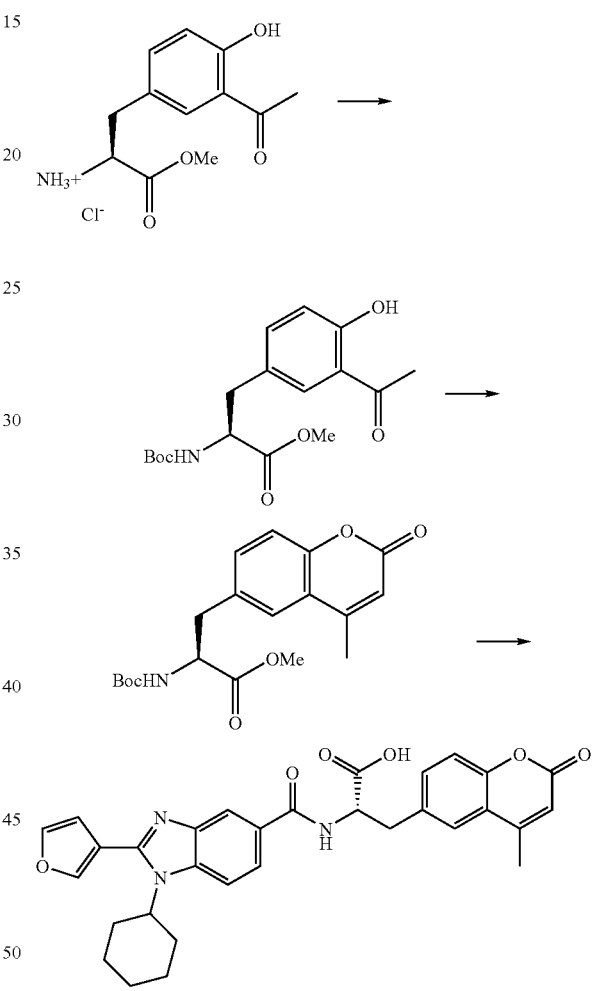

(S)-3-(3-Acetyl-4-hydroxy-phenyl)-2-tert-butoxycarbonylamino-propionic acid methyl ester: To a solution of (S)-3-(3-acetyl-4-hydroxyphenyl)alanine methyl ester hydrochloride (1.50 g, 5.48 mmol), prepared according to the method of D. L. Boger et al. (*J. Org. Chem.* 1987, 52, 5283), in DMF (15 mL) was added di-tert-butyldicarbonate (1.20 g, 5,48 mmol) and DIEA (1.91 mL, 10.96 mmol). The solution was stirred under an argon atmosphere for 16 h. It was poured in a 0.5 N solution of KHSO₄ (200 mL), extracted with EtOAc (2×75 mL) and the combined organic solutions were washed with brine (50 mL). The extract was dried (MgSO₄) and the solvent evaporated to yield 1.80 g (97%) of the title compound.

(S)-2-tert-Butoxycarbonylamino-3-(4-methyl-2-oxo-2H-1-benzopyran-6-yl)-propionic acid methyl ester: To a solution of the above ketone (0.250 g, 0.74 mmol) in benzene (4 mL) was added methyl (triphenylphosphoranylidene)acetate (0.496 g, 1.48 mmol). The solution was refluxed for 5 h then evaporated to dryness. The residue was purified by flash chromatography (gradient 20 to 35% EtOAc/hexane) to yield 70 mg (26%) of the title compound.

(S)-2-{[1-(1-Cyclohexyl-2-furan-3-yl-1H-benzimidazol-5-yl)-methanoyl]-amino}-3-(4-methyl-2-oxo-2H-1-benzopyran-6-yl)-propionic acid (Entry 1126, Table 1)

The amino ester derivative from above was deprotected with 4N HCl in dioxane and coupled to the carboxylic acid of example 2 in the usual manner to give after saponification the title compound of example 82.

Example 83

(E)-3-[5-((S)-2-Carboxy-2-{[1-(1-cyclohexyl-2-furan-3-yl-1H-benzimidazol-5-yl)-methanoyl]-amino}-ethyl)-2-methoxy-phenyl]-acrylic acid (Entry 16051, Table 16)

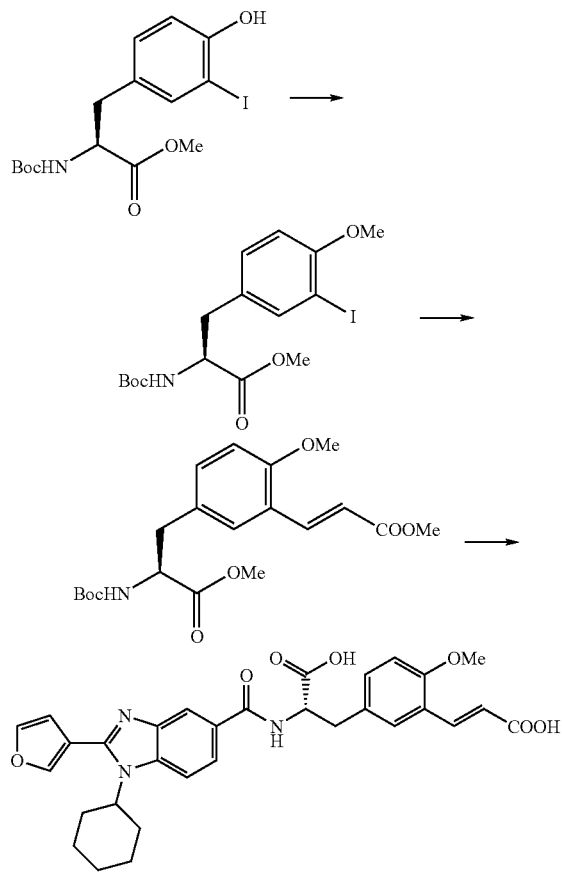

To a solution of Boc-3'-iodo-L-tyrosine methyl ester (B. Rzeszotarska et al. *Liebigs Ann. Chem.*, 1981, 7,1294-1302) (0.200 g, 0.47 mmol) in DMF (1 mL) was added iodomethane (32 μL, 0.52 mmol) and DIEA (125 μL, 0.71 mmol). The solution was stirred at room temperature for 16 h then poured in water (15 mL) and the product extracted with EtOAc (15 mL). The organic solution was evaporated and the residue purified by flash chromatography (gradient 20 to 25% EtOAc/hexane) to yield 127 mg (62%) of the title compound.

A solution of the above iodotyrosine derivative (0.110 g, 0.25 mmol) in MeCN (3 mL) was stirred vigorously and argon was diffused in it for 20 min. Methyl acrylate (225 μL, 2.50 mmol), DIEA (132 μL, 0.75 mmol), tri-o-tolylphosphine (11 mg) and palladium acetate (11 mg) were added. Argon diffusion was continued for 5 min then the system was sealed and heated at 80° C. with vigorous stirring for 18 h. After cooling to room temperature, argon was diffused again for 20 min, additional palladium acetate (20 mg) and tri-o-tolylphosphine (20 mg) were added and the system sealed and heated at 90° C. for 16 h. The solvent was then evaporated, the residue taken in EtOAc (20 mL) washed with 1 M $KHSO_4$ (10 mL), 5% aqueous sodium bicarbonate (10 mL) and brine (10 mL). The solution was dried (MgSO4) and the solvent evaporated. The residue was purified by flash chromatography (25% EtOAc/hexane) to yield 102 mg (100%) of the title compound.

The above tyrosine fragment was deprotected with 4N HCl—dioxane and coupled in the usual manner to the carboxylic acid of example 2. Following saponification of the ester groups the title compound of example 83 was isolated by preparative C18 reversed-phase HPLC.

Example 84

(S)-2-{[1-(1-Cyclohexyl-2-furan-3-yl-1H-benzimidazol-5-yl)-methanoyl]-amino}-3-[3-(2H-tetrazol-5-yl)-phenyl]-propionic acid (Entry 16057, Table 16)

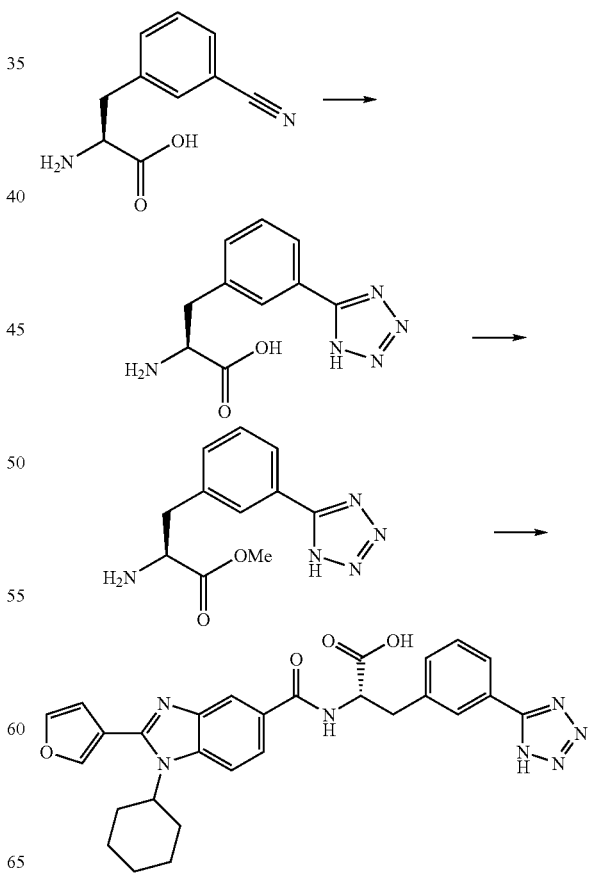

A suspension of L-3-cyano-phenylalanine (0.150 g, 0.79 mmol), lithium chloride (0.060 g, 1.43 mmol) and sodium azide (0.067 g, 1.03 mmol) in methoxyethanol (500 µL) was heated at 125° C. for 18 h. The solvent was evaporated to yield 370 mg of crude 3-tetrazolyl-L-phenylalanine.

The crude tetrazole prepared above was dissolved in MeOH (20 mL), a 4N HCl in dioxane solution (4 mL) was added and the solution refluxed for 3 h. The solution was evaporated to dryness to yield 307 mg of the crude methyl ester hydrochloride.

The methyl ester from above was coupled to the carboxylic acid of example 2 in the usual manner to give after saponification and purification by preparative C18 reversed-phase HPLC the title compound of example 84.

Example 85

(S)-2-{[1-(1-Cyclohexyl-2-furan-3-yl-1H-benzimidazol-5-yl)-methanoyl]-amino}-3-[4-hydroxy-3-(2H-tetrazol-5-yl)-phenyl]-propionic acid (Entry 16056, Table 16)

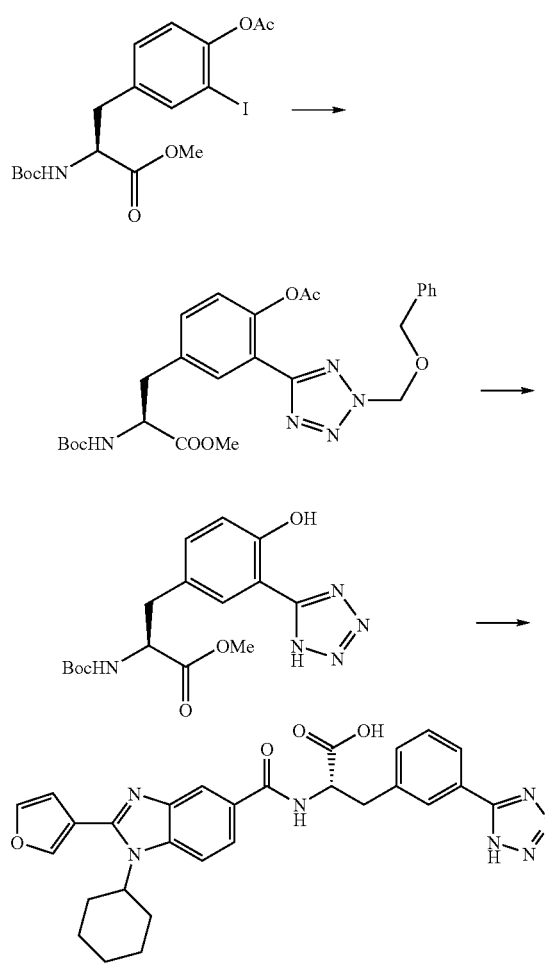

To a solution of Boc-3'-iodo-L-tyrosine methyl ester (B. Rzeszotarska et al. *Liebigs Ann. Chem.*, 1981, 7, 1294-1302) (0.300 g, 0.71 mmol) in DMF (2 mL) were added DIEA (250 µL, 1.43 mmol), and acetic anhydride (80 µL, 0.85 mmol).

The solution was stirred at room temperature for 2 h then poured in a 1 M solution of $KHSO_4$ (40 mL). The mixture was extracted with EtOAc (20 mL) and the organic extract washed with 5% aqueous sodium bicarbonate and brine. Drying ($MgSO_4$) and removal of the solvent gave the acetylated tyrosine derivative (330 mg, >100%).

A solution of the above acetylated iodotyrosine derivative (0.120 g, 0.26 mmol) in toluene (5 mL) was stirred vigorously and flushed with argon for 30 min. Then were added 2-benzyloxymethyl-5-(tributylstannyl)tetrazole (B. C. Bookser, *Tetrahedron Lett.*, 2000, 41, 2805) (0.149 g, 0.31 mmol), tetrakis(triphenylphosphine) palladium (0) (15 mg, 0.013 mmol) and copper(1) iodide (5 mg, 0.026 mmol). The system was sealed and heated at 110° C. for 18 h. The mixture was cooled to room temperature, a 15% aqueous solution of KF (2 mL) was added and the mixture vigorously stirred for 45 min. It was filtered over celite and the cake was washed with EtOAc (4×20 mL). The filtrate was dried ($MgSO_4$) and the solvent evaporated. The residue was purified by flash chromatography (gradient 10 to 30% EtOAc/hexane) to yield 54 mg (40%) of the protected 3-tetrazolyl-tyrosine derivative.

The tetrazole derivative prepared above was dissolved in MeOH (8 mL) and 10% Pd/C (50 mg) was added. The mixture was stirred under one atmosphere of hydrogen gas for 16 h. The suspension was filtered over celite washed with MeOH, the filtrate was evaporated and the residue re-dissolved in MeOH (20 mL). It was then hydrogenated at 50 psi with palladium acetate (100 mg) on a Parr shaker for 18 h. After filtration over celite, washing and evaporation of the filtrate 32 mg (93%) of the deprotected tetrazole derivative were obtained.

The N-Boc derivative from above was deprotected with 4 N HCl—dioxane and coupled in the usual manner to the carboxylic acid of example 2. Following removal of ester groups by saponification, the title compound of example 85 was isolated by preparative C18 reversed-phase HPLC.

Example 86

Carbonic acid 3-[(S)-2-tert-butoxycarbonylamino-2-(2-methylamino-thiazol-4-yl)-ethyl]-1H-indol-5-yl ester tert-butyl ester

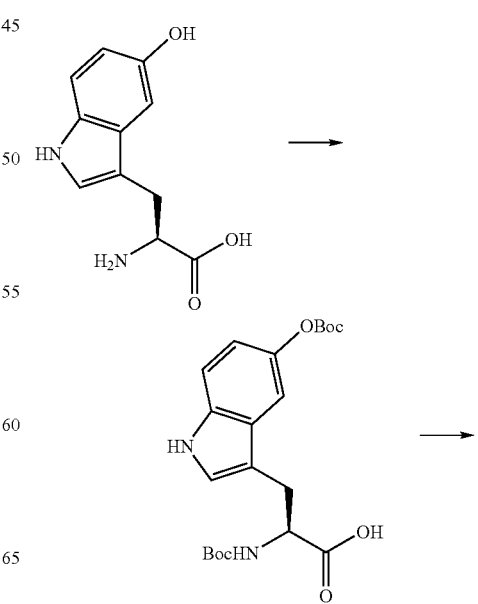

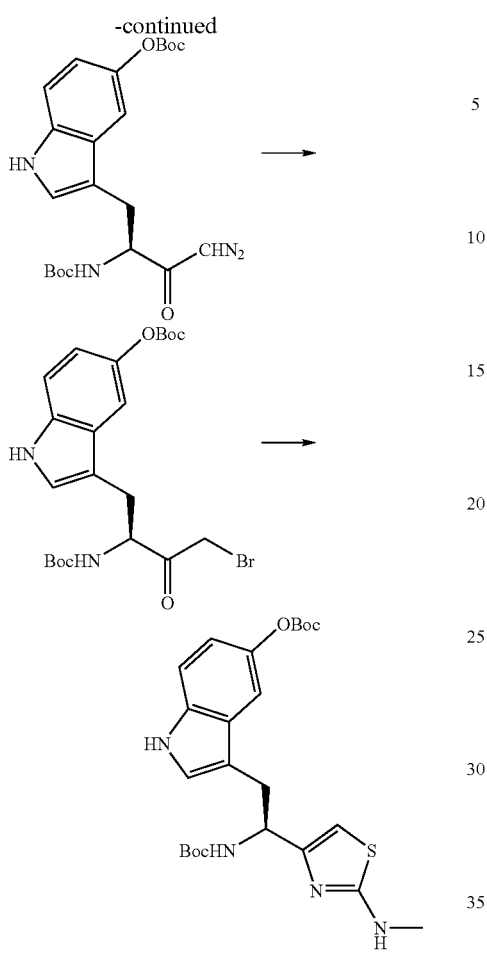

(S)-5-Hydroxytryptophan was converted to the bis-Boc derivative by the method of V. F. Pozdnev, *Chem. Nat. Compd.* (*Engl. Transl.*) 1982, 18 (1), 125) which was isolated as the free carboxylic acid. This material (1.0377 g, 2.47 mmol) was dissolved in THF (5 mL), DIEA (0.645 mL, 3.7 mmol) was added and the mixture cooled in ice. Isobutyl chloroformate (0.384 mL, 2.96 mmol) was added and the mixture stirred at 0-5° C. for 18 h. Excess diazomethane in Et$_2$O (0.6 M, 15 mL) was then added and the mixture stirred for 1 h. Another portion of diazomethane (10 mL) was added and after 40 min, the reaction was diluted with Et$_2$O (75 mL). The solution was washed successively with 10% aqueous citric acid (25 mL) and saturated aqueous NaHCO$_3$ (25 mL), and dried (MgSO$_4$). Volatiles were removed under reduced pressure and the residue purified by flash chromatography with 40% EtOAc/hexane. The diazomethylketone was obtained as a yellow foam (0.783 g).

The diazomethylketone from above was dissolved in EtOAc (10 mL) and the solution cooled to −30° C. A solution of HBr in AcOH (48% w/w, 0.384 mL) was added dropwise over 60 min. The cold reaction mixture was then diluted with Et$_2$O (100 mL) and washed successively with 10% aqueous citric acid (2×25 mL) and saturated aqueous NaHCO$_3$ (25 mL), and dried (MgSO$_4$). Volatiles were removed under reduced pressure and the residue coevaporated with hexane to give the bromomethylketone as a white foam (0.870 g). The bromomethylketone from above was reacted with N-methylthiourea as described for example 63.

Example 87

Carbonic acid 3-[(S)-2-tert-butoxycarbonylamino-2-(2-dimethylamino-thiazol-4-yl)-ethyl]-1H-indol-5-yl ester tert-butyl ester

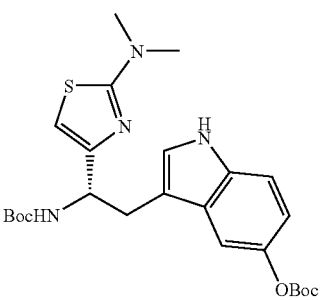

The bromomethylketone of example 86 was reacted with N,N-dimethylthiourea as described for example 64.

Example 88

Carbonic acid 3-[(S)-2-(2-acetylamino-thiazol-4-yl)-2-tert-butoxycarbonylamino-ethyl]-1H-indol-5-yl ester tert-butyl ester

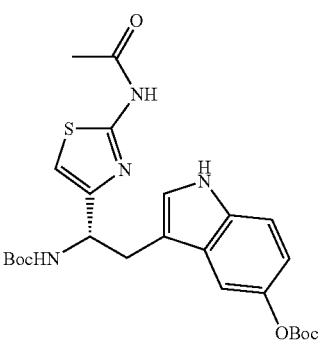

The bromomethylketone of example 86 was reacted with N-acetyl-2-thiourea as described for example 63.

Example 89

Carbonic acid 3-((S)-2-tert-butoxycarbonylamino-2-thiazol-4-yl-ethyl)-1H-indol-5-yl ester tert-butyl ester

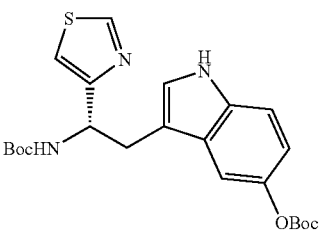

The bromomethylketone of example 86 was converted to the thiazole heterocycle as described for example 68.

Example 90

Carbonic acid 3-[(S)-2-tert-butoxycarbonylamino-2-(2-methyl-thiazol-4-yl)-ethyl]-1H-indol-5-yl ester tert-butyl ester

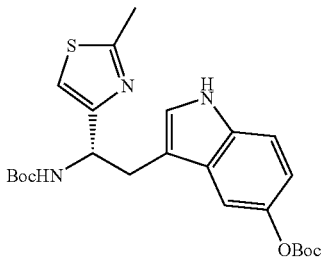

The bromomethylketone of example 86 (0.423 g, 0.85 mmol) was reacted with thioacetamide (0.128 g, 1.70 mmol) in MeCN (5 mL) at room temperature for 18 h. The solvent was then removed under reduced pressure and the residue dissolved in DMSO (1.5 mL). This solution was added dropwise with stirring to a mixture of water (15 mL) and DIEA (0.2 mL). The precipitate that formed was collected by filtration, washed with water and dried to give the title compound of example 90 (0.383 g).

Example 91

Carbonic acid 3-[(S)-2-(2-amino-thiazol-4-yl)-2-tert-butoxycarbonylamino-ethyl]-1H-indol-5-yl ester tert-butyl ester

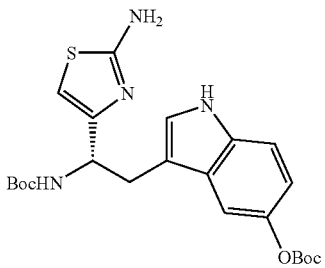

Prepared as described for example 90, except that thiourea was used instead of thioacetamide.

Example 92

1-Cyclohexyl-2-furan-3-yl-1H-benzimidazole-5-carboxylic acid [(S)-2-(5-hydroxy-1H-indol-3-yl)-1-(2-methyl-thiazol-4-yl)-ethyl]-amide (Entry 14001, Table 14)

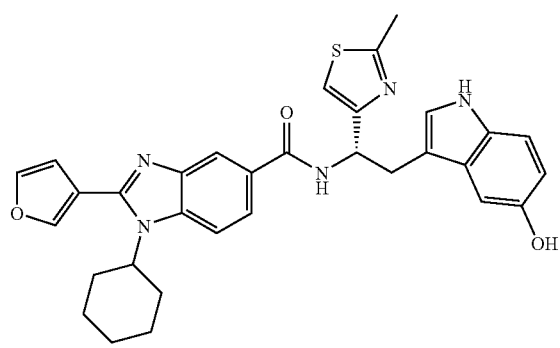

The Bis-Boc thiazole fragment of example 90 was deprotected using 4 N HCl—dioxane and the resulting hydrochloride salt was coupled in the usual manner to the carboxylic acid of example 2. The title compound of example 92 was isolated by preparative C18 reversed-phase HPLC.

Example 93

1-Cyclohexyl-2-furan-3-yl-1H-benzimidazole-5-carboxylic acid [(S)-1-(2-amino-thiazol-4-yl)-2-(5-hydroxy-1H-indol-3-yl)-ethyl]-amide (Entry 14002, Table 14)

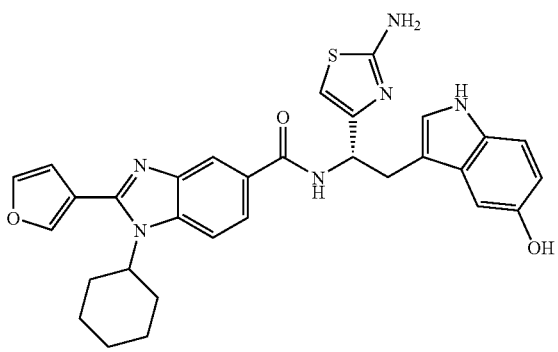

The Bis-Boc aminothiazole fragment of example 91 was deprotected using 4 N HCl—dioxane and the resulting hydrochloride salt was coupled in the usual manner to the carboxylic acid of example 2. The title compound of example 93 was isolated by preparative C18 reversed-phase HPLC.

Example 94

1-Cyclohexyl-2-furan-3-yl-1H-benzimidazole-5-carboxylic acid [(S)-2-(5-hydroxy-1H-indol-3-yl)-1-(2-methylamino-thiazol-4-yl)-ethyl]-amide (Entry 14004, Table 14)

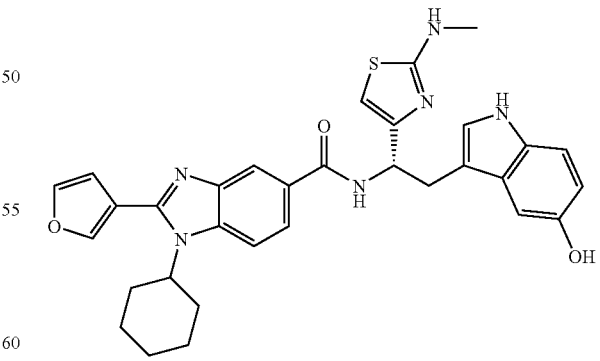

The Bis-Boc aminothiazole fragment of example 86 was deprotected using 4 N HCl—dioxane and the resulting hydrochloride salt was coupled in the usual manner to the carboxylic acid of example 2. The title compound of example 93 was isolated by preparative C18 reversed-phase HPLC.

Example 95

1-Cyclohexyl-2-furan-3-yl-1H-benzimidazole-5-carboxylic acid [(S)-1-(2-dimethylamino-thiazol-4-yl)-2-(5-hydroxy-1H-indol-3-yl)-ethyl]-amide (Entry 13005 Table 14)

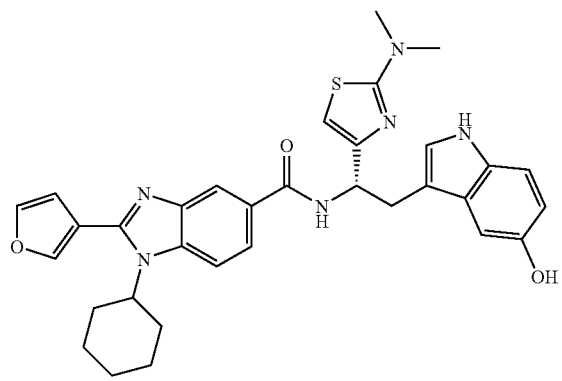

The Bis-Boc aminothiazole fragment of example 87 was deprotected using 4 N HCl—dioxane and the resulting hydrochloride salt was coupled in the usual manner to the carboxylic acid of example 2. The title compound of example 94 was isolated by preparative C18 reversed-phase HPLC.

Example 96

1-Cyclohexyl-2-furan-3-yl-1H-benzimidazole-5-carboxylic acid [(S)-1-(2-acetylamino-thiazol-4-yl)-2-(5-hydroxy-1H-indol-3-yl)-ethyl]-amide (Entry 14006, Table 14)

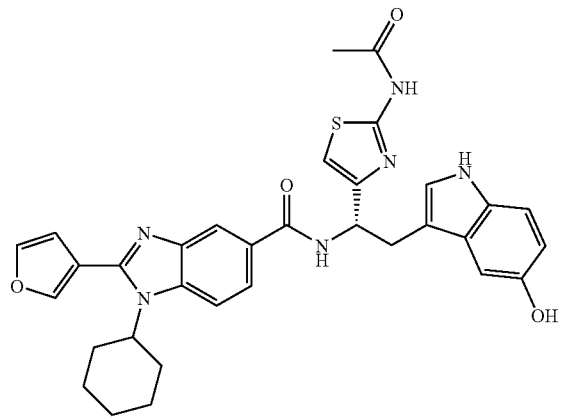

The Bis-Boc aminothiazole fragment of example 88 was deprotected using 4 N HCl—dioxane and the resulting hydrochloride salt was coupled in the usual manner to the carboxylic acid of example 2. The title compound of example 96 was isolated by preparative C18 reversed-phase HPLC.

Example 97

1-Cyclohexyl-2-furan-3-yl-1H-benzimidazole-5-carboxylic acid [(S)-2-(5-hydroxy-1H-indol-3-yl)-1-thiazol-4-yl-ethyl]-amide (Entry 14007, Table 14)

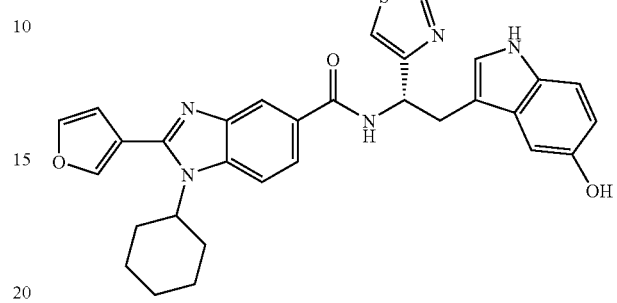

The Bis-Boc thiazole fragment of example 89 was deprotected using 4 N HCl—dioxane and the resulting hydrochloride salt was coupled in the usual manner to the carboxylic acid of example 2. The title compound of example 97 was isolated by preparative C18 reversed-phase HPLC.

Example 98

[4-((S)-4-Bromo-2-tert-butoxycarbonylamino-3-oxo-butyl)-phenoxy]-acetic acid methyl ester

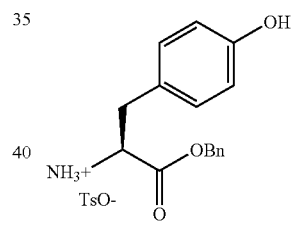

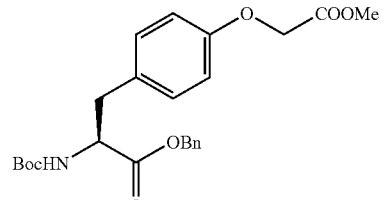

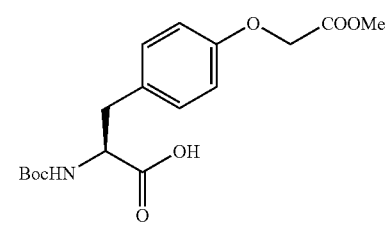

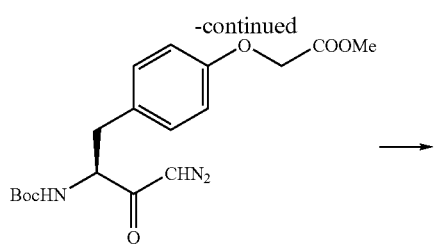

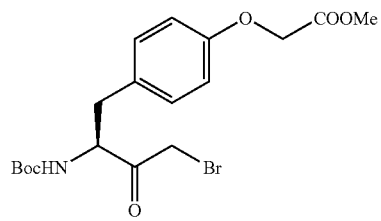

The para-toluenesulfonic acid salt of tyrosine benzyl ester (5.05 g, 11.4 mmol) was dissolved in THF (50 mL) containing DIEA (2.18 mL, 12.5 mmol) and di-tert-butyidicarbonate (2.98 g, 13.7 mmol) was added in one portion. The reaction was stirred 1.5 h at room temperature. Volatiles were removed under reduced pressure and the residue was dissolved in Et$_2$O (150 mL). The solution was washed successively with water (25 mL), 5% citric acid (25 mL) and 5% NaHCO$_3$ (25 mL). After drying (MgSO$_4$), the solvent was evaporated under reduced pressure and the residue dissolved in acetone (100 mL). Cesium carbonate (4.83 g, 14.8 mmol) and methyl bromoacetate (1.3 mL, 13.7 mmol) were added and the heterogeneous mixture was stirred overnight at room temperature. Solids were then removed by filtration (acetone for washings) and the filtrate evaporated. The residue was dissolved in Et$_2$O (150 mL) and washed with water (25 mL) and brine (25 mL). After drying (MgSO$_4$), the solution was concentrated and the residue purified by flash chromatography using 25-50% EtOAc/hexane as eluent. The fully protected tyrosine derivative was obtained as a colorless oil (3.61 g).

The benzyl ester from above (3.60 g, 8.1 mmol) was dissolved in EtOAc (25 mL) and hydrogenated (1 atm H$_2$ gas) over 20% Pd(OH)$_2$/C (350 mg) for 2.5 h. The catalyst was removed by filtration and the solvent removed under reduced pressure to give the free acid derivative as a colorless oil (3.19 g).

The tyrosine derivative from above (1.20 g, 3.4 mmol) was dissolved in THF (15 mL) and the solution cooled to −20° C. N-Methylmorpholine (0.45 mL, 4.1 mmol) was added followed by isobutylchloroformate (0.48 mL, 3.74 mmol). The mixture was stirred at −20° C. for 30 min. Diazomethane in Et$_2$O (0.6 M, excess) was added and the solution stirred for 30 min at room temperature. A second portion of diazomethane was added and stirring resumed for an additional 30 min (complete by TLC and HPLC). The reaction mixture was diluted with Et$_2$O (100 mL) and the solution washed successively with water (2×25 mL), 5% NaHCO$_3$ (25 mL) and brine (25 mL). The extract was dried (MgSO$_4$) and concentrated to give the desired diazomethylketone as a yellow oil (1.26 g).

The diazomethylketone from above (1.10 g, 3.4 mmol) was dissolved in EtOAc (10 mL) and the solution cooled to 0° C. A solution of HBr in AcOH (48% w/w, 0.44 mL, 3.4 mmol) was added dropwise over 5 min, followed by an additional portion (0.22 mL, 1.7 mmol). After stirring for 10 min, the reaction mixture was diluted with Et$_2$O (150 mL) and washed successively with water (25 mL), 10% citric acid (25 mL) and 5% NaHCO$_3$ (2×25 mL). After drying (MgSO$_4$), the solvent was evaporated under reduced pressure to give the desired bromomethylketone as a light yellow solid (1.14 g).

Example 99

{4-[(S)-2-{[1-(1-Cyclohexyl-2-furan-3-yl-1H-benz-imidazol-5-yl)-methanoyl]-amino}-2-(2-methyl-thiazol-4-yl)-ethyl]-phenoxy}-acetic acid (Entry 1131, Table 1, R=CH$_3$)

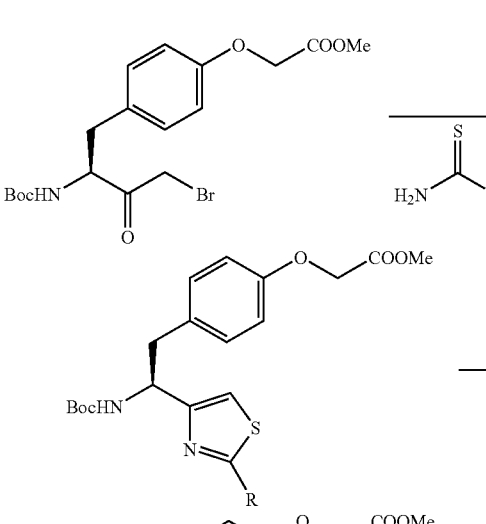

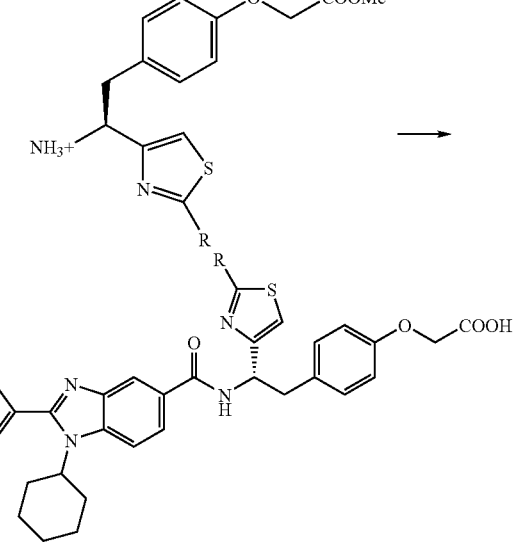

R = CH$_3$, NH$_2$, NHCH$_3$, N(CH$_3$)$_2$, NHiPr, NHCOCH$_3$, H

Following the procedure of example 90, the bromoketone of example 98 was reacted with thioacetamide. Following removal of the Boc protecting group (if necessary) with 4N HCl in dioxane, the amine hydrochloride salt was coupled to the carboxylic acid of example 2 in the usual manner. The ester protecting group was then removed by saponification (NaOH) and the final product isolated by preparative C18 reversed-phase HPLC.

Example 100

[4-((S)-2-(2-Amino-thiazol-4-yl)-2-{[1-(1-cyclo-hexyl-2-furan-3-yl-1H-benzimidazol-5-yl)-methanoyl]-amino}-ethyl)-phenoxy]-acetic acid (Entry 19002 Table 19, R=NH$_2$ in example 99)

Following the procedure of example 99 but replacing the thioacetamide by thiourea, the title compound of example 100 was obtained.

Example 101

{4-[(S)-2-{[1-(1-Cyclohexyl-2-furan-3-yl-1H-benzimidazol-5-yl)-methanoyl]-amino}-2-(2-isopropylamino-thiazol-4-yl)-ethyl]-phenoxy}-acetic acid (Entry 1133, Table 1, R=NH$^1$Pr in example 99)

Following the procedure of example 99 but replacing the thioacetamide by N-isopropyl-2-thiourea, the title compound of example 101 was obtained.

Example 102

[4-((S)-2-(2-Acetylamino-thiazol-4-yl)-2-{[1-(1-cyclohexyl-2-furan-3-yl-1H-benzimidazol-5-yl)-methanoyl]-amino}-ethyl)-phenoxy]-acetic acid (Entry 1134, Table 1, R=NHAC in example 99)

Following the procedure of example 99 but replacing the thioacetamide by N-acetyl-2-thiourea, the title compound of example 102 was obtained.

Example 103

{4-[(S)-2-{[1-(1-Cyclohexyl-2-furan-3-yl-1H-benzimidazol-5-yl)-methanoyl]-amino}-2-(2-methylamino-thiazol-4-yl)-ethyl]-phenoxy}-acetic acid (Entry 1140, Table 1, R=NHMe in example 99)

Following the procedure of example 99 but replacing the thioacetamide by N-methyl-2-thiourea, the title compound of example 103 was obtained.

Example 104

{4-[(S)-2-([1-(1-Cyclohexyl-2-furan-3-yl-1H-benzimidazol-5-yl)-methanoyl]-amino}-2-(2-dimethylamino-thiazol-4-yl)-ethyl]-phenoxy}-acetic acid (Entry 1141, Table 1, R=N(CH$_3$)$_2$ in example 99)

Following the procedure of example 99 but replacing the thioacetamide by N,N-dimethyl-2-thiourea, the title compound of example 104 was obtained.

Example 105

[4-((S)-2-{[1-(1-Cyclohexyl-2-furan-3-yl-1H-benzimidazol-5-yl)-methanoyl]-amino}-2-thiazol-4-yl-ethyl)-phenoxy]-acetic acid (Entry 1150, Table 1, R=H in example 99)

Following the procedure of example 68, the title compound of example 104 was obtained.

Example 106

Solid Phase Synthesis of Inhibitors, Wherein, X=CH, Y=O, Z=OH, n=0

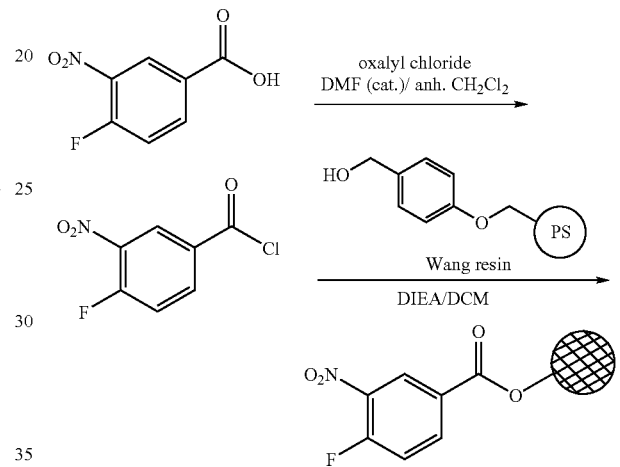

To a solution of the 4-fluoro-3-nitrobenzoic acid (0.12 mol, 22.2 g) in 100 mL of anhydrous DCM was added 10 drops of anhydrous DMF. To this solution was added dropwise over 60 min, oxalyl chloride (0.144 mol, 12.6 mL). During the addition, the solid slowly dissolved to give rise to a yellow solution. The mixture was stirred for an additional 4 h and the solvent was stripped down to give a yellow oil. This oil was distilled under vacuum (110° C., 1.5 mm Hg) to give 4-fluoro-3-nitrobenzoyl chloride as a light yellow liquid (22.0 g, 90% yield).

On a solid phase synthesizer (Advanced Chemtech ACT 90), Wang resin (Nova Biochem, loading: 1.2 mmol/g, 20 mmol, 16.7 g) was washed twice with DCM (100 mL), twice with i-PrOH (100 mL) and was dried overnight under high vacuum over P$_2$O$_5$. The following day, the resin was washed with anhydrous DCM (2×100 mL) and was suspended in anhydrous DCM (100 mL). To the suspension was added DIEA (30 mmol, 5.2 mL) followed by a solution of 4-fluoro-3-nitrobenzoyl chloride (22 mmol, 4.48 g) dissolved in 10 ml of anhydrous DCM. The slurry was shaken for 3 h, the solution was drained and the resin was washed twice with 100 mL-portions of anhydrous DCM. The resin was then suspended in anhydrous DCM (100 mL) and was treated with DIEA (30 mmol, 5.2 mL) followed by acetic anhydride (24 mmol, 2.3 mL). After shaking for 2 h, the solution was drained and the resin was washed successively with DCM (2×100 mL), i-PrOH (2×100 mL), DCM (2×100 mL) and finally with i-PrOH (3×100 mL). The resin was dried overnight under high vacuum. To calculate the level of incorporation, the resin (45.9 mg) was treated with a 1:1 mixture of TFA/1,2-dichloroethane (1.5 mL) for 1 h. The resin was filtered and was washed twice with 1,2-dichloroethane (1.5 mL). The filtrates were combined and concentrated under vacuum. The residue was lyophilized from MeCN/$H_2O$ to give 4-fluoro-3-nitro benzoic acid as a yellow solid (6.3 mg, 0.033 mmol). Based on recovered compound, the loading was calculated to be 0.74 mmol/g.

The following steps were performed on a solid-phase synthesizer (ACT 496 from Advanced Chemtech), using the 96-well reaction block:

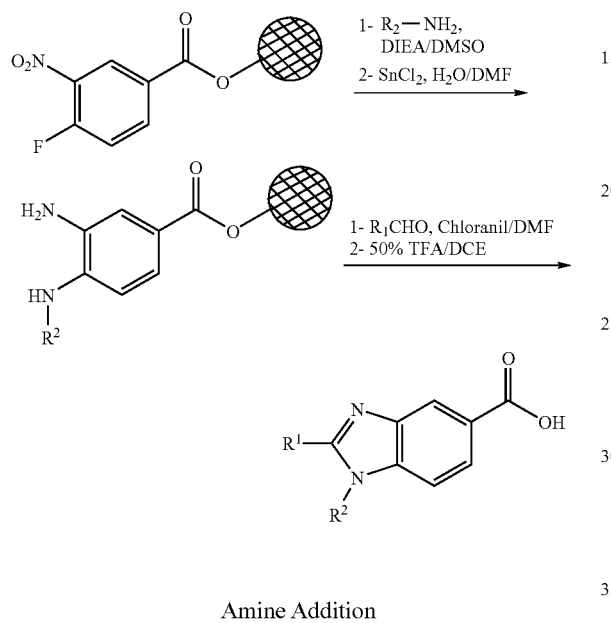

Amine Addition

Each well was filled with the benzoic acid resin from above (0.03 mmol, 40 mg) and was washed with DMF (3×1.2 mL) and DMSO (2×1.2 mL). To each well was added DMSO (530 μL), a 1 M solution of the amine $R_2$—$NH_2$ (600 μL, 0.6 mmol) and DIEA (0.4 mmol, 70 μL). The resins were shaken for 15 h at room temperature and the solvent was drained. The resins were washed successfully with 1.2-mL portions of DMF (3×), MeOH (3×), and DMF (4×).

Reduction of the Nitro Group

The resins were then suspended in DMF (600 μL) and were shaken with a 1 M solution of $SnCl_2.2H_2O$ (600 μL, 0.6 mmol) for 25 h. The solvent was drained, the resins were washed successively with 1.2-mL portions of 1:1 DMF-$H_2O$ (4×), DMF (4×), MeOH (4×) and NMP (4×).

Formation of the Benzimidazole Ring

Each resin was suspended in DMF (200 μL) and a 1 M solution of the aldehyde in DMF was added (0.20 mmol, 200 μL), followed by a 0.25 M solution of chloranil in NMP (0.20 mmol, 800 μL). The resins were shaken for 18 h, the liquid was drained and the resins were washed successively with 1.2-mL portions of NMP (3×), 1 M DIEA/NMP (2×), NMP (3×), MeOH (3×) and DCM (4×). The reaction block was placed in a vacuum chamber for 30 min in order to dry the resin.

Cleavage from the Resin

In each well was added 1.0 mL of a 1:1 solution of TFA/1,2-dichloroethane and the resins were shaken for 1 h. The wells were drained and the resins washed once with 1.0 mL of the cleavage solution. Volatiles were evaporated in a vacuum centrifuge to give the crude benzimidazole 5-carboxylic acids in which X=CH, Y=0, Z=OH and n=0.

Example 107

(Entries 2110, 2111, 2112, 2114-2117, 2120-2123, 2125-2128, 2139-2143, Table 2)

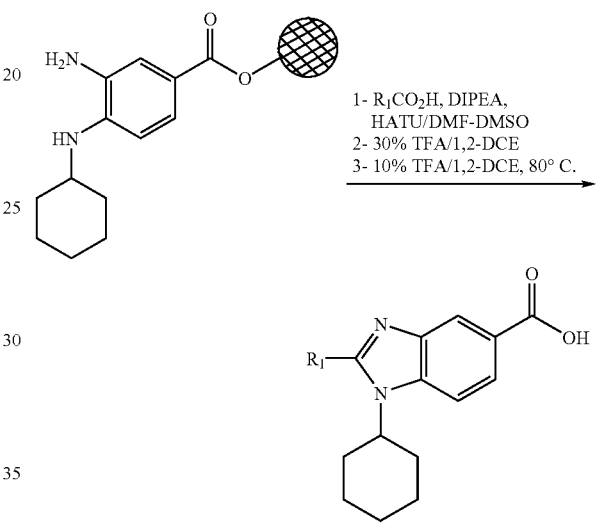

The following steps were performed on a solid-phase synthesizer (ACT 496 from Advanced Chemtech), using the 96-well reaction block.

The starting diamine resin was prepared as described in example 106. Each well was filled with resin (0.0203 mmol, 35 mg) and was washed with DMF (3 X 1.2 mL). To each well was added a 0.5 M solution of DIEA in DMF (200 μL, 0.1 mmol), a 0.2 M solution of the acid $R_1$—$CO_2H$ in DMSO (500 μL, 0.1 mmol) and a 0.2 M solution of HATU in DMF (500 μL, 0.1 mmol). The resins were shaken for 6 h at room temperature and the solvent was drained. The coupling was repeated for another 6 h with fresh reagent. The resins were washed successfully with 1.2-mL portions of DMF (3×), MeOH (3×), and DCM (3×).

Cleavage from the Resin

In each well was added 1.0 mL of a 30% solution of TFA/1,2-dichloroethane and the resins were shaken for 1.5 h. The wells were drained and the resins washed once with 2 mL of 1,2-dichloroethane. The resulting filtrates containing 10% TFA in 1,2-dichloroethane was heated at 80° C. for 13 h. The volatiles were removed under vacuum and the residue was lyophilized from MeCN/$H_2O$. The crude benzimidazole 5-carboxylic acid derivatives thus obtained were coupled with 5-(S)-hydroxytryptophan methyl ester hydrochloride, saponified and purified in the usual manner:

Example 108

(Entries 1157-1169, 1178, 1179, 1236-1239, Table 1)

Reduction of the Nitro Group and Coupling of Fmoc-β-amino Butyric Acid

The nitro group was reduced to the corresponding aniline using tin (II) chloride dihydrate (1.2 mL of a 0.5 M solution in

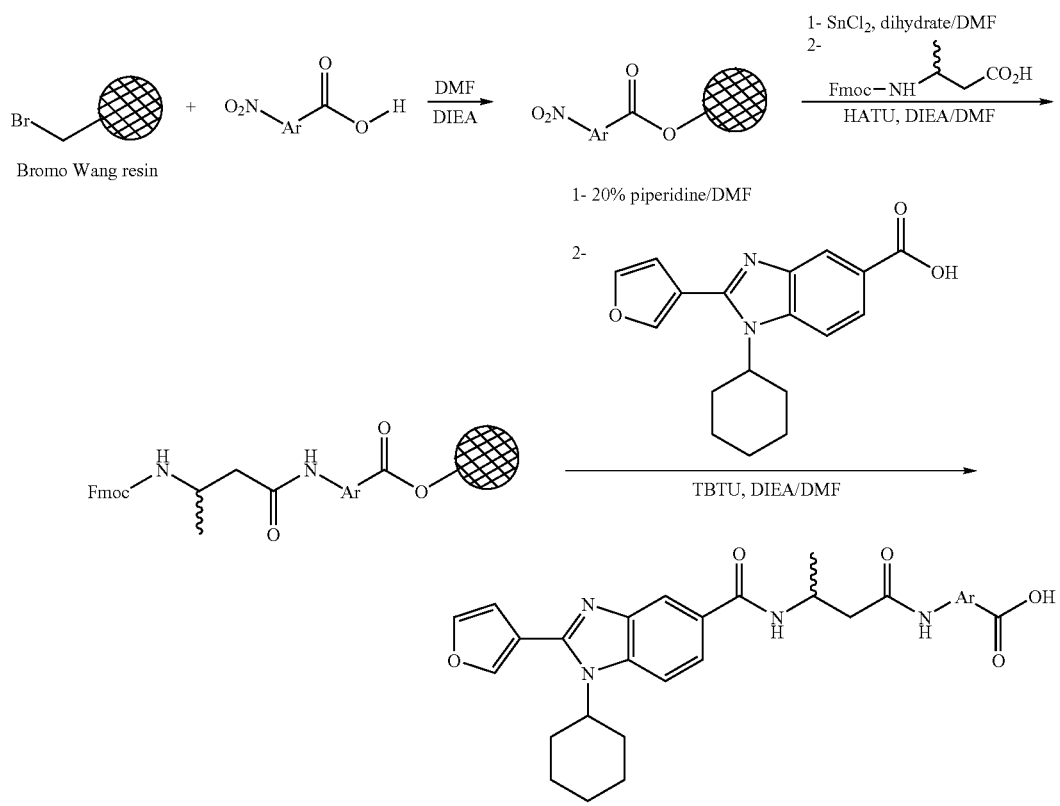

Note 1: In the case of compound entries 1157, 1158. 1236, 1237, 1238 and 1239, the coupling with the γ-amino butyryl fragment was omitted.

Note 2: In the case of compound entries 1159 and 1178, the amino acid fragment was coupled directly on the bromo Wang resin and, in the former case, Fmoc-d,l-alanine was used.

Note 3: In case of compound entries 1236, 1237, 1238, and 1239, the nitroacid was coupled to standard Wang resin using the MSNT method of J. Nielsen and L. O. LyngsØ (*Tetrahedron Lett.* 1996, 37, 8439).

The following steps were performed on a solid-phase synthesizer (ACT 496 from Advanced Chemtech), using the 96-well reaction block:

Anchoring on the Resin

Each well was filled with the bromo Wang resin (0.044 mmol, 40 mg) and was washed with DMF (3×1.2 mL). To each well was added DMF (200 μL), a 1 M solution of DIEA in DMF (300 μL, 0.3 mmol), and each of the nitro acid derivatives (0.176 mmol) dissolved in 500 μL of DMF. The resins were shaken for 15 h at room temperature and the solvent was drained. The resins were washed successively with 1.2-mL portions of DMF (3×), MeOH (3×), and DMF (3×).

DMF, 0.6 mmol) for 24 h followed by washing (3×1.2 mL) with DMF, DMF/H$_2$O, DMF, MeOH and DMF. The resin was then suspended in DMF (200 μL) and treated with a 0.5 M solution of DIEA in DMF (300 μL, 0.15 mmol), a 0.13 M solution of Fmoc-d,l-β-aminobutyric acid (500 μL, 0.066 mmol) and a 0.13 M solution of TBTU in DMF (500 μL, 0.066 mmol). After shaking for 5 h at 60° C., and since several reactions were not complete as indicated by the cleavage of a few resin beads, fresh reagents were added and a second coupling was done using HATU as coupling agent at room temperature for 18 h.

Coupling of the Core Benzimidazole and Cleavage from the Resin

The Fmoc group was cleaved with 20% piperidine/DMF (20 min) and after washing, the core benzimidazole was coupled under standard conditions to the carboxylic acid of example 2 using TBTU as coupling agent (room temperature, 18 h).

Cleavage from the Resin

In each well was added 1.0 mL of a 50% solution of TFA/1,2-dichloroethane and the resins were shaken for 1 h.

The wells were drained and the resins washed once with 1 mL of the 50% TFA/1,2-DCE solution. The volatiles were removed under vacuum and the compounds were purified by semi-prep reversed phase chromatography.

Example 109

(Entries 1180-1185, Table 1)

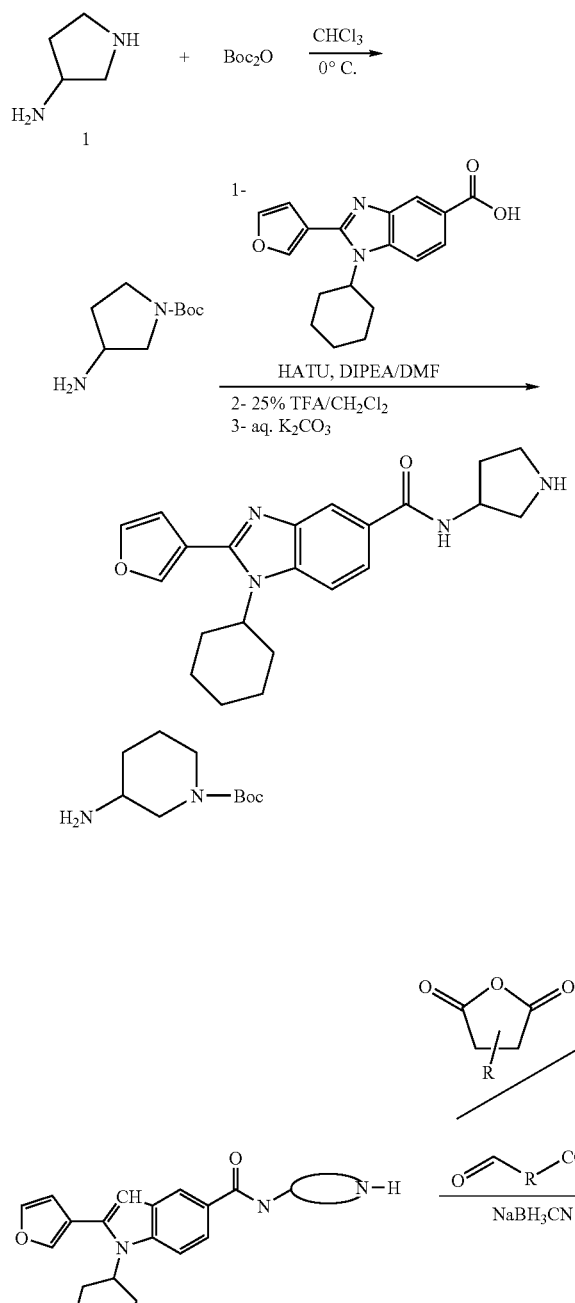

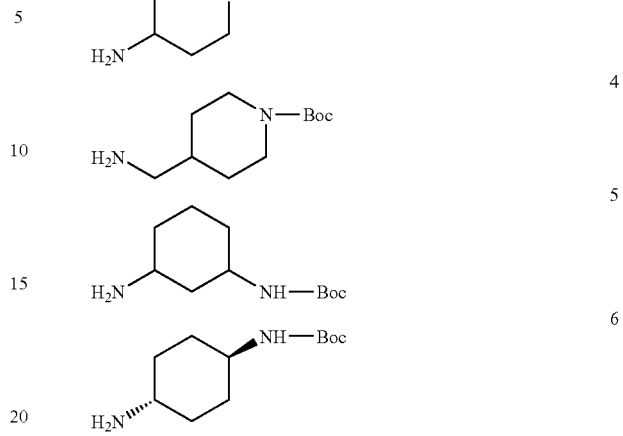

The mono-Boc diamines 1-6 were synthesized from the corresponding diamino compounds according to a literature procedure (see Carceller, E.; Merlos, M.; Giral, M.; Balsa, D.; Garcia-Rafanell, J.; Form, J. *J. Med. Chem.* 1996, 39, 487). 3-Aminopiperidine was prepared by hydrogenation of 3-aminopyridine at 45 psi $H_2$ over 5% w/w $Rh/Al_2O_3$ for 9 days. Coupling of the mono-protected diamino compound to the carboxylic acid of example 2 was performed using HATU. Following removal of the carbamate protecting group (TFA), the title compounds of example 109 were isolated by preparative C18 reversed-phase HPLC:

Example 110

(Entry 1191-1204,1205-1209,1210,1211-1227,1261-1274, and 1275-1292, Table 1)

The following steps were performed on a solid-phase synthesizer (ACT 496 from Advanced Chemtech), using the 96-well reaction block.

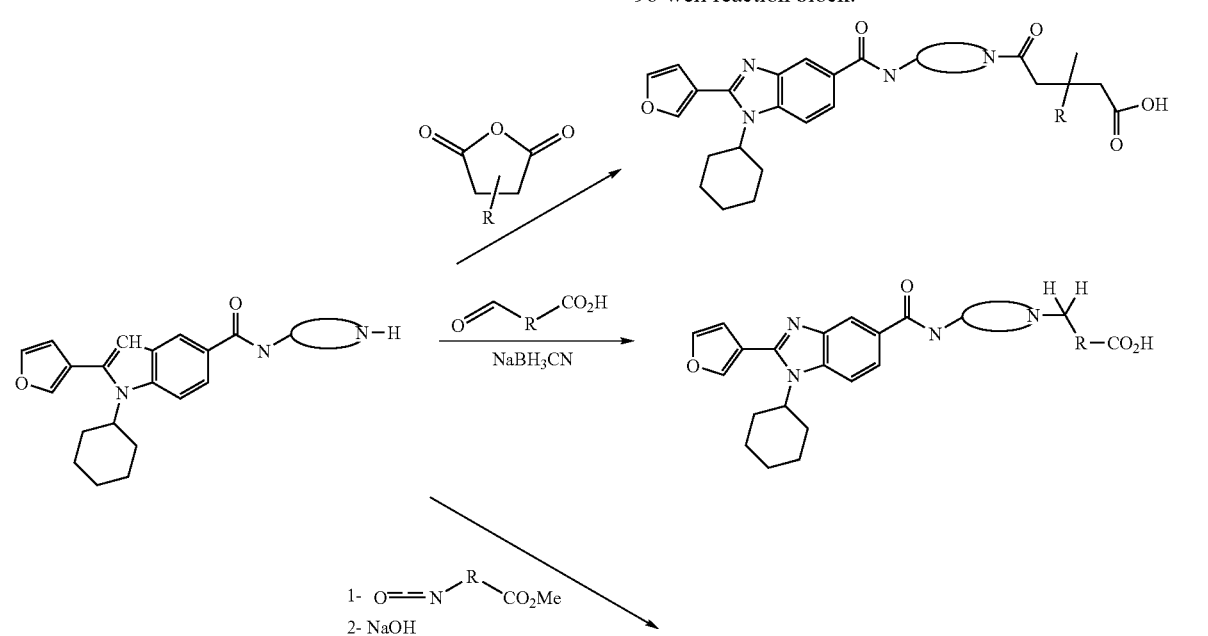

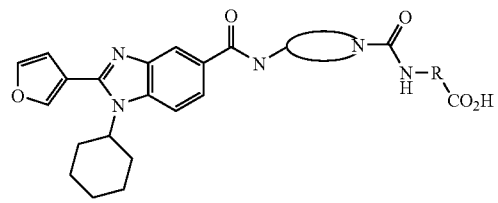

Reaction with Anhydrides and Isocyanates

In each well of the reaction block was added 0.5 mL of DMF followed by a 0.06 M solution of the appropriate amine from example 109 in DMF (0.5 mL, 0.03 mmol). In the case of anhydride additions, DIEA was added to the well (8.7 µL, 0.05 mmol). The isocyanates or anhydrides were added to the appropriate wells as a 0.45 M solution in DMF (0.10 mL, 0.045 mmol).

Anhydrides addition: After shaking 5 h, a 1 M solution of NaOH/H$_2$O was added (0.10 mL, 0.01 mmol) and the mixture was shaken for 14 h.

Isocyanates addition: The mixture was shaken for 19 h.

Work-up: In all the wells was added AcOH (11 µL, 0.2 mmol) and after shaking for 5 minutes, the solutions were sequentially purified by semi-Preparative C18 reversed-phase HPLC (20 mm×50 mm YMC column, 5 um, 120A) using a water-MeCN gradient containing 0.06% TFA.

Reaction with Aldehydes

In each well of the reaction block was added 0.2 mL of trimethylorthoformate followed by a 0.345 M solution of each of the appropriate amines from example 109 dissolved in trimethylorthoformate (0.30 mL, 0.115 mmol). Each of the aldehydes was dissolved in a 1% AcOH solution in trimethylorthoformate to make a 1.15 M solution. Each aldehyde solution was added to the appropriate well (0.10 mL, 0.115 mmol) and the solutions were shaken for 30 minutes. A solution 0.57 M of sodium cyanoborohydride in trimethylorthoformate was then added in each well (0.10 mL, 0.057 mmol) and the mixture was shaken for 3 h after which time, a 0.1 M solution of HCl in water was added (0.10 mL, 0.010 mmol). After shaking for 5 minutes, the solutions were filtered into a 8-mL vial and the well was washed with 1 mL of MeOH. The volatile solvents were removed under vacuum and the residue was dissolved in DMSO for purification by semi-preparative C18 reversed-phase HPLC.

Example 111

1-Cyclohexyl-2-furan-3-yl-1H-benzimidazole-5-carboxylic acid {(S)-1-(2-amino-thiazol-4-yl)-2-[4-(2H-tetrazol-5-yl)-phenyl]-ethyl}-amide (Entry 16059, Table 16)

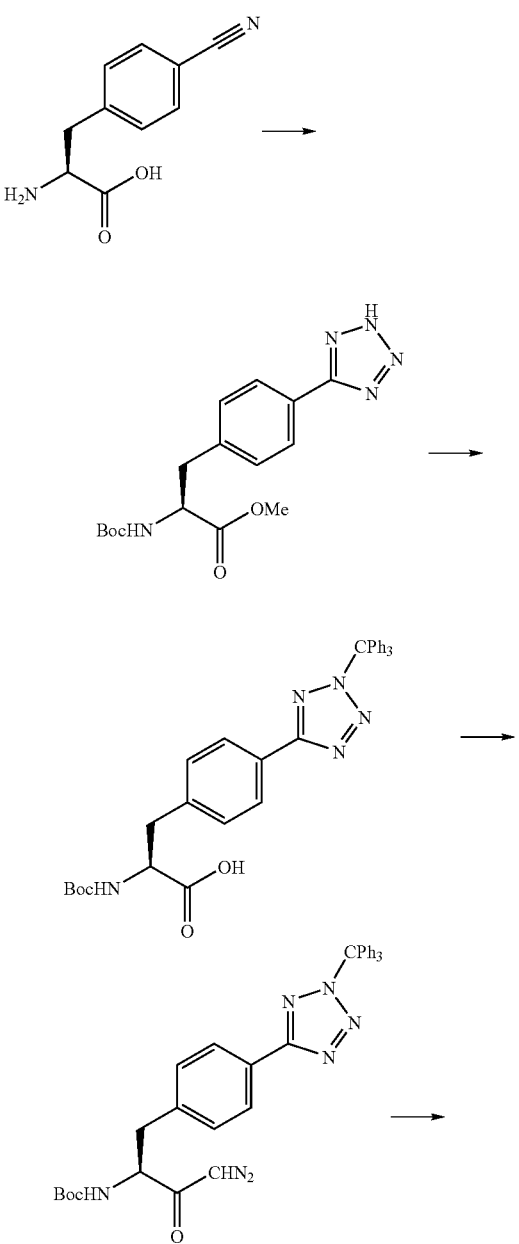

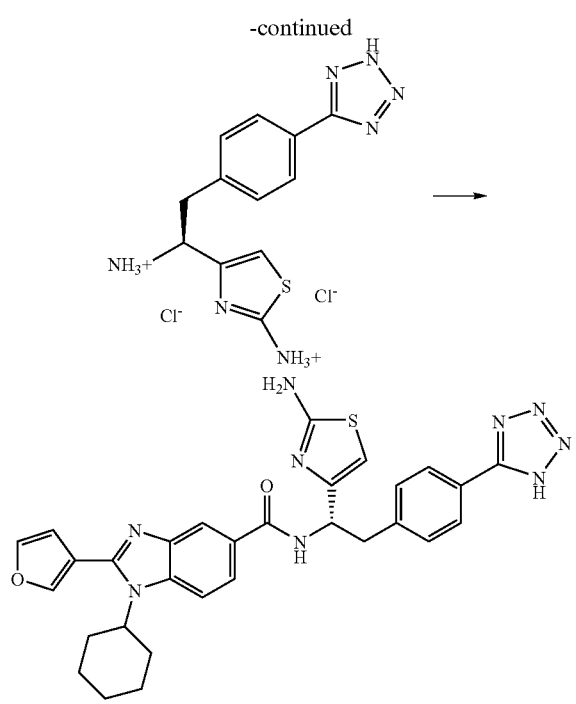

4-Cyano-L-phenylalanine (0.500 g, 2.63 mmol) was dissolved in DMF (10 mL) and sodium azide (0.342 g, 5.26 mmol) was added. The mixture was purged with argon gas and heated in a sealed tube at 100-120° C. for 18 h followed by 48 h at room temperature. HCl (1 M, 5 mL) was added and the mixture evaporated to dryness under vacuum. MeOH (25 mL) was added followed by thionyl chloride (1 mL, 13.7 mmol) and the mixture refluxed for 3 h. After cooling to room temperature, the solution was filtered to remove insoluble material and the filtrate evaporated to dryness. The residue was taken up in MeCN (20 mL), DIEA (2.74 mL, 15.8 mmol) and di-tert-butyldicarbonate (1.15 g, 5.26 mmol) were added, and the mixture stirred overnight at room temperature. Saturated aqueous $NaHCO_3$ (6 mL) was added, and after stirring for 1 h at room temperature, the reaction was quenched with AcOH (3.5 mL). After diluting with water (50 mL), the product was extracted into EtOAc (2×50 mL), washed with brine (25 mL) and dried ($Na_2SO_4$). After evaporation of the solvent, the desired tetrazole derivative was obtained as a tan-colored solid (0.775 g).

The tetrazole compound from above (0.752 g, 2.16 mmol) was dissolved in THF (20 mL) and DIEA (0.75 mL, 4.3 mmol) and triphenylchloromethane (trityl chloride, 0.604 g, 2.16 mmol) were added. The reaction was stirred for 1 h at room temperature and then quenched with 1 N NaOH (13 mL, 13 mmol). After stirring overnight at room temperature, the reaction mixture was cooled in ice and acidified to pH 3-4 with 1 N HCl. The product was extracted into EtOAc (50 mL), washed with brine and the solution dried ($Na_2SO_4$). Evaporation of the solvent gave a yellow residue that was purified by passing through a pad of silica gel using EtOAc as eluent. The product was then dissolved in TBME (5 mL) and hexane (10 mL) was added. The precipitated material was collected by filtration and dried to give the desired 4-tetrazolyl-L-phenylalanine free acid as a white solid (0.784 g).

The free carboxylic acid from above (0.278 g, 0.5 mmol) was dissolved in THF (10 mL) and the solution cooled to −30° C. DIEA (105 μL, 0.6 mmol) was added followed by isobutylchloroformate (72 μL, 0.55 mmol). The mixture was stirred for 30 min and excess diazomethane (0.6 M in $Et_2O$, 5 mL) was added. After stirring for 30 min at room temperature, $Et_2O$ (100 mL) was added and the mixture was washed successively with 10% citric acid (25 mL), 5% $NaHCO_3$ (25 mL) and brine (25 mL). After drying over $MgSO_4$, the solution was concentrated to give the diazomethylketone as a yellow foam (0.300 g).

The diazomethylketone from above (0.300 g, 0.5 mmol) was dissolved in EtOAc (3 mL) and cooled to −15° C. A solution of HBr in AcOH (48% w/w, 100 μL) was added dropwise and the reaction mixture stirred for 5 min. The reaction was warmed to room temperature and volatiles removed under a stream of nitrogen. The residue was dissolved in MeCN (5 mL) and thiourea (0.075 g, 1.0 mmol) was added. After stirring for 45 min at 60° C., the reaction mixture was cooled and the solvent removed under a stream on nitrogen. Water (0.5 mL) was added followed by 4 N HCl in dioxane (5 mL) and the mixture stirred for 30 min. Dioxane was evaporated under reduced pressure and 1 N HCl (10 mL) was added. The aqueous phase was washed with ether (3×10 mL) and liophilized to give a brown foam. The material was coevaporated once with MeOH then with MeCN to give a pale yellow solid (0.150 g).

The hydrochloride salt from above was coupled to the carboxylic acid of example 2 in the usual manner to give, after purification by preparative C18 reversed-phase HPLC, the title compound of example 111.

Example 112

(S)-3-{[1-(1-Cyclohexyl-2-furan-3-yl-1H-benzimidazol-5-yl)-methanoyl]-amino}-4-(5-hydroxy-1H-indol-3-yl)-butyric acid (Entry 16061, Table 16)

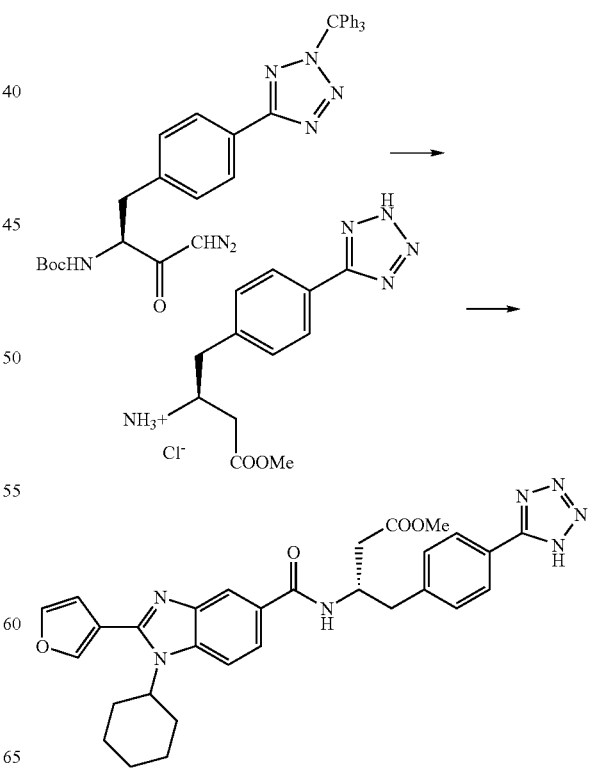

The diazomethylketone of example 111 (0.100 g, 0.17 mmol) was dissolved in a mixture of THF (0.2 mL) and MeOH (0.3 mL). A solution of silver benzoate in triethylamine (100 mg/mL, 0.1 mL) was added slowly, causing vigorous gas evolution. After 1 min, the reaction mixture turned brown. It was diluted with ether (2 mL) and 4N HCl in dioxane (0.2 mL) was added. The precipitate that formed was removed by filtration (ether for washings) and the filtrate evaporated to dryness. It was then stirred with additional 4N HCl in dioxane (0.5 mL) for 1 h. Et$_2$O (10 mL) and 1 N HCl (10 mL) were added and the aqueous phase was liophilized to give a yellow residue (0.078 g).

The amine hydrochloride from above was coupled to the carboxylic acid of example 2 in the usual manner, saponified and purified by preparative C18 reversed-phase HPLC to give the title compound of example 112).

Example 113

1-Cyclohexyl-2-furan-3-yl-1H-benzimidazole-5-carboxylic acid [(S)-1-carbamoyl-2-(5-hydroxy-1-methyl-1H-indol-3-yl)-ethyl]-amide (Entry 13002, Table 13)

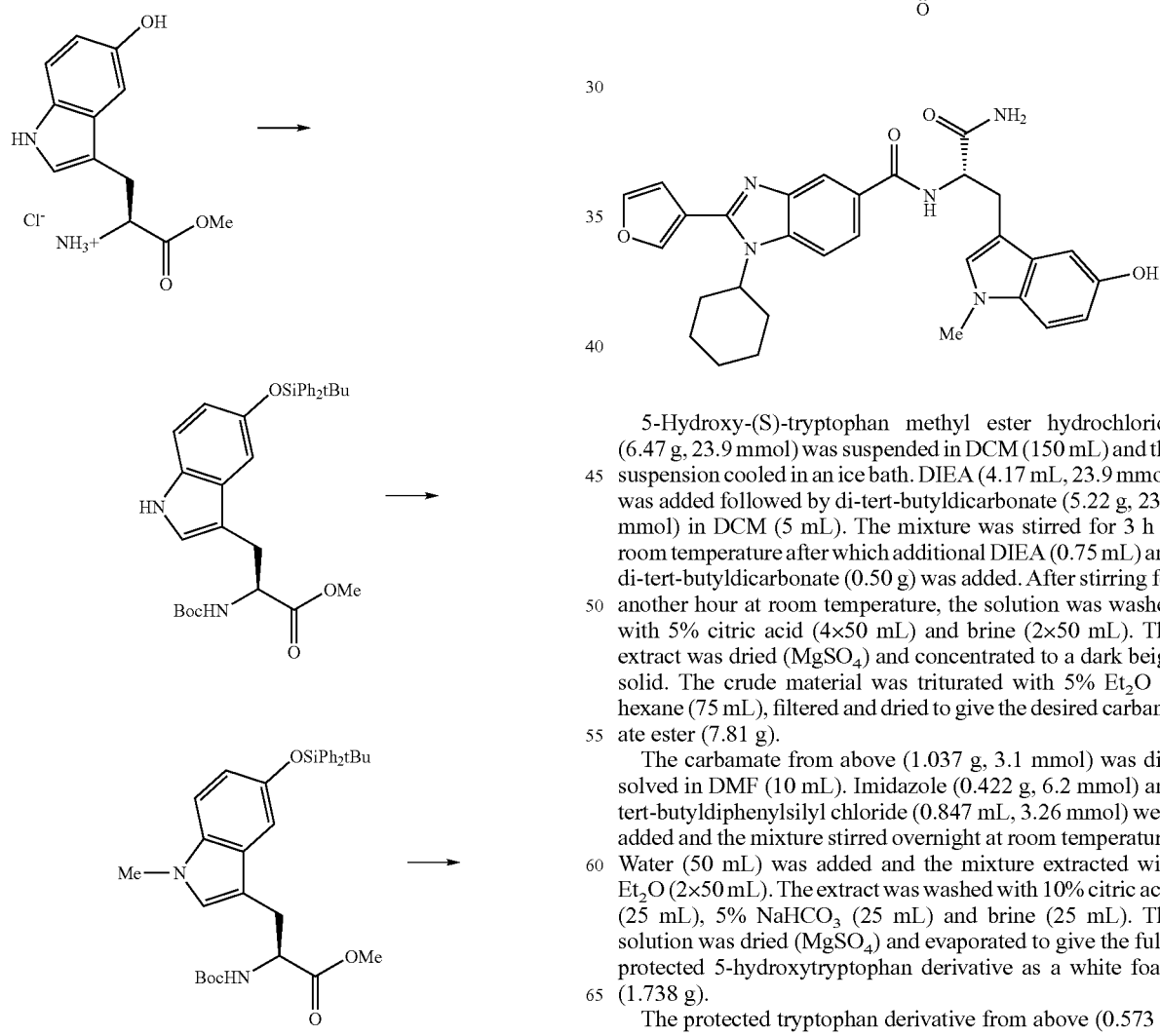

5-Hydroxy-(S)-tryptophan methyl ester hydrochloride (6.47 g, 23.9 mmol) was suspended in DCM (150 mL) and the suspension cooled in an ice bath. DIEA (4.17 mL, 23.9 mmol) was added followed by di-tert-butyldicarbonate (5.22 g, 23.9 mmol) in DCM (5 mL). The mixture was stirred for 3 h at room temperature after which additional DIEA (0.75 mL) and di-tert-butyldicarbonate (0.50 g) was added. After stirring for another hour at room temperature, the solution was washed with 5% citric acid (4×50 mL) and brine (2×50 mL). The extract was dried (MgSO$_4$) and concentrated to a dark beige solid. The crude material was triturated with 5% Et$_2$O in hexane (75 mL), filtered and dried to give the desired carbamate ester (7.81 g).

The carbamate from above (1.037 g, 3.1 mmol) was dissolved in DMF (10 mL). Imidazole (0.422 g, 6.2 mmol) and tert-butyldiphenylsilyl chloride (0.847 mL, 3.26 mmol) were added and the mixture stirred overnight at room temperature. Water (50 mL) was added and the mixture extracted with Et$_2$O (2×50 mL). The extract was washed with 10% citric acid (25 mL), 5% NaHCO$_3$ (25 mL) and brine (25 mL). The solution was dried (MgSO$_4$) and evaporated to give the fully protected 5-hydroxytryptophan derivative as a white foam (1.738 g).

The protected tryptophan derivative from above (0.573 g, 1.00 mmol) was dissolved in DMF (3 mL) and the solution cooled in ice. Sodium hydride (60% oil dispersion, 0.048 g, 1.2 mmol) was added and the mixture stirred for 30 min. Iodomethane (0.093 mL, 1.5 mmol) was added and stirring continued for an additional hour. The reaction was then quenched with 10% citric acid (2 mL) and water (25 mL), and extracted with Et$_2$O (100 mL). The extract was dried (MgSO$_4$) and concentrated, and the residue purified by flash chromatography (20-30% EtOAc/hexane as eluent) to give the desired N-methyltryptophan derivative (0.284 g).

The N-methyltryptophan derivative from above (0.711 g, 1.21 mmol) was dissolved in MeOH (10 mL) and thionyl chloride (0.6 mL) was added dropwise. The mixture was heated to 60° C. for 3 h. Volatiles were removed under reduced pressure and the residue triturated with TBME (25 mL). The precipitated white solid was collected, washed with TBME and dried to give N-methyl-5-hydroxytryptophan methyl ester hydrochloride (0.339 g): MS (ES+) m/z 249 (MH$^+$).

The methyl ester hydrochloride from above (0.170 g, 0.6 mmol) was suspended in concentrated aqueous ammonia (15 mL) and the mixture was stirred overnight at room temperature. Volatiles were then removed under vacuum and the residue triturated with MeOH (3-4 mL) and Et$_2$O (15 mL). The amide derivative was obtained as a brown solid (0.136 g).

The tryptophan amide derivative from above was coupled to the carboxylic acid of example 2 in the usual manner to give after purification by HPLC the title compound of example 113.

Example 114

(S)-2-{[1-(1-Cyclohexyl-2-furan-3-yl-1H-benzimidazol-5-yl)-methanoyl]-amino}-3-(5-hydroxy-1-methyl-1H-indol-3-yl)-propionic acid methyl ester (Entry 11028, Table 11)

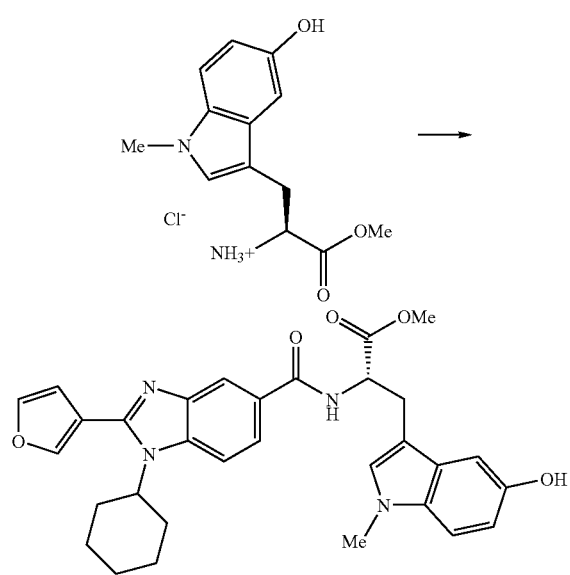

N-Methyl-5-hydroxytryptophan methyl ester hydrochloride (example 113) was coupled to the carboxylic acid of example 2 in the usual manner to give after purification by HPLC the title compound of example 114.

Example 115

(S)-3-[5-(1-Carboxy-1-methyl-ethoxy)-1-methyl-1H-indol-3-yl]-2-{[1-(1-cyclohexyl-2-furan-3-yl-1H-benzimidazol-5-yl)-methanoyl]-amino}-propionic acid methyl ester (Entry 11029, Table 11)

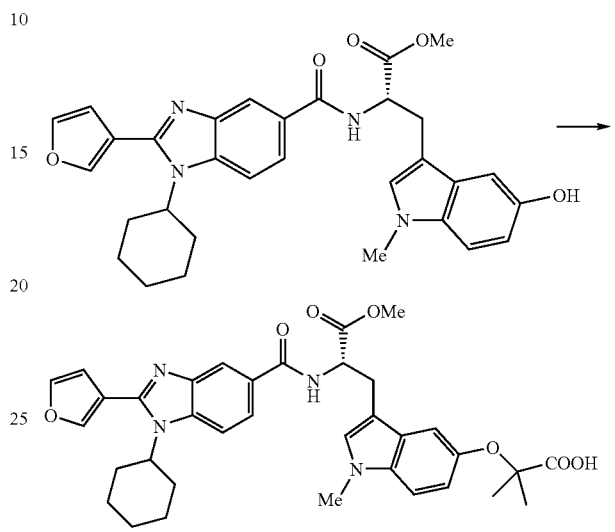

The title compound of example 114 (0.097 g, 0.18 mmol) was dissolved in acetone (1.5 mL). Cesium carbonate (0.175 g, 0.54 mmol) and tert-butylbromoisobutyrate (0.080 g, 0.36 mmol) were added and the mixture stirred at 60° C. overnight in a sealed tube. The reaction mixture was then diluted with water (10 mL) and the product extracted with EtOAc (50 mL). The organic phase was dried (MgSO$_4$), concentrated and the residue purified by flash chromatography using 60-80% EtOAc in hexane as eluent. The purified diester was dissolved in DCM (0.5 mL) and TFA (0.5 mL) was added. After stirring at room temperature for 1.5 h, volatiles were removed under a stream of nitrogen and the residue purified by preparative C18 reversed-phase HPLC to give the title compound of example 115.

Example 116

(S)-3-[5-(1-Carboxy-1-methyl-ethoxy)-1-methyl-1H-indol-3-yl]-2-{[1-(1-cyclohexyl-2-furan-3-yl-1H-benzimidazol-5-yl)-methanoyl]-amino}-propionic acid (Entry 11030, Table 11)

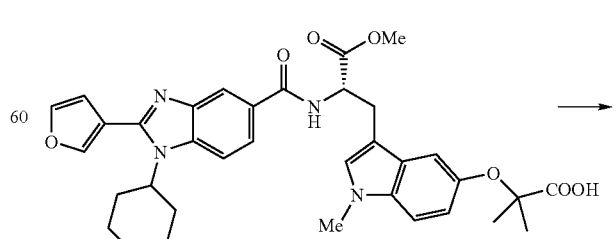

-continued

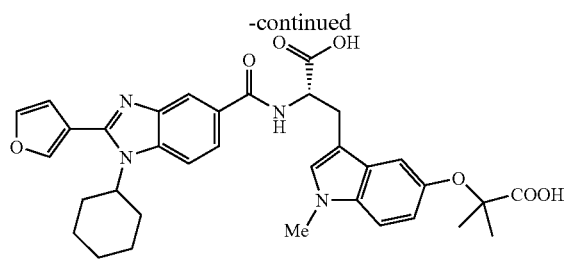

The title compound of example 115 (6 mg) was dissolved in DMSO (0.4 mL) and 2.5N NaOH (0.2 mL) was added. After stirring for 30 min at room temperature, the reaction mixture was acidified with TFA (0.1 mL) and the product of example 116 isolated directly by preparative C18 reversed-phase HPLC.

Example 117

2-[3-((S)-2-Carbamoyl-2-{[1-(1-cyclohexyl-2-furan-3-yl-1H-benzimidazol-5-yl)-methanoyl]-amino)-ethyl}-1-methyl-1H-indol-5-yloxy]-2-methyl-propionic acid (Entry 1176, Table 1)

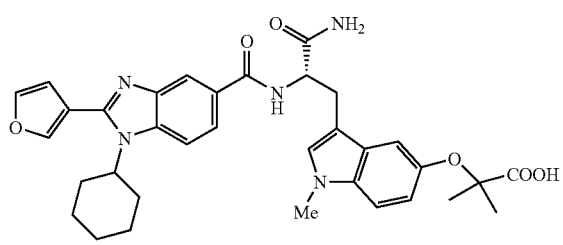

Following the procedure described for example 115, the title compound of example 113 was alkylated with tert-butyl-bromoisobutyrate and the protecting group removed to give the title compound of example 117 after purification by preparative C18 reversed-phase HPLC.

Example 118

[3-((S)-2-Carbamoyl-2-[{1-(1-cyclohexyl-2-furan-3-yl-1H-benzimidazol-5-yl)-methanoyl]-amino}-ethyl)-1-methyl-1H-indol-5-yloxy]-acetic acid (Entry 13003, Table 13)

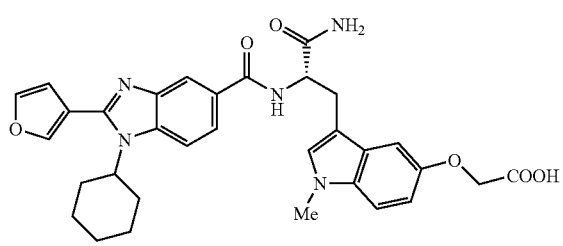

Following the procedure described for example 117, the title compound of example 113 was alkylated with tert-butyl-bromoacetate and the protecting group removed to give the title compound of example 118 after purification by preparative C18 reversed-phase HPLC.

Example 119

Substituted Racemic Phenylalanine Fragments

A variety of racemic substituted phenylalanine derivatives were prepared from the corresponding bromobenzene derivatives via palladium-catalyzed Heck coupling with 2-acetamido methyl acrylate as described in the scheme below. For this purpose, phenolic functions were protected as acetate and carboxyl groups as methyl esters. Following Heck coupling, the resulting protected dehydroamino acids were hydrogenated to the racemic phenylalanine derivatives which were deprotected to the free amino acids by hydrolysis under acidic conditions. Free carboxylic acid functions were then reprotected as methyl esters prior to coupling with the carboxylic acid of example 2. The following examples are representative and are meant to illustrate the process:

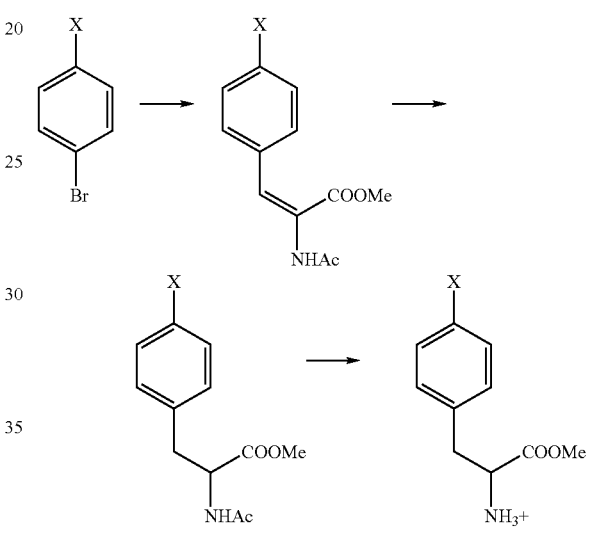

X = COOMe, OAc (meta or para to Br)
aromatic ring substituted with halo, Me, COOMe, OAc Racemic 3-fluoro-4-(carboxymethyl)phenylalanine methyl ester hydrochloride 4-Bromo-2-fluorobenzoic acid (3.00 g, 13.7 mmol) was dissolved in MeOH (25 mL) and thionyl chloride (1.5 mL, 20.1 mmol) was added dropwise. The mixture was refluxed overnight and then volatiles were removed under reduced pressure. The residue was triturated with a small amount of MeOH and the methyl ester collected by filtration (3.02 g).

The methyl ester from above (2.66 g, 11.4 mmol) was dissolved in MeCN (15 mL) and triethylamine (4.0 mL, 28.5 mmol) was added, followed by 2-acetamido methyl acrylate (1.80 g, 12.6 mmol) and tri-o-tolylphosphine (0.28 g, 0.91 mmol). The mixture was degassed with argon for 15 min and palladium acetate (0.17 g, 0.80 mmol) was added. Following an additional 15 min of degassing, the mixture was refluxed for 20 h. EtOAc was added and the solution washed with water, dried (MgSO$_4$) and concentrated. The residue was crystallized from EtOAc to give the desired dehydroamino ester (1.30 g).

The dehydroaminoester from above was dissolved in MeOH and hydrogenated over 20% Pd(OH)$_2$ under one atmosphere of hydrogen gas for 20 h. After removal of the catalyst by filtration and removal of the solvent under reduced pressure, the desired protected phenylalanine derivative was obtained.

The protected phenylalanine derivative from above (0.210 g, 0.71 mmol) was added to 4N HCl and the mixture refluxed overnight. Volatiles were then removed under vacuum to give the desired free amino acid as the hydrochloride salt (0.182 g). The fully deprotected phenylalanine derivative from above (0.187 g, 0.69 mmol) was dissolved in MeOH (30 mL) and thionyl chloride (3 mL) was added dropwise. The mixture was refluxed overnight and then evaporated under vacuum. The residue was triturated with MeOH to give the title compound (0.193 g).

Following adaptations of the above protocols, the following racemic phenylalanine esters were prepared:

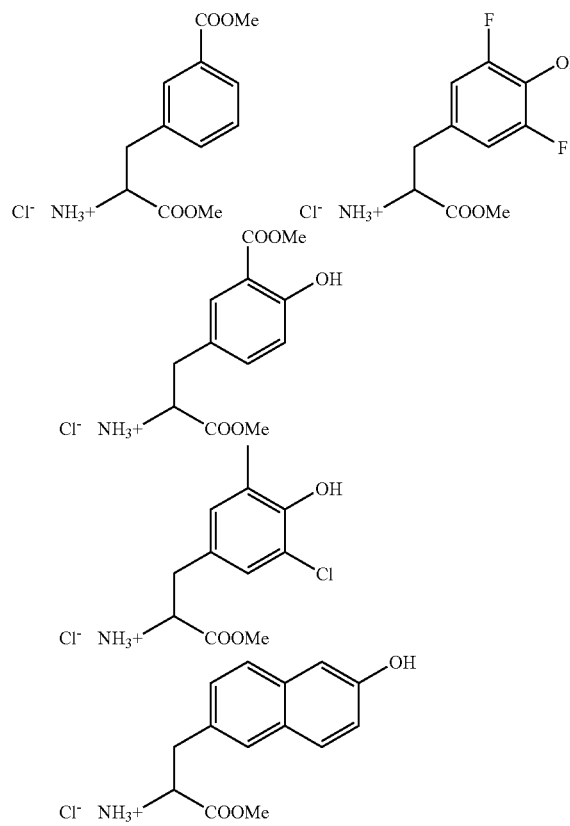

Example 120
Racemic 4-(2-Carboxy-2-{[1-(1-cyclohexyl-2-furan-3-yl-1H-benzimidazol-5-yl)-methanoyl]-amino}-ethyl)-2-fluoro-benzoic acid (Entry 1142, Table 1)

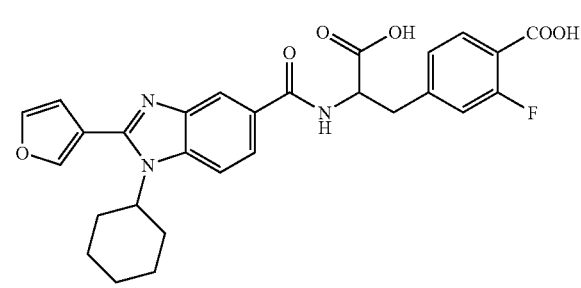

Racemic 3-fluoro-4-(carbomethoxy)phenylalanine methyl ester hydrochloride (example 119) was coupled to the carboxylic acid of example 2 in the usual manner and saponified to give the title compound of example 120.

Example 121

Racemic 5-(2-Carboxy-2-{[1-(1-cyclohexyl-2-furan-3-yl-1H-benzimidazol-5-yl)-methanoyl]-amino}-ethyl)-2-hydroxy-benzoic acid (Entry 16058, Table 16)

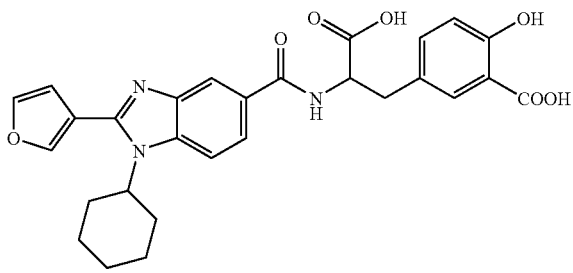

Racemic 3-(carbomethoxy)tyrosine methyl ester hydrochloride (example 119) was coupled to the carboxylic acid of example 2 in the usual manner and saponified to give the title compound of example 121.

Example 122

Racemic 3-(3-Chloro-4-hydroxy-5-methyl-phenyl)-2-{[1-(1-cyclohexyl-2-furan-3-yl-1H-benzimidazol-5-yl)-methanoyl]-amino}-propionic acid (Entry 1152, Table 1)

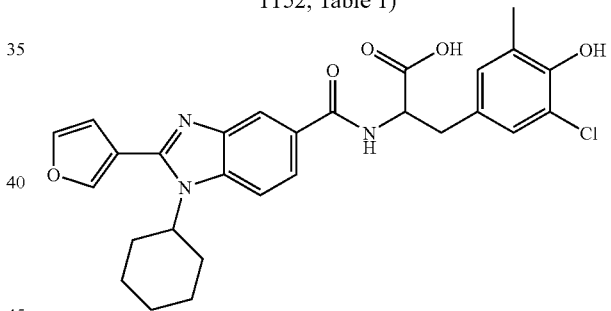

Racemic 3-chloro-5-methyltyrosine methyl ester hydrochloride (example 119) was coupled to the carboxylic acid of example 2 in the usual manner and saponified to give the title compound of example 121.

Example 123

Racemic 2-{[1-(1-Cyclohexyl-2-furan-3-yl-1H-benzimidazol-5-yl)-methanoyl]-amino}-3-(3,5-difluoro-4-hydroxy-phenyl)-propionic acid (Entry 1153, Table 1)

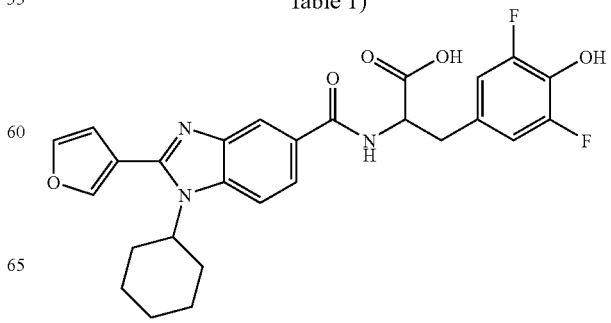

Racemic 3,5-difluorotyrosine methyl ester hydrochloride (example 119) was coupled to the carboxylic acid of example 2 in the usual manner and saponified to give the title compound of example 123.

Example 124

Racemic 3-(2-Carboxy-2-{[1-(1-cyclohexyl-2-furan-3-yl-1H-benzimidazol-5-yl)-methanoyl]-amino}-ethyl)-benzoic acid (Entry 16053, Table 16)

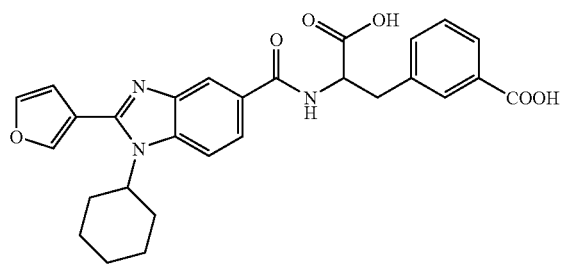

Racemic 3-(carbomethoxy)phenylalanine methyl ester hydrochloride (example 119) was coupled to the carboxylic acid of example 2 in the usual manner and saponified to give the title compound of example 1234.

Example 125

Racemic 3-(4-Carboxymethoxy-3,5-difluoro-phenyl)-2-({[1-(1-cyclohexyl-2-furan-3-yl-1H-benzimidazol-5-yl)-methanoyl]-amino}-propionic acid (Entry 1144, Table 1)

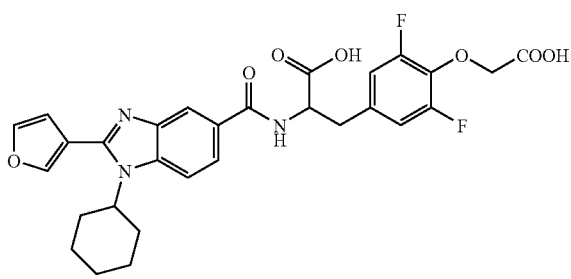

Racemic 3,5-difluorotyrosine methyl ester hydrochloride (example 119) was coupled to the carboxylic acid of example 2 in the usual manner. The phenolic hydroxyl group was alkylated with methyl bromoacetate in the usual manner ($K_2CO_3$/acetone at reflux) and ester groups saponified to give the title compound of example 125.

Example 126

Racemic 5-(2-Carboxy-2-{[1-(1-cyclohexyl-2-furan-3-yl-1H-benzimidazol-5-yl)-methanoyl]-amino}-ethyl)-2-carboxymethoxy-benzoic acid (Entry 16054, Table 16)

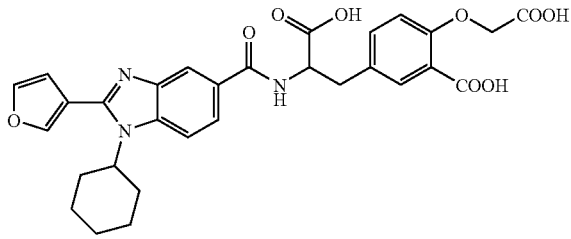

Racemic 3-(carbomethoxy)tyrosine methyl ester hydrochloride (example 119) was coupled to the carboxylic acid of example 2 in the usual manner. The phenolic hydroxyl group was alkylated with methyl bromoacetate in the usual manner ($K_2CO_3$/acetone at reflux) and saponified to give the title compound of example 126.

Example 127

Racemic 3-(4-Carboxymethoxy-3-chloro-5-methyl-phenyl)-2-{[1-(1-cyclohexyl-2-furan-3-yl-1H-benzimidazol-5-yl)-methanoyl]-amino}-propionic acid (Entry 16055, Table 16)

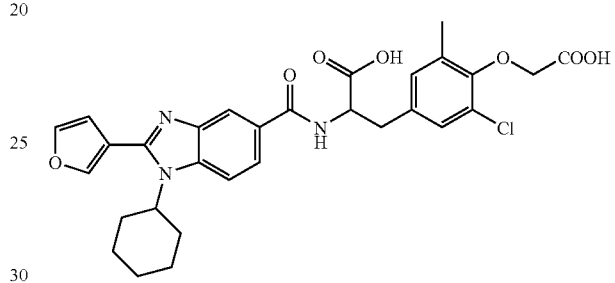

Racemic 3-chloro-5-methyltyrosine methyl ester hydrochloride (example 119) was coupled to the carboxylic acid of example 2 in the usual manner. The phenolic hydroxyl group was alkylated with methyl bromoacetate in the usual manner ($K_2CO_3$/acetone at reflux) and ester groups saponified to give the title compound of example 127.

Example 128

Racemic 2-{[1-(1-Cyclohexyl-2-furan-3-yl-1H-benzimidazol-5-yl)-methanoyl]-amino}-3-(6-hydroxy-naphthalen-2-yl)-propionic acid (Entry 21001, Table 21)

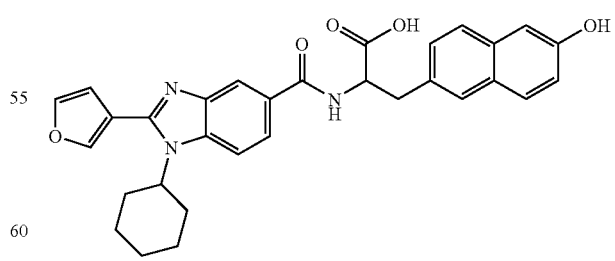

Racemic 5-hydroxynaphthylalanine methyl ester hydrochloride (example 119) was coupled to the carboxylic acid of example 2 in the usual manner and saponified to give the title compound of example 128.

Example 129

Racemic 3-(6-Carboxymethoxy-naphthalen-2-yl)-2-{[1-(1-cyclohexyl-2-furan-3-yl-1H-benzimidazol-5-yl)-methanoyl]-amino}-propionic acid (Entry 21002, Table 21)

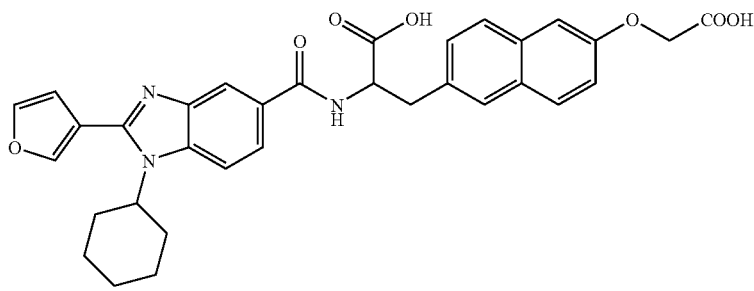

Racemic 5-hydroxynaphthylalanine methyl ester hydrochloride (example 119) was coupled to the carboxylic acid of example 2 in the usual manner. The phenolic hydroxyl group was alkylated with methyl bromoacetate in the usual manner ($K_2CO_3$/acetone at reflux) and ester groups saponified to give the title compound of example 129.

Example 130

1-Cyclohexyl-2-furan-3-yl-1H-benzimidazole-5-carboxylic acid [(S)-1-(2-amino-thiazol-4-yl)-2-(5-hydroxy-1-methyl-1H-indol-3-yl)-ethyl]-amide (Entry 14003, Table 14)

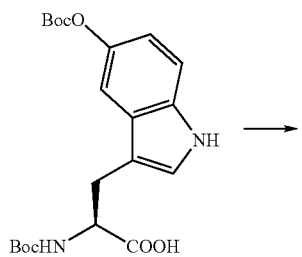

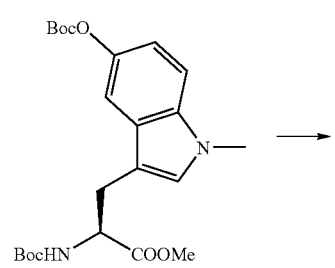

-continued

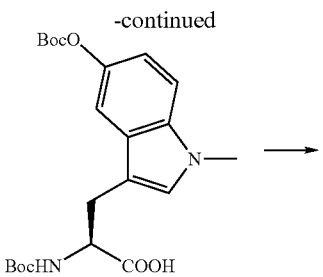

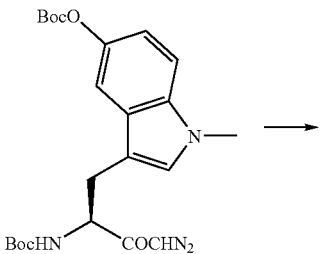

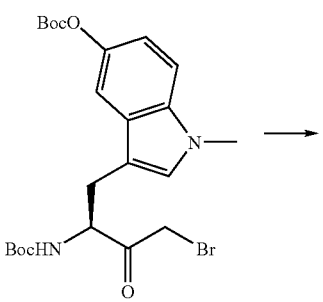

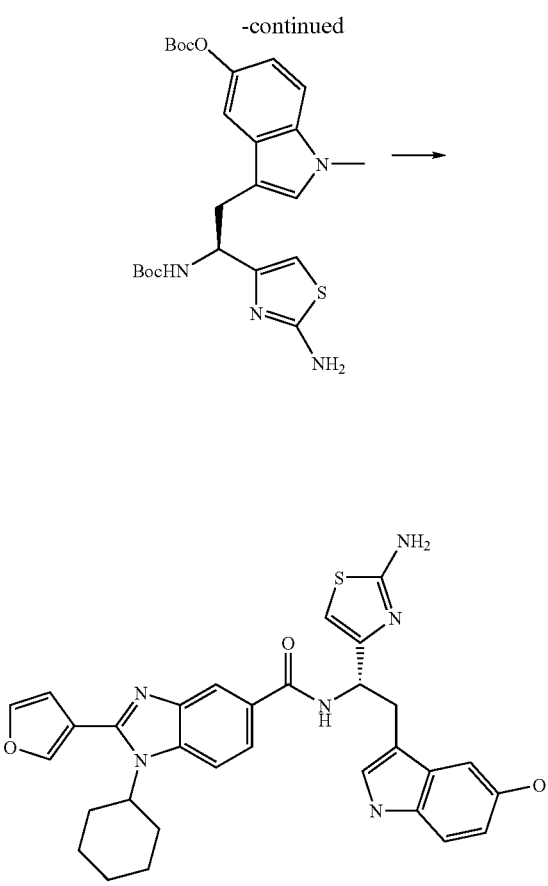

N,O-Bis-Boc-5-hydroxy-L-tryptophan (Example 86, 0.600 g, 1.43 mmol) was converted to its methyl ester using diazomethane in Et$_2$O. Following removal of volatiles under reduced pressure, the residue was dissolved in DMF and the solution cooled in ice. Iodomethane (0.178 mL, 2.86 mmol) was added followed by a 60% oil dispersion of NaH (0.086 g, 2.14 mmol). The mixture was stirred in the ice bath for 1 h and then quenched with AcOH (0.20 mL). Water (15 mL) was added and the mixture extracted with Et$_2$O (2×50 mL). The extract was dried (MgSO$_4$) and concentrated and the residue purified by flash chromatography (25%-50% EtOAc in hexane as eluent) to give the N-methyltryptophan derivative as a white foam (0.400 g).

The methyl ester from above (0.385 g, 0.86 mmol) was dissolved in THF (4 mL). Water (0.8 mL) and lithium hydroxide monohydrate (0.036 g, 0.86 mmol) was added and the mixture stirred vigorously for 1 h at room temperature. The mixture was poured into a solution of K$_2$CO$_3$ (1.0 g) in water (30 mL) and the solution washed with ether (2×25 mL). The aqueous phase was acidified to pH 4 by slow addition of 4 N HCl and extracted with Et$_2$O (2×25 mL). The extract was dried (Na$_2$SO$_4$) and evaporated to give the free carboxylic acid as a white foam (0.346 g).

The free acid from above (0.334 g, 0.77 mmol) was dissolved in THF (5 mL) and the solution cooled to −20 C. DIEA (0.200 mL, 1.15 mmol) and isobutylchloroformate (0.130 mL, 1.0 mmol) were added and the mixture stirred for 2 h at −20 C. Additional DIEA (0.100 mL) and isobutylchloroformate (0.065 mL) were added to complete the reaction (additional 30 min). Diazomethane (0.6 M in Et$_2$O, 10 ml) was added and stirring continued for another hour. Et$_2$O (100 mL) was added and the solution washed successively with 10% citric acid (2×20 mL) and saturated aqueous NaHCO$_3$ (20 mL). The extract was dried (MgSO$_4$) and concentrated to give a residue that was purified by flash chromatography using 40-50% EtOAc in hexane as eluent. The diazomethylketone derivative (0.294 g) was obtained as a yellow foam.

The diazomethylketone was converted to the bromomethylketone with 48% HBr in AcOH as described previously (Example 86).

The bromomethylketone from above was converted to the aminothiazole derivative with thiourea as described previously (Example 91).

The thiazole derivative obtained above was deprotected using 50% TFA in DCM and the hydrochloride derivative was coupled to the carboxylic acid of example 2 to give the title compound of example 130.

Example 131

(S)-3-[5-(2-{[2-(Bis-carboxymethyl-amino)-ethyl]-carboxymethyl-amino}-ethanoylamino)-1H-indol-3-yl]-2-{[1-(cyclohexyl-furan-3-yl-1H-benzimidazol-5-yl)-methanoyl]-amino}-propionic acid (Entry 111031, Table 11)

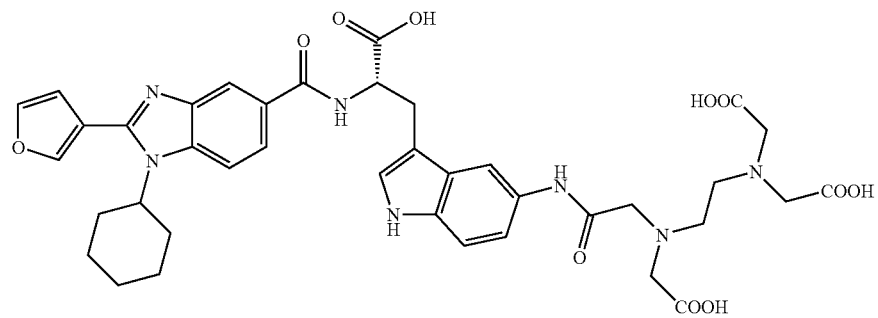

The 5-aminotryptophan methyl ester derivative of example 48 was coupled to ethylenediamine tetraAcetic acid trimethylester in the usual manner and the product saponified to give the title compound of example 131.

Example 132

1-Cyclohexyl-2-furan-3-yl-1H-benzimidazole-5-carboxylic acid [(S)-1-(2-hydroxy-1-hydroxymethyl-ethylcarbamoyl)-2-(5-hydroxy-1H-indol-3-yl)-ethyl]-amide (Entry 13014, Table 13)

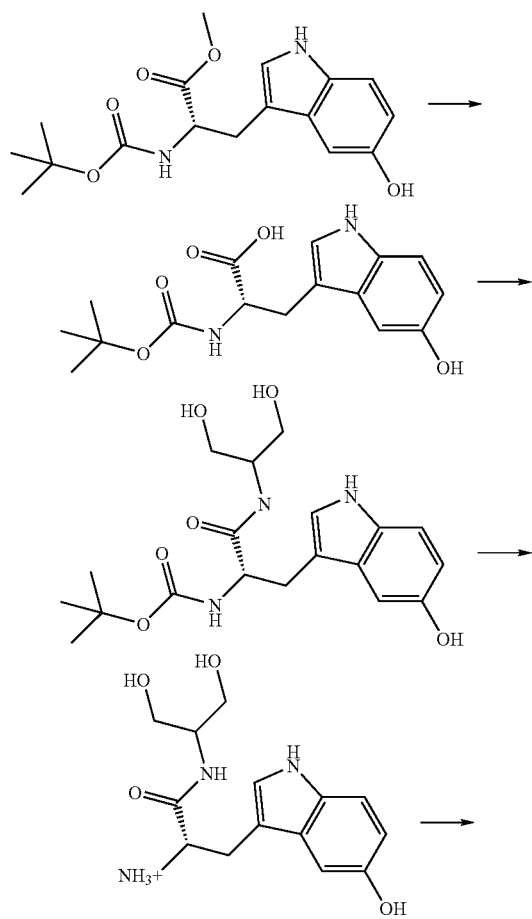

-continued

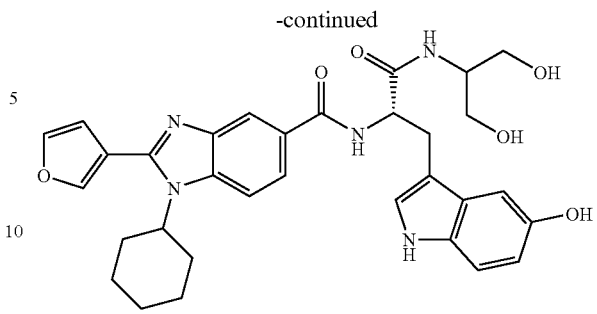

N-Boc-5-hydroxytryptophan methyl ester (example 113, 0.500 g, 1.5 mmol) was dissolved in MeOH (4 mL) and 2 N NaOH (2.24 mL, 4.5 mmol) was added. The mixture was stirred under an atmosphere of argon for 3 h. The solution was then added to a vigorously stirred 1 N KHSO$_4$ (15 mL). After 10 min the solid was filtered and air dried 18 h.

To the carboxylic acid prepared above (0.157 g, 0.5 mmol) in DMF (2 mL) were added TBTU (0.157 g, 0.5 mmol) and DIEA (256 µL, 1.5 mmol). The solution was stirred 30 min at room temperature and serinol (0.045 g, 0.5 mmol) was added. After 2 h the solution was poured into 50% NaCl (100 mL) and the product extracted with EtOAC (25 mL). The organic solution was washed with 5% citric acid (2×50 mL), 5% NaHCO$_3$ (3×50 mL) and brine (50 mL). The extract was dried (MgSO$_4$) and evaporated to yield 105 mg of the 5-hydroxytryptophan amide.

The Boc derivative prepared above was deprotected with 4N HCl-dioxane and coupled with the acid of example 2 in the usual manner to give the title compound of example 132.

Example 133

1-Cyclohexyl-2-furan-3-yl-1H-benzimidazole-5-carboxylic acid [(S)-1-(2-dimethylamino-ethylcarbamoyl)-2-(5-hydroxy-1H-indol-3-yl)-ethyl]-amide (Entry 13015, Table 15)

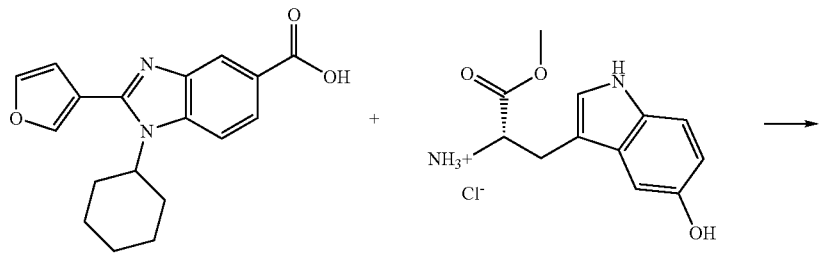

151 152
-continued
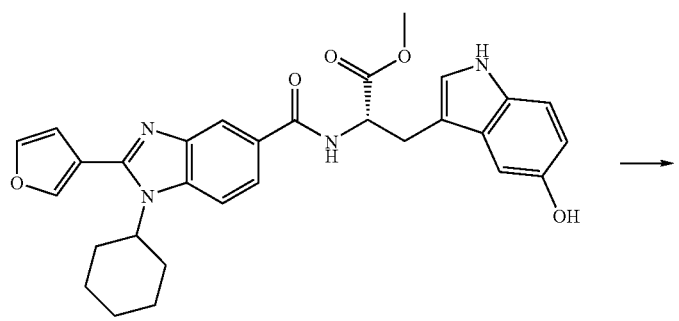
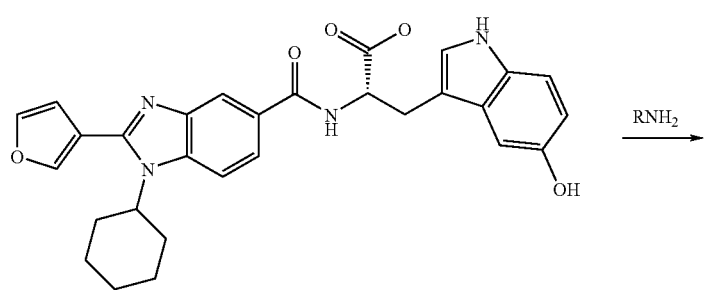
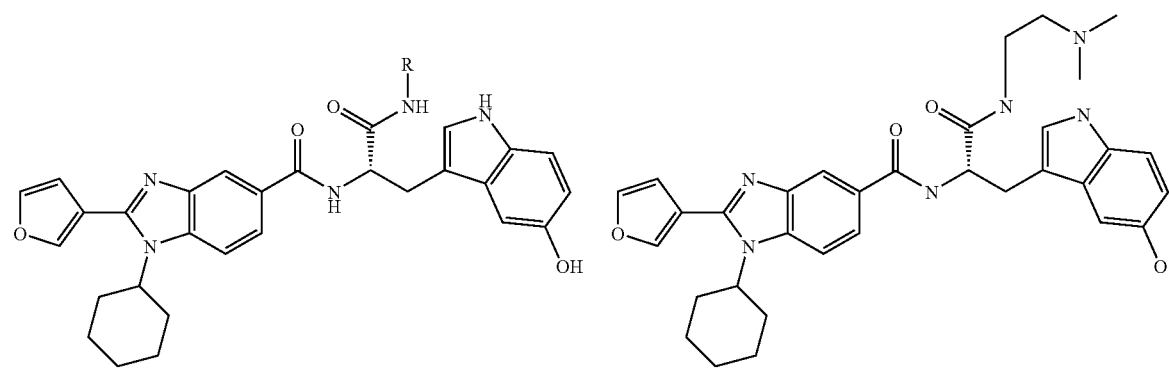

The carboxylic acid from example 2 was coupled to (S)-5-hydroxytryptophan methyl ester hydrochloride and the methyl ester saponified in the usual manner.

The carboxylic acid from above was coupled with N,N-dimethylethylene diamine under standard TBTU conditions example to yield the title compound of example 133.

Example 134

1-Cyclohexyl-2-furan-3-yl-1H-benzimidazole-5-carboxylic acid [(S)-1-(2-hydroxy-ethylcarbamoyl)-2-(5-hydroxy-1H-indol-3-yl)-ethyl]-amide (Entry 13016, Table 13)

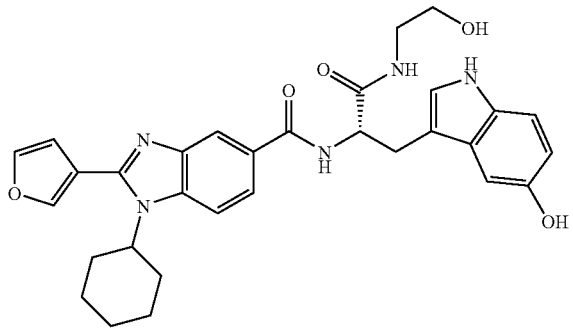

The carboxylic acid from example 133 was coupled to aminoethanol under standard TBTU conditions to yield the title compound of example 134.

Example 135

1-Cyclohexyl-2-furan-3-yl-1H-benzimidazole-5-carboxylic acid [(S)-2-(5-hydroxy-1H-indol-3-yl)-1-(2-morpholin-4-yl-ethylcarbamoyl)-ethyt]-amide (Entry 13017, Table 13)

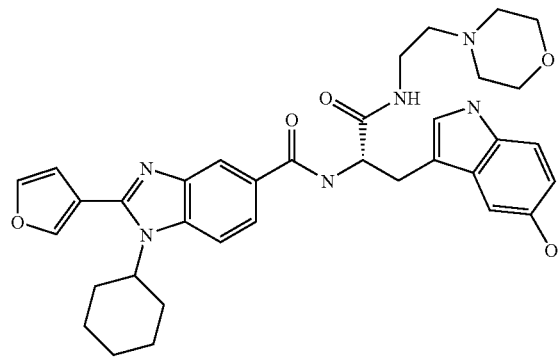

The carboxylic acid of example 133 was coupled to aminoethylmorpholine under standard TBTU conditions to yield the title compound of example 135.

Example 136

1-Cyclohexyl-2-furan-3-yl-1H-benzimidazole-5-carboxylic acid [(S)-1-(3-dimethylamino-propylcarbamoyl)-2-(5-hydroxy-1H-indol-3-yl)-ethyl]-amide (Entry 13018, Table 13)

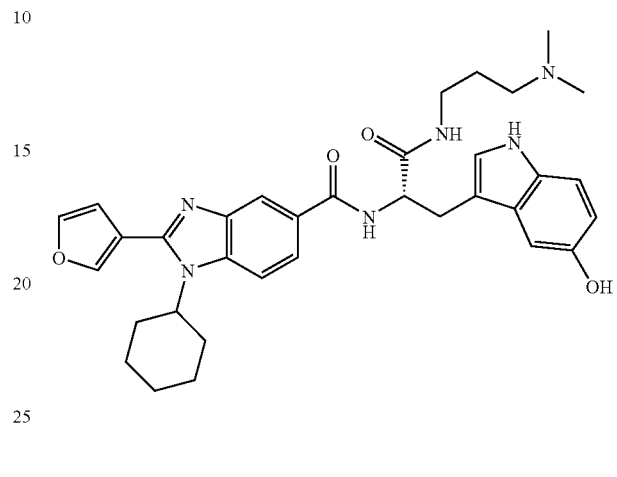

The carboxylic acid of example 133 was coupled to dimethylaminopropylamine under standard TBTU conditions to yield the title compound of example 136.

Example 137

1-Cyclohexyl-2-furan-3-yl-1H-benzimidazole-5-carboxylic acid [(S)-2-(5-hydroxy-1H-indol-3-yl)-1-(2-pyrrolidin-1-yl-ethylcarbamoyl)-ethyl]-amide (Entry 13019, Table 13)

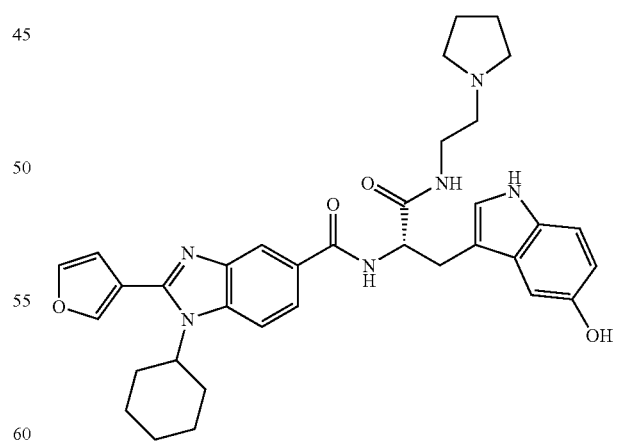

The carboxylic acid of example 133 was coupled to 1-(2-aminoethyl)pyrrolidine under standard TBTU conditions to yield the title compound of example 137.

Example 138

1-Cyclohexyl-2-furan-3-yl-1H-benzimidazole-5-carboxylic acid {(S)-2-(5-hydroxy-1H-indol-3-yl)-1-[2(RS)-(1-methyl-pyrrolidin-2-yl)-ethylcarbamoyl]-ethyl}-amide (Entry 13020, Table 13)

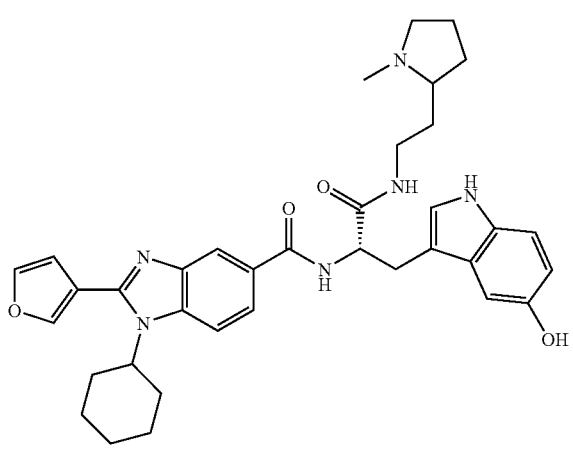

The carboxylic acid of example 133 was coupled to 2-(2-aminoethyl-1-methyl) pyrrolidine under standard TBTU conditions to yield the title compound of example 138.

Example 139

1-Cyclohexyl-2-furan-3-yl-1H-benzimidazole-5-carboxylic acid [(S)-1-(2-hydroxy-1,1-dimethyl-ethylcarbamoyl)-2-(5-hydroxy-1H-indol-3-yl)-ethyl]-amide (Entry 13021, Table 13)

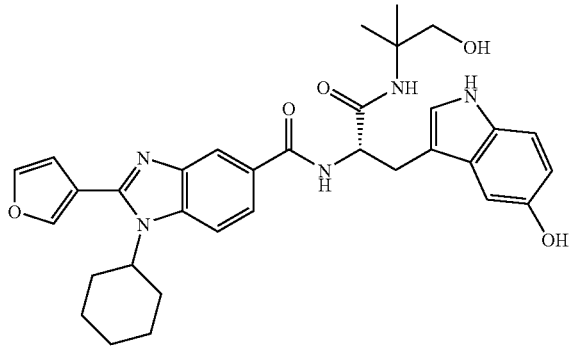

The carboxylic acid of example 133 was coupled to 2-amino-2-methyl-1-propanol under standard TBTU conditions to yield the title compound of example 139.

Example 140

1-Cyclohexyl-2-furan-3-yl-1H-benzimidazole-5-carboxylic acid [(S)-1-(2(RS),3-dihydroxy-propyl-carbamoyl)-2-(5-hydroxy-1H-indol-3-yl)-ethyl]-amide(Entry 13022, Table 13)

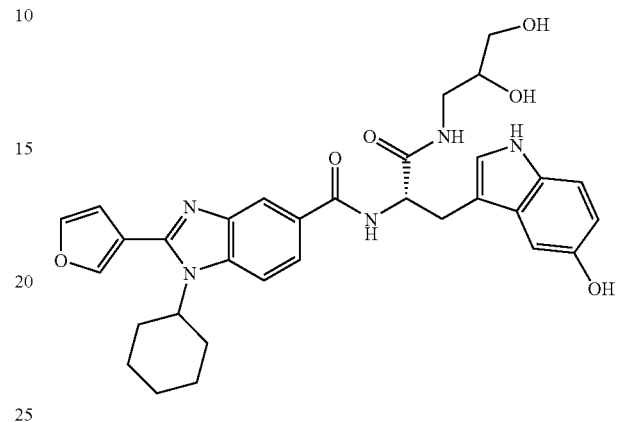

The carboxylic acid of example 133 was coupled to racemic 3-amino-1,2-propanediol under standard TBTU conditions to yield the title compound of example 140.

Example 141

(S)-3-{[1-(1-Cyclohexyl-2-furan-3-yl-1H-benzimi-dazol-5-yl)-methanoyl]-amino}-4-(4-hydroxy-phenyl)-butyric acid (Entry 1230, Table 1)

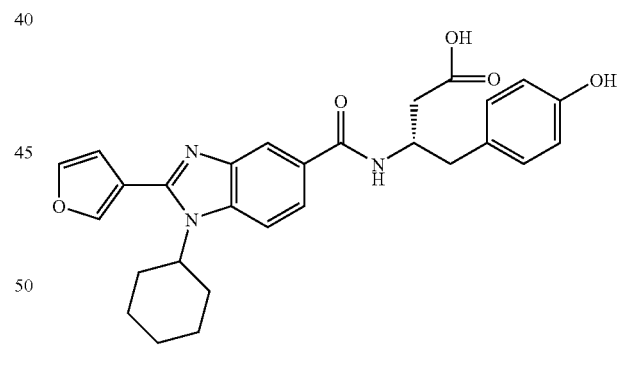

The diazomethylketone derived from Bis-Boc-Tyr (Example 64, 0.750 g, 1.85 mmol) was dissolved in a 1/1 mixture of THF/MeOH (10 mL). A solution of silver benzoate (50 mg) in triethylamine (1 mL) was added. After 15 min of stirring at room temperature the solvent was evaporated and the residue purified by flash chromatography (gradient 10-25% EtOAc/hexane) to yield 749 mg of protected tyrosine methyl ester.

The bis-Boc derivative prepared above was deprotected with 4N HCl in dioxane and coupled with the acid of example

Example 142

(E)-3-[5-((S)-2-Carbamoyl-2-{[1-(1-cyclohexyl-2-furan-3-yl-1H-benzimidazol-5-yl)-methanoyl]-amino}-ethyl)-2-hydroxy-phenyl]-acrylic acid (Entry 16062, Table 16)

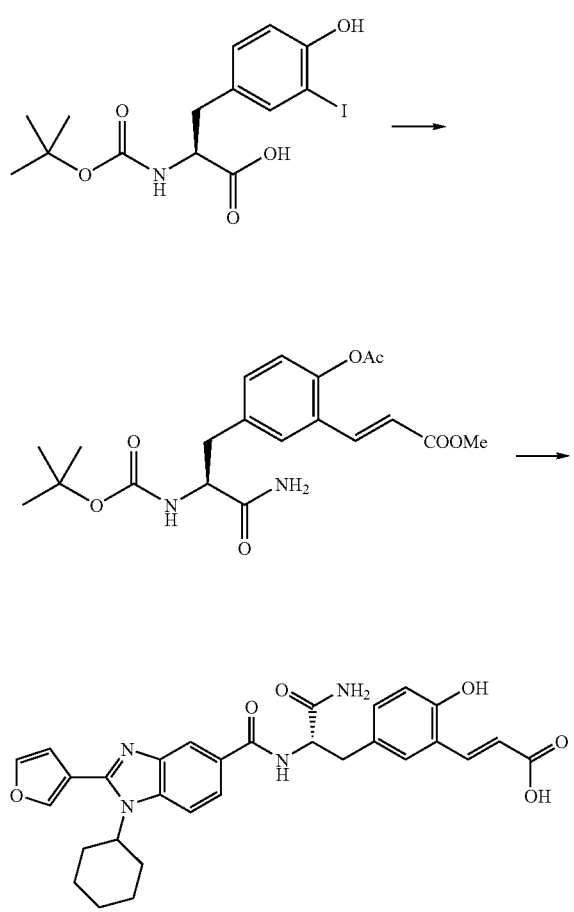

To a solution of N-Boc-3-iodotyrosine (0.380 g, 0.93 mmol) in pyridine (1 mL) were added acetic anhydride (105 μL, 1.1 mmol) and DMAP (10 mg, cat). The solution was stirred 1.5 h then diluted in 5% citric acid (20 mL), and the product extracted with EtOAc. The organic solution was evaporated and the residue dissolved in MeCN (4 mL). To the stirred cold (ice bath) solution were added EDC (0.196 g, 1.0 mmol) and HOBt (0.135 g, 1.0 mmol). After stirring for 1 h, a 2 N solution of ammonia in iPrOH (3 mL) was added. The suspension was stirred 1 h at 5° C., the solid was filtered, the filtrate evaporated and the residue purified by flash chromatography (gradient 3-5% MeOH/chloroform) to yield N-Boc-O-acety-3-iodotyrosine amide.

The iodo tyrosine derivative prepared above was coupled to methyl acrylate according to the procedure of example 83: MS (ES+) m/z 307 (MH⁺-Boc). The N-Boc-tyrosine derivative prepared above was deprotected with 4 N HCl in dioxane and coupled with the acid of example 2 in the usual manner. Following saponification of the O-acetyl group the title compound of example 142 was obtained.

2 in the usual manner. Following saponification of the methyl ester, the title compound of example 141 was obtained.

Example 143

4-{N'-[1-(1-Cyclohexyl-2-furan-3-yl-1H-benzimidazol-5-yl)-methanoyl]-hydrazinocarbonyl}-benzoic acid (Entry 1302, Table 1)

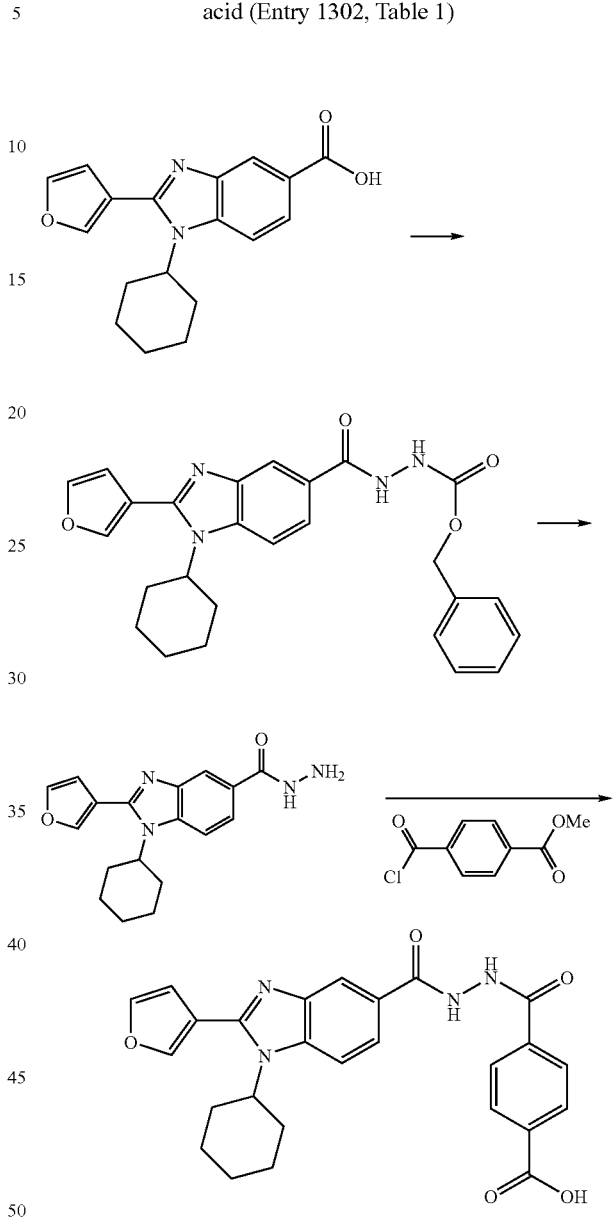

The benzimidazole carboxylic acid of example 2 (0.500 g, 1.61 mmol) was stirred in DMF (10 mL) with N-Cbz-hydrazine (0.268 g, 1.61 mmol), TBTU (0.620 g, 1.93 mmol) and DIEA (0.727 g, 563 mmol) for 3 days. EtOAc was added and the reaction mixture was washed twice with 10% aqueous citric acid, twice with saturated aqueous NaHCO₃ and once with brine. The organic layer was dried over anhydrous MgSO₄, filtered and concentrated to give a brown foam that was hydrogenolyzed in THF—EtOH (1:1) with 10% Pd/C (70 mg) under an atmosphere of hydrogen for 8 h. The suspension was filtered and concentrated to dryness to give 1-cyclohexyl-2-furan-3-yl-1H-benzoimidazole-5-carboxylic acid hydrazide as a brown foam.

1-Cyclohexyl-2-furan-3-yl-1H-benzoimidazole-5-carboxylic acid hydrazide (0.022 g, 0.068 mmol) and methyl-4-chlorocarbonylbenzoate (0.013 g, 0.068 mmol) were stirred in DMF (1 mL) in the presence of DIEA (0.018 g, 0.14 mmol) for 2 h. An aqueous solution of NaOH (2.5 N, 0.22 mL, 0.55 mmol) was then added and the mixture was stirred for 2 h at room temperature. The reaction mixture was acidified by the addition of AcOH and purified by reversed phase C18 preparative HPLC to give the title compound of example 143.

Example 144

Racemic 1-cyclohexyl-2-furan-3-yl-1H-benzimidazole-5-carboxylic acid 1-carboxy-2-(4-carboxymethoxy-phenyl)-ethyl ester (Entry 5005, Table 5)

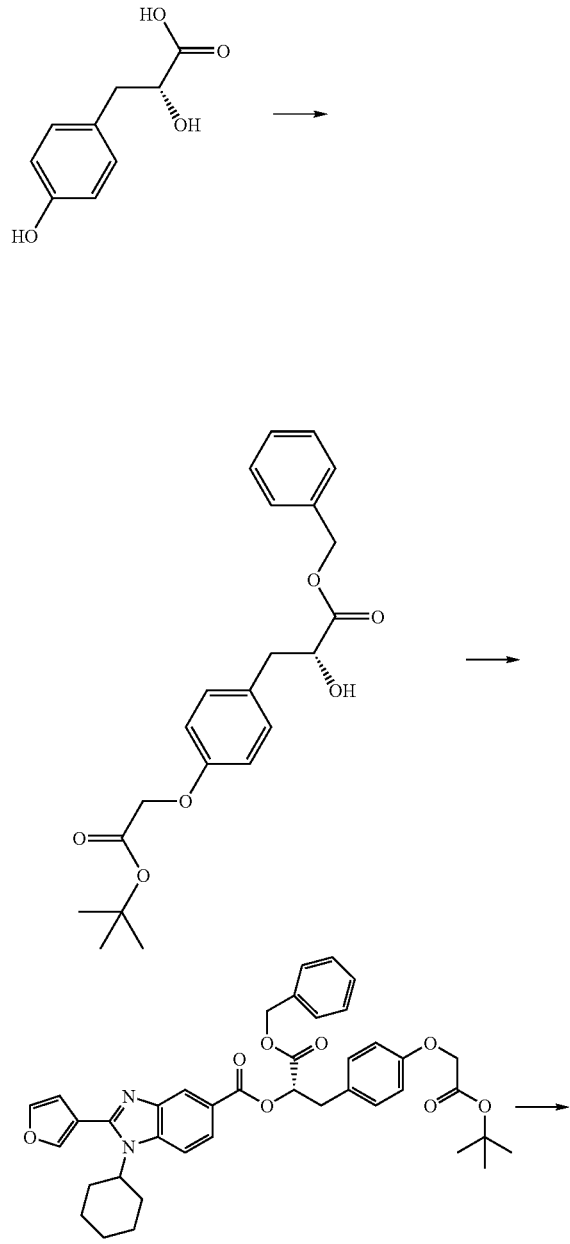

-continued

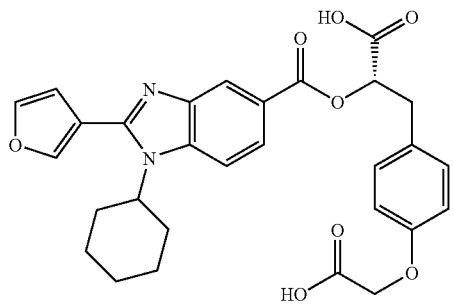

Racemic 2-hydroxy-3-(4-hydroxyphenyl)-propionic acid (0.100 g, 0.55 mmol) was stirred in acetone (10 mL) with triethylamine (0.17 mL, 1.2 mmol) and benzyl bromide (0.14 mL, 2.2 mmol) for 16 h at room temperature. The mixture was concentrated to dryness, taken up in EtOAc and washed once with water and twice with brine, dried over anhydrous MgSO$_4$, filtered and concentrated to dryness. The crude product was purified by flash chromatography to give the benzyl ester (150 mg). The ester (150 mg) was then dissolved in acetone (10 mL), t-butyl bromoacetate (0.1 mL, 0.65 mmol) and cesium carbonate (0.540 g, 1.7 mmol) were added and the reaction was stirred at 50° C. for 2.5 h. The mixture was concentrated to dryness, taken up in EtOAc and washed once with water and twice with brine, dried over anhydrous MgSO$_4$, filtered and concentrated to dryness. The crude product was purified by flash column chromatography, using 20% EtOAc in hexane as eluent, to give 3-(4-t-butoxycarbonylmethoxyphenyl)-2-hydroxy-propionic acid benzyl ester in 70% yield (146 mg).

To a solution of the above compound (0.060 g, 0.155 mmol) in DCM (5 mL), the carboxylic acid of example 2 (0.058 g, 0.19 mmol), DCC (0.039 g, 0.19 mmol) and DMAP (0.023 g, 0.19 mmol) were added and the reaction mixture was stirred at room temperature for 16 h. The reaction mixture was then concentrated and purified by flash chromatography to give 160 mg of 1-cyclohexyl-2-furan-3-yl-1H-benzoimidazole-5-carboxylic acid 1-benzyloxycarbonyl-2-(4-tert-butoxycarbonylmethoxy-phenyl)-ethyl ester.

The benzyl ester from above (0.040 g, 0.059 mmol) was stirred in a mixture of EtOAc:EtOH (4 mL, 3:1 ratio) with 10% Pd/C (10 mg) under an atmosphere of hydrogen gas for 4 h. The suspension was filtered and concentrated, then dissolved in 1 mL of 4 N HCl in dioxane and stirred for 1 h. The mixture was concentrated to dryness and purified by reversed phase C18 preparative HPLC to give the title compound of example 143.

Example 145

Racemic 2-(3-{[1-(1-Cyclohexyl-2-furan-3-yl-1H-benzimidazol-5-yl)-methanoyl]-amino}-propanoylamino)-3-(3H-imidazol-4-yl)-propionic acid (Entry 1228, Table 1)

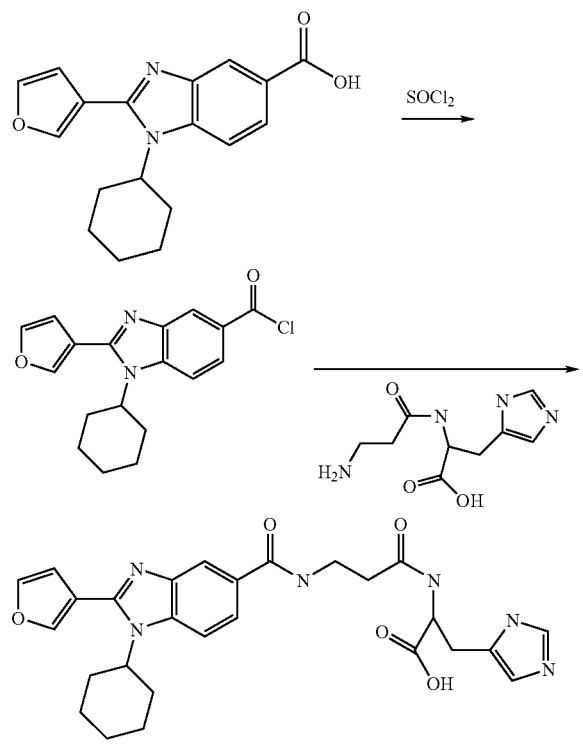

The carboxylic acid of example 2 (0.550 g, 1.8 mmol) was dissolved in SOCl₂ (20 mL) and DMF (~0.1 mL). The reaction mixture was stirred at room temperature for 20 h and then concentrated to dryness and co-evaporate with EtOAc to give a 1-cyclohexyl-2-furan-3-yl-1H-benzoimidazole-5-carbonyl chloride as a brown solid (580 mg). The acid chloride (0.050 g, 0.16 mmol) was dissolved in DMF (1 mL) and reacted with 1-carnosine (0.036 g, 0.159 mmol) in the presence of DIEA (82 μL, 0.476 mmol). The reaction mixture was stirred for 3 days at room temperature before it was acidified with AcOH (1 mL) and purified by reversed phase C18 preparative HPLC. The title compound of example 145 was obtained as a white solid.

Example 146

(S)-3-(3-Azido-4-hydroxy-phenyl)-2-{[1-(1-cyclohexyl-2-furan-3-yl-1H-benzimidazol-5-yl)-methanoyl]-amino}-propionic acid (Entry 1248, Table 1)

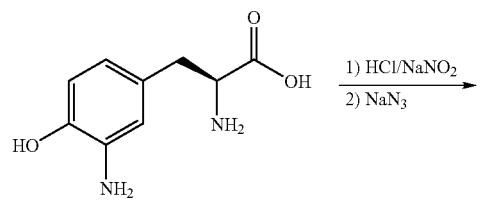

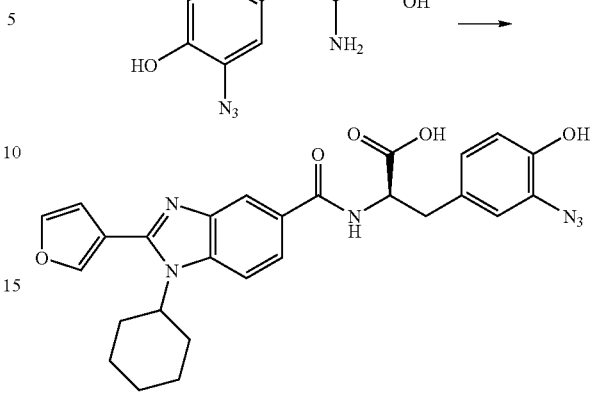

To a solution of 3-amino-L-tyrosine.2HCl.H₂O (2.50 g, 8.8 mmol) in 0.5 N HCl (28 mL) at 0° C., an aqueous solution of NaNO₂ (0.724 g, 10.5 mmol, in 10 mL H₂O) was added slowly. The reaction mixture was stirred for 10 min at 0° C., in the dark, and then a solution of NaN₃ (1.43 g, 21.9 mmol, in 10 mL H₂O) was added and stirring was continued for 1 h at 0° C. The white solid formed was filtered and dried to give (S)-2-amino-3-(3-azido-4-hydroxy-phenyl)-propionic acid (1.16 g) as of a beige solid. This amino acid was coupled to the carboxylic acid of example 2 in the usual manner to give the title compound of example 146 after purification by preparative C18 reversed-phase HPLC.

Example 147

(S)-3-(3-Azido-4-carboxymethoxy-phenyl)-2-{[1-(1-cyclohexyl-2-furan-3-yl-1H-benzimidazol-5-yl)-methanoyl]-amino}-propionic acid (Entry 16063, Table 16)

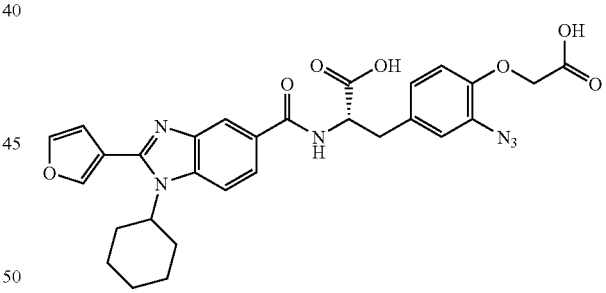

(S)-3-(3-Azido-4-hydroxy-phenyl)-2-{[1-(1-cyclohexyl-2-furan-3-yl-1 H-benzoimidazol-5-yl)-methanoyl]-amino}-propionic acid (Example 146, 0.230 g, 0.44 mmol) and methyl bromoacetate (0.136 g, 0.89 mmol) were stirred in acetone (4 mL) in the presence of Cs₂CO₃ (0.058 g, 0.18 mmol) for 20 h at room temperature. The reaction mixture was concentrated to dryness and dissolved in water, acidify to pH 4 and extracted with EtOAc (3x). The combined organic layers were dried over anhydrous MgSO₄ and concentrated to give a brown oil. This oil was stirred in THF:MeOH (6 mL, 2:1 ratio) in the presence of LiOH monohydrate (0.18 mmol) for 3 h at room temperature. The reaction mixture was concentrated to remove most of the THF and MeOH, acidified with AcOH and purified by reversed phase C18 preparative HPLC to obtain the title compound of example 147.

Example 148

1-Cyclohexyl-2-furan-3-yl-1H-imidazo[4,5-b]pyridine-5-carboxylic acid (Entry 5001, Table 5)

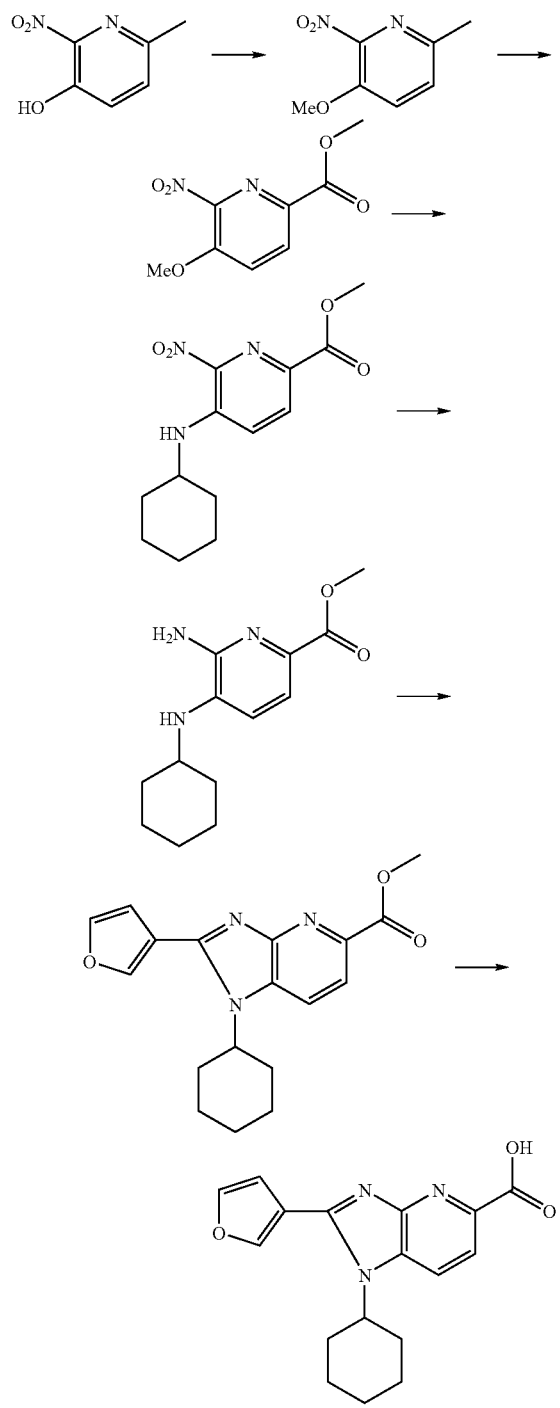

3-Methoxy-6-methyl-2-nitro-pyridine

A solution of 3-hydroxy-6-methyl-2-nitropyridine (4.00 g, 26 mmol) in MeOH—DCM (30 mL, 2:1 ratio) was treated with diazomethane in $Et_2O$ until all starting material was converted to 3-methoxy-6-methyl-2-nitropyridine (TLC). The solution was concentrated to dryness to give the desired product as a yellow solid (4.25 g).

5-Methoxy-6-nitro-pyridine-2-carboxylic acid methyl ester

A solution of 3-methoxy-6-methyl-2-nitro-pyridine (2.25 g, 13.4 mmol) in $H_2O$ containing $MgSO_4$ (5.24 g, 43.7 mmol) was heated to reflux. A solution of $KMnO_4$ (5.72 g, 36.2 mmol) was added slowly over a period of 1 h and reflux was maintained for an additional 5 h. The reaction mixture was cooled to room temperature and concentrated ammonia was added (6 mL). The brown solid formed was filtered and washed twice with water. The filtrate was concentrated and the new precipitate formed, composed mostly of starting material, was removed by filtration. The filtrate was acidified and extracted twice with EtOAc. The combined organic layers were washed with brine and dried over anhydrous $MgSO_4$, filtered and concentrated. The residue was taken up in MeOH-DCM (40 mL, 1:1 ratio) and a solution of diazomethane in $Et_2O$ was added until a persisting yellow color was observed. The solution was then concentrated to dryness and purify by flash column chromatography, using a gradient of hexane/EtOAc from 6/4 to 4/6 as the eluent, to give 5-methoxy-6-nitro-pyridine-2-carboxylic acid methyl ester (585 mg).

5-Cyclohexylamino-6-nitro-pyridine-2-carboxylic acid methyl ester

A solution of 5-methoxy-6-nitro-pyridine-2-carboxylic acid methyl ester (0.585 g, 2.75 mmol) and cyclohexylamine (0.636 mL, 5.51 mmol) in DMF (8 mL) was heated at 70° C. for 20 h. The mixture was poured on brine (50 mL) while mixing vigorously. The solid formed was filtered, washed with water and then dissolved in EtOAc. The solution was washed with water, saturated $NaHCO_3$ and brine, dried over anhydrous $MgSO_4$, filtered and concentrated to give 5-cyclohexylamino-6-nitro-pyridine-2-carboxylic acid methyl ester as a brown oil (0.558 g) which was used in the subsequent step without purification.

6-Amino-5-cyclohexylamino-pyridine-2-carboxylic acid methyl ester

The crude 5-cyclohexyl-6-nitro-pyridine-2-carboxylic acid methyl ester from above (0.530 g, 1.90 mmol) was stirred in EtOH (10 mL) and 10% Pd/C (50 mg), under 1 atm of $H_2$ gas at room temperature for 3 days. The suspension was filtered through a pad of celite and concentrated to dryness. The product was purified by flash column chromatography, using a gradient from 60% hexane in EtOAc to 100% EtOAc as the eluent, to give 6-amino-5-cyclohexylamino-pyridine-2-carboxylic acid methyl ester (0.210 g).

1-Cyclohexyl-2-furan-3-yl-1H-imidazo[4,5-b]pyridine-5-carboxylic acid methyl ester To a solution of the methyl ester from above (0.100 g, 0.40 mmol) in DMF (3 mL) and $H_2O$ (0.300 mL), oxone® (0.813 g, 1.32 mmol) and 3-furaldehyde (0.138 g, 1.32 mmol) were added. The reaction mixture was stirred at room temperature for 5 h and then stored at 5° C. for 3 days. The mixture was diluted with EtOAc and washed twice with water, twice with saturated $NaHCO_3$ and once with brine. The organic layer was then dried over magnesium sulfate, filtered and concentrated to give an oil that was purified by flash chromatography, using EtOAc as the eluent, to give 1-cyclohexyl-2-furan-3-yl-1H-imidazo[4,5-b]pyridine-5-carboxylic acid methyl ester (0.058 g).

1-Cyclohexyl-2-furan-3-yl-1H-imidazo[4,5-b]pyridine-5-carboxylic acid (Entry 5001, Table 5)

The ester from above (0.058 g, 0.178 mmol) was dissolved in MeOH (2 mL) and aqueous LiOH (0.700 mL, 1 M) was added. The solution was stirred at room temperature for 2 h and then purified by C18 reversed phase preparative HPLC to give the title compound of example 148.

Example 149

(S)-2-{[1-(1-Cyclohexyl-2-furan-3-yl-1H-imidazo[4,5-b]pyridin-5-yl)-methanoyl]-amino}-3-(5-hydroxy-1H-indol-3-yl)-propionic acid (Entry 5002, Table 5)

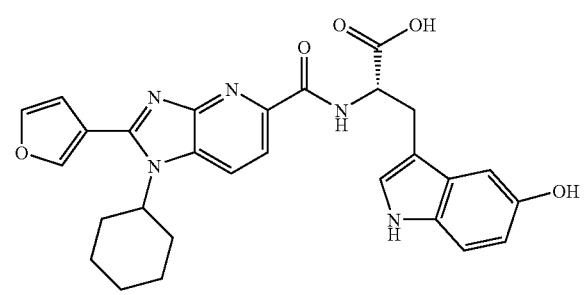

The carboxylic acid derivative of example 148 was coupled to 5-hydroxy-(S)-tryptophan methyl ester hydrochloride in the usual manner. Saponification followed by purification by preparative C18 reversed-phase HPLC gave the title compound of example 149.

Example 150

(S)-3-(5-Carboxymethoxy-1-carboxymethyl-1H-indol-3-yl)-2-{[1-(1-cyclohexyl-2-furan-3-yl-1H-imidazo[4,5-b]pyridin-5-yl)-methanoyl]-amino}-propionic acid (Entry 5003, Table 5)

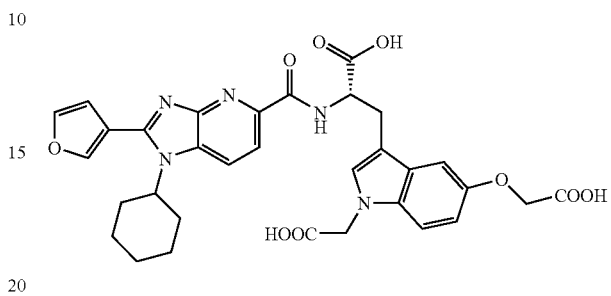

The carboxylic acid derivative of example 148 was coupled to 5-hydroxy-(S)-tryptophan methyl ester hydrochloride in the usual manner. The material was then alkylated with excess methyl bromoacetate as described previously to give after deprotection by saponification and preparative C18 reversed-phase HPLC, the title compound of example 150.

Example 151

1-Cyclohexyl-2-furan-3-yl-4-methyl-1H-benzimidazole-5-carboxylic acid (Entry 5004, Table 5)

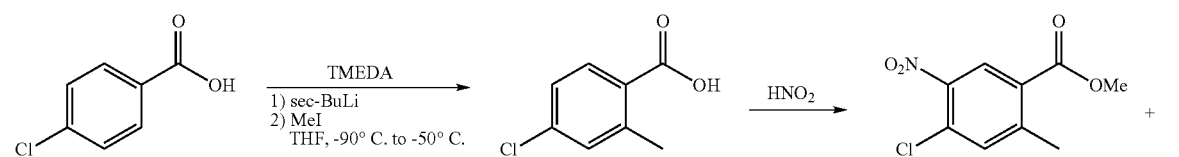

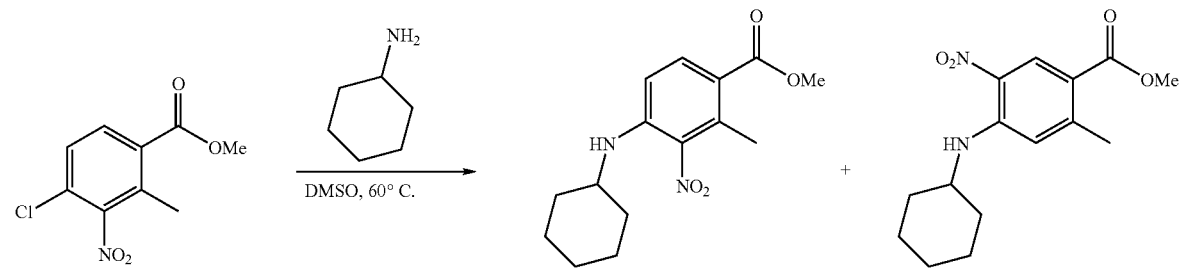

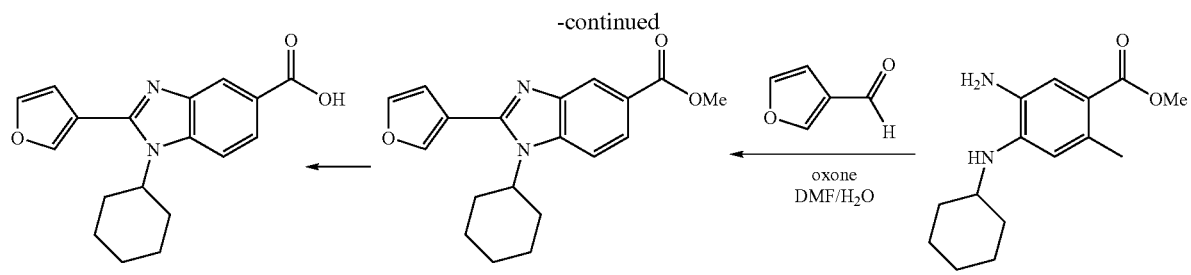

4-Chloro-2-methylbenzoic

In a dry round-bottomed flask (3L) equipped with a mechanical stirrer under $N_2$, anhydrous N,N,N',N'-tetramethylethylethylenediamine (TMEDA, 99.7 mL, 660 mmol, 2.2 eq.) and anhydrous THF (600 mL) were added and the mixture was cooled to −90° C. in a bath of liquid $N_2$/EtOH. Freshly titrated sec-BuLi (550 mL, 1.2M in cyclohexane, 660 mmol., 2.2 eq.) was added slowly via cannula as to maintain the temperature at −50° C. The solution was cooled to −90° C. and 4-chlorobenzoic acid (47.0 g in 400 mL anhydrous THF, 300 mmol) was added slowly via cannula, while stirring carefully to maintain the temperature at −90° C. The reaction mixture was stirred at −90° C. for 1 h before allowed to warm-up to −80° C. and $CH_3I$ (80 mL, 1.28 moles) was added very slowly. The reaction mixture was stirred for 10 min at −80° C., then quenched slowly with $H_2O$ (600 mL) and allowed to warm-up to room temperature. The aqueous layer was separated, washed with $Et_2O$ (2×500 mL) and then acidified with HCl (2.5 N, 600 mL) while cooling in an ice bath; cooling was continued for 16 h at 4° C. to allow crystallization of the desired product. The crude product was dried under vacuum and over anhydrous $P_2O_5$ and then re-crystallized from hot toluene (700 mL) to obtain pure 4-chloro-2-methylbenzoic acid (40 g).

Mixture of 4-chloro-2-methyl-5-nitrobenzoic acid methyl ester and 4-chloro-2-methyl-3-nitrobenzoic acid methyl ester These compounds were prepared using a modification of the procedure reported by M. Baumgarth et al. (*J. Med. Chem.* 1997, 40, 2017-2034). 4-Chloro-2-methylbenzoic acid (6 g) was added to fuming $HNO_3$ (100%, 36 g) in small portions over a period of 20 min, at 10° C., while stirring vigorously. The reaction mixture was stirred vigorously for a period of 1 h and the temperature allowed to warm-up to 20°C. The reaction mixture was then poured onto ice (100 g) and the yellow precipitate formed was collected, washed with $H_2O$, dissolved in EtOAc (25 mL) and the solution was dried over $Na_2CO_3$ and filtered. After concentration of the remaining mother liquor to ½ of the original volume, more precipitate was formed, however, the solid formed was always a mixture of 4-chloro-2-methyl-5-nitrobenzoic acid and 4-chloro-2-methyl-3-nitrobenzoic acid. Thus, all of the solid material formed was collected by filtration (~6.5 g), stirred in MeOH/HCl at 0° C. for 1 h to form a mixture of methyl esters. This mixture was used in the following step without further purification.

4-Cyclohexylamino-2-methyl-5-nitrobenzoic acid methyl ester and 4-cyclohexylamino-2-methyl-3-nitrobenzoic acid methyl ester The mixture of esters from above (1.1 g, 4.8 mmol) and cyclohexylamine (1.7 mL, 14.4 mmol) in DMSO (2 mL) were stirred at 60° C. for 16 h. The reaction mixture was then cooled and poured onto ice (~5 g) and mixed vigorously to allow the formation of a precipitate. The solid material was filtered, washed with $H_2O$ and dissolved in EtOAc. The solution was washed with $H_2O$ and brine, dried over anhydrous $MgSO_4$ and evaporated to an oil containing the desired products. The oil was triturated with hexane (~5 mL) to allow precipitation of relatively pure 4-cyclohexylamino-2-methyl-5-nitrobenzoic acid methyl ester (600 mg), whereas the mother liquor contained mostly 4-cyclohexylamino-2-methyl-3-nitrobenzoic acid methyl ester (600 mg).

3-Amino-4-cyclohexylamino-2-methylbenzoic acid methyl ester

4-Cyclohexylamino-2-methyl-3-nitrobenzoic acid methyl ester (150 mg) was dissolved in THF/MeOH (30 mL, 1:2 ratio) and stirred in the presence of $H_2$ (1 atm) and a catalytic amount of $Pd(OH)_2$ (20 mg) at room temperature for 14 h. The reaction mixture was then filtered, evaporated to dryness and purified by flash column chromatography, using 25% EtOAc in hexane with 0.2% $NH_4OH$ as the eluent, to give the pure aniline (106 mg).

1-Cyclohexyl-2-furan-3-yl-4-methyl-1H-benzimidazole-5-carboxylic acid

To a solution of the diamine from above (500 mg, 1.9 mmol) in DMF (3 mL) and $H_2O$ (0.15 mL), 3-furaldehyde (0.22 mL, 2.5 mmol) and oxone® (1.29 g, 2.1 mmol) were added and the reaction mixture was stirred at room temperature for 1 h.

Subsequently, $H_2O$ (60 mL) was added and the pH was adjusted to 8 with aqueous $NaHCO_3$. The reaction mixture was then extracted with DCM, the organic layer was washed with brine, dried over anhydrous $Na_2SO_4$ and evaporated to dryness. The desired benzimidazole methyl ester (446 mg) was obtained pure after column chromatography, using 25% EtOAc in hexane.

Hydrolysis of the methyl ester was achieved with an aqueous solution of NaOH (1.0 N, 0.66 mL, 6.6 mmol) in a solution of MeOH/THF (10 mL, 1:1 ratio) at 60° C. for 1.5 h. The reaction mixture was then cooled to room temperature, the pH was adjusted to 4 with AcOH and the organic solvents were evaporated to dryness. The remaining aqueous mixture was extracted with DCM (3×15 mL) and the combined organic layers were washed with H₂O, dried over anhydrous Na₂SO₄ and evaporated to dryness to give the desired title compound of example 151, 1-cyclohexyl-2-furan-3-yl-4-methyl-1H-benzimidazole-5-carboxylic acid (392 mg).

Example 152

(S)-2-{[1-(1-Cyclohexyl-2-furan-3-yl-4-methyl-1H-benzimidazol-5-yl)-methanoyl]-amino}-3-(5-hydroxy-1H-indol-3-yl)-propionic acid (Entry 5007, Table 5)

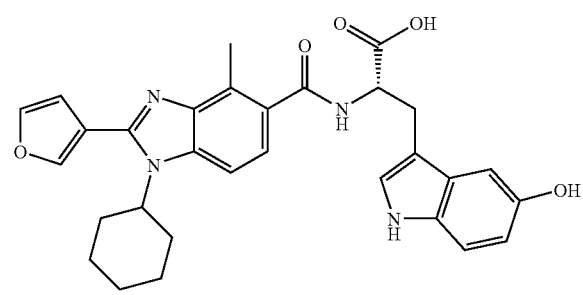

The carboxylic acid derivative of example 151 was coupled to 5-hydroxy-(S)-tryptophan methyl ester hydrochloride in the usual manner. Saponification followed by purification by preparative C18 reversed-phase HPLC gave the title compound of example 152.

Example 153

(S)-3-(5-Carboxymethoxy-1H-indol-3-yl)-2-{[1-(1-cyclohexyl-2-furan-3-yl-4-methyl-1H-benzimidazol-5-yl)-methanoyl]-amino}-propionic acid (Entry 5008, Table 5)

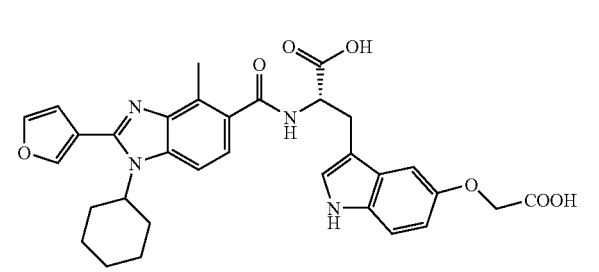

The carboxylic acid derivative of example 152 was coupled to 5-hydroxy-(S)-tryptophan methyl ester hydrochloride in the usual manner. The material was then alkylated with methyl bromoacetate as described previously to give after deprotection by saponification and preparative C18 reversed-phase HPLC, the title compound of example 153.

Example 154

(S)-2-{[1-(1-Cyclohexyl-2-furan-3-yl-6-methyl-1H-benzimidazol-5-yl)-methanoyl]-amino}-3-(5-hydroxy-1H-indol-3-yl)-propionic acid (Entry 5006, Table 5)

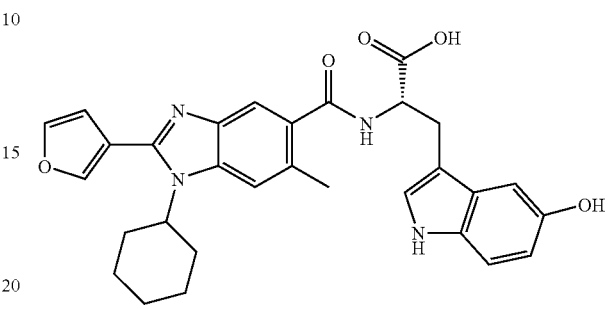

1-Cyclohexyl-2-furan-3-yl-6-methyl-1H-benzimidazole-5-carboxylic acid was prepared from 4-cyclohexylamino-2-methyl-5-nitrobenzoic acid methyl ester (Example 151) as described for the 4-methyl derivative (Example 151). The acid was coupled to 5-hydroxy-(S)-tryptophan methyl ester hydrochloride in the usual manner and following saponification of the methyl ester and purification by preparative C18 reversed-phase HPLC, the title compound of example 154 was obtained.

Example 155

(S)-3-(5-Carboxymethoxy-1H-indol-3-yl)-2-{[1-(1-cyclohexyl-2-furan-3-yl-6-methyl-1H-benzimidazol-5-yl)-methanoyl]-amino}-propionic acid (Entry 5009, Table 5)

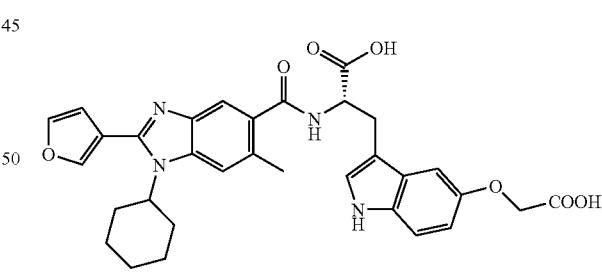

1-Cyclohexyl-2-furan-3-yl-6-methyl-1H-benzimidazole-5-carboxylic acid was coupled to 5-hydroxy-(S)-tryptophan methyl ester hydrochloride in the usual manner (Example 154). The material was then alkylated with methyl bromoacetate as described previously to give after deprotection by saponification and preparative C18 reversed-phase HPLC, the title compound of example 155.

Example 156

(E)-3-(4-((S)-1-[1-(1-Cyclohexyl-2-furan-3-yl-1H-benzimidazol-5-yl)-methanoyl]-pyrrolidin-3-yloxy)-phenyl)-acrylic acid (Entry 6004, Table 6)

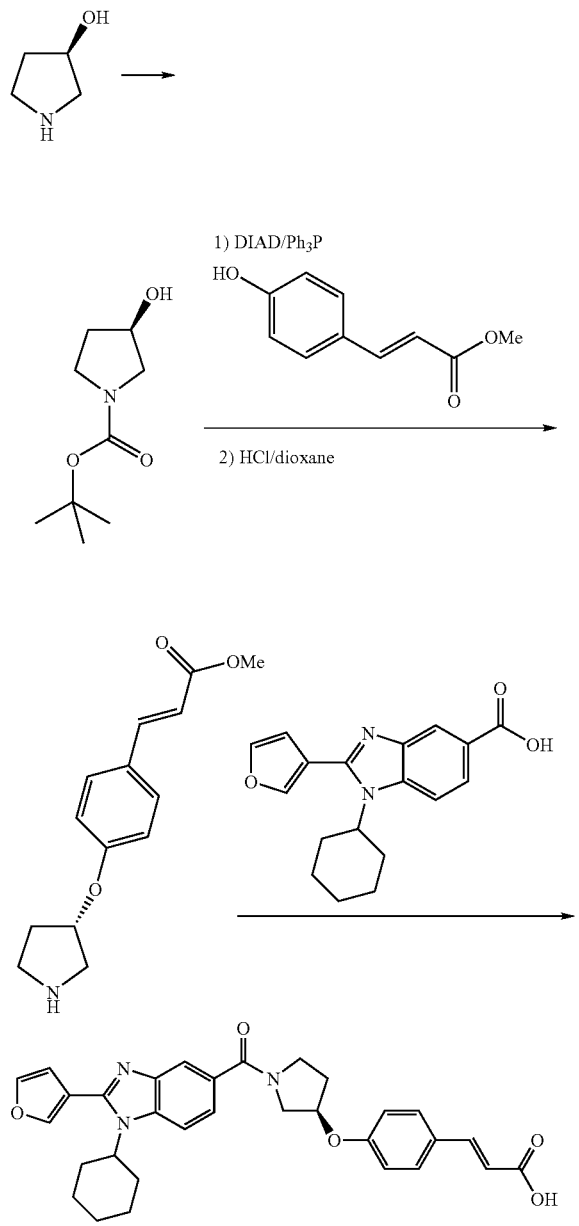

To a solution of (R)-(−)-3-pyrrolidinol hydrochloride (1.12 g, 9.1 mmol) in anhydrous THF (20 mL), a solution of di-tert-butyldicarbonate (2.07 g, 9.5 mmol) in THF (15 mL), followed by DIEA (4.74 mL, 27.2 mmol) were added. The reaction mixture was stirred at room temperature for 18 h then the solvent was evaporated. The residue was dissolved in EtOAc and the solution was washed with 10% aqueous HCl, saturated NaHCO₃ and brine. The organic layer was dried over anhydrous MgSO₄ and then evaporated to dryness to give the (R)-3-hydroxypyrrolidine-1-carboxylic acid tert-butyl ester as a white solid (1.54 g).

To a solution of 4-hydroxycinnamic acid (0.407 g, 2.48 mmol) in EtOAc, a solution of diazomethane in Et₂O was added until the yellow color persisted. Excess diazomethane was quenched by the addition of AcOH and the reaction mixture was evaporated to dryness. The residue was dissolved in EtOAc and washed with 10% aqueous HCl, saturated NaHCO₃ and brine. The organic layer was dried over anhydrous MgSO₄ and evaporated to dryness. The residue was purified by flash column chromatography, using a gradient from 10%-20% EtOAc in hexane, to give E-3-(4-hydroxyphenyl)acrylic acid methyl ester as a white solid (0.362 g).

To a solution of (R)-3-hydroxypyrrolidine-1-carboxylic acid tert-butyl ester (0.215 g, 1.15 mmol) in THF at 0° C., triphenylphosphine (0.316 g, 1.21 mmol), diisopropyl azodicarboxylate (236 µL, 1.21 mmol) and E-3-(4-hydroxy-phenyl)-acrylic acid methyl ester (0.215 g, 1.21 mmol) were added. The reaction mixture was stirred for 2 h at 0° C., followed by 4 h at room temperature and then the solvent was evaporated in vacuo. The residue was purified by flash column chromatography, using 20%-30% EtOAc in hexane, to give crude (S)-3-[4-(E)-2-methoxycarbonylvinyl)phenoxy] pyrrolidine-1-carboxylic acid tert-butyl ester as a yellow solid.

The product from above was dissolved in 4 N HCl in dioxane (4 mL) and stirred 30 min at room temperature. The solvent was evaporated to dryness and the solid residue was triturated with EtOAc (3×) to give the amine hydrochloride product as a white solid (0.260 g).

The amine hydrochloride from above was coupled to the carboxylic acid of example 2 in the usual manner. Following ester hydrolysis under basic conditions and purification using reversed phase C18 HPLC the title compound of example 155 was obtained.

Example 157

(S)-2-{[1-(1-Cyclohexyl-2-furan-3-yl-1H-benzimidazol-5-yl)-methanoyl]-amino}-3-(4-methoxycarbonylmethoxy-phenyl)-propionic acid (Entry 1124, Table 1)

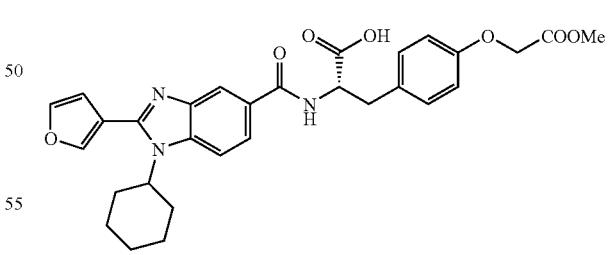

The N-Boc-O-alkylated-L-tyrosine benzyl ester intermediate described in example 98 was deprotected on nitrogen using 4 N HCl in dioxane and coupled to the carboxylic acid of example 2. Following hydrogenolysis of the benzyl ester with Pd(OH)₂ and H₂ (gas), the title compound of example 157 was purified by preparative C18 reversed-phase HPLC.

Example 158

(2S,4R)-4-[4-((Z)-2-Carboxy-vinyl)-phenoxy]-1-[1-(1-cyclohexyl-2-furan-3-yl-1H-benzimidazol-5-yl)-methanoyl]-pyrrolidine-2-carboxylic acid (Entry 6003, Table 6)

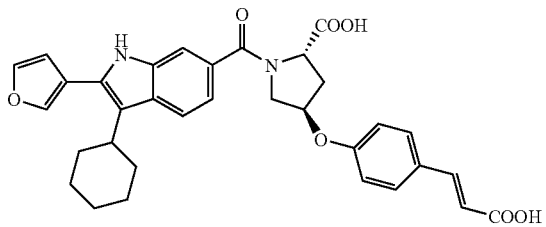

To a solution of N-Boc-protected cis-3-hydroxy-L-proline methyl ester (0.202 g, 0.82 mmol) in THF at 0° C., triphenylphosphine (0.433 g), diisopropylazodicarboxylate (333 uL) and E-3-(4-hydroxy-phenyl)-acrylic acid methyl ester (0.294 g) were added. The reaction mixture was stirred for 2 h at 0° C., followed by 4 h at room temperature and then the solvent was evaporated to dryness. The residue was purified by flash column chromatography, using 10%-50% EtOAc in hexane, to give the crude O-alkylated proline derivative as a yellow solid.

The material from above was dissolved in a 4N HCl in dioxane (10 mL) and stirred 30 min at room temperature. The solvent was evaporated to dryness and the solid residue coupled to the carboxylic acid of example 2 in the usual manner. Following saponification of ester protecting groups the title compound of example 158 was purified by reversed phase C18 HPLC.

The compounds of formula (I) can be obtained in the form of therapeutically acceptable salts. (see, for example Pharmaceutical salts, Birge, S. M. et al., J. Pharm. Sci. (1977), 66,1-19, incorporated herein by reference).

Example 159

Inhibition of NS5B RNA Dependent RNA Polymerase Activity

The compounds of the invention were tested for inhibitory activity against the hepatitis C virus RNA dependant polymerase (NS5B), according to the following assay The substrates are:
a 12 nucleotide RNA oligo-uridylate (or oligo-uridine-monophosphate) (oligo-U) primer modified with biotin at the free 5'C position;
a complementary poly-adenylate (or adenosine monophospahte) (polyA) template of heterogeneous length (1000-10000 nucleotides); and
UTP-[5,6 $^3$H].

Polymerase activity is measured as the incorporation of UMP-[5,6 $^3$H] into the chain elongated from the oligo-U primer. The $^3$H-labelled reaction product is captured by SPA-beads coated with streptavidin and quantified on the Top-Count.

All solutions were made from DEPC treated MilliQ water [2 ml of DEPC is added to 1 l of MilliQ water; the mixture is shaken vigorously to dissolve the DEPC, then autoclaved at 121° C. for 30 minutes].

Enzyme: The full length HCV NS5B (SEQ ID NO.1) was purified as an N-terminal hexa-histidine fusion protein from baculovirus infected insect cells. The enzyme can be stored at –20° C. in storage buffer (see below). Under these conditions, it was found to maintain activity for at least 6 months.

Substrates: The biotinylated oligo-$U_{12}$ primer, the Poly(A) template, and the UTP-[5,6 $^3$H] were dissolved in water. The solutions can be stored at –80° C.

| Assay buffer: | 20 mM Tris-HCl pH 7.5 |
| --- | --- |
| | 5 mM MgCl$_2$ |
| | 25 mM KCl |
| | 1 mM EDTA |
| | 1 mM DTT |
| NS5B storage buffer: | 0.1 μM NS5B |
| | 25 mM Tris-HCl pH 7.5 |
| | 300 mM NaCl |
| | 5 mM DTT |
| | 1 mM EDTA |
| | 0.1% n-Dodecyl maltoside |
| | 30% glycerol |

Test compound cocktail: Just prior to assay, test compounds of the invention were dissolved in assay buffer containing 15% DMSO.

Substrate cocktail: Just prior to assay, the substrates were mixed in assay buffer to the following concentrations:

| Component | Concentration in substrate cocktail | Final Concentration in assay |
| --- | --- | --- |
| RNAsin ™ | 0.5 U/μl | 1.67 U/μl |
| Biotin-oligo-$U_{12}$ primer | 3 ng/μl | 1 ng/μl |
| PolyA template | 30 ng/μl | 10 ng/μl |
| UTP-[5,6-$^3$H] 35 Ci/mmol | 0.025 μCi/μl | 0.0083 μCi/μl |
| | | 0.25 μM |
| UTP | 2.25 μM | 0.75 μM |

Enzyme cocktail: Just prior to assay, the RNA polymerase (NS5B) cocktail was prepared in assay buffer to the following specifications:

| Component | Concentration in cocktail |
| --- | --- |
| Tris-HCl at pH 7.5 | 20 mM |
| MgCl$_2$ | 5 mM |
| KCl | 25 mM |
| EDTA | 1 mM |
| DTT | 1 mM |
| n-Dodecyl maltoside | 1% |
| NS5B | 30 nM |

Protocol:

The assay reaction was performed in a Microfluorx™ white "U" bottom plate (Dynatech™ #7105), by successively adding:

20 μl of test compound cocktail;
20 μl of substrate cocktail; and
20 μl of enzyme cocktail
(final [NS5B] in assay=10 nM; final [n-dodecyl maltoside] in assay=0.33%; final DMSO in assay=5%).

The reaction was incubated at room temperature for 1.5 hours. STOP solution (20 µl; 0.5 M EDTA, 150 ng/µl tRNA) was added, followed by 30 µl streptavidin coated PVT beads (8 mg/ml in 20 mM Tris-HCl, pH 7.5, 25 mM KCl, 0.025% NaN$_3$). The plate was then shaken for 30 minutes. A solution of CsCl was added (70 µl, 5 M), to bring the CsCl concentration to 1.95 M. The mixture was then allowed to stand for 1 hour. The beads were then counted on a Hewlett Packard TopCount™ instrument using the following protocol:

Data mode: counts per minute
Scintillator: liq/plast
Energy range: low
Efficiency mode: normal
Region: 0-50
Count delay: 5 Minutes
Count time: 1 minute
Expected results: 6000 cpm/well
200 cpm/well no enzyme control Based on the results at ten different concentrations of test compound, standard concentration-% inhibition curves were plotted and analysed to determine IC$_{50}$'s for the compounds of the invention. For some compounds the IC$_{50}$ was estimated from two points.

Example 160

Specificity for NS5B RNA Dependent RNA polymerase inhibition

The compounds of the invention were tested for inhibitory activity against polio virus RNA dependent RNA polymerase and calf thymus DNA dependent RNA polymerase II in the format that is described for the HCV polymerase with the exception that poliovirus polymerase was used in place of the HCV NS5B polymerase.

Table of Compounds

The compounds listed in Tables 1 to 22 were found to be active in the above-described NS5B assay, with IC$_{50}$'s of less than 25 µM. None of these compounds were found to exhibit significant inhibition of poliovirus RNA dependent RNA polymerase or calf thymus DNA dependent RNA polymerase II at 25 µM concentration.

In Tables 1 to 22, the following ranges apply: A:-25-10 µM; B: 10-5 µM; C: 5-1 µM; and D: <1 µM

TABLE 1

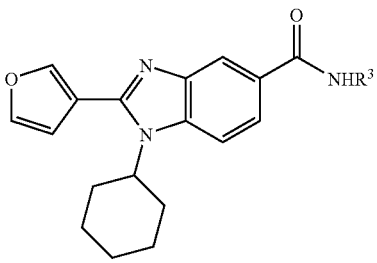

| Entry # | IC$_{50}$ µM | R$^3$ | m/z |
|---|---|---|---|
| 1001 | A | 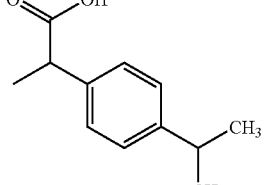 | 486(MH$^+$) |
| 1002 | A | 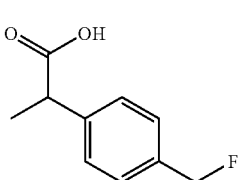 | 512(MH$^+$) |
| 1003 | B | 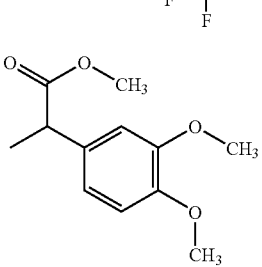 | 518(MH$^+$) |

TABLE 1-continued
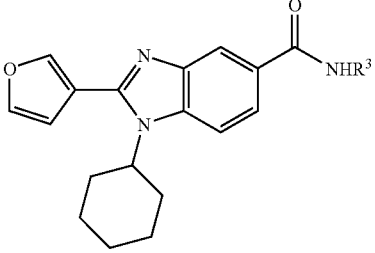
| Entry # | IC$_{50}$ μM | R$^3$ | m/z |
|---|---|---|---|
| 1004 | C | 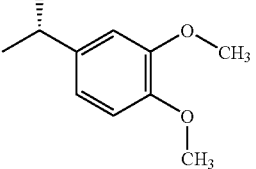 | 474(MH$^+$) |
| 1005 | C | 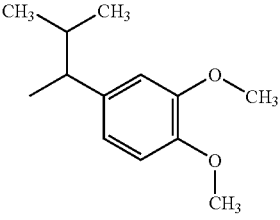 | 400(MH$^+$) |
| 1006 | B | 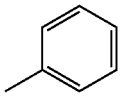 | 502(MH$^+$) |
| 1007 | C | 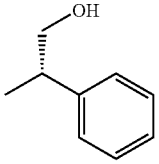 | 386(MH$^+$) |
| 1008 | C | 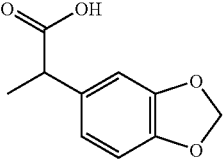 | 430(MH$^+$) |
| 1009 | C | 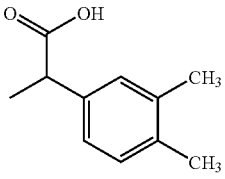 | 488(MH$^+$) |
| 1010 | C |  | 472(MH$^+$) |

TABLE 1-continued
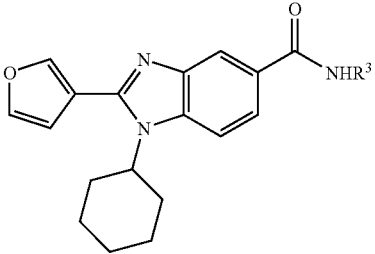
| Entry # | IC$_{50}$ µM | R$^3$ | m/z |
|---|---|---|---|
| 1011 | C | 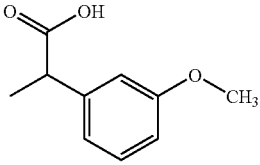 | 474(MH$^+$) |
| 1012 | C | 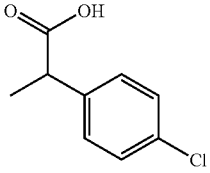 | 478(MH$^+$) |
| 1013 | C | 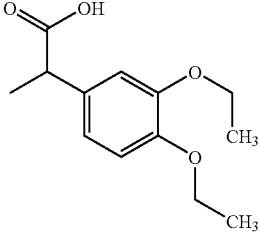 | 532(MH$^+$) |
| 1014 | C | 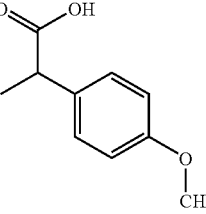 | 474(MH$^+$) |
| 1030 | B | 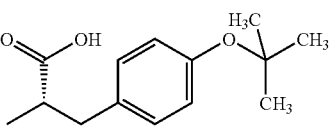 | 530(MH$^+$) |
| 1015 | B | 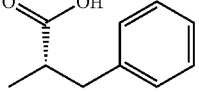 | 458(MH$^+$) |

TABLE 1-continued
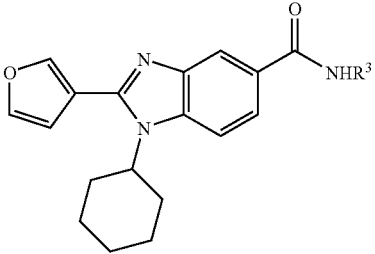
| Entry # | IC$_{50}$ μM | R$^3$ | m/z |
|---|---|---|---|
| 1016 | C | 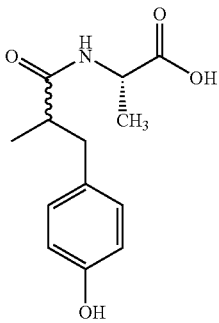 | 545(MH$^+$) |
| 1017 | B | 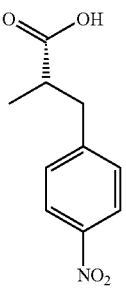 | 503(MH$^+$) |
| 1019 | C | 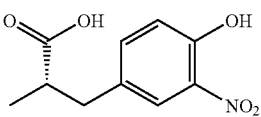 | 519(MH$^+$) |
| 1020 | C | 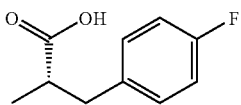 | 476(MH$^+$) |
| 1021 | C | 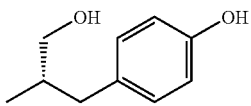 | 460(MH$^+$) |
| 1022 | C | 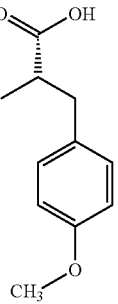 | 488(MH$^+$) |

TABLE 1-continued
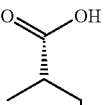
| Entry # | IC$_{50}$ μM | R$^3$ | m/z |
|---|---|---|---|
| 1023 | C | 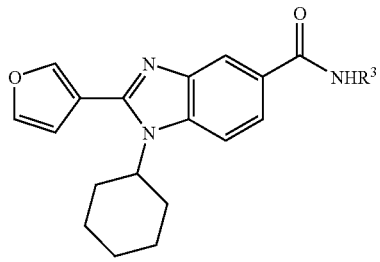 | 474(MH$^+$) |
| 1024 | C | 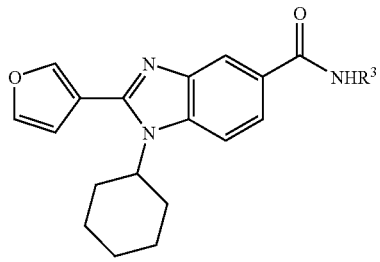 | 483(MH$^+$) |
|  | D | 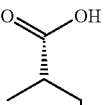 | 497(MH$^+$) |
| 1025 | B | 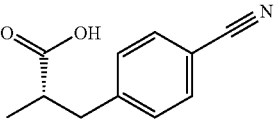 | 430(MH$^+$) |
| 1026 | C | 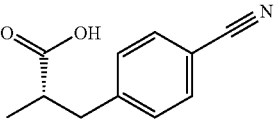 | 474(MH$^+$) |
| 1027 | C | 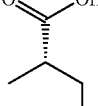 | 499(MH$^+$) |
| 1028 | C | 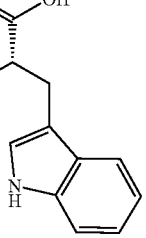 | 488(MH$^+$) |
| 1029 | B | 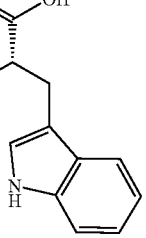 | 508(MH$^+$) |

TABLE 1-continued
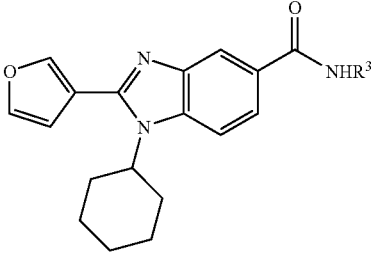
| Entry # | IC$_{50}$ µM | R$^3$ | m/z |
|---|---|---|---|
| 1031 | C | 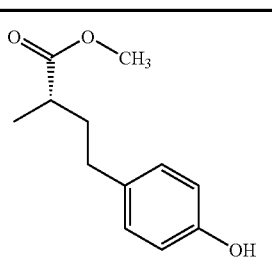 | 502(MH$^+$) |
| 1033 | C | 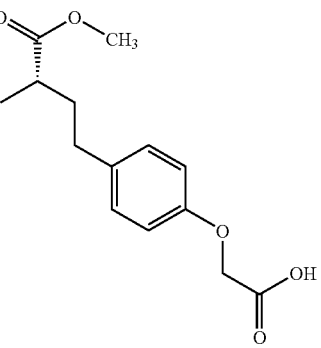 | 560(MH$^+$) |
| 1034 | C | 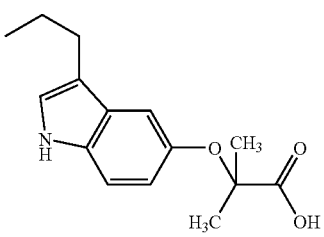 | 555(MH$^+$) |
| 1040 | D | 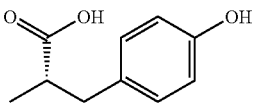 | 474(MH$^+$) |
| 1063 | C | 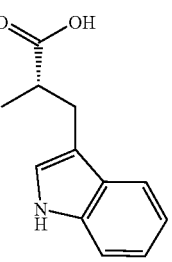 | 511(MH$^+$) |

TABLE 1-continued
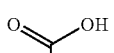
| Entry # | IC$_{50}$ μM | R$^3$ | m/z |
|---|---|---|---|
| 1069 | C | 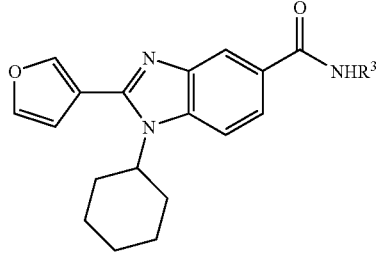 | 502(MH$^+$) |
| 1071 | C | 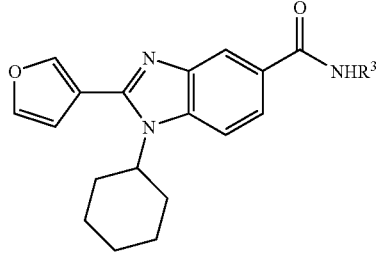 | 488(MH$^+$) |
| 1072 | C | 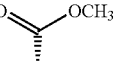 | 444(MH$^+$) |
| 1080 | C | 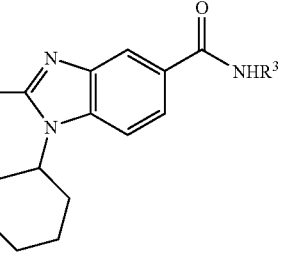 | 577(MH$^+$) |
| 1083 | A | 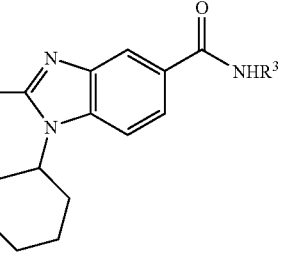 | 637(MH$^+$) |

TABLE 1-continued
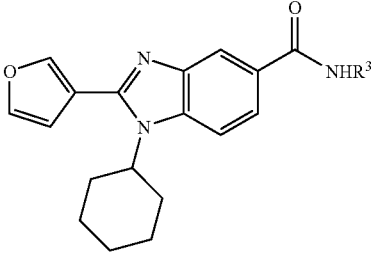
| Entry # | IC$_{50}$ μM | R$^3$ | m/z |
|---|---|---|---|
| 1086 | C | 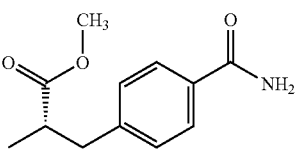 | 515(MH$^+$) |
| 1088 | C | 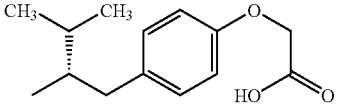 | 530(MH$^+$) |
| 1089 | C | 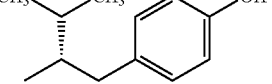 | 472(MH$^+$) |
| 1111 | C | 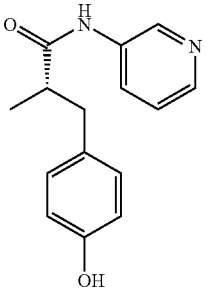 | 550(MH$^+$) |
| 1112 | C | 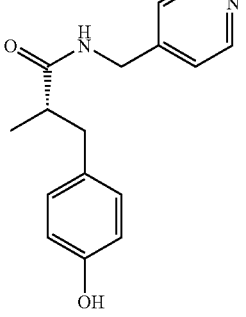 | 564(MH$^+$) |

TABLE 1-continued

| Entry # | IC$_{50}$ μM | R$^3$ | m/z |
|---|---|---|---|
| 1114 | C | | 564(MH$^+$) |
| 1117 | C | | 544(MH$^+$) |
| 1118 | C | | 586(MH$^+$) |
| 1119 | C | | 518(MH$^+$) |
| 1122 | B | | 498(MH$^+$) |

TABLE 1-continued

| Entry # | IC$_{50}$ µM | R$^3$ | m/z |
|---|---|---|---|
| 1123 | C | 4-(2-(trifluoromethyl)propyl)phenoxyacetic acid group | 556(MH$^+$) |
| 1124 | C | (S)-2-methyl-3-(4-(2-methoxy-2-oxoethoxy)phenyl)propanoic acid group | 546(MH$^+$) |
| 1125 | C | (S)-2-methyl-3-(5-nitro-1H-indol-3-yl)propanoic acid group | 540(MH$^+$) |
| 1126 | C | (S)-2-methyl-3-(4-methyl-2-oxo-2H-chromen-6-yl)propanoic acid group | 540(MH$^+$) |

TABLE 1-continued

| Entry # | IC$_{50}$ μM | R$^3$ | m/z |
|---|---|---|---|
| 1131 | C | (4-((2S)-2-methyl-3-(2-methylthiazol-4-yl)propyl)phenoxy)acetic acid group | 585(MH$^+$) |
| 1133 | C | (4-((2S)-2-methyl-3-(2-(isopropylamino)thiazol-4-yl)propyl)phenoxy)acetic acid group | 628(MH$^+$) |
| 1134 | C | (4-((2S)-2-methyl-3-(2-acetamidothiazol-4-yl)propyl)phenoxy)acetic acid group | 628(MH$^+$) |

TABLE 1-continued

| Entry # | IC₅₀ μM | R³ | m/z |
|---|---|---|---|
| 1140 | C | | 600(MH⁺) |
| 1141 | C | | 614(MH⁺) |
| 1142 | C | | 520(MH⁺) |
| 1144 | C | | 568(MH⁺) |

TABLE 1-continued
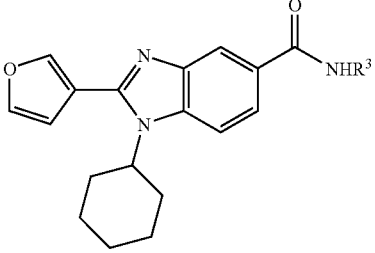
| Entry # | IC$_{50}$ µM | R$^3$ | m/z |
|---|---|---|---|
| 1147 | C | 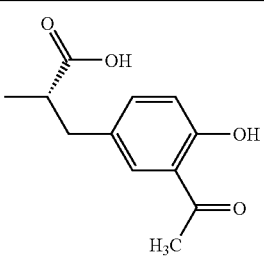 | 516(MH$^+$) |
| 1150 | C | 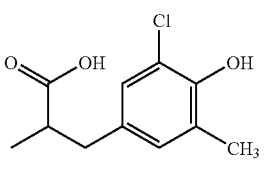 | 571(MH$^+$) |
| 1152 | C | 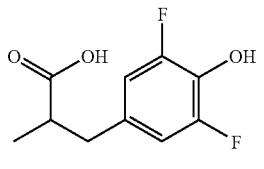 | 522(MH$^+$) |
| 1153 | C | 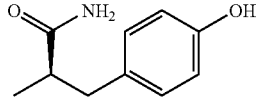 | 510(MH$^+$) |
| 1156 | B | 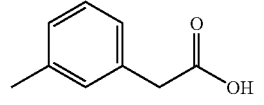 | 473(MH$^+$) |
| 1157 | A | 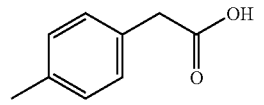 | 442.2(MH$^+$) |
| 1158 | A |  | 442.2(MH$^+$) |

TABLE 1-continued
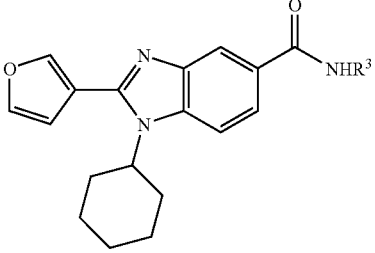
| Entry # | IC$_{50}$ μM | R$^3$ | m/z |
|---|---|---|---|
| 1159 | A | 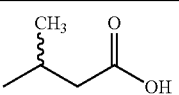 | 396.1(MH$^+$) |
| 1160 | C | 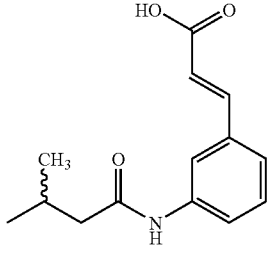 | 541.2(MH$^+$) |
| 1161 | C | 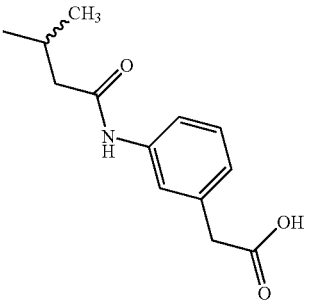 | 529.2(MH$^+$) |
| 1162 | C | 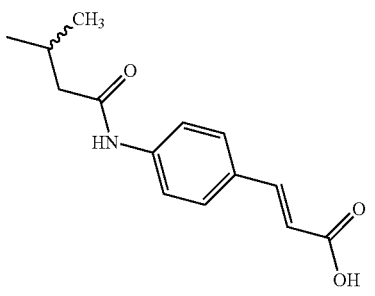 | 541.2(MH$^+$) |
| 1163 | B | 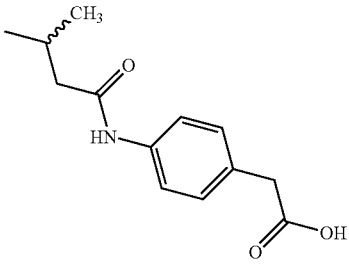 | 529.3(MH$^+$) |

TABLE 1-continued
| Entry # | IC$_{50}$ μM | R$^3$ | m/z |
|---|---|---|---|
| 1164 | A | 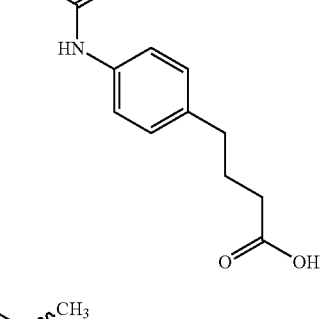 | 557.3(MH$^+$) |
| 1165 | A | 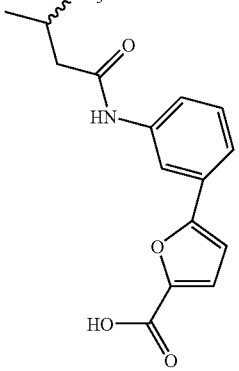 | 715.3(MH$^+$) |
| 1166 | B |  | 581.3(MH$^+$) |

TABLE 1-continued

| Entry # | IC$_{50}$ μM | R$^3$ | m/z |
|---|---|---|---|
| 1167 | C | 3-methylbutanoyl-NH-(2-hydroxy-5-carboxyphenyl) | 531.2(MH$^+$) |
| 1168 | A | 3-methylbutanoyl-NH-CH(CH$_3$)-CH$_2$-C(O)NH-(3-carboxymethylphenyl) | 614.3(MH$^+$) |
| 1169 | A | 3-methylbutanoyl-NH-CH(CH$_3$)-CH$_2$-C(O)NH-(4-carboxymethylphenyl) | 614.3(MH$^+$) |
| 1170 | A | (S)-CH(CN)-CH(CH$_3$)-(4-hydroxyphenyl) | 455(MH$^+$) |

TABLE 1-continued
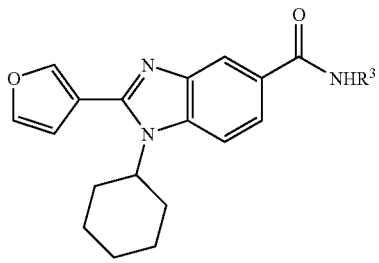
| Entry # | IC$_{50}$ μM | R$^3$ | m/z |
|---|---|---|---|
| 1171 | A | 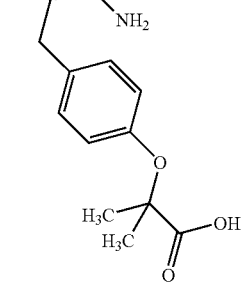 | 559(MH$^+$) |
| 1176 | C | 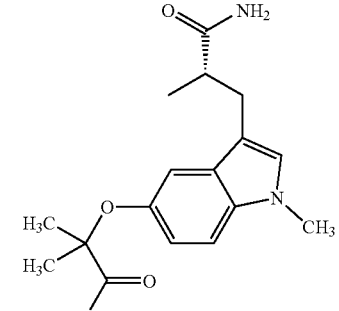 | 612(MH$^+$) |
| 1178 | C | 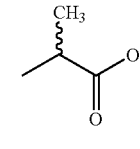 | 382.1(MH$^+$) |
| 1179 | C | 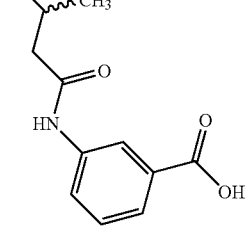 | 515.1(MH$^+$) |
| 1180 | B | 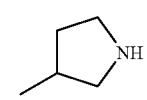 | 379.2(MH$^+$) |

TABLE 1-continued

| Entry # | IC$_{50}$ μM | R³ | m/z |
|---|---|---|---|
| 1181 | B | 4-ethylpiperidine | 407.3(MH⁺) |
| 1182 | B | 3-methylcyclohexylamine | 407.3(MH⁺) |
| 1183 | C | 4-methylcyclohexylamine | 407.3(MH⁺) |
| 1184 | B | 3-methylpiperidine | 393.2(MH⁺) |
| 1185 | B | 4-methylpiperidine | 393.2(MH⁺) |
| 1187 | C | 2-methylthiazole tyrosine derivative | 527(MH⁺) |
| 1191 | A | 3-methylpyrrolidine-1-carbonyl-glycine | 480.2(MH⁺) |
| 1192 | A | 4-ethylpiperidine-1-carbonyl-glycine | 508.3(MH⁺) |

TABLE 1-continued
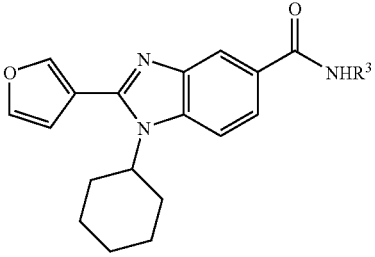
| Entry # | IC$_{50}$ μM | R$^3$ | m/z |
|---|---|---|---|
| 1193 | A | 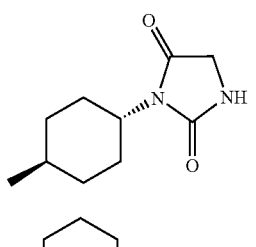 | 490.4(MH$^+$) |
| 1194 | A | 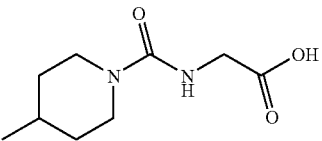 | 494.3(MH$^+$) |
| 1195 | A | 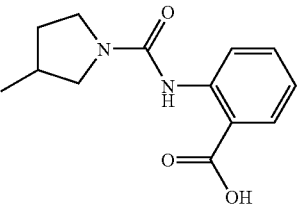 | 494.3(MH$^+$) |
| 1196 | C | 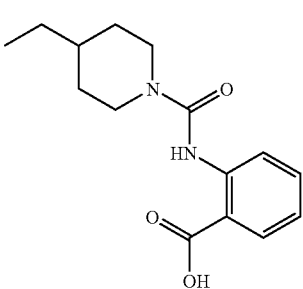 | 542.3(MH$^+$) |
| 1197 | A | 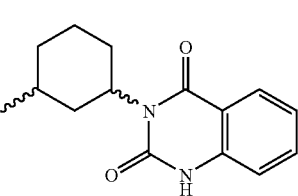 | 570.3(MH$^+$) |
| 1198 | A |  | 552.3(MH$^+$) |

TABLE 1-continued
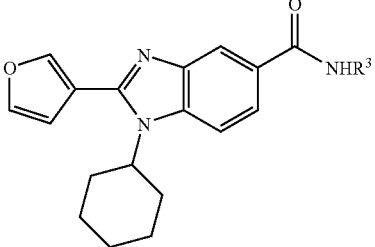
| Entry # | IC₅₀ μM | R³ | m/z |
|---|---|---|---|
| 1199 | A | 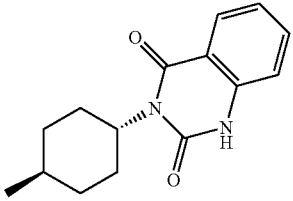 | 552.3(MH⁺) |
| 1200 | A | 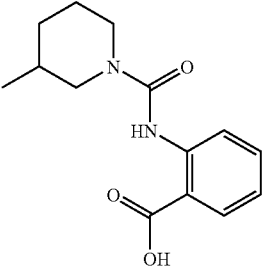 | 556.2(MH⁺) |
| 1201 | A | 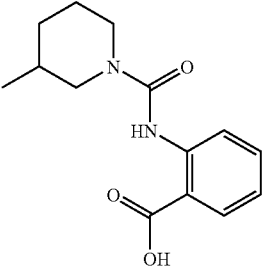 | 556.2(MH⁺) |
| 1202 | C | 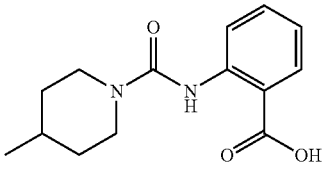 | 542.3(MH⁺) |
| 1203 | A | 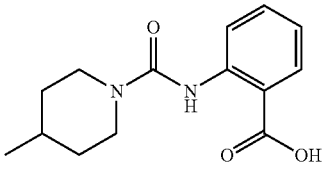 | 570.3(MH⁺) |

TABLE 1-continued
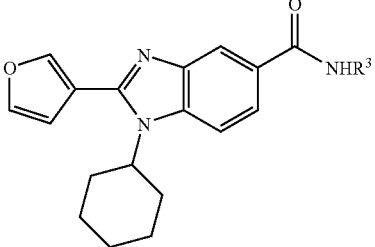
| Entry # | IC$_{50}$ µM | R³ | m/z |
|---|---|---|---|
| 1204 | B | 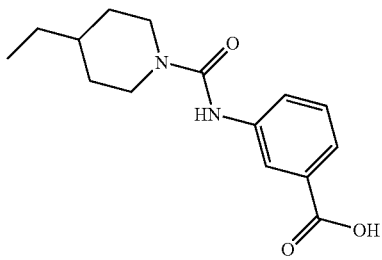 | 570.3(MH⁺) |
| 1205 | C | 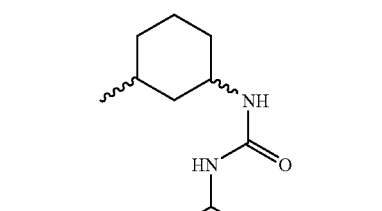 | 570.3(MH⁺) |
| 1206 | A | 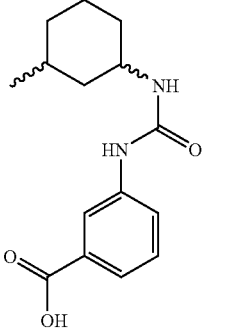 | 598.4(MH⁺) |
| 1207 | B | 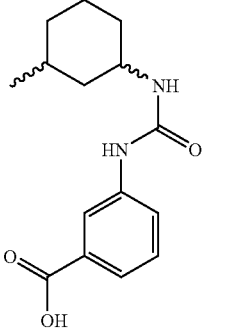 | 570.3(MH⁺) |

TABLE 1-continued
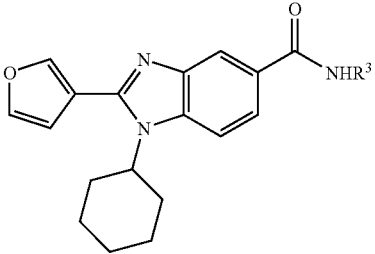
| Entry # | IC$_{50}$ μM | R$^3$ | m/z |
|---|---|---|---|
| 1208 | A | 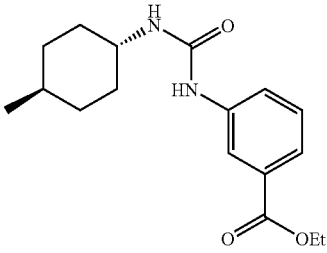 | 598.4(MH$^+$) |
| 1209 | C | 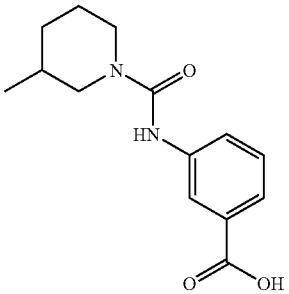 | 556.2(MH$^+$) |
| 1210 | A | 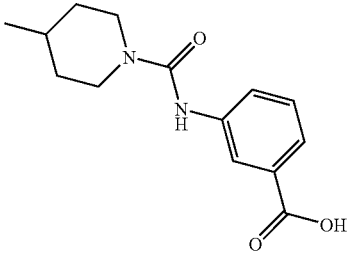 | 556.2(MH$^+$) |
| 1211 | A | 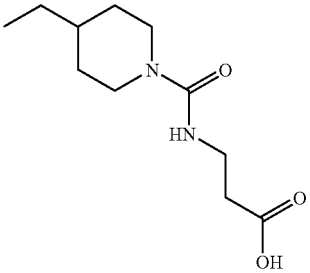 | 522.3(MH$^+$) |

TABLE 1-continued
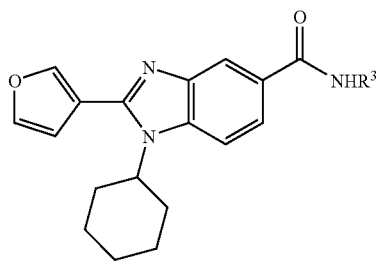
| Entry # | IC$_{50}$ μM | R$^3$ | m/z |
|---|---|---|---|
| 1212 | A | 4-ethylpiperidine-N-C(O)NH-CH$_2$CH$_2$C(O)OEt | 550.3(MH$^+$) |
| 1213 | A | cyclohexyl-NH-C(O)NH-CH$_2$CH$_2$C(O)OH | 522.3(MH$^+$) |
| 1214 | A | cyclohexyl-NH-C(O)NH-CH$_2$CH$_2$C(O)OEt | 550.3(MH$^+$) |
| 1215 | A | trans-4-methylcyclohexyl-NH-C(O)NH-CH$_2$CH$_2$C(O)OH | 522.3(MH$^+$) |

TABLE 1-continued

| Entry # | IC₅₀ μM | R³ | m/z |
|---|---|---|---|
| 1216 | A | (trans-4-methylcyclohexyl)-NH-C(O)-NH-CH₂CH₂-C(O)-OEt | 550.3(MH⁺) |
| 1217 | A | (3-methylpiperidin-1-yl)-C(O)-NH-CH₂CH₂-C(O)-OEt | 536.3(MH⁺) |
| 1218 | A | (4-methylpiperidin-1-yl)-C(O)-NH-CH₂CH₂-C(O)-OH | 508.3(MH⁺) |
| 1219 | A | (4-methylpiperidin-1-yl)-C(O)-NH-CH₂CH₂-C(O)-OEt | 536.3(MH⁺) |

TABLE 1-continued
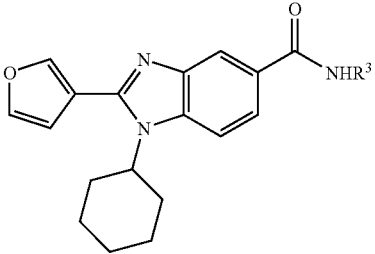
| Entry # | IC$_{50}$ µM | R$^3$ | m/z |
|---|---|---|---|
| 1220 | A | 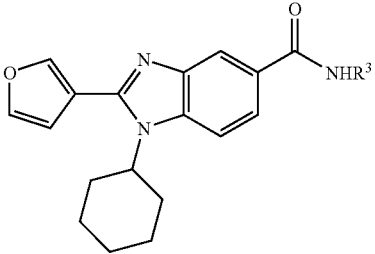 | 479.3(MH$^+$) |
| 1221 | A | 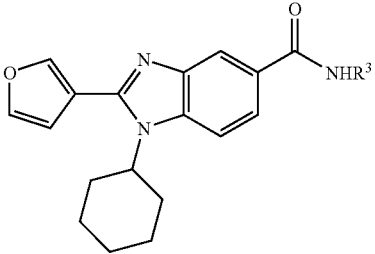 | 507.3(MH$^+$) |
| 1222 | A | 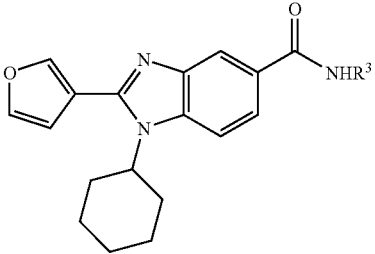 | 507.3(MH$^+$) |
| 1223 | A | 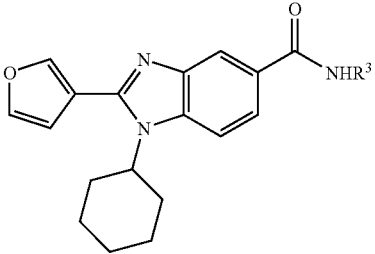 | 519.3(MH$^+$) |

TABLE 1-continued
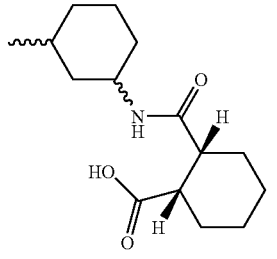
| Entry # | IC₅₀ μM | R³ | m/z |
|---|---|---|---|
| 1224 | A | 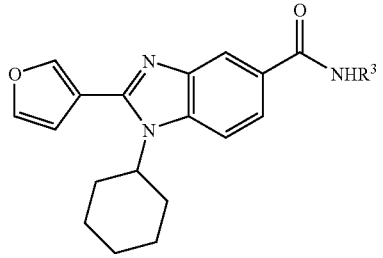 | 561.3(MH⁺) |
| 1225 | B | 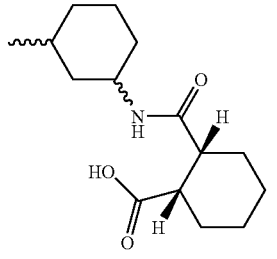 | 561.3(MH⁺) |
| 1226 | B | 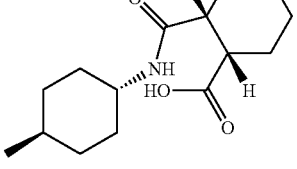 | 535.4(MH⁺) |
| 1227 | A | 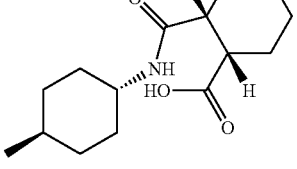 | 535.4(MH⁺) |

TABLE 1-continued
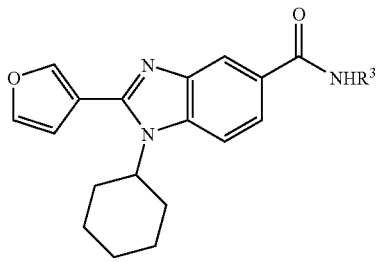
| Entry # | IC$_{50}$ μM | R$^3$ | m/z |
|---|---|---|---|
| 1228 | A | 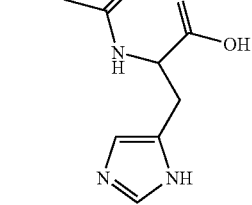 | 519(MH$^+$) |
| 1230 | C | 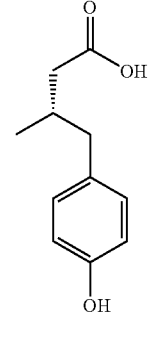 | 488(MH$^+$) |
| 1231 | C | 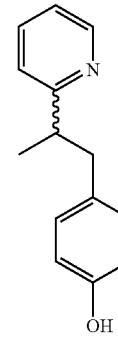 | 507(MH$^+$) |
| 1233 | B | 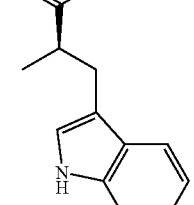 | 497(MH$^+$) |

TABLE 1-continued
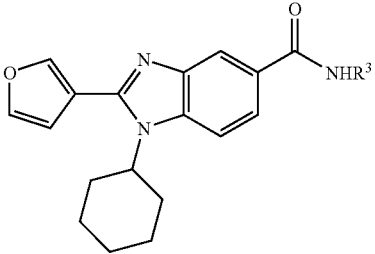
| Entry # | IC$_{50}$ µM | R$^3$ | m/z |
|---|---|---|---|
| 1236 | B | 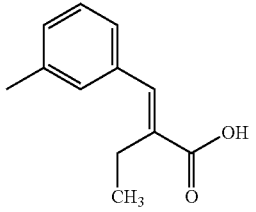 | 484.3(MH$^+$) |
| 1237 | B | 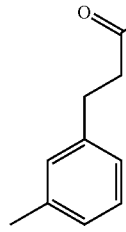 | 458.2(MH$^+$) |
| 1238 | A | 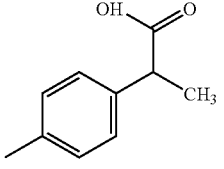 | 458.2(MH$^+$) |
| 1239 | C | 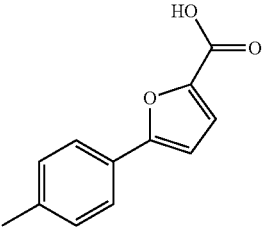 | 496.2(MH$^+$) |
| 1240 | C | 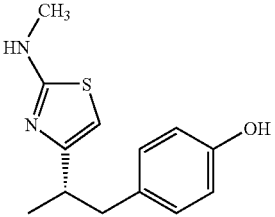 | 542(MH$^+$) |

TABLE 1-continued

| Entry # | IC$_{50}$ μM | R$^3$ | m/z |
|---|---|---|---|
| 1241 | C | (2-dimethylamino-thiazol-4-yl with CH(CH$_3$)-CH$_2$-C$_6$H$_4$-OH) | 556(MH$^+$) |
| 1242 | C | (2-acetamido-thiazol-4-yl with CH(CH$_3$)-CH$_2$-C$_6$H$_4$-OH) | 570(MH$^+$) |
| 1243 | B | (2-acetamido-1H-imidazol-4-yl with CH(CH$_3$)-CH$_2$-C$_6$H$_4$-OH) | 553(MH$^+$) |
| 1248 | C | (2-(4-hydroxy-3-azido-phenyl)-1-methyl-acetic acid) | 515(MH$^+$) |
| 1250 | C | (thiazol-4-yl with CH(CH$_3$)-CH$_2$-C$_6$H$_4$-OH) | 513(MH$^+$) |

TABLE 1-continued

| Entry # | IC$_{50}$ µM | R$^3$ | m/z |
|---|---|---|---|
| 1259 | B | | 506(MH$^+$) |
| 1260 | C | | 507(MH$^+$) |
| 1261 | A | | 543.2(MH$^+$) |
| 1262 | A | | 571.3(MH$^+$) |

TABLE 1-continued
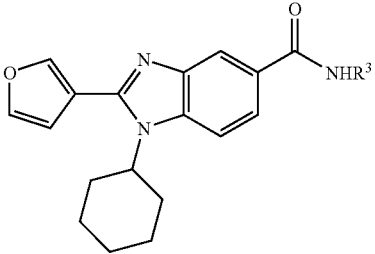
| Entry # | IC$_{50}$ μM | R$^3$ | m/z |
|---|---|---|---|
| 1263 | B | 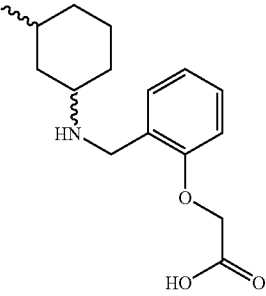 | 571.3(MH$^+$) |
| 1264 | B | 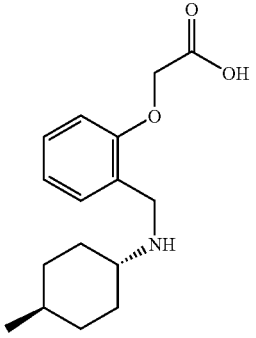 | 571.3(MH$^+$) |
| 1265 | C | 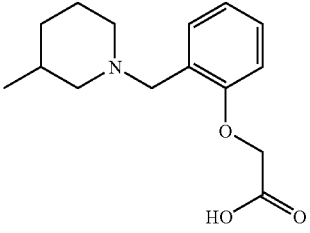 | 557.3(MH$^+$) |
| 1266 | B | 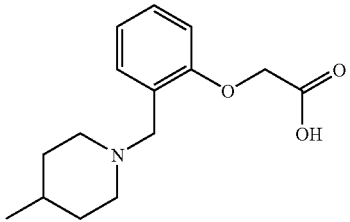 | 557.3(MH$^+$) |

TABLE 1-continued
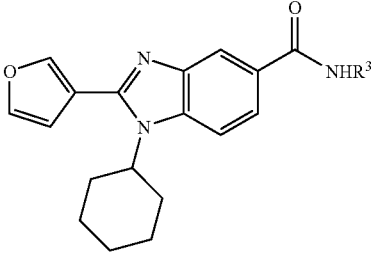
| Entry # | IC$_{50}$ μM | R$^3$ | m/z |
|---|---|---|---|
| 1267 | A | 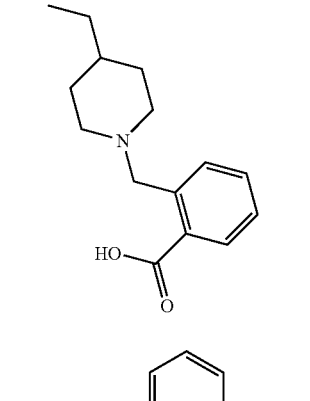 | 541.3(MH$^+$) |
| 1268 | A | 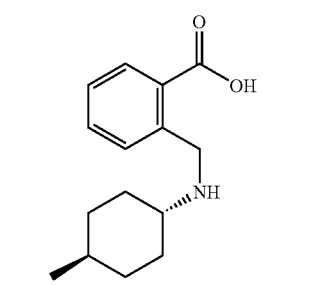 | 541.3(MH$^+$) |
| 1269 | A | 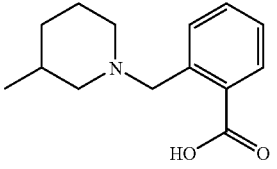 | 541.3(MH$^+$) |
| 1270 | A | 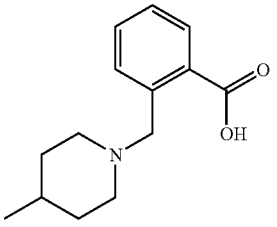 | 527.3(MH$^+$) |
| 1271 | A | | 527.3(MH$^+$) |

TABLE 1-continued

| Entry # | IC$_{50}$ µM | R$^3$ | m/z |
|---|---|---|---|
| 1272 | A | 4-((3-methylpyrrolidin-1-yl)methyl)benzoic acid | 513.2(MH$^+$) |
| 1273 | A | 4-((4-ethylpiperidin-1-yl)methyl)benzoic acid | 541.3(MH$^+$) |
| 1274 | A | 4-(((trans-4-methylcyclohexyl)amino)methyl)benzoic acid | 541.3(MH$^+$) |
| 1275 | B | 4-((3-methylpiperidin-1-yl)methyl)benzoic acid | 527.3(MH$^+$) |
| 1276 | A | 4-((4-methylpiperidin-1-yl)methyl)benzoic acid | 527.3(MH$^+$) |

TABLE 1-continued

| Entry # | IC$_{50}$ μM | R$^3$ | m/z |
|---|---|---|---|
| 1277 | C | | 539.3(MH$^+$) |
| 1278 | C | | 567.4(MH$^+$) |
| 1279 | C | | 567.4(MH$^+$) |

TABLE 1-continued

| Entry # | IC$_{50}$ μM | R$^3$ | m/z |
|---|---|---|---|
| 1280 | C | | 553.3(MH$^+$) |
| 1281 | A | | 553.3(MH$^+$) |
| 1282 | B | | 543.2(MH$^+$) |

TABLE 1-continued
| Entry # | IC$_{50}$ μM | R³ | m/z |
|---|---|---|---|
| 1283 | A | 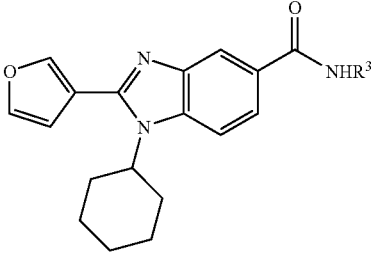 | 571.3(MH⁺) |
| 1284 | A | 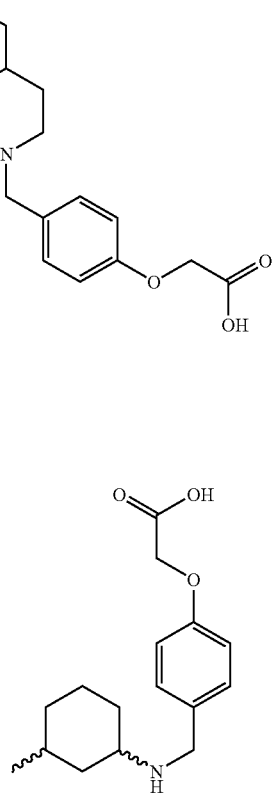 | 571.3(MH⁺) |
| 1285 | B | 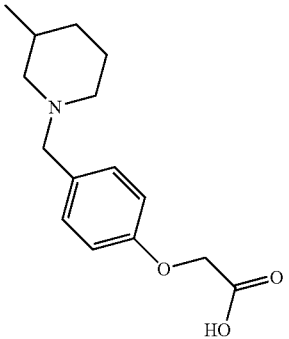 | 557.3(MH⁺) |

TABLE 1-continued
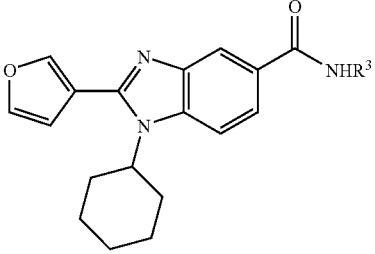
| Entry # | IC$_{50}$ µM | R$^3$ | m/z |
|---|---|---|---|
| 1286 | A | 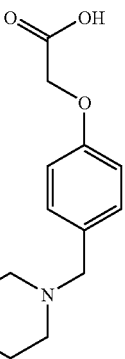 | 557.3(MH$^+$) |
| 1287 | C | 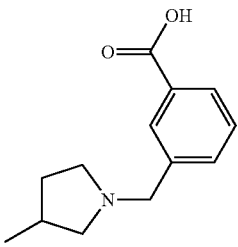 | 513.2(MH$^+$) |
| 1288 | C | 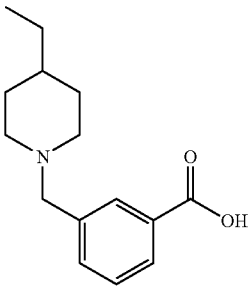 | 541.3(MH$^+$) |
| 1289 | C | 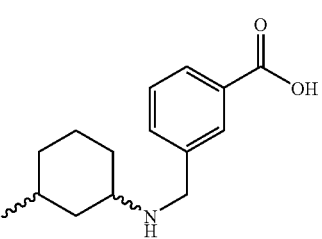 | 541.3(MH$^+$) |

TABLE 1-continued

| Entry # | IC$_{50}$ μM | R$^3$ | m/z |
|---|---|---|---|
| 1290 | C | 3-(trans-4-methylcyclohexylaminomethyl)benzoic acid | 541.3(MH$^+$) |
| 1291 | C | 3-((3-methylpiperidin-1-yl)methyl)benzoic acid | 527.3(MH$^+$) |
| 1292 | A | 3-((4-methylpiperidin-1-yl)methyl)benzoic acid | 527.3(MH$^+$) |
| 1298 | B | 4-(2-(5-(trifluoromethyl)-1,2,4-oxadiazol-3-yl)propyl)phenol | 566(MH$^+$) |
| 1300 | B | N,N-dimethyl | 353(MH$^+$) |
| 1301 | B | benzyl methylcarbamate | 459(MH$^+$) |

TABLE 1-continued
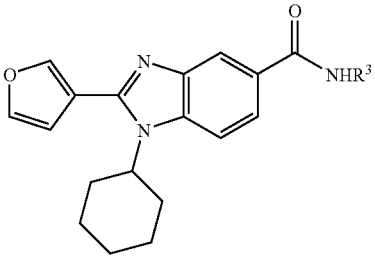
| Entry # | IC$_{50}$ μM | R$^3$ | m/z |
|---|---|---|---|
| 1302 | C | [4-(methylcarbamoyl)benzoic acid group] | 473(MH$^+$) |
TABLE 2
| Entry # | IC$_{50}$ μM | R$^1$ | R$^3$ | m/z |
|---|---|---|---|---|
| 2001 | A | 4-hydroxyphenyl | propyl-3,4-dimethoxyphenyl | 500(MH$^+$) |
| 2002 | A | 2-hydroxy-5-methylpyridyl | propyl-3,4-dimethoxyphenyl | 500(MH$^+$) |
| 2003 | A | 4-pyridyl | propyl-3,4-dimethoxyphenyl | 485(MH$^+$) |
| 2004 | A | phenyl | propyl-3,4-dimethoxyphenyl | 484(MH$^+$) |

TABLE 2-continued

| Entry # | IC$_{50}$ µM | R$^1$ | R$^3$ | m/z |
|---|---|---|---|---|
| 2005 | A | 2-fluorophenyl | 3,4-dimethoxyphenylpropyl | 502(MH$^+$) |
| 2006 | A | 2-pyridyl | (S)-2-methylbutanoic acid | 421(MH$^+$) |
| 2007 | A | 2-pyridyl | 2-ethyl-5-methoxy-phenyl (with OMe) | 471(MH$^+$) |
| 2008 | A | 2-pyridyl | 4-ethyl-2,3,6-trimethoxyphenyl | 501(MH$^+$) |
| 2009 | A | 2-pyridyl | 1,2-diphenyl-1-hydroxypropyl | 517(MH$^+$) |
| 2010 | A | 2-pyridyl | (S)-2-phenyl-1-propanol | 441(MH$^+$) |

TABLE 2-continued

| Entry # | IC$_{50}$ μM | R$^1$ | R$^3$ | m/z |
|---|---|---|---|---|
| 2011 | A | N-methylpyrrole | ethyl-(3,4-dimethoxyphenyl) | 459(MH$^+$) |
| 2012 | A | 2-pyridyl | 3-methyl-2-butyl-(3,4-dimethoxyphenyl) | 513(MH$^+$) |
| 2013 | A | 2-pyridyl | pent-4-en-2-yl-(3,4-dimethoxyphenyl) | 511(MH$^+$) |
| 2014 | A | 2-pyridyl | (S)-2-phenylpropanoic acid | 455(MH$^+$) |
| 2015 | A | 2,6-dimethylpyridyl | ethyl-(3,4-dimethoxyphenyl) | 485(MH$^+$) |
| 2016 | A | 2-pyridyl | propanoic acid | 379(MH$^+$) |
| 2017 | A | 2-pyridyl | 2,3-dimethylpentanoic acid | 435(MH$^+$) |

TABLE 2-continued
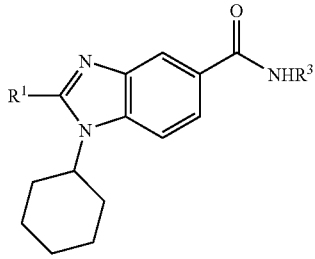
| Entry # | IC$_{50}$ μM | R$^1$ | R$^3$ | m/z |
|---|---|---|---|---|
| 2018 | A | 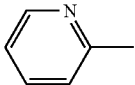 | 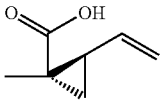 | 431(MH$^+$) |
| 2019 | A | 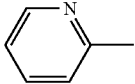 | 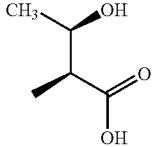 | 423(MH$^+$) |
| 2020 | A | 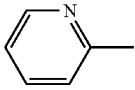 | 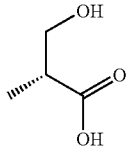 | 409(MH$^+$) |
| 2021 | A | 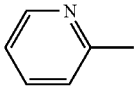 | 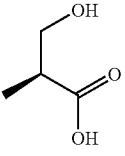 | 409(MH$^+$) |
| 2022 | B | 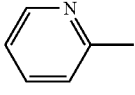 | 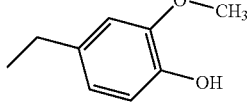 | 457(MH$^+$) |
| 2023 | A | 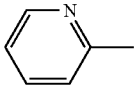 | 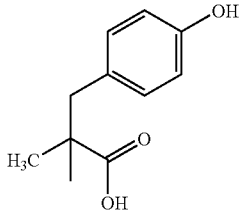 | 499(MH$^+$) |
| 2024 | A | 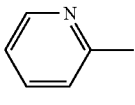 | 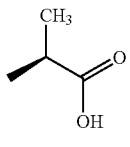 | 393(MH$^+$) |

TABLE 2-continued
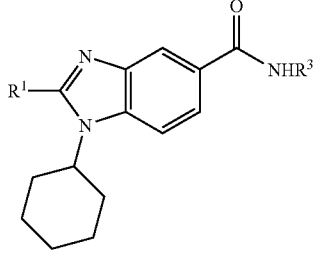
| Entry # | IC$_{50}$ μM | R$^1$ | R$^3$ | m/z |
|---|---|---|---|---|
| 2025 | B | 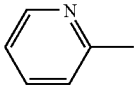 | 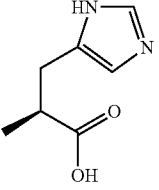 | 459(MH$^+$) |
| 2026 | A | 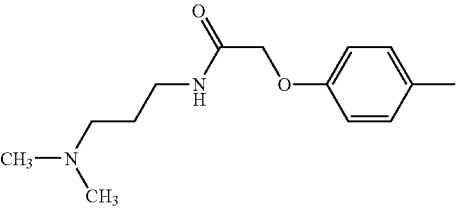 | 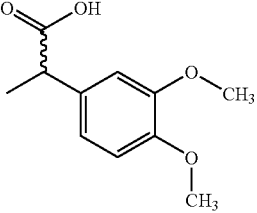 | 672(MH$^+$) |
| 2027 | A | 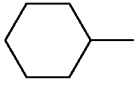 | 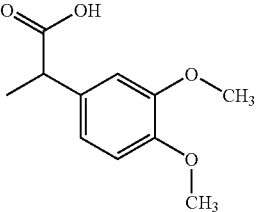 | 520(MH$^+$) |
| 2028 | A | 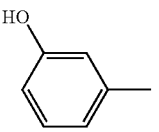 | 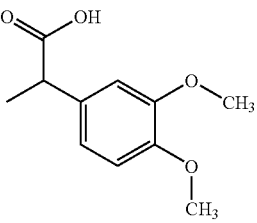 | 530(MH$^+$) |
| 2029 | A | 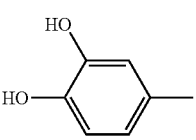 | 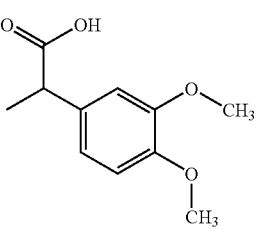 | 546(MH$^+$) |

TABLE 2-continued
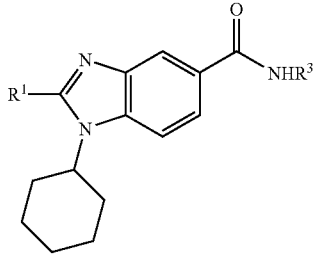
| Entry # | IC$_{50}$ μM | R$^1$ | R$^3$ | m/z |
|---|---|---|---|---|
| 2030 | A | 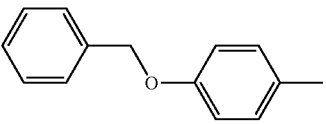 | 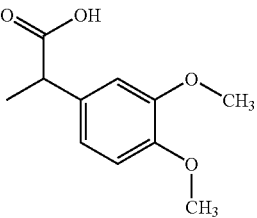 | 620(MH$^+$) |
| 2031 | A | 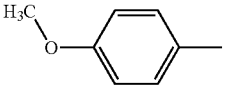 | 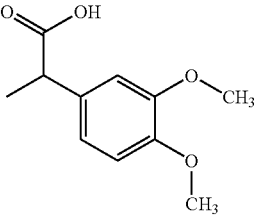 | 544(MH$^+$) |
| 2032 | A | 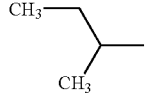 | 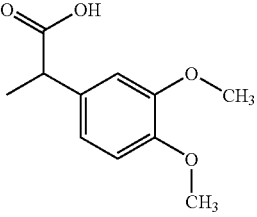 | 494(MH$^+$) |
| 2033 | A | 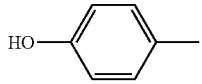 | 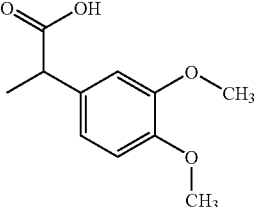 | 530(MH$^+$) |
| 2034 | A |  | 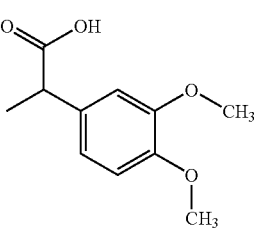 | 478(MH$^+$) |

TABLE 2-continued

| Entry # | IC$_{50}$ μM | R$^1$ | R$^3$ | m/z |
|---|---|---|---|---|
| 2035 | A | 3-methylbenzoic acid | 2-(3,4-dimethoxyphenyl)propanoic acid | 558(MH$^+$) |
| 2036 | A | 2,3-dihydro-1,4-benzodioxin-6-ylmethyl | 2-(3,4-dimethoxyphenyl)propanoic acid | 572(MH$^+$) |
| 2037 | A | 2-methylbut-2-enyl | 2-(3,4-dimethoxyphenyl)propanoic acid | 492(MH$^+$) |
| 2038 | A | benzofuran-2-yl | 2-(3,4-dimethoxyphenyl)propanoic acid | 554(MH$^+$) |
| 2039 | A | N-(3-(dimethylamino)propyl)-2-(p-tolyloxy)acetamide | 4-ethylphenyl methyl sulfone | 646(MH$^+$) |

TABLE 2-continued
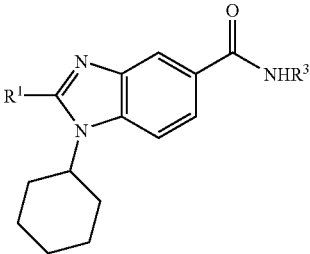
| Entry # | IC$_{50}$ μM | R$^1$ | R$^3$ | m/z |
|---|---|---|---|---|
| 2040 | A | CH$_3$ | 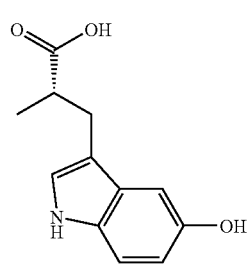 | 461(MH$^+$) |
| 2041 | C | 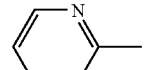 | 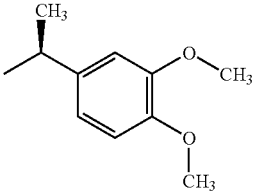 | 485(MH$^+$) |
| 2042 | C | 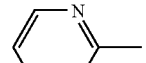 | 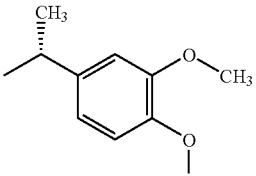 | 485(MH$^+$) |
| 2043 | B | 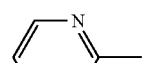 | 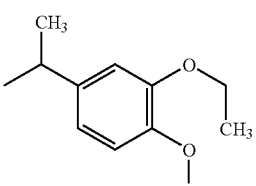 | 499(MH$^+$) |
| 2044 | B | 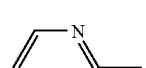 | 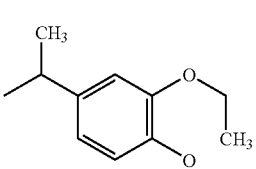 | 499(MH$^+$) |

US 7,439,258 B2
TABLE 2-continued
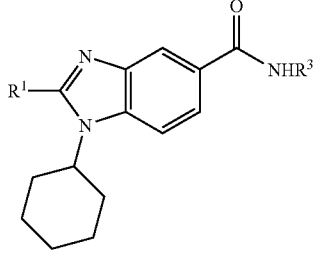
| Entry # | IC$_{50}$ μM | R$^1$ | R$^3$ | m/z |
|---|---|---|---|---|
| 2045 | C | 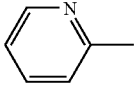 | 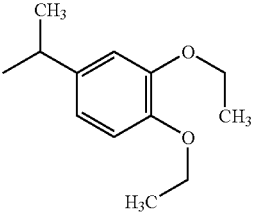 | 513(MH$^+$) |
| 2046 | B | 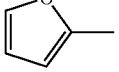 | 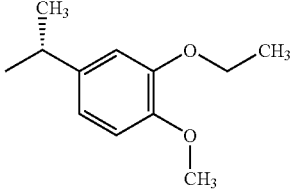 | 474(MH$^+$) |
| 2047 | B | 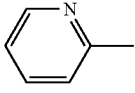 | 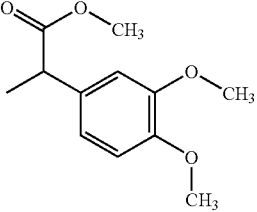 | 529(MH$^+$) |
| 2048 | C | 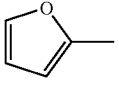 | 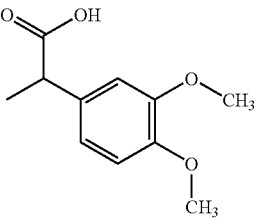 | 504(MH$^+$) |
| 2049 | C | 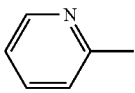 | 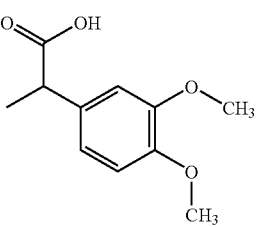 | 515(MH$^+$) |

TABLE 2-continued
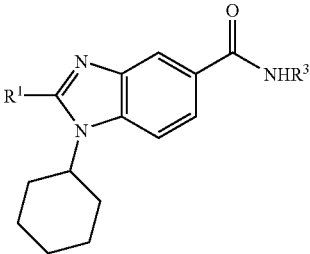
| Entry # | IC$_{50}$ μM | R$^1$ | R$^3$ | m/z |
|---|---|---|---|---|
| 2050 | B | 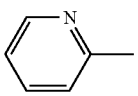 | 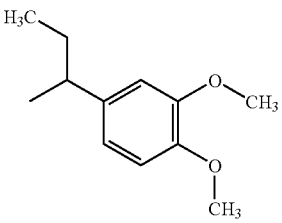 | 499(MH$^+$) |
| 2051 | B | 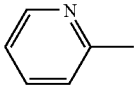 | 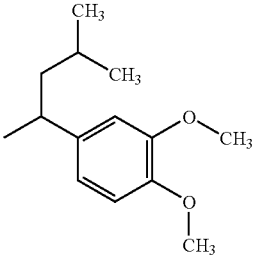 | 527(MH$^+$) |
| 2054 | B | 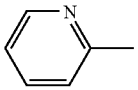 | 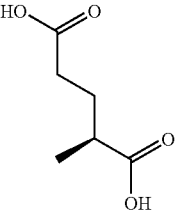 | 451(MH$^+$) |
| 2055 | C | 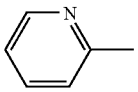 | 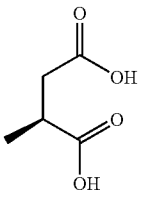 | 437(MH$^+$) |
| 2056 | B | 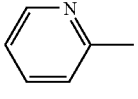 | 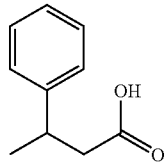 | 469(MH$^+$) |

TABLE 2-continued
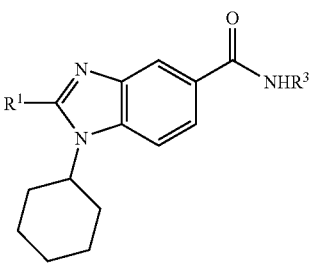
| Entry # | IC$_{50}$ μM | R$^1$ | R$^3$ | m/z |
|---|---|---|---|---|
| 2057 | B | 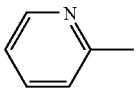 | 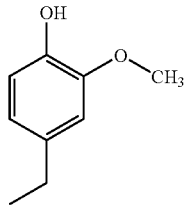 | 457(MH$^+$) |
| 2058 | C | 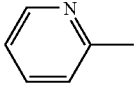 | 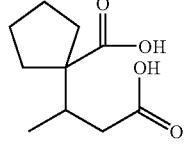 | 491(MH$^+$) |
| 2059 | C | 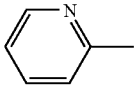 | 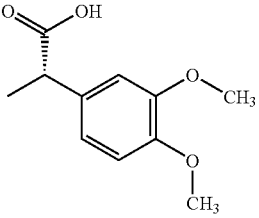 | 515(MH$^+$) |
| 2060 | C | 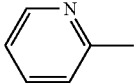 | 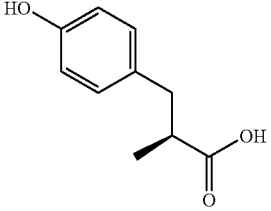 | 485(MH$^+$) |
| 2061 | B | 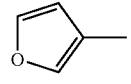 | 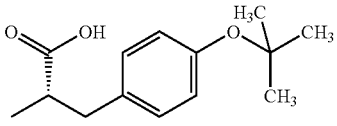 | 530 |
| 2062 | B | 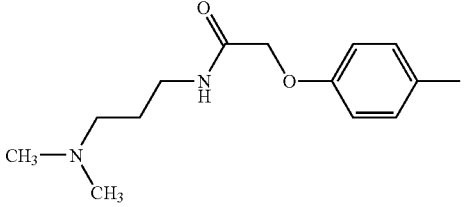 | 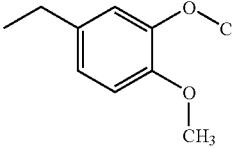 | 628(MH$^+$) |

TABLE 2-continued
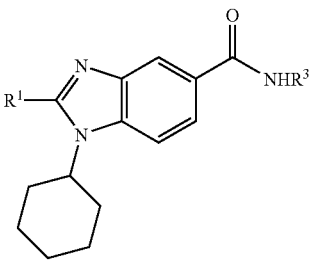
| Entry # | IC$_{50}$ μM | R$^1$ | R$^3$ | m/z |
|---|---|---|---|---|
| 2063 | C | 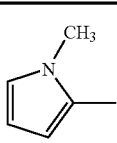 | 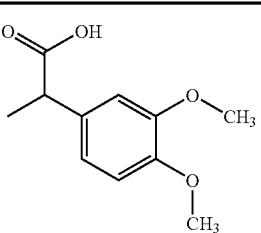 | 517(MH$^+$) |
| 2064 | C | 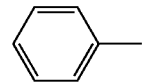 | 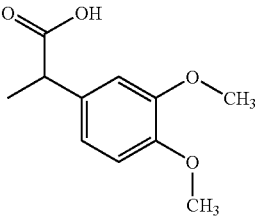 | 514(MH$^+$) |
| 2065 | C | 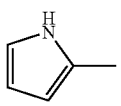 | 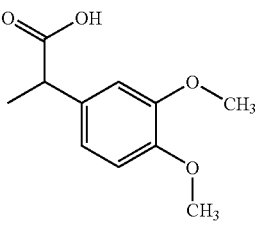 | 503(MH$^+$) |
| 2067 | C | 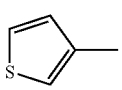 | 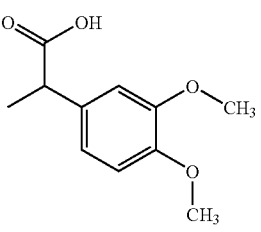 | 520(MH$^+$) |
| 2068 | B | 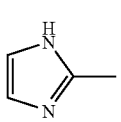 | 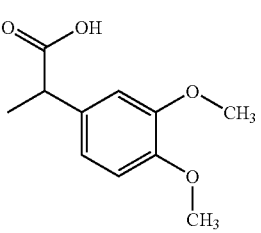 | 504(MH$^+$) |

TABLE 2-continued

[Structure: 1-cyclohexyl-benzimidazole-5-carboxamide core with R¹ at 2-position and NHR³ on the carboxamide]

| Entry # | IC$_{50}$ μM | R¹ | R³ | m/z |
|---|---|---|---|---|
| 2069 | C | 4-(isopropoxy)phenyl (CH₃)₂CHO-C₆H₄- | 2-(3,4-dimethoxyphenyl)-1-carboxyethyl (α-methyl, COOH, 3,4-diOMe-Ph) | 572(MH⁺) |
| 2070 | B | 4-[(3-(dimethylamino)propylaminocarbonylmethoxy)]phenyl | 4-ethylphenylsulfonamide (4-SO₂NH₂-C₆H₄-CH₂CH₂-) | 647(MH⁺) |
| 2071 | C | 4-[(3-(dimethylamino)propylaminocarbonylmethoxy)]phenyl | 1-(naphthalen-2-yl)ethyl | 632(MH⁺) |
| 2073 | B | pyridin-2-yl | 2-(3,4-dihydroxyphenyl)ethyl | 443(MH⁺) |
| 2074 | B | pyridin-2-yl | 2-(2-ethyl-1H-benzimidazol-yl) | 451(MH⁺) |
| 2075 | C | pyridin-2-yl | 2-(3,4-dimethoxyphenyl)ethyl | 471(MH⁺) |

TABLE 2-continued

| Entry # | IC$_{50}$ μM | R$^1$ | R$^3$ | m/z |
|---|---|---|---|---|
| 2076 | B | 2-pyridyl-methyl | (R)-1-phenyl-1-carboxyethyl | 455(MH$^+$) |
| 2077 | B | 4-methoxyphenyl-methyl | 3,4-dimethoxyphenyl-propyl | 514(MH$^+$) |
| 2082 | B | 2-hydroxy-5-methyl benzoic acid | 2-(3,4-dimethoxyphenyl)propanoic acid | 574(MH$^+$) |
| 2083 | A | 4-(2-carboxyvinyl)phenyl-methyl | 2-(3,4-dimethoxyphenyl)propanoic acid | 584(MH$^+$) |
| 2084 | C | 3-phenoxyphenyl-methyl | (S)-2-methyl-3-(5-hydroxy-1H-indol-3-yl)propanoic acid | 615(MH$^+$) |
| 2085 | C | 4-acetamidophenyl-methyl | (S)-2-methyl-3-(5-hydroxy-1H-indol-3-yl)propanoic acid | 580(MH$^+$) |

TABLE 2-continued
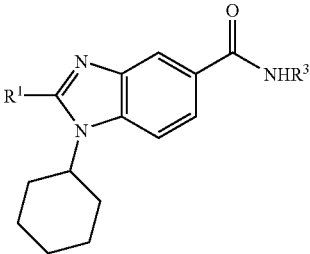
| Entry # | IC$_{50}$ µM | R$^1$ | R$^3$ | m/z |
|---|---|---|---|---|
| 2087 | C | 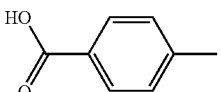 | 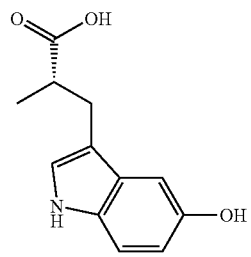 | 567(MH$^+$) |
| 2088 | A | 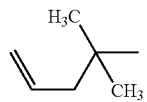 | 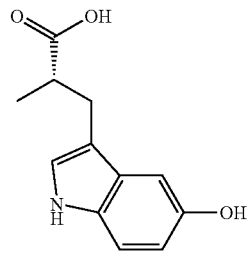 | 529(MH$^+$) |
| 2089 | C | 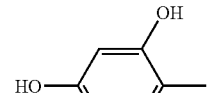 | 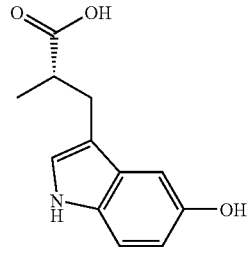 | 555(MH$^+$) |
| 2091 | C | 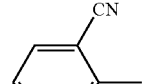 | 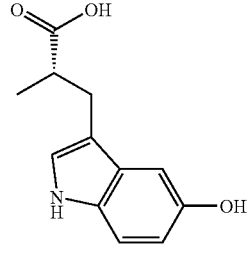 | 548(MH$^+$) |

TABLE 2-continued
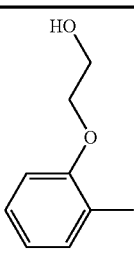
| Entry # | IC$_{50}$ μM | R$^1$ | R$^3$ | m/z |
|---|---|---|---|---|
| 2093 | C | 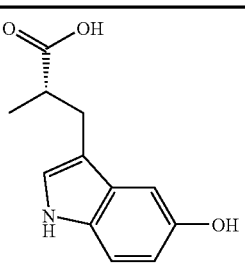 | 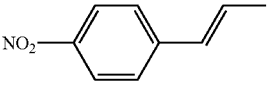 | 583(MH$^+$) |
| 2097 | C | 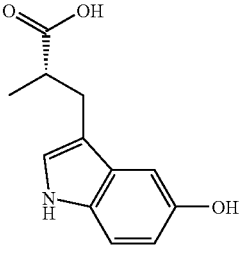 | 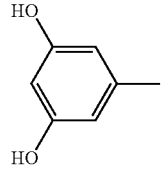 | 594(MH$^+$) |
| 2100 | C | 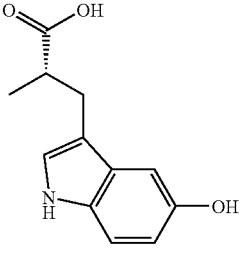 | 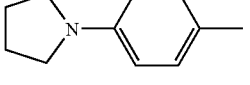 | 555(MH$^+$) |
| 2101 | C | 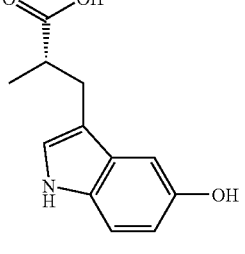 | 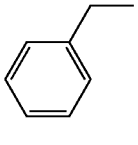 | 592(MH$^+$) |
| 2102 | C | 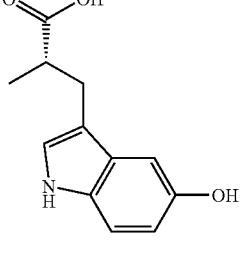 | | 537(MH$^+$) |

TABLE 2-continued

| Entry # | IC$_{50}$ μM | R$^1$ | R$^3$ | m/z |
|---|---|---|---|---|
| 2105 | C | 2-methoxy-6-methylphenol | (S)-2-methyl-3-(5-hydroxy-1H-indol-3-yl)propanoic acid | 569(MH$^+$) |
| 2107 | C | 5-methylfuran-2-sulfonic acid | (S)-2-methyl-3-(5-hydroxy-1H-indol-3-yl)propanoic acid | 593(MH$^+$) |
| 2108 | A | 2-methylpyridine | 3-(3,4-dimethoxyphenyl)propyl | 485(MH$^+$) |
| 2110 | C | 2-methyl-1H-indole | (S)-2-methyl-3-(5-hydroxy-1H-indol-3-yl)propanoic acid | 562.2(MH$^+$) |
| 2111 | C | CF$_3$ | (S)-2-methyl-3-(5-hydroxy-1H-indol-3-yl)propanoic acid | 515.1(MH$^+$) |

TABLE 2-continued
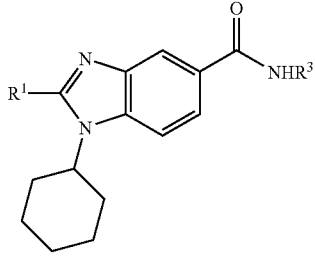
| Entry # | IC$_{50}$ μM | R$^1$ | R$^3$ | m/z |
|---|---|---|---|---|
| 2112 | D | 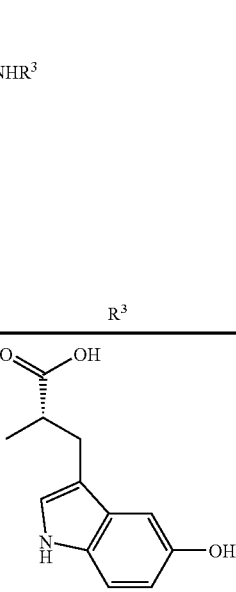 | 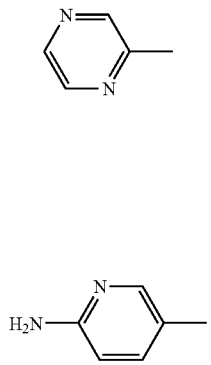 | 525.3(MH$^+$) |
| 2114 | C | 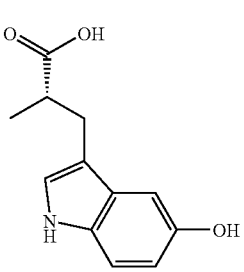 | 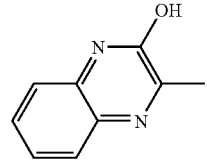 | 539.2(MH$^+$) |
| 2115 | B | 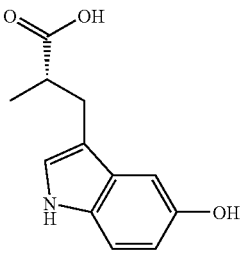 | 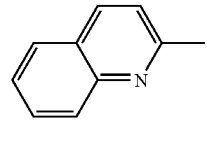 | 591.2(MH$^+$) |
| 2116 | B | 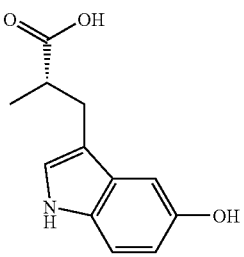 | 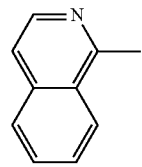 | 574.2(MH$^+$) |
| 2117 | C | 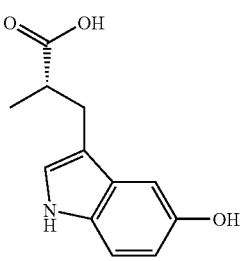 | | 574.2(MH$^+$) |

TABLE 2-continued
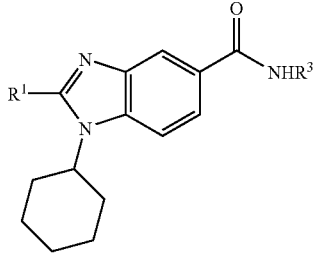
| Entry # | IC$_{50}$ μM | R$^1$ | R$^3$ | m/z |
|---|---|---|---|---|
| 2120 | C | 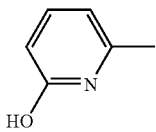 | 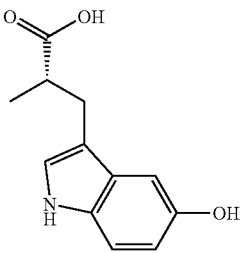 | 540.2(MH$^+$) |
| 2121 | C | 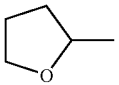 | 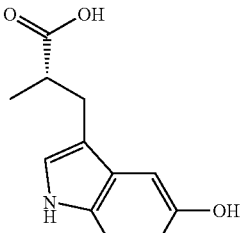 | 517.2(MH$^+$) |
| 2122 | B | 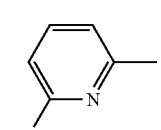 | 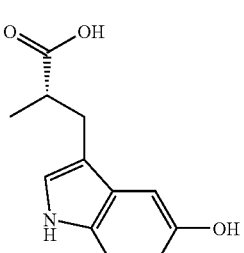 | 538.2(MH$^+$) |
| 2123 | C | 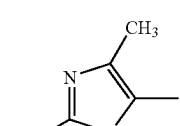 | 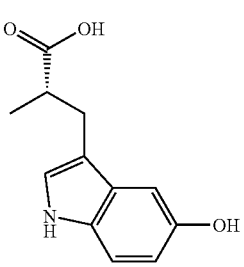 | 558.1(MH$^+$) |

TABLE 2-continued
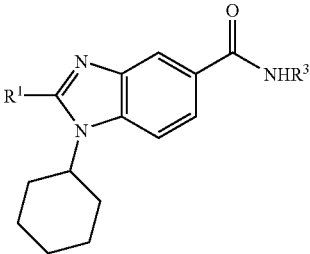
| Entry # | IC$_{50}$ µM | R$^1$ | R$^3$ | m/z |
|---|---|---|---|---|
| 2125 | B | 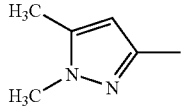 | 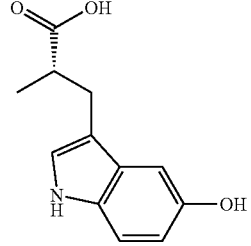 | 541.2(MH$^+$) |
| 2126 | C | 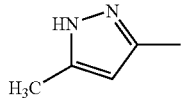 | 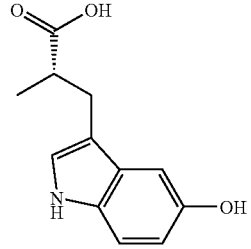 | 527.2(MH$^+$) |
| 2127 | D | 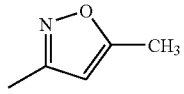 | 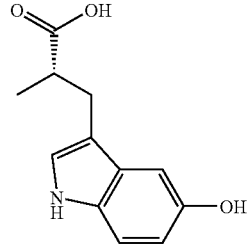 | 528.2(MH$^+$) |
| 2128 | C | 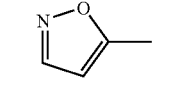 | 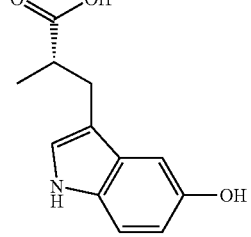 | 514.1(MH$^+$) |

TABLE 2-continued
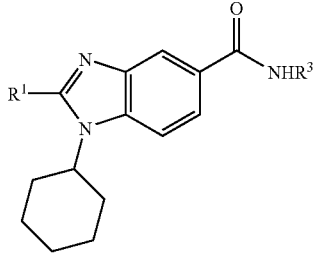
| Entry # | IC$_{50}$ μM | R$^1$ | R$^3$ | m/z |
|---|---|---|---|---|
| 2129 | C | 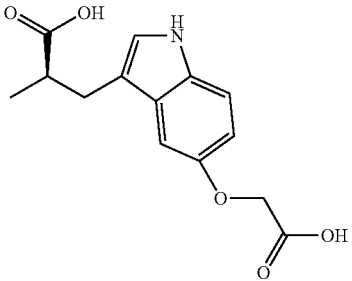 | 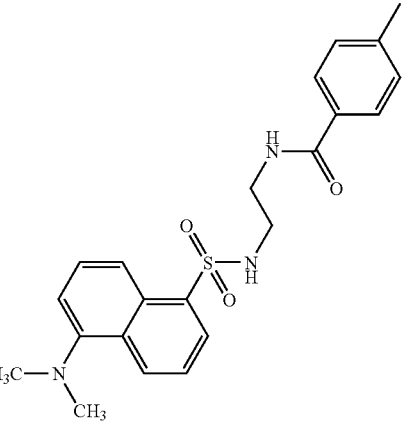 | 930(MH$^+$) |
| 2130 | C | 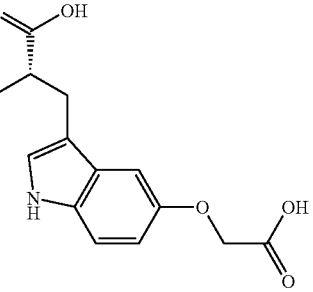 | | 900(MH$^+$) |

TABLE 2-continued

| Entry # | IC$_{50}$ μM | R$^1$ | R$^3$ | m/z |
|---|---|---|---|---|
| 2135 | C | 2-pyridyl | (S)-CH(CH$_3$)CH$_2$-(4-hydroxyphenyl)-C(O)NH$_2$ | 484(MH$^+$) |
| 2138 | C | 4-(CF$_3$)phenyl | (S)-CH(CH$_3$)CH$_2$-(5-hydroxyindol-3-yl)-COOH | 591(MH$^+$) |
| 2139 | D | phenyl | (S)-CH(CH$_3$)CH$_2$-(5-hydroxyindol-3-yl)-COOH | 523.2(MH$^+$) |
| 2140 | D | 6-hydroxypyridin-3-yl | (S)-CH(CH$_3$)CH$_2$-(5-hydroxyindol-3-yl)-COOH | 540.2(MH$^+$) |
| 2141 | D | 4,5-dimethyl-1,2,3-thiadiazol-yl | (S)-CH(CH$_3$)CH$_2$-(5-hydroxyindol-3-yl)-COOH | 545.1(MH$^+$) |

TABLE 2-continued
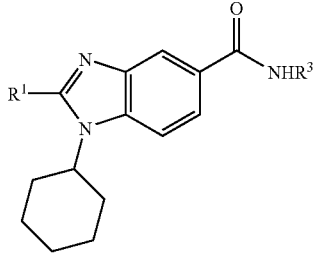
| Entry # | IC$_{50}$ μM | R$^1$ | R$^3$ | m/z |
|---|---|---|---|---|
| 2142 | D | 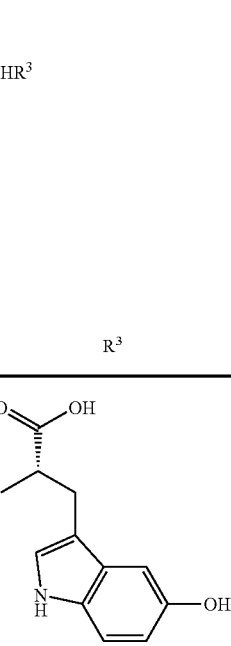 | 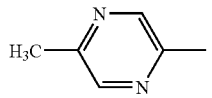 | 513.2(MH$^+$) |
| 2143 | D | 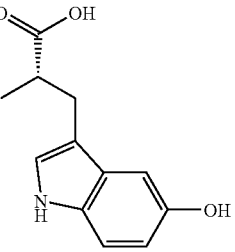 | 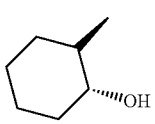 | 539.2(MH$^+$) |
TABLE 3
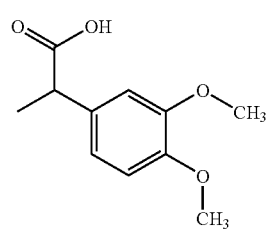
| Entry # | IC$_{50}$ μM | R$^2$ | R$^3$ | m/z |
|---|---|---|---|---|
| 3001 | B |  |  | 520(MH$^+$) |

TABLE 3-continued
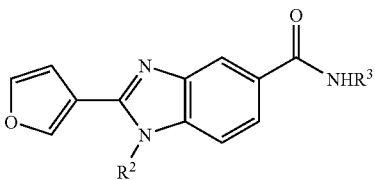
| Entry # | IC$_{50}$ μM | R$^2$ | R$^3$ | m/z |
|---|---|---|---|---|
| 3002 | D | 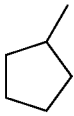 | 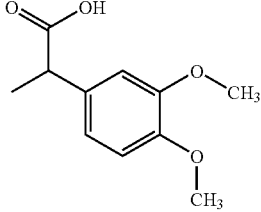 | 490(MH$^+$) |
| 3005 | C | 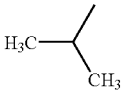 | 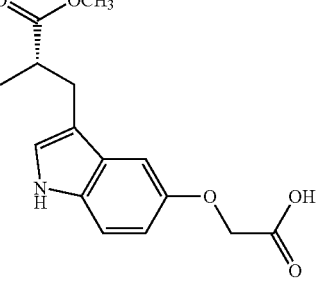 | 545(MH$^+$) |
| 3024 | C | 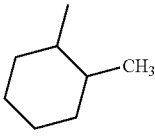 | 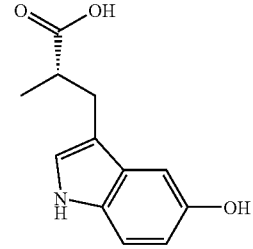 | 527(MH$^+$) |
| 3029 | C | 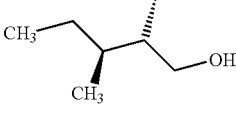 | 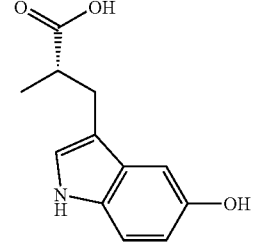 | 531(MH$^+$) |
| 3033 | C | 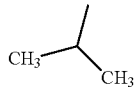 | 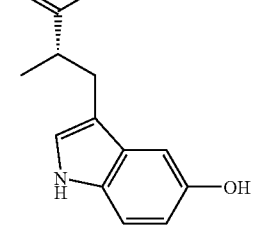 | 473(MH$^+$) |

TABLE 3-continued
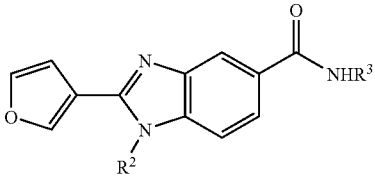
| Entry # | IC$_{50}$ μM | R$^2$ | R$^3$ | m/z |
|---|---|---|---|---|
| 3034 | B | 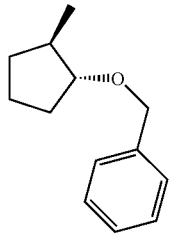 | 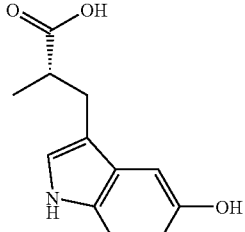 | 605(MH$^+$) |
| 3035 | C | 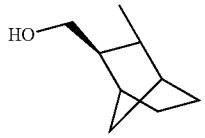 | 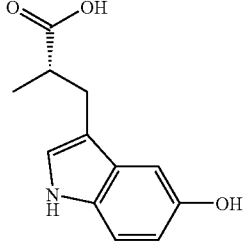 | 555(MH$^+$) |
| 3037 | B | 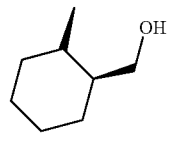 | 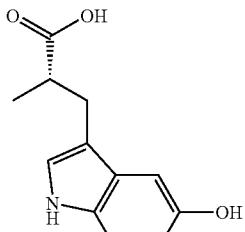 | 543(MH$^+$) |
| 3040 | C | 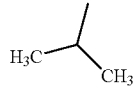 | 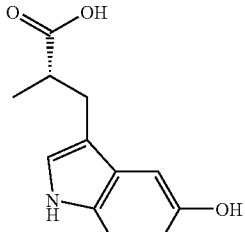 | 472(MH$^+$) |

TABLE 4
| Entry # | IC$_{50}$ μM | R$^1$ | R$^2$ | R$^3$ | m/z |
|---|---|---|---|---|---|
| 4001 | D |  |  | 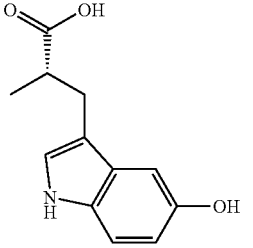 | 525 (MH$^+$) |
TABLE 5
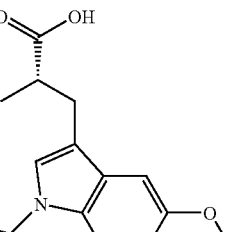
| Entry # | IC$_{50}$ μM | A | R$^5$ | Z | R$^3$ | m/z |
|---|---|---|---|---|---|---|
| 5001 | B | N | H | OH | — | 312(MH$^+$) |
| 5002 | D | N | H | NHR$^3$ | (structure) | 514(MH$^+$) |
| 5003 | D | N | H | NHR$^3$ | (structure) | 630(MH$^+$) |
| 5004 | C | CMe | H | OH | — | 325(MH$^+$) |

TABLE 5-continued
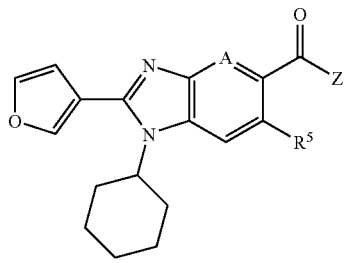
| Entry # | IC$_{50}$ μM | A | R$^5$ | Z | R$^3$ | m/z |
|---|---|---|---|---|---|---|
| 5005 | D | CH | H | OR$^3$ | 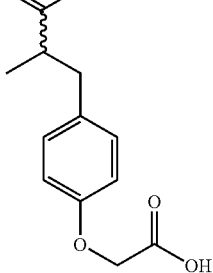 | 533(MH$^+$) |
| 5006 | C | CH | CH$_3$ | NHR$^3$ | 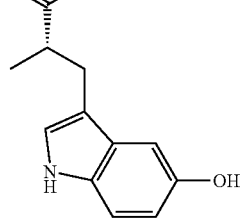 | 527(MH$^+$) |
| 5007 | D | CMe | H | NHR$^3$ | 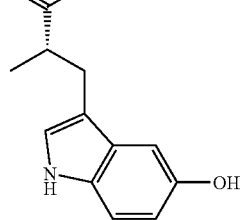 | 527(MH$^+$) |

TABLE 5-continued

| Entry # | IC₅₀ μM | A | R⁵ | Z | R³ | m/z |
|---|---|---|---|---|---|---|
| 5008 | D | CMe | H | NHR³ | (2-methyl-3-(5-(carboxymethoxy)-1H-indol-3-yl)propanoic acid) | 583(M − H) |
| 5009 | C | CH | CH₃ | NHR³ | (2-methyl-3-(5-(carboxymethoxy)-1H-indol-3-yl)propanoic acid) | 583(M − H) |

TABLE 6

| Entry # | IC₅₀ μM | Z | m/z |
|---|---|---|---|
| 6001 | A | (1-methyl-4-hydroxypyrrolidine-2-carboxylic acid) | 424 (MH⁺) |
| 6002 | A | (1-methyl-4-hydroxypyrrolidine-2-carboxylic acid) | 424 (MH⁺) |

TABLE 6-continued

[Structure: 2-(furan-3-yl)-1-cyclohexyl-1H-benzimidazole-5-carbonyl-Z]

| Entry # | IC$_{50}$ μM | Z | m/z |
|---|---|---|---|
| 6003 | B | (2S,4R)-1-methyl-4-(4-((E)-2-carboxyvinyl)phenoxy)pyrrolidine-2-carboxylic acid | 570 (MH$^+$) |
| 6004 | B | (3R)-1-methyl-3-(4-((E)-2-carboxyvinyl)phenoxy)pyrrolidine | 526 (MH$^+$) |

TABLE 6-continued

[Structure: 2-(furan-3-yl)-1-cyclohexyl-1H-benzimidazole-5-carbonyl-Z]

| Entry # | IC$_{50}$ μM | Z | m/z |
|---|---|---|---|
| 6005 | B | (3S)-2-methyl-6-hydroxy-2,3,4,9-tetrahydro-1H-pyrido[3,4-b]indole-3-carboxylic acid | 525 (MH$^+$) |

TABLE 7

[Structure: 1H-benzimidazole-5-carboxylic acid with R$^1$ at 2-position and R$^2$ on N1]

| Entry # | IC$_{50}$ μM | R$^1$ | R$^2$ | m/z |
|---|---|---|---|---|
| 7001 | A | pyridin-2-yl | 2-methylcyclohexyl | 336(MH$^+$) |
| 7002 | A | 4-cyanophenyl | cyclohexyl | 346(MH$^+$) |
| 7003 | A | 2-methylprop-1-enyl | cyclohexyl | 299(MH$^+$) |

TABLE 7-continued
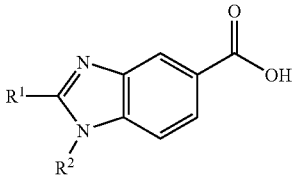
| Entry # | IC$_{50}$ μM | R$^1$ | R$^2$ | m/z |
|---|---|---|---|---|
| 7004 | A | 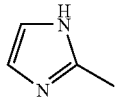 | 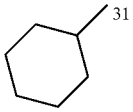 | 311(MH$^+$) |
| 7005 | A | 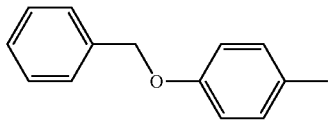 | 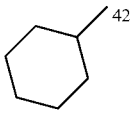 | 427(MH$^+$) |
| 7006 | A | 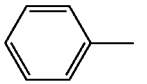 | 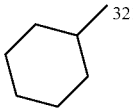 | 321(MH$^+$) |
| 7007 | A | 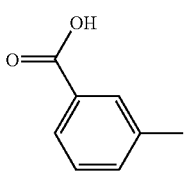 | 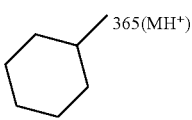 | 365(MH$^+$) |
| 7008 | A | 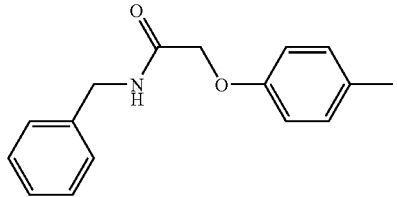 | 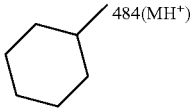 | 484(MH$^+$) |
| 7009 | A | 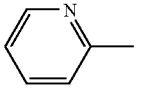 | 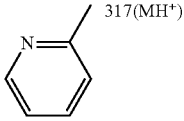 | 317(MH$^+$) |
| 7026 | C | 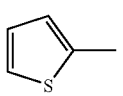 | 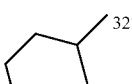 | 327(MH$^+$) |
| 7027 | B | 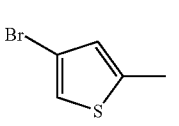 | 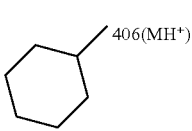 | 406(MH$^+$) |
| 7010 | A | 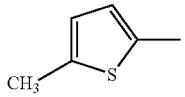 | 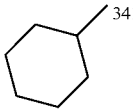 | 341(MH$^+$) |

TABLE 7-continued
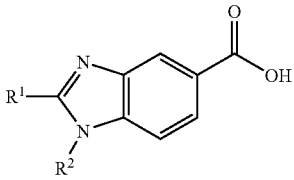
| Entry # | IC$_{50}$ μM | R$^1$ | R$^2$ | m/z |
|---|---|---|---|---|
| 7011 | A | 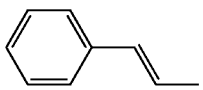 |  | 347(MH$^+$) |
| 7012 | A | 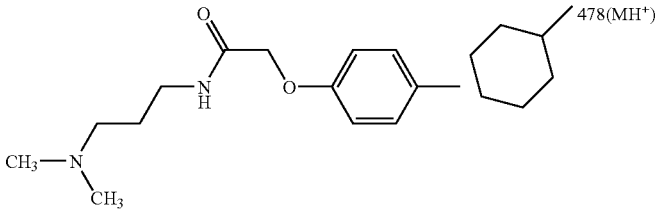 |  | 478(MH$^+$) |
| 7013 | C | 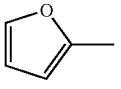 |  | 311(MH$^+$) |
| 7014 | C | 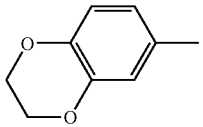 |  | 379(MH$^+$) |
| 7015 | C | 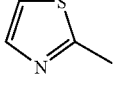 |  | 328(MH$^+$) |
| 7016 | B | 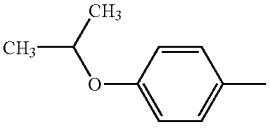 |  | 379(MH$^+$) |
| 7017 | B | 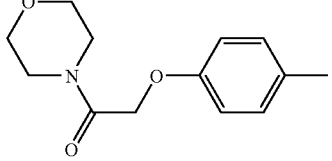 |  | 464(MH$^+$) |
| 7018 | C | 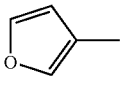 |  | 311(MH$^+$) |
| 7019 | C | 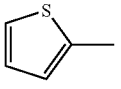 |  | 327(MH$^+$) |

TABLE 7-continued
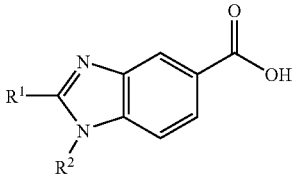
| Entry # | IC$_{50}$ μM | R$^1$ | R$^2$ | m/z |
|---|---|---|---|---|
| 7020 | B | 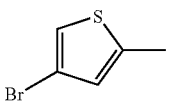 | 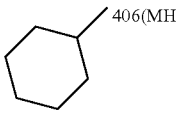 | 406(MH$^+$) |
| 7021 | C | 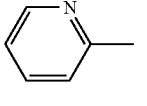 | 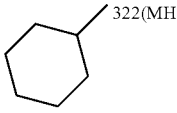 | 322(MH$^+$) |
| 7022 | B | 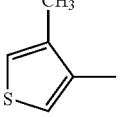 | 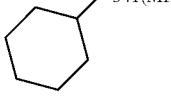 | 341(MH$^+$) |
| 7023 | A | 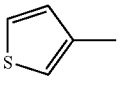 | 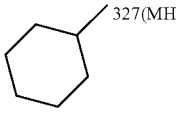 | 327(MH$^+$) |
| 7024 | C | 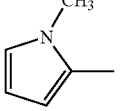 | 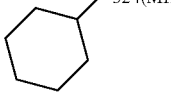 | 324(MH$^+$) |
| 7025 | A | 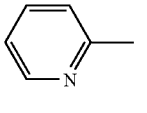 | 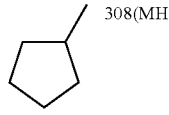 | 308(MH$^+$) |
TABLE 8
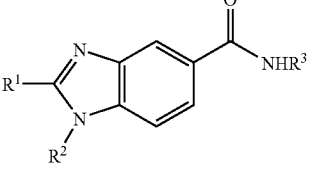
| Entry # | IC$_{50}$ μM | R$^1$ | R$^2$ | R$^3$ | m/z |
|---|---|---|---|---|---|
| 8001 | A | 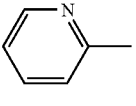 | 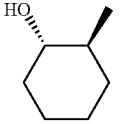 | 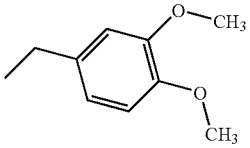 | 487(MH$^+$) |

TABLE 8-continued
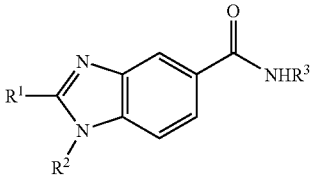
| Entry # | IC$_{50}$ µM | R$^1$ | R$^2$ | R$^3$ | m/z |
|---|---|---|---|---|---|
| 8002 | B |  | 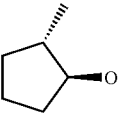 | 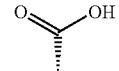 | 519(MH$^+$) |
| 8003 | A |  | 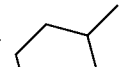 | 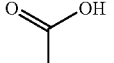 | 520(MH$^+$) |
TABLE 9
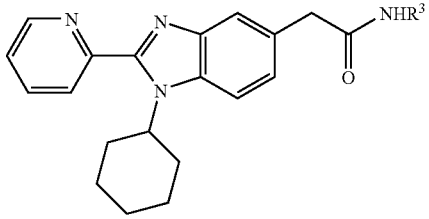
| Entry # | IC$_{50}$ µM | R$^3$ | m/z |
|---|---|---|---|
| 9001 | B | 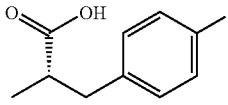 | 499(MH$^+$) |
| 9002 | B | 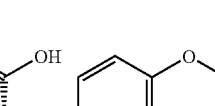 | 557(MH$^+$) |
TABLE 10
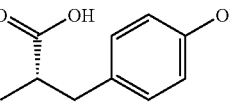
| Entry # | IC$_{50}$ µM | R$^3$ | m/z |
|---|---|---|---|
| 10001 | A | 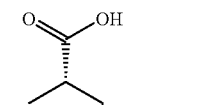 | 488(MH$^+$) |
| 10063 | C | | 511(MH$^+$) |

TABLE 11

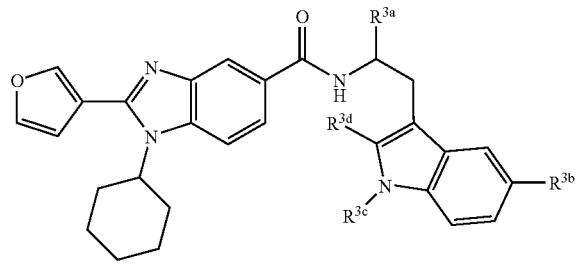

| Entry # | IC$_{50}$ | R$^{3a}$ | R$^{3b}$ | R$^{3c}$ | R$^{3d}$ | m/z |
|---|---|---|---|---|---|---|
| 11001 | D | H | OH | H | H | 469(MH$^+$) |
| 11002 | D | ⋯C(O)OH | OH | H | H | 513(MH$^+$) |
| 11003 | D | ⋯C(O)OH | H | H | H | 497(MH$^+$) |
| 11004 | D | ⋯C(O)OH | OCH$_2$COOH | H | H | 497(MH$^+$) |
| 11005 | D | ⋯C(O)OCH$_3$ | OH | H | H | 527(MH$^+$) |
| 11006 | D | ⋯C(O)OH | OH | H | H | 513(MH$^+$) |
| 11007 | D | ⋯C(O)OH | OCH$_2$COOH | CH$_2$COOH | H | 629(MH$^+$) |
| 11008 | D | ⋯C(O)OCH$_3$ | OCH$_2$COOH | H | H | 585(MH$^+$) |
| 11009 | D | ⋯C(O)OH | OCH$_2$COOH | H | H | 571(MH$^+$) |
| 11010 | D | ⋯C(O)OH | OC(CH$_3$)$_2$COOH | H | H | 599(MH$^+$) |
| 11011 | D | H | OCH$_2$COOH | H | H | 527(MH$^+$) |
| 11012 | D | H | OCH$_2$COOH | CH$_2$COOH | H | 585(MH$^+$) |
| 11013 | D | C(O)OH | OH | H | H | 513(MH$^+$) |
| 11014 | D | C(O)OH | OCH$_2$COOH | H | H | 571(MH$^+$) |
| 11015 | D | ⋯C(O)OCH$_3$ | OCH$_2$COOH | H | CH$_3$ | 599(MH$^+$) |

TABLE 11-continued
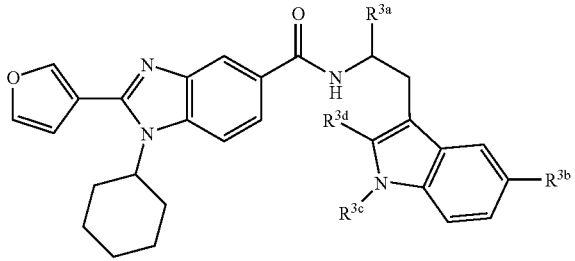
| Entry # | IC$_{50}$ | R$^{3a}$ | R$^{3b}$ | R$^{3c}$ | R$^{3d}$ | m/z |
|---|---|---|---|---|---|---|
| 11016 | D | 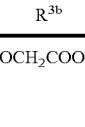 | OCH$_2$COOH | CH$_3$ | H | 585(MH$^+$) |
| 11017 | D |  | OCH$_2$COOH | CH$_3$ | H | 599(MH$^+$) |
| 11018 | D |  | COOH | H | H | 541(MH$^+$) |
| 11019 | D |  | CONH$_2$ | H | H | 540(MH$^+$) |
| 11020 | D |  | OH | H | CH$_3$ | 527(MH$^+$) |
| 11021 | D |  | OH | CH$_3$ | H | 527(MH$^+$) |
| 11022 | D |  | 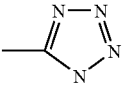 | H | H | 565(MH$^+$) |
| 11023 | D |  | NH$_2$ | H | H | 512(MH$^+$) |
| 11024 | D |  | NHCOCOOH | H | H | 584(MH$^+$) |
| 11025 | D |  | NHSO$_2$CH$_3$ | H | H | 590(MH$^+$) |
| 11026 | D |  | NHSO$_2$CF$_3$ | H | H | 644(MH$^+$) |
| 11027 | D |  | 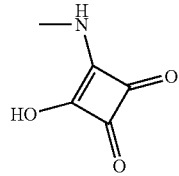 | H | H | 608(MH$^+$) |

TABLE 11-continued
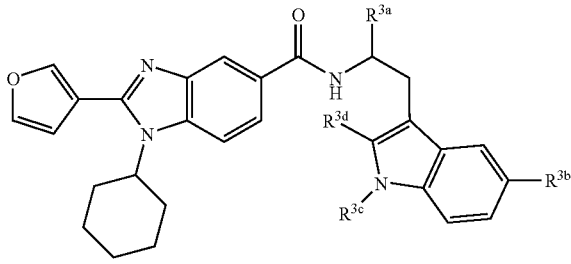
| Entry # | IC$_{50}$ | R$^{3a}$ | R$^{3b}$ | R$^{3c}$ | R$^{3d}$ | m/z |
|---|---|---|---|---|---|---|
| 11028 | D | 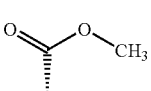 | OH | CH$_3$ | H | 541(MH$^+$) |
| 11029 | D | 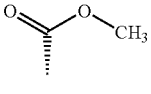 | OC(CH$_3$)$_2$COOH | CH$_3$ | H | 584(MH$^+$) |
| 11030 | D | 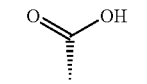 | OC(CH$_3$)$_2$COOH | CH$_3$ | H | 613(MH$^+$) |
| 11031 | D | 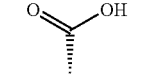 | 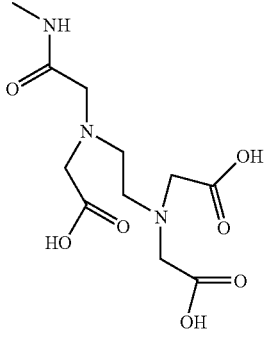 | H | H | 786(MH$^+$) |
| 11032 | D | 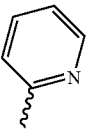 | OH | H | H | 546(MH$^+$) |
| 11033 | D | 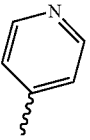 | OH | H | H | 546(MH$^+$) |

TABLE 12
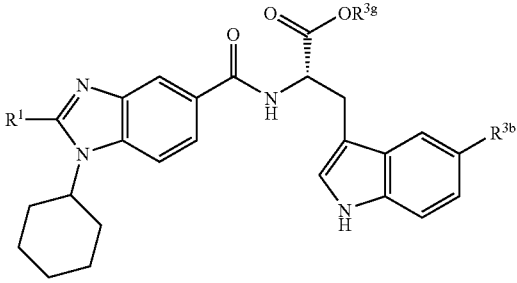
| Entry # | IC$_{50}$ | R$^1$ | R$^{3g}$ | R$^{3b}$ | m/z |
|---|---|---|---|---|---|
| 12001 | D | 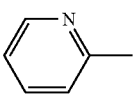 | CH$_3$ | OH | 583(MH$^+$) |
| 12002 | D | 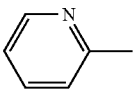 | CH$_3$ | OCH$_2$COOH | 458(MH$^+$) |
| 12003 | D | 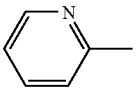 | H | OCH$_2$COOH | 582(MH$^+$) |
| 12004 | D | 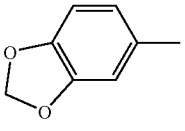 | H | OH | 567(MH$^+$) |
| 12005 | D | 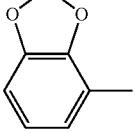 | H | OH | 567(MH$^+$) |
| 12006 | D | 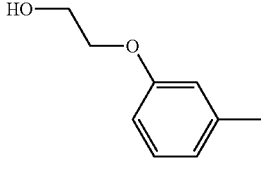 | H | OH | 583(MH$^+$) |
| 12007 | D | 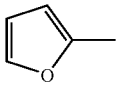 | H | OH | 513(MH$^+$) |
| 12008 | D | 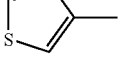 | H | OH | 529(MH$^+$) |
| 12009 | D | 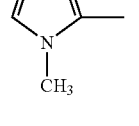 | H | OH | 527(MH$^+$) |

TABLE 12-continued
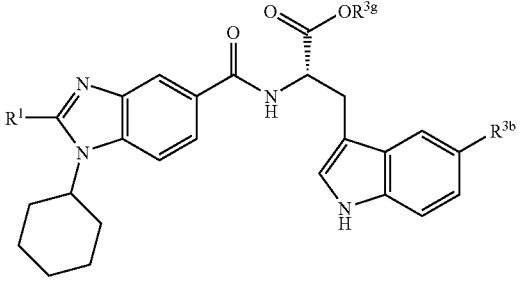
| Entry # | IC$_{50}$ | R$^1$ | R$^{3g}$ | R$^{3b}$ | m/z |
|---|---|---|---|---|---|
| 12010 | D | 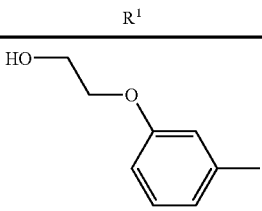 | H | OH | 583(MH$^+$) |
| 12011 | D | 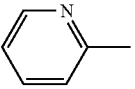 | H | OH | 524(MH$^+$) |
| 12012 | D | 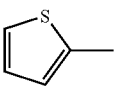 | H | OH | 529(MH$^+$) |
| 12013 | D | 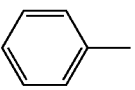 | H | OH | 523(MH$^+$) |
| 12014 | D | 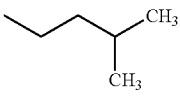 | H | OH | 517(MH$^+$) |
| 12015 | D | 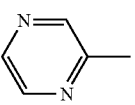 | H | OH | 525(MH$^+$) |
| 12016 | D | 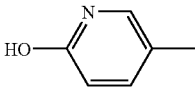 | H | OH | 540(MH$^+$) |
| 12017 | D |  | H | OH | 545(MH$^+$) |
| 12018 | D | 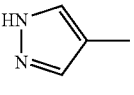 | H | OH | 513(MH$^+$) |
| 12019 | D | 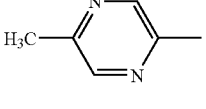 | H | OH | 539(MH$^+$) |
| 12020 | D | 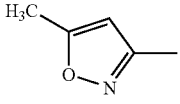 | H | OH | 528(MH$^+$) |

TABLE 12-continued
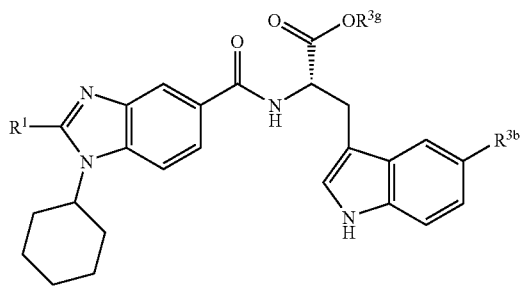
| Entry # | IC$_{50}$ | R$^1$ | R$^{3g}$ | R$^{3b}$ | m/z |
|---|---|---|---|---|---|
| 12021 | D | (4-methylbenzamidoethyl-thiourea-fluorescein substituent) | H | OCH$_2$COOH | 1057(MH$^+$) |
| 12022 | D | (4-methylphenoxyacetamidoethyl-thiourea-fluorescein substituent) | H | OCH$_2$COOH | 1087(MH$^+$) |
| 12023 | D | 4-fluorophenyl | H | OCH$_2$COOH | 599(MH$^+$) |
| 12024 | D | 4-trifluoromethylphenyl | H | OCH$_2$COOH | 649(MH$^+$) |

TABLE 12-continued
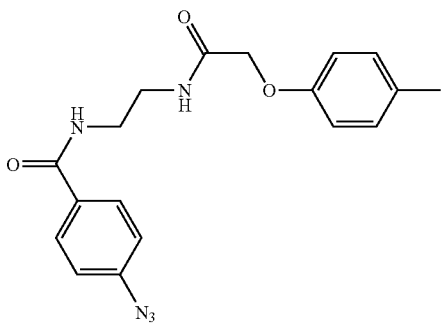
| Entry # | IC$_{50}$ | R$^1$ | R$^{3g}$ | R$^{3b}$ | m/z |
|---|---|---|---|---|---|
| 12025 | D | (structure with azidobenzamide-ethylenediamine-tolyloxyacetamide) | H | OCH$_2$COOH | 842(MH$^+$) |
| 12026 | D | (structure with benzoylbenzamide-ethylenediamine-tolyloxyacetamide) | H | OCH$_2$COOH | 905(MH$^+$) |
TABLE 13
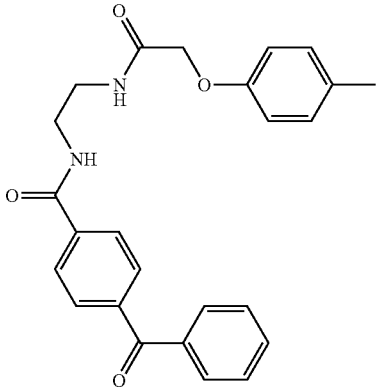
| Entry # | IC$_{50}$ | R$^{3b}$ | R$^{3c}$ | R$^{3f}$ | m/z |
|---|---|---|---|---|---|
| 13001 | D | OH | H | H | 512(MH$^+$) |
| 13002 | D | OH | CH$_3$ | H | 526(MH$^+$) |
| 13003 | D | OCH$_2$COOH | CH$_3$ | H | 584(MH$^+$) |

TABLE 13-continued
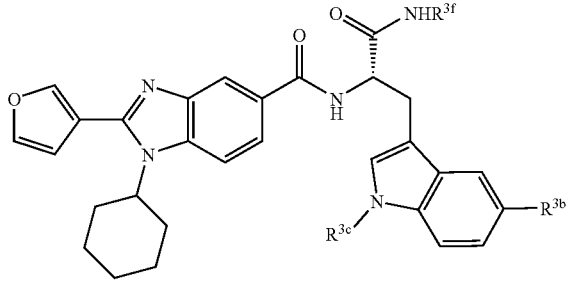
| Entry # | IC$_{50}$ | R$^{3b}$ | R$^{3c}$ | R$^{3f}$ | m/z |
|---|---|---|---|---|---|
| 13004 | D | 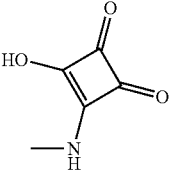 | H | H | 607(MH$^+$) |
| 13005 | D | NH$_2$ | H | H | 511(MH$^+$) |
| 13006 | D | NHSO$_2$CH$_3$ | H | H | 589(MH$^+$) |
| 13007 | D | NHSO$_2$CF$_3$ | H | H | 643(MH$^+$) |
| 13008 | D | NHCOCOOH | H | H | 583(MH$^+$) |
| 13009 | D | NHCOCONH$_2$ | H | H | 582(MH$^+$) |
| 13010 | D | NHCOCONHCH$_3$ | H | H | 596(MH$^+$) |
| 13011 | D | NHCOCONHOH | H | H | 598(MH$^+$) |
| 13012 | D | 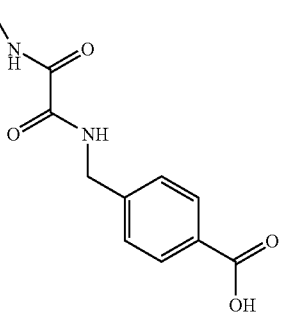 | H | H | 716(MH$^+$) |
| 13013 | D | NHCOCONH$_2$ | H | H | 554(MH$^+$) |
| 13014 | D | OH | H | CH(CH$_2$OH)$_2$ | 586(MH$^+$) |
| 13015 | D | OH | H | CH$_2$CH$_2$N(CH$_3$)$_2$ | 583(MH$^+$) |
| 13016 | D | OH | H | CH$_2$CH$_2$OH | 556(MH$^+$) |
| 13017 | D | OH | H | 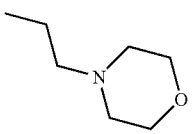 | 625(MH$^+$) |

TABLE 13-continued
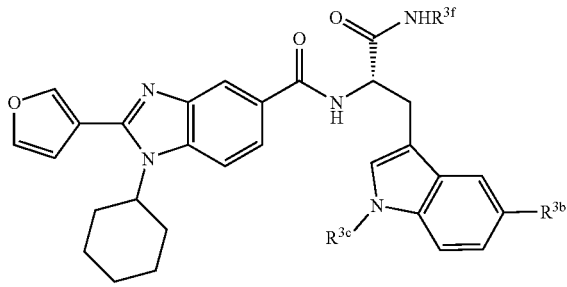
| Entry # | IC$_{50}$ | R$^{3b}$ | R$^{3c}$ | R$^{3f}$ | m/z |
|---|---|---|---|---|---|
| 13018 | D | OH | H | CH$_2$CH$_2$CH$_2$N(CH$_3$)$_2$ | 597(MH$^+$) |
| 13019 | D | OH | H | 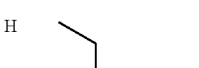 | 609(MH$^+$) |
| 13020 | D | OH | H |  | 623(MH$^+$) |
| 13021 | D | OH | H | C(CH$_3$)$_2$CH$_2$OH | 584(MH$^+$) |
| 13022 | D | OH | H | CH$_2$CH(OH)CH$_2$OH | 586(MH$^+$) |
TABLE 14
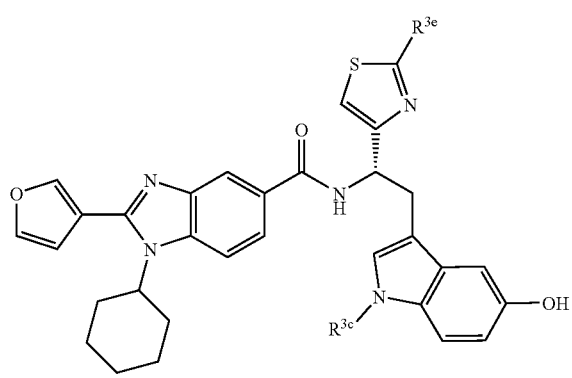
| Entry # | IC$_{50}$ | R$^{3c}$ | R$^{3e}$ | m/z |
|---|---|---|---|---|
| 14001 | D | H | CH$_3$ | 566(MH$^+$) |
| 14002 | D | H | NH$_2$ | 567(MH$^+$) |
| 14003 | D | CH$_3$ | NH$_2$ | 581(MH$^+$) |
| 14004 | D | H | NHCH$_3$ | 472(MH$^+$) |
| 14005 | D | H | N(CH$_3$)$_2$ | 595(MH$^+$) |
| 14006 | D | H | NHCOCH$_3$ | 609(MH$^+$) |
| 14007 | D | H | H | 552(MH$^+$) |
TABLE 15
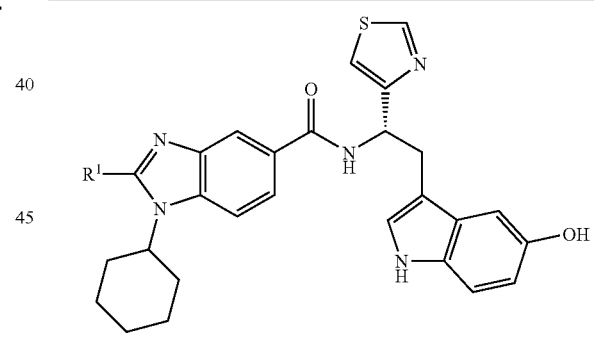
| Entry # | IC$_{50}$ | R$^1$ | m/z |
|---|---|---|---|
| 15001 | D | 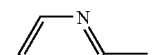 | 563(MH$^+$) |
| 15002 | D | 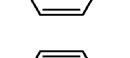 | 562(MH$^+$) |
| 15003 | D | 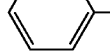 | 551(MH$^+$) |

TABLE 16

| Entry # | IC$_{50}$ | R$^{3a}$ | R$^{3j}$ | R$^{3k}$ | R$^{3l}$ | m | m/z |
|---|---|---|---|---|---|---|---|
| 16001 | D | COOH | H | OH | H | 0 | 460(MH$^+$) |
| 16002 | D | COOH | H | CH$_2$COOH | H | 1 | 516(MH$^+$) |
| 16003 | D | COOH | H | NH$_2$ | H | 1 | 473(MH$^+$) |
| 16004 | D | COOH | OMe | OMe | H | 0 | 504(MH$^+$) |
| 16005 | D | H | OMe | OMe | H | 0 | 460(MH$^+$) |
| 16006 | D | COOH | OMe | OMe | H | 0 | 504(MH$^+$) |
| 16007 | D | COOH | OMe | OMe | H | 1 | 518(MH$^+$) |
| 16008 | D | COOH | H | OH | H | 1 | 474(MH$^+$) |
| 16009 | D | COOH | H | NHCOCOOH | H | 1 | 545(MH$^+$) |
| 16010 | D | COOH | H | NHCH$_2$COOH | H | 1 | 531(MH$^+$) |
| 16011 | D | COOH | H | OCH$_2$COOH | H | 1 | 532(MH$^+$) |
| 16012 | D | COOH | H | COOH | H | 1 | 502(MH$^+$) |
| 16013 | D | COOH | H | OH | H | 2 | 488(MH$^+$) |
| 16014 | D | COOH | H | OCH$_2$COOH | H | 2 | 546(MH$^+$) |

TABLE 16-continued

| Entry # | IC$_{50}$ | R$^{3a}$ | R$^{3j}$ | R$^{3k}$ | R$^{3l}$ | m | m/z |
|---|---|---|---|---|---|---|---|
| 16015 | D | COOH | OH | OH | H | 1 | 490(MH$^+$) |
| 16016 | D | COOH | H | OCH$_2$COOH | H | 0 | 518(MH$^+$) |
| 16017 | D | COOH | H | tetrazole | H | 1 | 526(MH$^+$) |
| 16018 | D | COOH | H | OC(CH$_3$)$_2$COOH | H | 1 | 560(MH$^+$) |
| 16019 | D | COOCH$_2$CH$_3$ | H | tetrazole | H | 1 | 554(MH$^+$) |
| 16020 | D | COOH | H | H | OCH$_2$COOH | 1 | 532(MH$^+$) |
| 16021 | D | CONH$_2$ | H | OH | H | 1 | 473(MH$^+$) |
| 16022 | D | COOH | H | tetrazole-CH$_2$OCH$_3$ | H | 1 | 556(MH$^+$) |
| 16023 | D | CONH$_2$ | H | tetrazole | H | 1 | 525(MH$^+$) |
| 16024 | D | COOH | H | ethylidene-thiazolidinedione-thione | H | 1 | 601(MH$^+$) |
| 16025 | D | COOH | H | methylamino-hydroxy-cyclobutenedione | H | 1 | 569(MH$^+$) |

TABLE 16-continued

| Entry # | IC$_{50}$ | R$^{3a}$ | R$^{3j}$ | R$^{3k}$ | R$^{3l}$ | m | m/z |
|---|---|---|---|---|---|---|---|
| 16026 | D | C(O)OH | H | NHCONH$_2$ | H | 1 | 516(MH$^+$) |
| 16027 | D | C(O)OMe | H | NHCN | H | 1 | 512(MH$^+$) |
| 16028 | D | C(O)OH | H | NHCHO | H | 1 | 501(MH$^+$) |
| 16029 | D | C(O)OMe | H | methylamino-hydroxy-cyclobutenedione | H | 1 | 569(MH$^+$) |
| 16030 | D | C(O)OH | H | NHSO$_2$CF$_3$ | H | 1 | 605(MH$^+$) |
| 16031 | D | C(O)OH | H | NHCOCH$_3$ | H | 1 | 515(MH$^+$) |
| 16032 | D | C(O)OH | H | NHSO$_2$CH$_3$ | H | 1 | 551(MH$^+$) |
| 16033 | D | C(O)OMe | H | 1-methyl-1H-1,2,3-triazole-4-carboxylic acid | H | 1 | 583(MH$^+$) |
| 16034 | D | C(O)OH | CH$_3$ | OH | CH$_3$ | 1 | 502(MH$^+$) |
| 16035 | D | C(O)OH | H | CONH$_2$ | H | 1 | 501(MH$^+$) |
| 16036 | D | C(O)OH | H | 2-methyl-2H-tetrazol-5-yl | H | 1 | 540(MH$^+$) |
| 16037 | D | C(O)OH | H | 1-methyl-1H-tetrazol-5-yl | H | 1 | 540(MH$^+$) |

TABLE 16-continued

| Entry # | IC$_{50}$ | R$^{3a}$ | R$^{3j}$ | R$^{3k}$ | R$^{3l}$ | m | m/z |
|---|---|---|---|---|---|---|---|
| 16038 | D | COOH | H | CH$_2$CH$_2$COOH | H | 1 | 530(MH$^+$) |
| 16039 | D | COOH | H | methylcyclopropanecarboxylic acid | H | 1 | 542(MH$^+$) |
| 16040 | D | COOH | H | crotonic acid | H | 1 | 528(MH$^+$) |
| 16041 | D | COOH | Br | OH | Br | 1 | 632(MH$^+$) |
| 16042 | D | COOH | H | O(CH$_2$)$_4$COOH | H | 1 | 574(MH$^+$) |
| 16043 | D | COOH | H | O(CH$_2$)$_3$COOH | H | 1 | 560(MH$^+$) |
| 16044 | D | COOH | H | N-methyl-(S)-hydroxysuccinamide | H | 1 | 589(MH$^+$) |
| 16045 | D | COOH | H | N-methyl-(R)-hydroxysuccinamide | H | 1 | 589(MH$^+$) |
| 16046 | D | CH$_2$C(O)NH-(3-pyridyl) | H | OH | H | 1 | 550(MH$^+$) |
| 16047 | D | CH$_2$C(O)NHCH$_2$-(3-pyridyl) | H | OH | H | 1 | 564(MH$^+$) |
| 16048 | D | CH$_2$C(O)NH(CH$_2$)$_3$N(CH$_3$)$_2$ | H | OH | H | 1 | 558(MH$^+$) |

TABLE 16-continued

| Entry # | IC$_{50}$ | R$^{3a}$ | R$^{3j}$ | R$^{3k}$ | R$^{3l}$ | m | m/z |
|---|---|---|---|---|---|---|---|
| 16049 | D | COOH | H | 1-methyl-1H-1,2,3-triazole-4-carboxylic acid | H | 1 | 569(MH$^+$) |
| 16050 | D | COOH | H | PO$_4$ | H | 1 | 554(MH$^+$) |
| 16051 | D | COOH | (E)-3-carboxy-allyl | OMe | H | 1 | 558(MH$^+$) |
| 16052 | D | COOH | CH(OH)CH$_3$ | OH | H | 1 | 518(MH$^+$) |
| 16053 | D | COOH | COOH | H | H | 1 | 502(MH$^+$) |
| 16054 | D | COOH | COOH | OCH$_2$COOH | H | 1 | 576(MH$^+$) |
| 16055 | D | COOH | Cl | OCH$_2$COOH | CH$_3$ | 1 | 581(MH$^+$) |
| 16056 | D | COOH | tetrazolyl | OH | H | 1 | 542(MH$^+$) |
| 16057 | D | COOH | tetrazolyl | H | H | 1 | 526(MH$^+$) |
| 16058 | D | COOH | COOH | OH | H | 1 | 518(MH$^+$) |
| 16059 | D | 2-amino-4-methylthiazol-4-yl | H | tetrazolyl | H | 1 | 580(MH$^+$) |

TABLE 16-continued
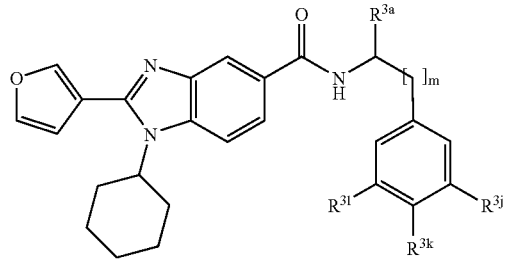
| Entry # | IC$_{50}$ | R$^{3a}$ | R$^{3j}$ | R$^{3k}$ | R$^{3l}$ | m | m/z |
|---|---|---|---|---|---|---|---|
| 16060 | D | 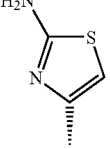 | H | OH | H | 1 | 528(MH$^+$) |
| 16061 | D | 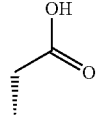 | H | 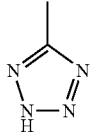 | H | 1 | 540(MH$^+$) |
| 16062 | D |  | 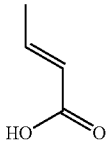 | OH | H | 1 | 543(MH$^+$) |
| 16063 | D |  | N$_3$ | OCH$_2$COOH | H | 1 | 573(MH$^+$) |
| 16064 | D |  | 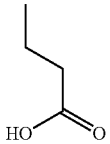 | OH | H | 1 | 544(MH$^+$) |
| 16065 | D |  | 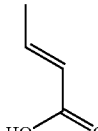 | OH | H | 1 | 546(MH$^+$) |

TABLE 17
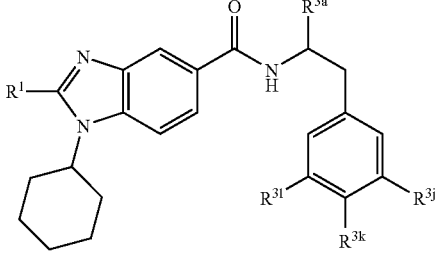
| Entry # | IC$_{50}$ μM | R$^1$ | R$^{3a}$ | R$^{3j}$ | R$^{3k}$ | R$^{3l}$ | m/z |
|---|---|---|---|---|---|---|---|
| 17001 | D | 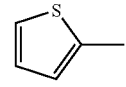 | 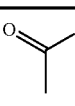 | OMe | OMe | H | 520(MH$^+$) |
| 17002 | D | 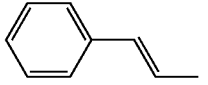 | H | OMe | OMe | H | 451(MH$^+$) |
TABLE 18
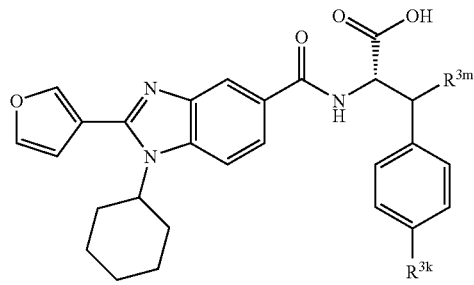
| Entry # | IC$_{50}$ | R$^{3m}$ | R$^{3k}$ | m/z |
|---|---|---|---|---|
| 18001 | D | 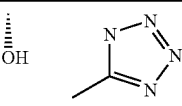 ＯＨ |  | 542(MH$^+$) |
TABLE 18-continued
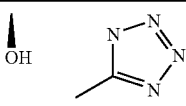
| Entry # | IC$_{50}$ | R$^{3m}$ | R$^{3k}$ | m/z |
|---|---|---|---|---|
| 18002 | D |  ＯＨ | 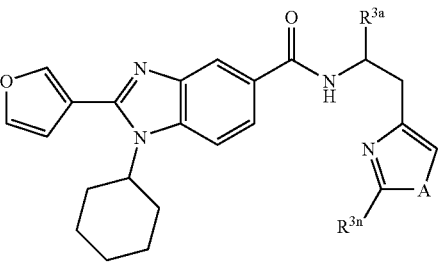 | 542(MH$^+$) |
TABLE 19
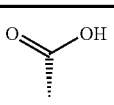
| Entry # | IC$_{50}$ | R$^{3a}$ | R$^{3n}$ | A | m/z |
|---|---|---|---|---|---|
| 19001 | D | O OH (acetic) | H | NCH$_2$COOH | 506(MH$^+$) |

TABLE 19-continued
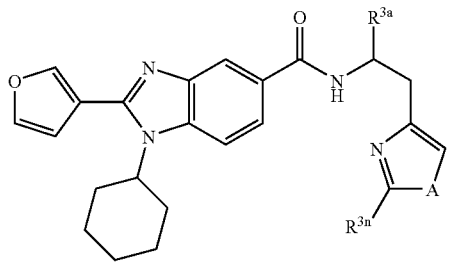
| Entry # | IC$_{50}$ | R$^{3a}$ | R$^{3n}$ | A | m/z |
|---|---|---|---|---|---|
| 19002 | D | ![structure](phenoxyacetic acid with ethyl) | NH$_2$ | S | 586(MH$^+$) |
TABLE 20
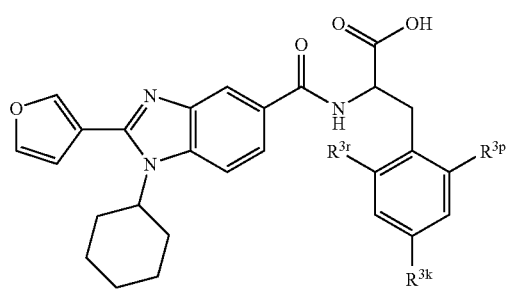
| Entry # | IC$_{50}$ | R$^{3k}$ | R$^{3p}$ | R$^{3r}$ | m/z |
|---|---|---|---|---|---|
| 20001 | D | OCH$_2$COOH | CH$_3$ | CH$_3$ | 560(MH$^+$) |
TABLE 21
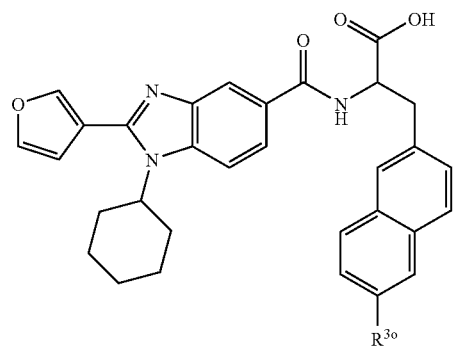
| Entry # | IC$_{50}$ | R$^{3o}$ | m/z |
|---|---|---|---|
| 21001 | D | OH | 524(MH$^+$) |
| 21002 | D | OCH$_2$COOH | 582(MH$^+$) |
TABLE 22
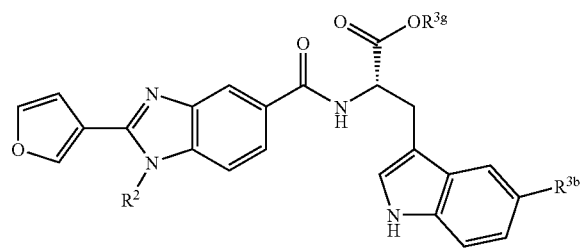
| Entry # | IC$_{50}$ μM | R$^2$ | R$^{3b}$ | R$^{3g}$ | m/z |
|---|---|---|---|---|---|
| 22001 | D |  | OH | H | 573(MH$^+$) |

TABLE 22-continued

| Entry # | IC$_{50}$ μM | R² | R$^{3b}$ | R$^{3g}$ | m/z |
|---|---|---|---|---|---|
| 22002 | D | cyclopentylmethyl | OH | H | 499(MH⁺) |
| 22003 | D | trans-2-hydroxycyclohexylmethyl | OH | H | 529(MH⁺) |
| 22004 | D | cyclopentylmethyl | OCH$_2$COOH | CH$_3$ | 571(MH⁺) |
| 22005 | D | trans-2-hydroxycyclohexylmethyl | OCH$_2$COOH | CH$_3$ | 601(MH⁺) |
| 22006 | D | isobutyl | OCH$_2$COOH | H | 531(MH⁺) |
| 22007 | D | cyclopentylmethyl | OCH$_2$COOH | H | 557(MH⁺) |
| 22008 | D | trans-2-hydroxycyclohexylmethyl | OCH$_2$COOH | H | 587(MH⁺) |
| 22009 | D | norbornylmethyl | OH | H | 525(MH⁺) |
| 22010 | D | (2,6-dimethylcyclohexyl)methyl | OH | H | 541(MH⁺) |
| 22011 | D | (2,5-dimethylcyclopentyl)methyl | OH | H | 527(MH⁺) |

TABLE 22-continued

| Entry # | IC$_{50}$ μM | R$^2$ | R$^{3b}$ | R$^{3g}$ | m/z |
|---|---|---|---|---|---|
| 22012 | D | (2,6-dimethylcyclohexyl) | OH | H | 541(MH$^+$) |
| 22013 | D | (norbornyl) | OH | H | 525(MH$^+$) |
| 22014 | D | (2-methyl-3-methylbutyl with OH) | OH | H | 517(MH$^+$) |
| 22015 | D | (cyclopropylmethyl-ethyl) | OH | H | 485(MH$^+$) |
| 22016 | D | (methylcycloheptyl) | OH | H | 527(MH$^+$) |
| 22017 | D | (2-methylcyclohexylmethyl) | OH | H | 527(MH$^+$) |
| 22018 | D | (2-benzyloxycyclohexylmethyl) | OH | H | 619(MH$^+$) |
| 22019 | D | (2-hydroxymethylcyclohexylmethyl) | OH | H | 543(MH$^+$) |

TABLE 22-continued

| Entry # | IC$_{50}$ μM | R$^2$ | R$^{3b}$ | R$^{3g}$ | m/z |
|---|---|---|---|---|---|
| 22020 | D | cyclobutylmethyl | OH | H | 485(MH$^+$) |
| 22021 | D | (2-methylcyclohexyl)methyl | OH | H | 527(MH$^+$) |

What is claimed is:

1. A compound of formula I:

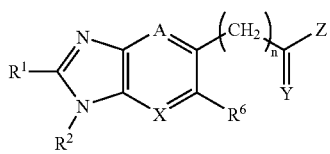

(I)

wherein:

X is CH

Y is O;

A is $COR^7$ or $CR^5$, wherein $R^5$ is H, halogen, or $(C_{1-6})$alkyl and $R^7$ is H or $(C_{1-6}$alkyl);

$R^6$ is H, halogen, $(C_{1-6}$alkyl) or $OR^7$, wherein $R^7$ is H or $(C_{1-6}$alkyl);

$R^1$ is selected from the group consisting of 5- or 6-membered heterocycle having 1 to 4 heteroatoms selected from O, N, and S, and 9-or 10-membered heterobicycle having 1 to 4 heteroatoms selected from O, N and S, wherein said heterocycle and heterobicycle are optionally substituted with from 1 to 4 substituents selected from: OH, halogen, $CF_3$, amino, cyano, phenyl$(C_{1-4})$alkoxy, COOH, —$OCH_2CONHCH_2Ph$, $(C_{1-4})$alkyl, —$OCH_2CONH(CH_2)_{2-3}N(CH_3)_2$, $(C_{1-4})$alkoxy, —$OCH_2CO$-(morpholino), pyrrole, pyrrolidinyl, carboxy$(C_{2-4})$alkenyl, phenoxy, —$NH(C_{2-4})$acyl, —$O(CH_2)_mOH$, m being an integer from 2 to 4, $SO_3H$, and $NO_2$;

$R^2$ is selected from $(C_{3-7})$cycloalkyl, $(C_{3-7})$cycloalkyl$(C_{1-3})$alkyl, $(C_{6-10})$bicycloalkyl, norbornane, phenyl, and pyridyl, all of which is optionally substituted with from 1 to 4 substituents selected from halogen, $(C_{1-6})$alkyl, —$CH_2OH$, O-benzyl and OH; and (1) n is zero and Z is OH or $OR^3$, wherein $R^3$ is H, $(C_{1-6})$ alkyl or $(C_{6-10})$aryl$(C_{1-6})$alkyl, wherein said alkyl and said aryl are optionally substituted with from 1 to 4 substituents selected from the group consisting of: OH, COOH, COO$(C_{1-6})$alkyl, $(C_{1-6})$alkyl, $(C_{1-6})$alkyl-hydroxy, halogen, $(C_{1-6})$alkylamino, di-$(C_{1-6})$alkyl-amino, C(halogen)$_3$, —$NH_{(2-4)}$acyl and $(C_2)_p$COOH in which p is an integer from 1 to 4;

or (2) n is zero and Z is $OR^3$ wherein $R^3$ is $(C_{1-6})$alkyl substituted with a 6- or 10-membered aryl, said aryl being optionally substituted with from 1 to 4 substituents selected from the group consisting of: cyano, $NO_2$, —$COCH_3$, —$CONH_2$, —$NH_2$, sulfonamido, —$SO_2CH_3$, —$NHSO_2CH_3$ and $(C_{1-4})$alkoxy;

or (3) n is zero and Z is $NH_2$, $NMeR^3$ or $NHR^3$, wherein $R^3$ is H, or $(C_{1-6})$alkyl optionally substituted with from 1 to 4 substituents selected from the group consisting of: OH, COOH, COO$(C_{1-6})$alkyl, halogen, $(C_{1-6})$alkylamino and di-$(C_{1-6})$alkyl-amino;

or (4) n is 1 and Z is OH or $OR^3$ wherein $R^3$ is $(C_{1-6})$alkyl;

or a detectable derivative or salt thereof;

wherein the detectable derivative is selected from a compound of the formula (I) labeled with a fluorescent label or a colorimetric label;

with the proviso that if X is CH, Y is O, Z is OH n=0, and $R^2$ is optionally substituted cycloalkyl, then $R^1$ is not 5-aryl-2-furyl; and with the further proviso that if X is CH, Y is O, Z is OH, n=0, and $R^2$ is cycloalkyl, then $R^1$ is not 6-phenylbenzofuran-2-yl;

and with the further proviso that if X is CH, Y is O, Z is OH, n=1, then $R^1$ is not 5-azabenzimidazol-2-yl;

and with the further proviso that if X is CH, Y is O, Z is OH, n=0 or 1, $R^1$ is heteroaryl, then $R^2$ is not heteroaryl or phenyl;

and with the further proviso that if X is CH, Y is O, Z is $NMeR^3$ or $NHR^3$ wherein $R^3$ is alkyl, n=0, and $R^2$ is cycloalkyl or aryl, then $R^1$ is not a substituted 2-benzofuryl group;

and with the further proviso that if X is CH, Y is O, Z is $NHR^3$ wherein $R^3$ is alkyl, n=0, and $R^2$ is cycloalkyl, then $R^1$ is not a substituted benzofuryl group or benzofuran-2-yl;

and with the further proviso that if X is CH, Y is O, Z is $NHR^3$ wherein $R^3$ is alkyl, n=0, and $R^2$ is cycloalkyl, then $R^1$ is not heteroaryl;

and with the further proviso that if X is CH, Y is O, Z is OH or $NHR^3$ wherein $R^3$ is H, or alkyl, n=0, and $R^2$ is cycloalkyl, then $R^1$ is not tetrazolyl.

2. A compound of formula Ia:

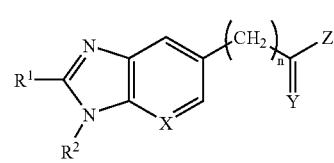

(Ia)

wherein:

X is CH;

Y is O;

$R^1$ is selected from 5- or 6-membered heteroaryl or heterocycle having 1 to 4 heteroatoms selected from O, N, and S and 9-or 10-atom heterobicycle having 1 to 4 heteroatoms selected from O, N and S, wherein said heteroaryl, and heterobicycle are all optionally substituted with 1 to 4 substituents selected from: OH, halogen, cyano, phenyl$(C_{1-4})$alkoxy, COOH, —$OCH_2CONHCH_2Ph$, $(C_{1-4})$alkyl, —$OCH_2CONH(CH_2)_{2-3}N(CH_3)_2$, $(C_{1-4})$alkoxy, —OCH$_2$CO-(morpholino), pyrrolidinyl, carboxy(C$_{2-4}$)alkenyl, phenoxy, —NH$_{(2-4)}$acyl, —O(CH$_2$)$_m$OH, m being an integer from 2 to 4, SO$_3$H and NO$_2$;

R$^2$ is selected from (C$_{3-7}$)cycloalkyl, (C$_{3-7}$)cycloalkyl(C$_{1-3}$) alkyl, (C$_{6-10}$)bicycloalkyl, norbornane, phenyl, and pyridyl, all of which is optionally substituted with from 1 to 4 substituents selected from:
halogen, (C$_{1-6}$)alkyl, —CH$_2$OH, O-benzyl and OH; and (1) n is zero or 1 and Z is OH;
or
(2) n is zero and Z is NH$_2$, NMeR$^3$ or NHR$^3$, wherein R$^3$ is (C$_{1-6}$)alkyl optionally substituted with from 1 to 4 substituents selected from the group consisting of: OH, COOH, COO(C$_{1-6}$)alkyl and halogen;
or a salt thereof;

with the proviso that if X is CH, Y is O, Z is OH, n=0, and R$^2$ is optionally substituted cycloalkyl, then R$^1$ is not 5-aryl-2-furyl; and with the further proviso that if X is CH, Y is O, Z is OH, n=0, and R$^2$ is cycloalkyl, then R$^1$ is not 6-phenylbenzofuran-2-yl;

and with the further proviso that if X is CH, Y is O, Z is OH, n=1, then R$^1$ is not 5-azabenzimidazol-2-yl;

and with the further proviso that if X is CH, Y is O, Z is OH, n=0 or 1, R$^1$ is heteroaryl, then R$^2$ is not heteroaryl or phenyl;

and with the further proviso that if X is CH, Y is O, Z is NMeR$^3$ or NHR$^3$ wherein R$^3$ is alkyl, n=0, and R$^2$ is cycloalkyl or aryl, then R$^1$ is not a substituted 2-benzofuryl group;

and with the further proviso that if X is CH, Y is O, Z is NHR$^3$ wherein R$^3$ is alkyl, n=0,
and R$^2$ is cycloalkyl, then R$^1$ is not a substituted benzofuryl group or benzofuran-2-yl;

and with the further proviso that if X is CH, Y is O, Z is NHR$^3$ wherein R$^3$ is alkyl, n=0,
and R$^2$ is cycloalkyl, then R$^1$ is not heteroaryl;

and with the further proviso that if X is CH, Y is O, Z is OH or NHR$^3$ wherein R$^3$ is H,
or alkyl, n=0, and R$^2$ is cycloalkyl, then R$^1$ is not tetrazolyl.

3. A compound of formula I as claimed in claim 1, having the following formula:

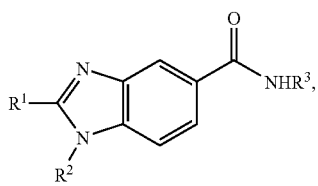

wherein
R$^1$ is selected from the group consisting of 5- or 6-membered heterocycle having 1 to 4 heteroatoms selected from O, N, and S and 9- or 10-membered heterobicycle having 1 to 4 heteroatoms selected from O, N and S,
wherein said heterocycle and heterobicycle are all optionally substituted with from 1 to 4 substituents selected from: OH, halogen, CF$_3$, amino, cyano, phenyl(C$_{1-4}$)alkoxy, COOH, —OCH$_2$CONHCH$_2$Ph, (C$_{1-4}$)alkyl, —OCH$_2$CONH(CH$_2$)$_{2-3}$N(CH$_3$)$_2$, (C$_{1-4}$) alkoxy, —OCH$_2$CO-(morpholino), pyrrolidinyl, carboxy(C$_{2-4}$)alkenyl, phenoxy, —NH$_{(2-4)}$acyl, —O(CH$_2$)$_m$OH, m being an integer from 2 to 4, SO$_3$H and NO$_2$;

R$^2$ is selected from (C$_{3-7}$)cycloalkyl, (C$_{3-7}$)cycloalkyl(C$_{1-3}$)alkyl, (C$_{6-10}$)bicycloalkyl, norbornane, phenyl, and pyridyl, all of which is optionally substituted with from 1 to 4 substituents selected from
halogen, (C$_{1-6}$)alkyl, —CH$_2$OH, O-benzyl and OH;

R$^3$ is selected from H and (C$_{1-6}$)alkyl optionally substituted with from 1 to 4 substituents selected from the group consisting of: OH, COOH, COO(C$_{1-6}$)alkyl, halogen, (C$_{1-6}$)alkylamino and di-(C$_{1-6}$)alkyl-amino;

or a detectable derivative or salt thereof,
wherein the detectable derivative is selected from a compound of the formula (I) labeled with a fluorescent label or a colorimetric label.

4. A compound of formula I as claimed in claim 1, having the following formula:

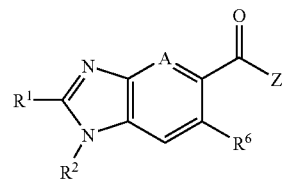

wherein
A is COR$^7$ or CR$^5$, wherein R$^5$ is H, halogen, or (C$_{1-6}$)alkyl and R$^7$ is H or (C$_{1-6}$alkyl);
R$^6$ is H, halogen, (C$_{1-6}$alkyl) or OR$^7$, wherein R$^7$ is H or (C$_{1-6}$alkyl);
R$^1$ is selected from the group consisting of 5- or 6-membered heterocycle having 1 to 4 heteroatoms selected from O, N, and S and 9- or 10-membered heterobicycle having 1 to 4 heteroatoms selected from O, N and S,
wherein said heterocycle and heterobicycle are all optionally substituted with from 1 to 4 substituents selected from: OH, halogen, CF$_3$, amino, cyano, phenyl(C$_{1-4}$)alkoxy, COOH, —OCH$_2$CONHCH$_2$Ph, (C$_{1-4}$)alkyl, —OCH$_2$CONH(CH$_2$)$_{2-3}$N(CH$_3$)$_2$, (C$_{1-4}$) alkoxy, —OCH$_2$CO-(morpholino), pyrrolidinyl, carboxy(C$_{2-4}$)alkenyl, phenoxy, —NH$_{(2-4)}$acyl, —O(CH$_2$)$_m$OH, m being an integer from 2 to 4, SO$_3$H, and NO$_2$;

R$^2$ is selected from (C$_{3-7}$)cycloalkyl, (C$_{3-7}$)cycloalkyl(C$_{1-3}$)alkyl, (C$_{6-10}$)bicycloalkyl, norbornane, phenyl, and pyridyl, all of which is optionally substituted with from 1 to 4 substituents selected from
halogen, (C$_{1-6}$)alkyl, —CH$_2$OH, O-benzyl and OH; and (1) Z is OH or OR$^3$, wherein R$^3$ is H, (C$_{1-6}$)alkyl or (C$_{6-10}$)aryl(C$_{1-6}$)alkyl, wherein said alkyl and said aryl are optionally substituted with from 1 to 4 substituents selected from the group consisting of: OH, COOH, COO(C$_{1-6}$)alkyl, (C$_{1-6}$)alkyl, (C$_{1-6}$)alkyl-hydroxy, halogen, (C$_{1-6}$)alkylamino, di-(C$_{1-6}$)alkyl-amino, C(halogen)$_3$, —NH(C$_{2-4}$)acyl and (CH$_2$)$_p$COOH in which p is an integer from 1 to 4;
or
(2) Z is OR$^3$ wherein R$^3$ is (C$_{1-6}$)alkyl substituted with a 6- or 10-membered aryl, said aryl being optionally substituted with from 1 to 4 substituents selected from the group consisting of: cyano, NO$_2$, —COCH$_3$, —CONH$_2$, —NH$_2$, sulfonamido, —SO$_2$CH$_3$, —NHSO$_2$CH$_3$ and (C$_{1-4}$)alkoxy;
or
(3) Z is NH$_2$, NMeR$^3$ or NHR$^3$, wherein R$^3$ is H, or (C$_{1-6}$) alkyl optionally substituted with from 1 to 4 substituents selected from the group consisting of: OH, COOH, COO($C_{1-6}$)alkyl, halogen, ($C_{1-6}$)alkylamino and di-($C_{1-6}$)alkyl-amino;

a detectable derivative or salt thereof, wherein the detectable derivative is selected from a compound of the formula (I) labeled with a fluorescent label or a colorimetric label.

5. A compound of formula I as claimed in claim 4, wherein $R^6$ is H or ($C_{1-6}$)alkyl.

6. A compound of formula I as claimed in claim 5 wherein $R^6$ is H.

7. A compound of formula I as claimed in claim 4, wherein Z is $NHR^3$, $OR^3$, or OH.

8. A compound of formula I as claimed in claim 7, wherein Z is $NHR^3$.

9. A compound of formula I as claimed in claim 1, wherein $R^1$ is selected from the group consisting of 5- or 6-membered heterocycle having 1 to 4 heteroatoms selected from O, N, and S and 9- or 10-membered heterobicycle having 1 to 4 heteroatoms selected from O, N and S, wherein said heterocycle and heterobicycle are all optionally substituted with from 1 to 4 substituents selected from: OH, halogen, $CF_3$, amino, cyano, phenyl($C_{1-4}$)alkoxy, COOH, —$OCH_2CONHCH_2Ph$, ($C_{1-4}$)alkyl, —$OCH_2CONH(CH_2)_{2-3}N(CH_3)_2$, ($C_{1-4}$)alkoxy, —$OCH_2CO$-(morpholino), pyrrole, pyrrolidinyl, carboxy($C_{2-4}$)alkenyl, phenoxy, —$NH(C_{2-4})$acyl, —$O(CH_2)_mOH$, m being an integer from 2 to 4, $SO_3H$, and $NO_2$.

10. A compound of formula I as claimed in claim 9, wherein $R^1$ is furanyl, tetrahydrofuranyl, pyridyl, N-methylpyrrolyl, pyrrolidinyl, pyrazine, imidazole, isoquinoline, thiazole, thiadiazole, pyrazole, isoxazole, indole, thiophene, 1,3-benzodioxazole or 1,4-benzodioxan,;

wherein said furanyl, tetrahydrofuranyl, pyridyl, N-methylpyrrolyl, pyrazine, isoquinoline, thiazole, pyrazole, isoxazole, indole, thiophene, 1,3-benzodioxazole, 1,4-benzodioxan or being optionally substituted with from 1 to 4 substituents selected from: ($C_{1-6}$alkyl), ($C_{1-4}$)alkoxy, —$OCH_2CONH(CH_2)_{2-3}N(CH_3)_2$, COOH, OH, halogen, $CF_3$, cyano, phenoxy, pyrrolidinyl, —NH($C_{2-4}$)acyl, —$O(CH_2)_2OH$, $NO_2$, and $SO_3H$.

11. A compound of formula I as claimed in claim 10, wherein $R^1$ is furanyl, pyridyl, thiophene, thiadiazole, 1,3-benzodioxazole, pyrazine, imidazole, pyrazole, or isooxazole, wherein said furanyl, pyridyl, thiophene, thiadiazole, 1,3-benzodioxazole, pyrazine, imidazole, pyrazole, isooxazole being optionally substituted with from 1 to 4 substituents selected from: ($C_{1-6}$alkyl), halogen, $CF_3$, OH, and —$O(CH_2)_2OH$.

12. A compound of formula I as claimed in claim 11, wherein $R^1$ is furanyl, pyridyl or thiophene.

13. A compound of formula I as claimed in claim 1, wherein $R^2$ is selected from ($C_{3-7}$)cycloalkyl, ($C_{3-7}$)cycloalkyl($C_{1-3}$)alkyl, ($C_{6-10}$)bicycloalkyl, norbornane, phenyl, and pyridyl, all of which is optionally substituted with from 1 to 4 substituents selected from:

halogen, ($C_{1-6}$)alkyl, —$CH_2OH$, O-benzyl and OH.

14. A compound of formula I as claimed in claim 13, wherein $R^2$ is norbornane, cyclobutyl, cyclopentyl, cyclohexyl, cycloheptyl,

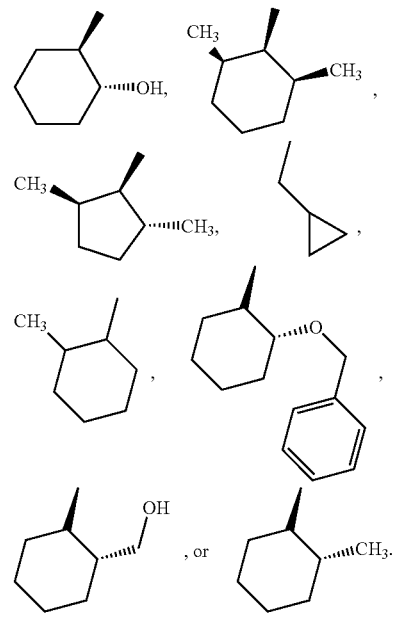

15. A compound of formula I as claimed in claim 14, wherein $R^2$ is cyclohexyl.

16. A compound of formula I as claimed in claim 1, wherein Z is $OR^3$, n=0, and $R^3$ is:

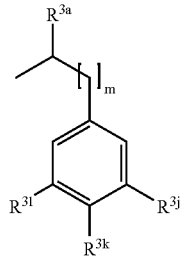

wherein
$R^{3a}$ is H, COOH or COO($C_{1-6}$)alkyl;
$R^{3j}$ is OH, ($C_{1-6}$alkyl), halogen; ($C_{1-6}$)alkyl-hydroxy or COOH;
$R^{3k}$ is OH, $(CH_2)_pCOOH$ where p is an integer from 1 to 4, or COOH;,
$R^{3l}$ is ($C_{1-6}$alkyl), or halogen; and
m is an integer from 0 to 4.

17. A compound of formula I as claimed in claim 16, wherein m is 1.

18. A compound of formula I as claimed in claim 1, wherein Z is $OR^3$, n=0, and $R^3$ is:

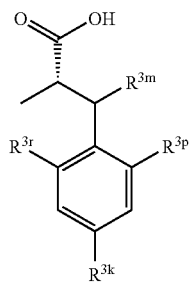

wherein $R^{3k}$ is OH, $(CH_2)_p$COOH where p is an integer from 1 to 4, or COOH, $R^{3m}$ is H or OH;

$R^{3p}$ is H, halogen, or ($C_{1-6}$alkyl); and $R^{3r}$ is H, halogen, or ($C_{1-6}$ alkyl).

19. A compound of formula I as claimed in claim 1, wherein $R^3$ is

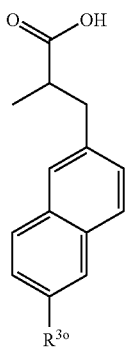

wherein $R^{3o}$ is OH.

20. A pharmaceutical composition comprising a compound of the formula I, as claimed in claim 1, or a pharmaceutically acceptable salt thereof, as an inhibitor of RNA dependent RNA polymerase activity of the enzyme NS5B encoded by HCV.

21. A pharmaceutical composition comprising a compound of the formula I, as claimed in claim 1, or a pharmaceutically acceptable salt thereof, as an inhibitor of HCV replication.

22. A method of treating HCV infection in a mammal, comprising administering to the mammal an effective amount of a compound of the following formula I, or a pharmaceutically acceptable salt thereof:

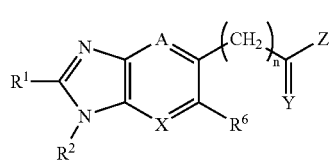

wherein:

X is CH;

Y is O;

A is $COR^7$ or $CR^5$, wherein $R^5$ is H, halogen, or ($C_{1-6}$)alkyl and $R^7$ is H or ($C_{1-6}$alkyl);

$R^6$ is H, halogen, ($C_{1-6}$alkyl) or $OR^7$, wherein $R^7$ is H or ($C_{1-6}$ alkyl);

$R^1$ is selected from the group consisting of 5- or 6-membered heterocycle having 1 to 4 heteroatoms selected from O, N, and S and 9- or 10-membered heterobicycle having 1 to 4 heteroatoms selected from O, N and S, wherein said heterocycle and heterobicycle are all optionally substituted with from 1 to 4 substituents selected from: OH, halogen, $CF_3$, amino, cyano, phenyl($C_{1-4}$)alkoxy, COOH, —$OCH_2CONHCH_2Ph$, ($C_{1-4}$)alkyl, —$OCH_2CONH(CH_2)_{2-3}N(CH_3)_2$, ($C_{1-4}$) alkoxy, —$OCH_2CO$-(morpholino), pyrrolidinyl, carboxy($C_{2-4}$)alkenyl, phenoxy, —$NH(C_{2-4})$acyl, —$O(CH_2)_mOH$, m being an integer from 2 to 4, $SO_3H$, and $NO_2$;

$R^2$ is selected from ($C_{1-6}$)alkyl, ($C_{3-7}$)cycloalkyl, ($C_{3-7}$) cycloalkyl($C_{1-3}$)alkyl, ($C_{6-10}$)bicycloalkyl, norbornane, phenyl, and pyridyl, all of which is optionally substituted with from 1 to 4 substituents selected from halogen, ($C_{1-6}$)alkyl, —$CH_2OH$, O-benzyl and OH; and (1) n is zero and Z is OH or $OR^3$, wherein $R^3$ is H, ($C_{1-6}$) alkyl or ($C_{6-10}$)aryl($C_{1-6}$)alkyl, wherein said alkyl and said aryl are optionally substituted with from 1 to 4 substituents selected from the group consisting of: OH, COOH, COO($C_{1-6}$)alkyl, ($C_{1-6}$)alkyl, ($C_{1-6}$)alkyl-hydroxy, halogen, ($C_{1-6}$)alkylamino, di-($C_{1-6}$)alkylamino, C(halogen)$_3$, —$NH(C_{2-4})$acyl and $(CH_2)_p$ COOH in which p is an integer from 1 to 4;

or (2) n is zero and Z is $OR^3$ wherein $R^3$ is ($C_{1-6}$)alkyl substituted with a 6- or 10-membered aryl, said aryl being optionally substituted with from 1 to 4 substituents selected from the group consisting of: cyano, $NO_2$, —$COCH_3$, —$CONH_2$, —$NH_2$, sulfonamido, —$SO_2CH_3$, —$NHSO_2CH_3$ and ($C_{1-4}$)alkoxy;

or (3) n is zero and Z is $NH_2$, $NMeR^3$ or $NHR^3$, wherein $R^3$ is H, or ($C_{1-6}$)alkyl optionally substituted with from 1 to 4 substituents selected from the group consisting of: OH, COOH, COO($C_{1-6}$)alkyl, halogen, ($C_{1-6}$)alkylamino and di-($C_{1-6}$)alkyl-amino;

or (4) n is 1 and Z is OH or $OR^3$ wherein $R^3$ is ($C_{1-6}$)alkyl.

23. A pharmaceutical composition for the treatment of HCV infection, comprising an effective amount of a compound of formula I, as claimed in claim 1, or a pharmaceutically acceptable salt thereof, and a pharmaceutically acceptable carrier.

24. A method of inhibiting the RNA dependent RNA polymerase activity of the enzyme NS5B encoded by Hey, comprising contacting said enzyme with a compound of the following formula I or a pharmaceutically acceptable salt thereof:

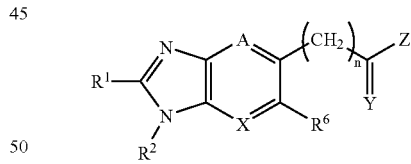

wherein:

X is CH;

Y is O;

A is $COR^7$ or $CR^5$, wherein $R^5$ is H, halogen, or ($C_{1-6}$)alkyl and $R^7$ is H or ($C_{1-6}$alkyl);

$R^6$ is H, halogen, ($C_{1-6}$alkyl) or $OR^7$, wherein $R^7$ is H or ($C_{1-6}$ alkyl);

$R^1$ is selected from the group consisting of 5- or 6-membered heterocycle having 1 to 4 heteroatoms selected from O, N, and S and 9- or 10-membered heterobicycle having 1 to 4 heteroatoms selected from O, N and S, wherein said heterocycle and heterobicycle are all optionally substituted with from 1 to 4 substituents selected from: OH, halogen, $CF_3$, amino, cyano, phenyl($C_{1-4}$)alkoxy, COOH, —$OCH_2CONHCH_2Ph$, $(C_{1-4})$alkyl, —OCH$_2$CONH(CH$_2$)$_{2-3}$N(CH$_3$)$_2$, $(C_{1-4})$ alkoxy, —OCH$_2$CO-(morpholino), pyrrolidinyl, carboxy$(C_{2-4})$ alkenyl, phenoxy, —NH$(C_{2-4})$acyl, —O(CH$_2$)$_m$OH, m being an integer from 2 to 4, SO$_3$H, and NO$_2$;

R$^2$ is selected from $(C_{1-6})$alkyl, $(C_{3-7})$cycloalkyl, $(C_{3-7})$cycloalkyl$(C_{1-3})$alkyl, $(C_{6-10})$bicycloalkyl, norbornane, phenyl, and pyridyl, all of which is optionally substituted with from 1 to 4 substituents selected from halogen, $(C_{1-6})$alkyl, —CH$_2$OH, O-benzyl and OH; and (1) n is zero and Z is OH or OR$^3$, wherein R$^3$ is H, $(C_{1-6})$ alkyl or $(C_{1-6})$aryl$(C_{1-6})$alkyl, wherein said alkyl and said aryl are optionally substituted with from 1 to 4 substituents selected from the group consisting of: OH, COOH, COO$(C_{1-6})$alkyl, $(C_{1-6})$alkyl, $(C_{1-6})$alkyl-hydroxy, halogen, $(C_{1-6})$alkylamino, di-$(C_{1-6})$alkyl-amino, C(halogen)$_3$, —NH$(C_{2-4})$acyl and (CH$_2$)$_p$COOH in which p is an integer from 1 to 4;

or (2) n is zero and Z is OR$^3$ wherein R$^3$ is $(C_{1-6})$alkyl substituted with a 6- or 10-membered aryl, said aryl being optionally substituted with from 1 to 4 substituents selected from the group consisting of: cyano, NO$_2$, —COCH$_3$, —CONH$_2$, —NH$_2$, sulfonamido, —SO$_2$CH$_3$, —NHSO$_2$CH$_3$ and $(C_{1-4})$alkoxy;

or (3) n is zero and Z is NH$_2$, NMeR$^3$ or NHR$^3$, wherein R$^3$ is H, or $(C_{1-6})$alkyl optionally substituted with from 1 to 4 substituents selected from the group consisting of: OH, COOH, COO$(C_{1-6})$alkyl, halogen, $(C_{1-6})$alkylamino and di-$(C_{1-6})$alkyl-amino;

or (4) n is 1 and Z is OH or OR$^3$ wherein R$^3$ is $(C_{1-6})$alkyl;

a detectable derivative thereof, wherein the detectable derivative is selected from a compound of the formula (I) labeled with a fluorescent label or a colorimetric label.

25. A method of inhibiting the replication of the hepatitis C virus, comprising contacting said virus with a compound of the following formula 1 or a pharmaceutically acceptable salt thereof:

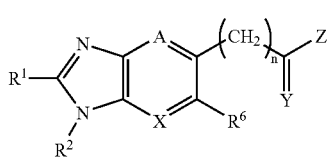

(I)

wherein:

X is CH;

Y is O;

A is COR$^7$ or CR$^5$, wherein R$^5$ is H, halogen, or $(C_{1-6})$alkyl and R$^7$ is H or $(C_{1-6}$alkyl);

R$^6$ is H, halogen, $(C_{1-6}$alkyl) or OR$^7$, wherein R$^7$ is H or $(C_{1-6}$alkyl);

R$^1$ is selected from the group consisting of 5- or 6-membered heterocycle having 1 to 4 heteroatoms selected from O, N, and S and 9- or 10-membered heterobicycle having 1 to 4 heteroatoms selected from O, N and S, wherein said heterocycle and heterobicycle are all optionally substituted with from 1 to 4 substituents selected from: OH, halogen, CF$_3$, amino, cyano, phenyl$(C_{1-4})$alkoxy, COOH, —OCH$_2$CONHCH$_2$Ph, $(C_{1-4})$alkyl, —OCH$_2$CONH(CH$_2$)$_{2-3}$N(CH$_3$)$_2$, $(C_{1-4})$ alkoxy, —OCH$_2$CO-(morpholino), pyrrolidinyl, carboxy$(C_{2-4})$alkenyl, phenoxy, —NH$(C_{2-4}$acyl, —O(CH$_2$)$_m$OH, m being an integer from 2 to 4, SO$_3$H, and NO$_2$;

R$^2$ is selected from $(C_{1-6})$alkyl, $(C_{3-7})$cycloalkyl, $(C_{3-7})$cycloalkyl$(C_{1-3})$alkyl, $(C_{6-10})$bicycloalkyl, norbornane, phenyl, and pyridyl, all of which is optionally substituted with from 1 to 4 substituents selected from halogen, $(C_{1-6})$alkyl, —CH$_2$OH, O-benzyl and OH; and (1) n is zero and Z is OH or OR$^3$, wherein R$^3$ is H, $(C_{1-6})$ alkyl or $(C_{6-10})$aryl$(C_{1-6})$alkyl, wherein said alkyl and said aryl are optionally substituted with from 1 to 4 substituents selected from the group consisting of: OH, COOH, COO$(C_{1-6})$alkyl, $(C_{1-6})$alkyl, $(C_{1-6})$alkyl-hydroxy, halogen, $(C_{1-6})$alkylamino, di-$(C_{1-6})$alkyl-amino, C(halogen)$_3$, —NH$(C_{2-4})$ acyl and (CH$_2$)$_p$COOH in which p is an integer from 1 to 4;

or (2) n is zero and Z is OR$^3$ wherein R$^3$ is $(C_{1-6})$alkyl substituted with a 6- or 10-membered aryl, said aryl being optionally substituted with from 1 to 4 substituents selected from the group consisting of: cyano, NO$_2$, —COCH$_3$, —CONH$_2$, —NH$_2$, sulfonamido, —SO$_2$CH$_3$, —NHSO$_2$CH$_3$ and $(C_{1-4})$alkoxy;

or (3) n is zero and Z is NH$_2$, NMeR$^3$ or NHR$^3$, wherein R$^3$ is H, or $(C_{1-6})$alkyl optionally substituted with from 1 to 4 substituents selected from the group consisting of: OH, COOH, COO$(C_{1-6})$alkyl, halogen, $(C_{1-6})$alkylamino and di-$(C_{1-6})$alkyl-amino;

or (4) n is 1 and Z is OH or OR$^3$ wherein R$^3$ is $(C_{1-6})$alkyl;

a detectable derivative thereof, wherein the detectable derivative is selected from a compound of the formula (I) labeled with a fluorescent label or a colorimetric label.

26. A method of treating HCV infection in a mammal, comprising giving written or oral instructions to administer a compound of the following formula I or a pharmaceutically acceptable salt thereof to a mammal in need of such treatment and administering said compound:

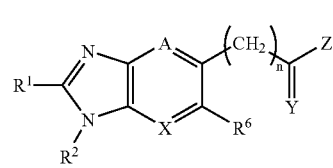

(I)

wherein:

X is OH;

Y is O;

A is COR$^7$ or CR$^5$, wherein R$^5$ is H, halogen, or $(C_{1-6})$alkyl and R$^7$ is H or $(C_{1-6}$alkyl);

R$^6$ is H, halogen, $(C_{1-6}$alkyl) or OR$^7$, wherein R$^7$ is H or $(C_{1-6}$alkyl);

R$^1$ is selected from the group consisting of 5- or 6-membered heterocycle having 1 to 4 heteroatoms selected from O, N, and S and 9- or 10-membered heterobicycle having 1 to 4 heteroatoms selected from O, N and S, wherein said heterocycle and heterobicycle are all optionally substituted with from 1 to 4 substituents selected from: OH, halogen, $CF_3$, amino, cyano, phenyl($C_{1-4}$)alkoxy, COOH, —$OCH_2CONHCH_2Ph$, ($C_{1-4}$)alkyl, —$OCH_2CONH(CH_2)_{2-3}N(CH_3)_2$, ($C_{1-4}$ alkoxy, —$OCH_2CO$-(morpholino), pyrrolidinyl, carboxy($C_{2-4}$)alkenyl, phenoxy, —$NH(C_{2-4})$acyl, —$O(CH_2)_mOH$, m being an integer from 2 to 4, $SO_3H$, and $NO_2$;

$R^2$ is selected from ($C_{1-6}$)alkyl, ($C_{3-7}$)cycloalkyl, ($C_{3-7}$)cycloalkyl($C_{1-3}$)alkyl, ($C_{6-10}$)bicycloalkyl, norbornane, phenyl, and pyridyl, all of which is optionally substituted with from 1 to 4 substituents selected from halogen, ($C_{1-6}$)alkyl, $CH_2OH$, O-benzyl and OH; and (1) n is zero and Z is OH or $OR^3$, wherein $R^3$ is H, ($C_{1-6}$) alkyl or ($C_{6-10}$)aryl($C_{1-6}$)alkyl, wherein said alkyl and said aryl are optionally substituted with from 1 to 4 substituents selected from the group consisting of: OH, COOH, COO($C_{1-6}$)alkyl, ($C_{1-6}$)alkyl, ($C_{1-6}$)alkyl-hydroxy, halogen, ($C_{1-6}$)alkylamino, di-($C_{1-6}$)alkylamino, C(halogen)$_3$, —$NH(C_{2-4})$acyl and $(CH_2)_p$ COOH in which p is an integer from 1 to 4;

or (2) n is zero and Z is $OR^3$ wherein $R^3$ is ($C_{1-6}$)alkyl substituted with a 6- or 10-membered aryl, said aryl being optionally substituted with from 1 to 4 substituents selected from the group consisting of: cyano, $NO_2$, —$COCH_3$, —$CONH_2$, —$NH_2$, sulfonamido, —$SO_2CH_3$, —$NHSO_2CH_3$ and ($C_{1-4}$)alkoxy;

or (3) n is zero and Z is $NH_2$, $NMeR^3$ or $NHR^3$, wherein $R^3$ is H, or ($C_{1-6}$)alkyl optionally substituted with from 1 to 4 substituents selected from the group consisting of: OH, COOH, COO($C_{1-6}$)alkyl, halogen, ($C_{1-6}$)alkylamino and di-($C_{1-6}$)alkyl-amino;

or (4) n is 1 and Z is OH or $OR^3$ wherein $R^3$ is ($C_{1-6}$)alkyl.

27. A compound of formula I as claimed in claim 1, having the following formula:

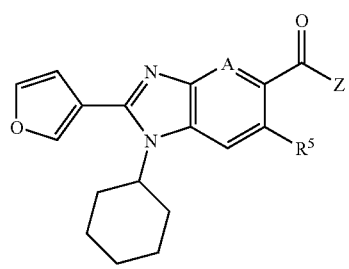

wherein A, $R^5$ and Z are as defined as follows:

| Entry # | A | $R^5$ | Z |
|---------|-----|-------|-----|
| 5004 | CMe | H | OH |

28. A compound of formula I as claimed in claim 1, having the following formula:

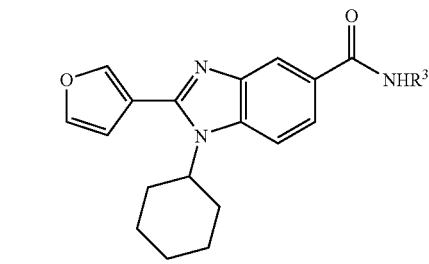

wherein $R^3$ is as defined as follows:

| Entry # | $R^3$ |
|---------|-------|
| 1159 | CH$_3$, propanoic acid group |
| 1178 | CH$_3$, 2-methylpropanoic acid group |

29. A compound of formula I as claimed in claim 1, having the following formula:

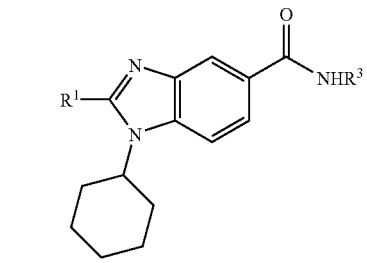

wherein $R^1$ and $R^3$ are as defined as follows:

| Entry # | $R^1$ | $R^3$ |
|---------|-------|-------|
| 2006 | 2-pyridyl | isopropyl-carboxylic acid |
| 2016 | 2-pyridyl | acetic acid |

-continued

| Entry # | R¹ | R³ |
|---|---|---|
| 2017 | 2-pyridyl | (2S,3S)-2-methyl-3-methylpentanoic acid |
| 2019 | 2-pyridyl | (2S,3R)-3-hydroxy-2-methylbutanoic acid |
| 2020 | 2-pyridyl | (2S)-3-hydroxy-2-methylpropanoic acid |
| 2021 | 2-pyridyl | (2R)-3-hydroxy-2-methylpropanoic acid |
| 2024 | 2-pyridyl | (2S)-2-methylpropanoic acid (isobutyric acid derivative) |
| 2054 | 2-pyridyl | (2S)-2-methyladipic acid |
| 2055 | 2-pyridyl | (2S)-2-methylsuccinic acid |

30. A compound of formula I as claimed in claim 1, having the following formula:

[benzimidazole-5-carboxylic acid core with R¹ at 2-position and R² on N1]

wherein R¹ and R² are as defined below:

| Entry # | R¹ | R² |
|---|---|---|
| 7001 | 2-pyridyl | 2-methylcyclohexyl |
| 7004 | 2-(1H-imidazolyl) | cyclohexyl |
| 7009 | 2-pyridyl | 3-pyridylmethyl |
| 7026 | 2-thienyl | cyclohexyl |
| 7027 | 4-bromo-5-methyl-2-thienyl | cyclohexyl |
| 7010 | 5-methyl-2-thienyl | cyclohexyl |
| 7013 | 2-furyl | cyclohexyl |

-continued
| Entry # | R¹ | R² |
|---|---|---|
| 7014 | 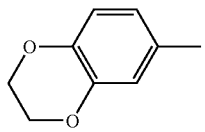 |  |
| 7015 | 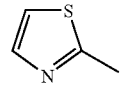 | 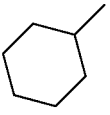 |
| 7018 | 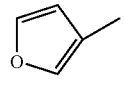 |  |
| 7019 | 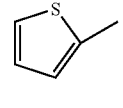 |  |
| 7020 | 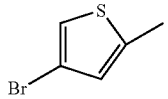 |  |
-continued
| Entry # | R¹ | R² |
|---|---|---|
| 7021 | 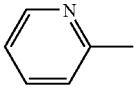 | 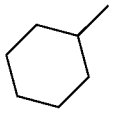 |
| 7022 | 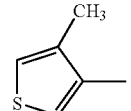 |  |
| 7023 | 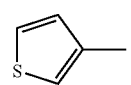 | 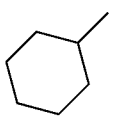 |
| 7024 | 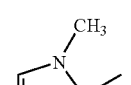 | 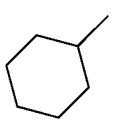 |
| 7025 | 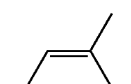 | 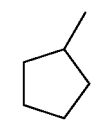 |
\* \* \* \* \*